United States Patent
Kim et al.

(10) Patent No.: US 11,299,478 B2
(45) Date of Patent: Apr. 12, 2022

(54) 2-CYANOPYRIMIDIN-4-YL CARBAMATE OR UREA DERIVATIVE OR SALT THEREOF, AND PHARMACEUTICAL COMPOSITION INCLUDING SAME

(71) Applicant: HANLIM PHARMACEUTICAL CO., LTD., Yongin-si (KR)

(72) Inventors: Kyung-Hee Kim, Daegu (KR); Jung-Wook Chin, Daegu (KR); Ji-Hoon Lee, Seoul (KR); Shin-Ae Kim, Daegu (KR); Kyung-Jin Jung, Daegu (KR); Jun-Woo Kim, Daegu (KR); Sang-Hyun Min, Daegu (KR); Ji-Hoon Yu, Seoul (KR); Ju-Suk Lee, Daegu (KR); Won-Seok Lee, Seoul (KR); Jae-Young Song, Daegu (KR); Eung-Seok Lee, Seoul (KR); Tae-Cheon Jeong, Daegu (KR); Jung-Ae Kim, Daegu (KR)

(73) Assignee: HANLIM PHARMACEUTICAL CO., LTD., Yongin-si (KR)

( * ) Notice: Subject to any disclaimer, the term of this patent is extended or adjusted under 35 U.S.C. 154(b) by 12 days.

(21) Appl. No.: 17/041,883

(22) PCT Filed: Mar. 20, 2019

(86) PCT No.: PCT/KR2019/003212
§ 371 (c)(1),
(2) Date: Sep. 25, 2020

(87) PCT Pub. No.: WO2019/190117
PCT Pub. Date: Oct. 3, 2019

(65) Prior Publication Data
US 2021/0047301 A1   Feb. 18, 2021

(30) Foreign Application Priority Data

Mar. 28, 2018 (KR) .................. 10-2018-0035639

(51) Int. Cl.
| | |
|---|---|
| *C07D 239/28* | (2006.01) |
| *C07D 403/12* | (2006.01) |
| *C07D 405/12* | (2006.01) |
| *C07D 401/12* | (2006.01) |
| *A61P 19/10* | (2006.01) |

(52) U.S. Cl.
CPC ............ *C07D 403/12* (2013.01); *A61P 19/10* (2018.01); *C07D 239/28* (2013.01); *C07D 401/12* (2013.01); *C07D 405/12* (2013.01)

(58) Field of Classification Search
CPC .. C07D 239/28; C07D 403/12; C07D 405/12; C07D 401/12; A61P 19/10
See application file for complete search history.

(56) References Cited

U.S. PATENT DOCUMENTS

| | | |
|---|---|---|
| 7,375,134 B2 | 5/2008 | Bayly et al. |
| 7,531,546 B2 | 5/2009 | Irie et al. |
| 7,973,037 B2 | 7/2011 | Bayly et al. |
| 8,318,748 B2 | 11/2012 | Bayly et al. |
| 8,772,336 B2 | 7/2014 | Bayly et al. |
| 9,458,181 B2 | 10/2016 | Stachel et al. |
| 2003/0232863 A1 | 12/2003 | Bayly et al. |
| 2005/0240023 A1 | 10/2005 | Bayly et al. |
| 2006/0258690 A1 | 11/2006 | Irie |
| 2007/0232586 A1 | 10/2007 | Ohmoto et al. |
| 2008/0188529 A1 | 8/2008 | Bayly et al. |
| 2009/0186889 A1 | 7/2009 | Irie et al. |
| 2010/0009956 A1 | 1/2010 | Coteron Lopez et al. |
| 2011/0230446 A1 | 9/2011 | Bayly et al. |
| 2013/0035312 A1 | 2/2013 | Bayly et al. |
| 2014/0256743 A1 | 9/2014 | Bayly et al. |
| 2015/0099719 A1 | 4/2015 | Stachel et al. |

FOREIGN PATENT DOCUMENTS

| | | |
|---|---|---|
| WO | 2007/025774 A2 | 3/2007 |
| WO | 2007/039470 A1 | 4/2007 |
| WO | 2014/181287 A1 | 11/2014 |

OTHER PUBLICATIONS

Costa et al., "Cathepsin K: its skeletal actions and role as a therapeutic target in osteoporosis", Nat. Rev. Rheumatol. 7, 447-456 (2011).

*Primary Examiner* — Laura L Stockton
(74) *Attorney, Agent, or Firm* — Vorys, Sater, Seymour and Pease LLP; Mih Suhn Koh

(57) ABSTRACT

Provided is a 2-cyanopyrimidin-4-yl carbamate or urea derivative or pharmaceutically acceptable salt thereof, a process for the preparation thereof, and a pharmaceutical composition comprising the same. The 2-cyanopyrimidin-4-yl carbamate or urea derivative or pharmaceutically acceptable salt thereof selectively inhibits cathepsin K and therefore can be usefully applied for preventing or treating osteoporosis.

12 Claims, No Drawings

2-CYANOPYRIMIDIN-4-YL CARBAMATE OR UREA DERIVATIVE OR SALT THEREOF, AND PHARMACEUTICAL COMPOSITION INCLUDING SAME

TECHNICAL FIELD

The present invention relates to a 2-cyanopyrimidin-4-yl carbamate or urea derivative or salt thereof and a pharmaceutical composition comprising the same.

BACKGROUND ART

Cathepsins are known as a lysosomal protease belonging to the papain-like cysteine protease family, including cathepsin B, C, F, H, L, O, S, V, X, W, etc. Among them, cathepsin K is a protease having strong collagenase activity and plays an important role in bone resorption. Cathepsin K is predominantly expressed in osteoclasts, while it is expressed in very low level in other tissues or cells. In case of osteoclasts, cathepsin K is expressed approximately 100 times or more, in comparison with other cathepsin L or S.

Cathepsin K is down-regulated by estrogen, and up-regulated by RANKL, TNF, vitamin D, PTH, interleukin, and the like. Cathepsin K cleaves the type I collagen that makes up the organic bone matrix. In addition to the collagen, cathepsin K also cleaves a variety of other proteins in bones or cartilage, such as osteonectin, aggrecan, IGF-1, and the like and thus the development for selective inhibitors against cathepsin K can be usefully applied as a therapeutic agent of osteoporosis (A. G. Costa, N. E. Cusano, B. C. Silva, S. Cremers. and J. P. Bilezikian, Cathepsin K: its skeletal actions and role as a therapeutic target in osteoporosis. Nat. Rev. Rheumatol. 7, 447-456 (2011)). For example, International Publication Nos. WO 03/075836, WO 04/076455 and the like have disclosed cathepsin K inhibitors useful for treating e.g. osteoporosis.

DETAILED DESCRIPTION OF THE INVENTION

Technical Problem

The present inventors found that a 2-cyanopyrimidin-4-yl carbamate or urea derivatives or pharmaceutically acceptable salt has a selective inhibitory activity against cathepsin K, and therefore can be usefully applied for preventing or treating osteoporosis.

Therefore, it is an object of the present invention to provide a 2-cyanopyrimidin-4-yl carbamate or urea derivative or pharmaceutically acceptable salt thereof, a process for the preparation thereof, and a pharmaceutical composition comprising the same.

It is another object of the present invention to provide a reagent for inhibiting cathepsin K comprising a 2-cyanopyrimidin-4-yl carbamate or urea derivative or salt thereof.

Technical Solution

According to an aspect of the present invention, there is provided a 2-cyanopyrimidin-4-yl carbamate or urea derivative or pharmaceutically acceptable salt thereof.

According to another aspect of the present invention, there is provided a process for preparing said compound or pharmaceutically acceptable salt thereof.

According to still another aspect of the present invention, there is provided a pharmaceutical composition for preventing or treating osteoporosis comprising said compound or pharmaceutically acceptable salt thereof as an active ingredient.

According to still another aspect of the present invention, there is provided a reagent for inhibiting cathepsin K comprising said compound or salt thereof.

Advantageous Effects

It was found by the present invention that the compound of the present invention, i.e., the 2-cyanopyrimidin-4-yl carbamate or urea derivative or pharmaceutically acceptable salt thereof has a selective inhibitory activity against cathepsin K. Therefore the compound of the present invention, i.e., the 2-cyanopyrimidin-4-yl carbamate or urea derivative or pharmaceutically acceptable salt thereof can be usefully applied for preventing or treating osteoporosis.

BEST MODE FOR CARRYING OUT THE INVENTION

The present invention provides a compound of Formula 1 or pharmaceutically acceptable salt thereof:

<Formula 1>

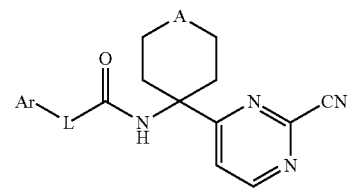

wherein,
A is a bond, —$CH_2$—, —O—, or —$C(CH_3)_2$—,
L is —$(CH_2)_m$—O—, —$(CH_2)_n$—NH—, —$CH(CH_3)$—NH—, or —$N(CH_3)$—,
m is 1 or 2,
n is 0, 1, or 2,
Ar is an aromatic ring selected from the group consisting of phenyl, phenoxy-phenyl, pyridinyl-phenyl, indazolyl-phenyl, morpholinyl-phenyl, piperazinyl-phenyl, piperidinyl-phenyl, pyrazolyl-phenyl, benzyl-phenyl, phenylamino-phenyl, biphenyl, piperazinyl-biphenyl, morpholinyl-biphenyl, naphthyl, benzodioxolyl, furanyl, indazolyl, quinoxalinyl, and indanyl, and the aromatic ring is optionally substituted with one to three substituents selected from the group consisting of halogen, cyano, hydroxy, trifluoromethyl, $C_1$~$C_4$ alkyl, $C_3$~$C_6$ cycloalkyl, $C_1$~$C_4$ alkoxy, hydroxy-$C_1$~$C_4$ alkyl, $C_1$~$C_4$ alkoxy-$C_1C_4$ alkyl, hydroxycarbonyl-$C_1$~$C_4$ alkyl, $C_1$~$C_4$ alkoxycarbonyl-$C_1$~$C_4$ alkyl, $C_1$~$C_4$ alkoxy-$C_1$~$C_4$ alkoxy-$C_1$~$C_4$ alkyl, $C_1$~$C_4$ alkylcarbonylamino-$C_1$~$C_4$ alkyl, amino-$C_1$~$C_4$ alkoxy, mono- or di-$C_1$~$C_4$ alkylamino-$C_1$~$C_4$ alkoxy, aminosulfonyl, $C_1$~$C_4$ alkyl-sulfonyl, trifluoromethylsulfonyl, $C_3$~$C_6$ cycloalkylaminosulfonyl, mono- or di-$C_1$~$C_4$ alkylamino, $C_1$~$C_4$ alkylcarbonylamino, methanesulfonylamino, $C_1$~$C_4$ alkylcarbonyl, hydroxycarbonyl, mono- or di-$C_1$~$C_4$ alkylaminocarbonyl, oxolanyl-$C_1$~$C_4$ alkylaminocarbonyl, di-$C_1$~$C_4$ alkylamino-$C_1$~$C_4$ alkylaminocarbonyl, imidazolyl-$C_1$~$C_4$ alkylaminocarbonyl, $C_1$~$C_4$ alkoxy-$C_1$~$C_4$ alkylaminocarbonyl, $C_3$~$C_6$ cycloalkylaminocarbonyl, pyrrolidinylcarbonyl, triazolyl-$C_1$~$C_4$ alkylaminocarbonyl, $C_1$~$C_4$ alkoxycarbonyl-$C_2$~$C_4$ alkynyl, hydroxycarbonyl-$C_2$~$C_4$ alkynyl, hydroxy-$C_1$~$C_4$ alkylphenyl-$C_2$~$C_4$ alkynyl, and $C_1$~$C_4$ alkoxy-$C_1$~$C_4$ alkyl-phenoxymethyl.

In the compound or pharmaceutically acceptable salt thereof according to the present invention, preferably, the aromatic ring is optionally substituted with one to three substituents selected from the group consisting of halogen, cyano, hydroxy, trifluoromethyl, $C_1$~$C_4$ alkyl, $C_3$~$C_6$ cycloalkyl, $C_1$~$C_4$ alkoxy, hydroxymethyl, methoxymethyl, hydroxycarbonylmethyl, hydroxycarbonylethyl, methoxycarbonylmethyl, methoxyethoxymethyl, acetylaminomethyl, aminoethoxy, methylaminoethoxy, dimethylaminoethoxy, aminosulfonyl, methanesulfonyl, trifluoromethylsulfonyl, cyclopropylaminosulfonyl, mono- or di-$C_1$~$C_4$ alkylamino, acetylamino, methanesulfonylamino, acetyl, hydroxycarbonyl, dimethylaminocarbonyl, oxolanylmethylaminocarbonyl, dimethylaminoethylaminocarbonyl, imidazolylethylaminocarbonyl, methoxyethylaminocarbonyl, cyclopropylaminocarbonyl, pyrrolidinylcarbonyl, triazolylethylaminocarbonyl, methoxycarbonylbutynyl, hydroxycarbonylbutynyl, hydroxymethylphenylethynyl, and methoxyethylphenoxymethyl. More preferably, the aromatic ring is substituted with one or two substituents selected from the group consisting of halogen, $C_1$~$C_4$ alkyl, and acetyl.

In the compound or pharmaceutically acceptable salt thereof according to the present invention, more preferably, A is —$CH_2$—, L is —$(CH_2)_n$—NH—, n is 0, Ar is an aromatic ring selected from the group consisting of biphenyl, piperazinyl-biphenyl, and morpholinyl-biphenyl, and the aromatic ring is substituted with one or two substituents selected from the group consisting of halogen, $C_1$~$C_4$ alkyl, and acetyl.

In the compound or pharmaceutically acceptable salt thereof according to the present invention, especially preferably, A is —$CH_2$—, L is —$(CH_2)_n$—NH—, n is 0, Ar is a piperazinyl-biphenyl group substituted with one or two substituents selected from the group consisting of halogen and $C_1$~$C_4$ alkyl.

In the compound of the present invention, preferable compounds or pharmaceutically acceptable salt thereof include the following compounds:

benzyl (1-(2-cyanopyrimidin-4-yl)cyclopentyl)carbamate;
4-bromobenzyl (1-(2-cyanopyrimidin-4-yl)cyclopentyl)carbamate;
3-bromobenzyl (1-(2-cyanopyrimidin-4-yl)cyclopentyl)carbamate;
phenethyl (1-(2-cyanopyrimidin-4-yl)cyclopentyl)carbamate;
3-methylbenzyl (1-(2-cyanopyrimidin-4-yl)cyclopentyl)carbamate;
3-methoxybenzyl (1-(2-cyanopyrimidin-4-yl)cyclopentyl)carbamate;
3-fluorobenzyl (1-(2-cyanopyrimidin-4-yl)cyclopentyl)carbamate;
3-chlorobenzyl (1-(2-cyanopyrimidin-4-yl)cyclopentyl)carbamate;
3-cyanobenzyl (1-(2-cyanopyrimidin-4-yl)cyclopentyl)carbamate;
benzyl (1-(2-cyanopyrimidin-4-yl)cyclohexyl)carbamate;
4-bromobenzyl (1-(2-cyanopyrimidin-4-yl)cyclohexyl)carbamate;
3-bromobenzyl (1-(2-cyanopyrimidin-4-yl)cyclohexyl)carbamate;
3-methylbenzyl (1-(2-cyanopyrimidin-4-yl)cyclohexyl)carbamate;
3-(trifluoromethyl)benzyl (1-(2-cyanopyrimidin-4-yl)cyclohexyl)carbamate;
3-fluorobenzyl (1-(2-cyanopyrimidin-4-yl)cyclohexyl)carbamate;
3-chlorobenzyl (1-(2-cyanopyrimidin-4-yl)cyclohexyl)carbamate;
2-methylbenzyl (1-(2-cyanopyrimidin-4-yl)cyclohexyl)carbamate;
2-fluorobenzyl (1-(2-cyanopyrimidin-4-yl)cyclohexyl)carbamate;
2-bromobenzyl (1-(2-cyanopyrimidin-4-yl)cyclohexyl)carbamate;
2-(trifluoromethyl)benzyl (1-(2-cyanopyrimidin-4-yl)cyclohexyl)carbamate;
2-methoxybenzyl (1-(2-cyanopyrimidin-4-yl)cyclohexyl)carbamate;
4-methylbenzyl (1-(2-cyanopyrimidin-4-yl)cyclohexyl)carbamate;
4-chlorobenzyl (1-(2-cyanopyrimidin-4-yl)cyclohexyl)carbamate;
4-(trifluoromethyl)benzyl (1-(2-cyanopyrimidin-4-yl)cyclohexyl)carbamate;
4-methoxybenzyl (1-(2-cyanopyrimidin-4-yl)cyclohexyl)carbamate;
naphthalen-1-ylmethyl (1-(2-cyanopyrimidin-4-yl)cyclohexyl)carbamate;
4-fluorobenzyl (1-(2-cyanopyrimidin-4-yl)cyclohexyl)carbamate;
2-chlorobenzyl (1-(2-cyanopyrimidin-4-yl)cyclohexyl)carbamate;
(4'-(methylsulfonyl)-[1,1'-biphenyl]-4-yl)methyl (1-(2-cyanopyrimidin-4-yl)cyclopentyl)carbamate;
(4'-(methylsulfonyl)-[1,1'-biphenyl]-3-yl)methyl (1-(2-cyanopyrimidin-4-yl)cyclopentyl)carbamate;
(4'-morpholino-[1,1'-biphenyl]-4-yl)methyl (1-(2-cyanopyrimidin-4-yl)cyclopentyl)carbamate;
(4'-morpholino-[1,1'-biphenyl]-3-yl)methyl (1-(2-cyanopyrimidin-4-yl)cyclopentyl)carbamate;
4-(6-fluoropyridin-3-yl)benzyl (1-(2-cyanopyrimidin-4-yl)cyclopentyl)carbamate;
4-(1-methyl-1H-indazol-6-yl)benzyl (1-(2-cyanopyrimidin-4-yl)cyclopentyl)carbamate;
3-(6-fluoropyridin-3-yl)benzyl (1-(2-cyanopyrimidin-4-yl)cyclopentyl)carbamate;
3-(1-methyl-1H-indazol-6-yl)benzyl (1-(2-cyanopyrimidin-4-yl)cyclopentyl)carbamate;
1-(1-(2-cyanopyrimidin-4-yl)cyclopentyl)-3-(ortho-tolyl)urea;
1-(1-(2-cyanopyrimidin-4-yl)cyclopentyl)-3-(meta-tolyl)urea;
1-(1-(2-cyanopyrimidin-4-yl)cyclopentyl)-3-(para-tolyl)urea;
1-(1-(2-cyanopyrimidin-4-yl)cyclopentyl)-3-(2-fluorobenzyl)urea;
1-(1-(2-cyanopyrimidin-4-yl)cyclopentyl)-3-phenylurea;
1-benzyl-3-(1-(2-cyanopyrimidin-4-yl)cyclopentyl)urea;
1-(benzo[d][1,3]dioxol-5-ylmethyl)-3-(1-(2-cyanopyrimidin-4-yl)cyclopentyl)urea;
1-(1-(2-cyanopyrimidin-4-yl)cyclopentyl)-3-(4-phenoxyphenyl)urea;
4-(2-(3-(1-(2-cyanopyrimidin-4-yl)cyclopentyl)ureido)ethyl)benzenesulfonamide;
1-(1-(2-cyanopyrimidin-4-yl)cyclopentyl)-3-(2-methylbenzyl)urea;
1-(1-(2-cyanopyrimidin-4-yl)cyclopentyl)-3-(3-methylbenzyl)urea;

1-(1-(2-cyanopyrimidin-4-yl)cyclopentyl)-3-(4-methylbenzyl)urea;
1-(1-(2-cyanopyrimidin-4-yl)cyclopentyl)-3-(3,4-dimethoxybenzyl)urea;
1-(1-(2-cyanopyrimidin-4-yl)cyclopentyl)-3-(2,5-dimethylphenyl)urea;
1-(1-(2-cyanopyrimidin-4-yl)cyclopentyl)-3-(1-phenylethyl)urea;
1-(1-(2-cyanopyrimidin-4-yl)cyclopentyl)-3-(4-(piperazin-1-yl)phenyl)urea;
1-(1-(2-cyanopyrimidin-4-yl)cyclopentyl)-3-(furan-3-ylmethyl)urea;
1-(1-(2-cyanopyrimidin-4-yl)cyclopentyl)-3-(4-fluorobenzyl)urea;
1-(1-(2-cyanopyrimidin-4-yl)cyclopentyl)-3-(naphthalen-1-ylmethyl)urea;
1-(1-(2-cyanopyrimidin-4-yl)cyclopentyl)-3-(2-(trifluoromethyl)benzyl)urea;
1-(1-(2-cyanopyrimidin-4-yl)cyclopentyl)-3-(3-(trifluoromethyl)benzyl)urea;
1-(1-(2-cyanopyrimidin-4-yl)cyclopentyl)-3-(4-(trifluoromethyl)benzyl)urea;
1-(1-(2-cyanopyrimidin-4-yl)cyclopentyl)-3-(2-(trifluoromethyl)phenyl)urea;
1-(1-(2-cyanopyrimidin-4-yl)cyclopentyl)-3-(3-(trifluoromethyl)phenyl)urea;
1-(1-(2-cyanopyrimidin-4-yl)cyclopentyl)-3-(4-(trifluoromethyl)phenyl)urea;
1-(1-(2-cyanopyrimidin-4-yl)cyclopentyl)-3-(3,4-dimethylphenyl)urea;
1-(1-(2-cyanopyrimidin-4-yl)cyclopentyl)-3-(3,5-dimethylphenyl)urea;
1-(1-(2-cyanopyrimidin-4-yl)cyclopentyl)-3-(2,3-dimethylphenyl)urea;
1-(1-(2-cyanopyrimidin-4-yl)cyclopentyl)-3-(2,5-difluorophenyl)urea;
1-(1-(2-cyanopyrimidin-4-yl)cyclopentyl)-3-(2-methyl-5-(trifluoromethyl)phenyl)urea;
1-(1-(2-cyanopyrimidin-4-yl)cyclopentyl)-3-(5-fluoro-2-(trifluoromethyl)phenyl)urea;
1-(1-(2-cyanopyrimidin-4-yl)cyclopentyl)-3-(2-methoxybenzyl)urea;
1-(1-(2-cyanopyrimidin-4-yl)cyclopentyl)-3-(3-methoxybenzyl)urea;
1-(1-(2-cyanopyrimidin-4-yl)cyclopentyl)-3-(4-methoxybenzyl)urea;
1-(1-(2-cyanopyrimidin-4-yl)cyclopentyl)-3-(3-hydroxyphenyl)urea;
4-(3-(1-(2-cyanopyrimidin-4-yl)cyclopentyl)ureido)benzenesulfonamide;
1-(1-(2-cyanopyrimidin-4-yl)cyclopentyl)-3-(2-hydroxyphenyl)urea;
1-(1-(2-cyanopyrimidin-4-yl)cyclopentyl)-3-(naphthalen-1-yl)urea;
1-(1-(2-cyanopyrimidin-4-yl)cyclopentyl)-3-(naphthalen-2-yl)urea;
1-(1-(2-cyanopyrimidin-4-yl)cyclopentyl)-3-(1-methyl-1H-indazol-5-yl)urea;
1-(1-(2-cyanopyrimidin-4-yl)cyclopentyl)-3-(quinoxalin-6-yl)urea;
1-(benzo[d][1,3]dioxol-5-yl)-3-(1-(2-cyanopyrimidin-4-yl)cyclopentyl)urea;
1-(1-(2-cyanopyrimidin-4-yl)cyclopentyl)-3-(2-methoxyphenyl)urea;
1-(1-(2-cyanopyrimidin-4-yl)cyclopentyl)-3-(3-methoxyphenyl)urea;
1-(1-(2-cyanopyrimidin-4-yl)cyclopentyl)-3-(4-methoxyphenyl)urea;
1-(1-(2-cyanopyrimidin-4-yl)cyclopentyl)-3-(2,3-dihydro-1H-inden-5-yl)urea;
1-(1-(2-cyanopyrimidin-4-yl)cyclopentyl)-3-(2-fluoro-5-(trifluoromethyl)phenyl)urea;
1-(1-(2-cyanopyrimidin-4-yl)-4,4-dimethylcyclohexyl)-3-(2,5-dimethylphenyl)urea;
1-(4-(2-cyanopyrimidin-4-yl)tetrahydro-2H-pyran-4-yl)-3-(4-fluoro-3-(trifluoromethyl)phenyl)urea;
1-(1-(2-cyanopyrimidin-4-yl)cyclohexyl)-3-phenylurea;
1-(1-(2-cyanopyrimidin-4-yl)cyclohexyl)-3-(2,5-dimethylphenyl)urea;
1-benzyl-3-(1-(2-cyanopyrimidin-4-yl)cyclohexyl)urea;
1-(1-(2-cyanopyrimidin-4-yl)cyclohexyl)-3-(3-(trifluoromethyl)phenyl)urea;
1-(1-(2-cyanopyrimidin-4-yl)cyclohexyl)-3-(4-(trifluoromethyl)phenyl)urea;
1-(1-(2-cyanopyrimidin-4-yl)cyclohexyl)-3-(2-(trifluoromethyl)benzyl)urea;
1-(1-(2-cyanopyrimidin-4-yl)cyclohexyl)-3-(2-(trifluoromethyl)phenyl)urea;
1-(4-chloro-3-(trifluoromethyl)phenyl)-3-(1-(2-cyanopyrimidin-4-yl)cyclohexyl)urea;
1-(1-(2-cyanopyrimidin-4-yl)cyclohexyl)-3-(2-fluoro-5-methylphenyl)urea;
1-(3,5-bis(trifluoromethyl)phenyl)-3-(1-(2-cyanopyrimidin-4-yl)cyclohexyl)urea;
1-(1-(2-cyanopyrimidin-4-yl)cyclohexyl)-3-(4-fluoro-3-(trifluoromethyl)phenyl)urea;
1-(1-(2-cyanopyrimidin-4-yl)cyclohexyl)-3-(2-fluoro-5-(trifluoromethyl)phenyl)urea;
2-(3-(1-(2-cyanopyrimidin-4-yl)cyclohexyl)ureido)-4-(trifluoromethyl)benzoic acid;
1-(1-(2-cyanopyrimidin-4-yl)cyclohexyl)-3-(2-methyl-5-(trifluoromethyl)phenyl)urea;
1-(4-benzylphenyl)-3-(1-(2-cyanopyrimidin-4-yl)cyclohexyl)urea;
1-(1-(2-cyanopyrimidin-4-yl)cyclohexyl)-3-(4-(phenylamino)phenyl)urea;
1-(1-(2-cyanopyrimidin-4-yl)cyclohexyl)-3-(2-hydroxyphenyl)urea;
1-(2,5-bis(trifluoromethyl)phenyl)-3-(1-(2-cyanopyrimidin-4-yl)cyclohexyl)urea;
3-(1-(2-cyanopyrimidin-4-yl)cyclohexyl)-1-methyl-1-phenylurea;
3-(1-(2-cyanopyrimidin-4-yl)cyclohexyl)-1-(4-fluoro-3-(trifluoromethyl)phenyl)-1-methylurea;
1-(1-(2-cyanopyrimidin-4-yl)cyclohexyl)-3-(2,4-difluoro-5-(trifluoromethyl)phenyl)urea;
1-(1-(2-cyanopyrimidin-4-yl)cyclohexyl)-3-(2-(methoxymethyl)-5-(trifluoromethyl)phenyl)urea;
1-(1-(2-cyanopyrimidin-4-yl)cyclohexyl)-3-(2-(hydroxymethyl)-5-(trifluoromethyl)phenyl)urea;
1-(3-bromophenyl)-3-(1-(2-cyanopyrimidin-4-yl)cyclohexyl)urea;
1-(4-bromophenyl)-3-(1-(2-cyanopyrimidin-4-yl)cyclohexyl)urea;
1-([1,1'-biphenyl]-3-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-3-yl)urea;
1-([1,1'-biphenyl]-4-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-4-yl)urea;

1-(1-(2-cyanopyrimidin-4-yl)cyclohexyl)-3-(4'-hydroxy-[1,1'-biphenyl]-4-yl)urea;
1-(1-(2-cyanopyrimidin-4-yl)cyclohexyl)-3-(4'-(methylsulfonyl)-[1,1'-biphenyl]-4-yl)urea;
1-(1-(2-cyanopyrimidin-4-yl)cyclohexyl)-3-(4'-morpholino-[1,1'-biphenyl]-4-yl)urea;
1-(1-(2-cyanopyrimidin-4-yl)cyclohexyl)-3-(4-(1-methyl-1H-indazol-6-yl)phenyl)urea;
1-(1-(2-cyanopyrimidin-4-yl)cyclohexyl)-3-(4-(pyridin-4-yl)phenyl)urea;
1-(1-(2-cyanopyrimidin-4-yl)cyclohexyl)-3-(4-(1-methyl-1H-pyrazol-4-yl)phenyl)urea;
1-(1-(2-cyanopyrimidin-4-yl)cyclohexyl)-3-(4'-fluoro-[1,1'-biphenyl]-4-yl)urea;
1-(1-(2-cyanopyrimidin-4-yl)cyclohexyl)-3-(4'-ethynyl-[1,1'-biphenyl]-4-yl)urea;
1-(1-(2-cyanopyrimidin-4-yl)cyclohexyl)-3-(3'-fluoro-[1,1'-biphenyl]-4-yl)urea;
1-(1-(2-cyanopyrimidin-4-yl)cyclohexyl)-3-(2'-fluoro-[1,1'-biphenyl]-4-yl)urea;
1-(1-(2-cyanopyrimidin-4-yl)cyclohexyl)-3-(4-(6-fluoropyridin-3-yl)phenyl)urea;
1-(1-(2-cyanopyrimidin-4-yl)cyclohexyl)-3-(4-(6-(trifluoromethyl)pyridin-3-yl)phenyl)urea;
1-(1-(2-cyanopyrimidin-4-yl)cyclohexyl)-3-(4-(6-methoxypyridin-3-yl)phenyl)urea;
1-(1-(2-cyanopyrimidin-4-yl)cyclohexyl)-3-(4-(pyridin-3-yl)phenyl)urea;
N-(4'-(3-(1-(2-cyanopyrimidin-4-yl)cyclohexyl)ureido)-[1,1'-biphenyl]-4-yl)acetamide;
4'-(3-(1-(2-cyanopyrimidin-4-yl)cyclohexyl)ureido)-N,N-dimethyl-[1,1'-biphenyl]-4-carboxamide;
3-(4'-(3-(1-(2-cyanopyrimidin-4-yl)cyclohexyl)ureido)-[1,1'-biphenyl]-4-yl)propanoic acid;
1-(1-(2-cyanopyrimidin-4-yl)cyclohexyl)-3-(4-iodophenyl)urea;
1-(4-bromo-3-(trifluoromethyl)phenyl)-3-(1-(2-cyanopyrimidin-4-yl)cyclohexyl)urea;
1-(4-bromo-2-fluorophenyl)-3-(1-(2-cyanopyrimidin-4-yl)cyclohexyl)urea;
4-(3-(1-(2-cyanopyrimidin-4-yl)cyclohexyl)ureido)benzoic acid;
1-(1-(2-cyanopyrimidin-4-yl)cyclohexyl)-3-(4-iodo-3-(trifluoromethyl)phenyl)urea;
1-(1-(2-cyanopyrimidin-4-yl)cyclohexyl)-3-(3-fluoro-4-iodophenyl)urea;
1-(1-(2-cyanopyrimidin-4-yl)cyclohexyl)-3-(4-(4-methylpiperazin-1-yl)phenyl)urea;
1-(1-(2-cyanopyrimidin-4-yl)cyclohexyl)-3-(4-morpholinophenyl)urea;
1-(1-(2-cyanopyrimidin-4-yl)cyclohexyl)-3-(4-(piperazin-1-yl)phenyl)urea;
1-(1-(2-cyanopyrimidin-4-yl)cyclohexyl)-3-(4-(4-(dimethylamino)piperidin-1-yl)phenyl)urea;
1-(1-(2-cyanopyrimidin-4-yl)cyclohexyl)-3-(4-(4-isopropylpiperazin-1-yl)phenyl)urea;
1-(4-(4-(tert-butyl)piperazin-1-yl)phenyl)-3-(1-(2-cyanopyrimidin-4-yl)cyclohexyl)urea;
1-(1-(2-cyanopyrimidin-4-yl)cyclohexyl)-3-(4-(4-cyclopropylpiperazin-1-yl)phenyl)urea;
1-(1-(2-cyanopyrimidin-4-yl)cyclohexyl)-3-(4-(4-isopropylpiperidin-1-yl)phenyl)urea;
1-(1-(2-cyanopyrimidin-4-yl)cyclohexyl)-3-(4-(4-ethylpiperazin-1-yl)phenyl)urea;
4'-(3-(1-(2-cyanopyrimidin-4-yl)cyclohexyl)ureido)-N-(2-methoxyethyl)-[1,1'-biphenyl]-4-carboxamide;
4'-(3-(1-(2-cyanopyrimidin-4-yl)cyclohexyl)ureido)-N-cyclopropyl-[1,1'-biphenyl]-4-sulfonamide;
4'-(3-(1-(2-cyanopyrimidin-4-yl)cyclohexyl)ureido)-N-cyclopropyl-[1,1'-biphenyl]-4-carboxamide;
1-(3'-chloro-4'-(pyrrolidin-1-carbonyl)-[1,1'-biphenyl]-4-yl)-3-(1-(2-cyanopyrimidin-4-yl)cyclohexyl)urea;
N-((4'-(3-(1-(2-cyanopyrimidin-4-yl)cyclohexyl)ureido)-[1,1'-biphenyl]-4-yl)methyl)acetamide;
1-(1-(2-cyanopyrimidin-4-yl)cyclohexyl)-3-(4'-((4-(2-methoxyethyl)phenoxy)methyl)-[1,1'-biphenyl]-4-yl)urea;
1-(1-(2-cyanopyrimidin-4-yl)cyclohexyl)-3-(4'-(2-(dimethylamino)ethoxy)-[1,1'-biphenyl]-4-yl)urea;
1-(1-(2-cyanopyrimidin-4-yl)cyclohexyl)-3-(4'-(4-isopropylpiperazin-1-yl)-[1,1'-biphenyl]-4-yl)urea;
1-(4'-(4-acetylpiperazin-1-yl)-[1,1'-biphenyl]-4-yl)-3-(1-(2-cyanopyrimidin-4-yl)cyclohexyl)urea;
methyl 2-(4'-(3-(1-(2-cyanopyrimidin-4-yl)cyclohexyl)ureido)-[1,1'-biphenyl]-4-yl)acetate;
1-(1-(2-cyanopyrimidin-4-yl)cyclohexyl)-3-(4'-((2-methoxyethoxy)methyl)-[1,1'-biphenyl]-4-yl)urea;
4'-(3-(1-(2-cyanopyrimidin-4-yl)cyclohexyl)ureido)-N-((tetrahydrofuran-2-yl)methyl)-[1,1'-biphenyl]-4-carboxamide;
4'-(3-(1-(2-cyanopyrimidin-4-yl)cyclohexyl)ureido)-N-(2-(dimethylamino)ethyl)-[1,1'-biphenyl]-4-carboxamide;
1-(1-(2-cyanopyrimidin-4-yl)cyclohexyl)-3-(4'-(4-ethylpiperazin-1-yl)-[1,1'-biphenyl]-4-yl)urea;
2-(4'-(3-(1-(2-cyanopyrimidin-4-yl)cyclohexyl)ureido)-[1,1'-biphenyl]-4-yl)acetic acid;
1-(1-(2-cyanopyrimidin-4-yl)cyclohexyl)-3-(4'-(methylsulfonyl)-2-(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-carboxylic acid;
N-(4'-(3-(1-(2-cyanopyrimidin-4-yl)cyclohexyl)ureido)-2'-fluoro-[1,1'-biphenyl]-4-yl)acetamide;
N-((4'-(3-(1-(2-cyanopyrimidin-4-yl)cyclohexyl)ureido)-2'-fluoro-[1,1'-biphenyl]-4-yl)methyl)acetamide;
1-(1-(2-cyanopyrimidin-4-yl)cyclohexyl)-3-(2-fluoro-4'-(4-isopropylpiperazin-1-yl)-[1,1'-biphenyl]-4-yl)urea;
1-(1-(2-cyanopyrimidin-4-yl)cyclohexyl)-3-(2-fluoro-4'-(methylsulfonyl)-[1,1'-biphenyl]-4-yl)urea;
1-(1-(2-cyanopyrimidin-4-yl)cyclohexyl)-3-(4'-(1-cyclopropylpiperidin-4-yl)-2-fluoro-[1,1'-biphenyl]-4-yl)urea;
1-(1-(2-cyanopyrimidin-4-yl)cyclohexyl)-3-(4'-((trifluoromethyl)sulfonyl)-[1,1'-biphenyl]-4-yl)urea;
1-(1-(2-cyanopyrimidin-4-yl)cyclohexyl)-3-(3'-fluoro-4'-(methylsulfonyl)-[1,1'-biphenyl]-4-yl)urea;
1-(1-(2-cyanopyrimidin-4-yl)cyclohexyl)-3-(4'-(methylsulfonyl)-3'-(trifluoromethyl)-[1,1'-biphenyl]-4-yl)urea;
1-(1-(2-cyanopyrimidin-4-yl)cyclohexyl)-3-(2'-(trifluoromethyl)-[1,1'-biphenyl]-4-yl)urea;
4'-(3-(1-(2-cyanopyrimidin-4-yl)cyclohexyl)ureido)-[1,1'-biphenyl]-4-sulfonamide;
N-(4'-(3-(1-(2-cyanopyrimidin-4-yl)cyclohexyl)ureido)-[1,1'-biphenyl]-4-yl)methanesulfonamide;
methyl 5-(4'-(3-(1-(2-cyanopyrimidin-4-yl)cyclohexyl)ureido)-[1,1'-biphenyl]-4-yl)pent-4-ynoate;
1-(2,2'-bis(trifluoromethyl)-[1,1'-biphenyl]-4-yl)-3-(1-(2-cyanopyrimidin-4-yl)cyclohexyl)urea;
1-(1-(2-cyanopyrimidin-4-yl)cyclohexyl)-3-(2-(trifluoromethyl)-4'-((trifluoromethyl)sulfonyl)-[1,1'-biphenyl]-4-yl)urea;
1-(1-(2-cyanopyrimidin-4-yl)cyclohexyl)-3-(4'-(methylsulfonyl)-2,3'-bis(trifluoromethyl)-[1,1'-biphenyl]-4-yl)urea;

4'-(3-(1-(2-cyanopyrimidin-4-yl)cyclohexyl)ureido)-2'-(trifluoromethyl)-[1,1'-biphenyl]-4-sulfonamide;
N-(4'-(3-(1-(2-cyanopyrimidin-4-yl)cyclohexyl)ureido)-2'-(trifluoromethyl)-[1,1'-biphenyl]-4-yl)methanesulfonamide;
1-(1-(2-cyanopyrimidin-4-yl)cyclohexyl)-3-((4'-(4-isopropylpiperazin-1-yl)-[1,1'-biphenyl]-4-yl)methyl)urea;
5-(4-(3-(1-(2-cyanopyrimidin-4-yl)cyclohexyl)ureido)phenyl)pent-4-ynoic acid;
1-(1-(2-cyanopyrimidin-4-yl)cyclohexyl)-3-(4-((4-(hydroxymethyl)phenyl)ethynyl)phenyl)urea;
N-(2-(1H-imidazol-4-yl)ethyl)-4'-(3-(1-(2-cyanopyrimidin-4-yl)cyclohexyl)ureido)-[1,1'-biphenyl]-4-carboxamide;
N-(2-(1H-imidazol-1-yl)ethyl)-4'-(3-(1-(2-cyanopyrimidin-4-yl)cyclohexyl)ureido)-[1,1'-biphenyl]-4-carboxamide;
N-(2-(1H-imidazol-1-yl)ethyl)-4'-(3-(1-(2-cyanopyrimidin-4-yl)cyclohexyl)ureido)-2'-fluoro-[1,1'-biphenyl]-4-carboxamide;
N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;
N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;
N-(2-(1H-imidazol-4-yl)ethyl)-4'-(3-(1-(2-cyanopyrimidin-4-yl)cyclohexyl)ureido)-2'-(trifluoromethyl)-[1,1'-biphenyl]-4-carboxamide;
1-(4'-(2-aminoethoxy)-[1,1'-biphenyl]-4-yl)-3-(1-(2-cyanopyrimidin-4-yl)cyclohexyl)urea;
1-(1-(2-cyanopyrimidin-4-yl)cyclohexyl)-3-(4'-(2-(methylamino)ethoxy)-[1,1'-biphenyl]-4-yl)urea.

In the compound of the present invention, more preferable compounds or pharmaceutically acceptable salt thereof include the following compounds:
1-([1,1'-biphenyl]-3-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-3-yl)urea;
1-([1,1'-biphenyl]-4-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-4-yl)urea;
1-(1-(2-cyanopyrimidin-4-yl)cyclohexyl)-3-(4'-hydroxy-[1,1'-biphenyl]-4-yl)urea;
1-(1-(2-cyanopyrimidin-4-yl)cyclohexyl)-3-(4'-(methylsulfonyl)-[1,1'-biphenyl]-4-yl)urea;
1-(1-(2-cyanopyrimidin-4-yl)cyclohexyl)-3-(4'-morpholino-[1,1'-biphenyl]-4-yl)urea;
1-(1-(2-cyanopyrimidin-4-yl)cyclohexyl)-3-(4'-fluoro-[1,1'-biphenyl]-4-yl)urea;
1-(1-(2-cyanopyrimidin-4-yl)cyclohexyl)-3-(4'-ethynyl-[1,1'-biphenyl]-4-yl)urea;
1-(1-(2-cyanopyrimidin-4-yl)cyclohexyl)-3-(3'-fluoro-[1,1'-biphenyl]-4-yl)urea;
1-(1-(2-cyanopyrimidin-4-yl)cyclohexyl)-3-(2'-fluoro-[1,1'-biphenyl]-4-yl)urea;
N-(4'-(3-(1-(2-cyanopyrimidin-4-yl)cyclohexyl)ureido)-[1,1'-biphenyl]-4-yl)acetamide;
4'-(3-(1-(2-cyanopyrimidin-4-yl)cyclohexyl)ureido)-N,N-dimethyl-[1,1'-biphenyl]-4-carboxamide;
3-(4'-(3-(1-(2-cyanopyrimidin-4-yl)cyclohexyl)ureido)-[1,1'-biphenyl]-4-yl)propanoic acid;
4'-(3-(1-(2-cyanopyrimidin-4-yl)cyclohexyl)ureido)-N-(2-methoxyethyl)-[1,1'-biphenyl]-4-carboxamide;
4'-(3-(1-(2-cyanopyrimidin-4-yl)cyclohexyl)ureido)-N-cyclopropyl-[1,1'-biphenyl]-4-sulfonamide;
4'-(3-(1-(2-cyanopyrimidin-4-yl)cyclohexyl)ureido)-N-cyclopropyl-[1,1'-biphenyl]-4-carboxamide;
1-(3'-chloro-4'-(pyrrolidin-1-carbonyl)-[1,1'-biphenyl]-4-yl)-3-(1-(2-cyanopyrimidin-4-yl)cyclohexyl)urea;
N-((4'-(3-(1-(2-cyanopyrimidin-4-yl)cyclohexyl)ureido)-[1,1'-biphenyl]-4-yl)methyl)acetamide;
1-(1-(2-cyanopyrimidin-4-yl)cyclohexyl)-3-(4'-((4-(2-methoxyethyl)phenoxy)methyl)-[1,1'-biphenyl]-4-yl)urea;
1-(1-(2-cyanopyrimidin-4-yl)cyclohexyl)-3-(4'-(2-(dimethylamino)ethoxy)-[1,1'-biphenyl]-4-yl)urea;
1-(1-(2-cyanopyrimidin-4-yl)cyclohexyl)-3-(4'-(4-isopropylpiperazin-1-yl)-[1,1'-biphenyl]-4-yl)urea;
1-(4'-(4-acetylpiperazin-1-yl)-[1,1'-biphenyl]-4-yl)-3-(1-(2-cyanopyrimidin-4-yl)cyclohexyl)urea;
methyl 2-(4'-(3-(1-(2-cyanopyrimidin-4-yl)cyclohexyl)ureido)-[1,1'-biphenyl]-4-yl)acetate;
1-(1-(2-cyanopyrimidin-4-yl)cyclohexyl)-3-(4'-((2-methoxyethoxy)methyl)-[1,1'-biphenyl]-4-yl)urea;
4'-(3-(1-(2-cyanopyrimidin-4-yl)cyclohexyl)ureido)-N-((tetrahydrofuran-2-yl)methyl)-[1,1'-biphenyl]-4-carboxamide;
4'-(3-(1-(2-cyanopyrimidin-4-yl)cyclohexyl)ureido)-N-(2-(dimethylamino)ethyl)-[1,1'-biphenyl]-4-carboxamide;
1-(1-(2-cyanopyrimidin-4-yl)cyclohexyl)-3-(4'-(4-ethylpiperazin-1-yl)-[1,1'-biphenyl]-4-yl)urea;
2-(4'-(3-(1-(2-cyanopyrimidin-4-yl)cyclohexyl)ureido)-[1,1'-biphenyl]-4-yl)acetic acid;
1-(1-(2-cyanopyrimidin-4-yl)cyclohexyl)-3-(4'-(methylsulfonyl)-2'-(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-carboxylic acid;
N-(4'-(3-(1-(2-cyanopyrimidin-4-yl)cyclohexyl)ureido)-2'-fluoro-[1,1'-biphenyl]-4-yl)acetamide;
N-((4'-(3-(1-(2-cyanopyrimidin-4-yl)cyclohexyl)ureido)-2'-fluoro-[1,1'-biphenyl]-4-yl)methyl)acetamide;
1-(1-(2-cyanopyrimidin-4-yl)cyclohexyl)-3-(2-fluoro-4'-(4-isopropylpiperazin-1-yl)-[1,1'-biphenyl]-4-yl)urea;
1-(1-(2-cyanopyrimidin-4-yl)cyclohexyl)-3-(2-fluoro-4'-(methylsulfonyl)-[1,1'-biphenyl]-4-yl)urea;
1-(1-(2-cyanopyrimidin-4-yl)cyclohexyl)-3-(4'-(1-cyclopropylpiperidin-4-yl)-2-fluoro-[1,1'-biphenyl]-4-yl)urea;
1-(1-(2-cyanopyrimidin-4-yl)cyclohexyl)-3-(4'-((trifluoromethyl)sulfonyl)-[1,1'-biphenyl]-4-yl)urea;
1-(1-(2-cyanopyrimidin-4-yl)cyclohexyl)-3-(3'-fluoro-4'-(methylsulfonyl)-[1,1'-biphenyl]-4-yl)urea;
1-(1-(2-cyanopyrimidin-4-yl)cyclohexyl)-3-(4'-(methylsulfonyl)-3'-(trifluoromethyl)-[1,1'-biphenyl]-4-yl)urea;
1-(1-(2-cyanopyrimidin-4-yl)cyclohexyl)-3-(2'-(trifluoromethyl)-[1,1'-biphenyl]-4-yl)urea;
4'-(3-(1-(2-cyanopyrimidin-4-yl)cyclohexyl)ureido)-[1,1'-biphenyl]-4-sulfonamide;
N-(4'-(3-(1-(2-cyanopyrimidin-4-yl)cyclohexyl)ureido)-[1,1'-biphenyl]-4-yl)methanesulfonamide;
methyl 5-(4'-(3-(1-(2-cyanopyrimidin-4-yl)cyclohexyl)ureido)-[1,1'-biphenyl]-4-yl)pent-4-ynoate;
1-(2,2'-bis(trifluoromethyl)-[1,1'-biphenyl]-4-yl)-3-(1-(2-cyanopyrimidin-4-yl)cyclohexyl)urea;
1-(1-(2-cyanopyrimidin-4-yl)cyclohexyl)-3-(2-(trifluoromethyl)-4'-((trifluoromethyl)sulfonyl)-[1,1'-biphenyl]-4-yl)urea;
1-(1-(2-cyanopyrimidin-4-yl)cyclohexyl)-3-(4'-(methylsulfonyl)-2,3'-bis(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-sulfonamide;

N-(4'-(3-(1-(2-cyanopyrimidin-4-yl)cyclohexyl)ureido)-2'-(trifluoromethyl)-[1,1'-biphenyl]-4-yl)methanesulfonamide;

1-(1-(2-cyanopyrimidin-4-yl)cyclohexyl)-3-((4'-(4-isopropylpiperazin-1-yl)-[1,1'-biphenyl]-4-yl)methyl)urea;

N-(2-(1H-imidazol-4-yl)ethyl)-4'-(3-(1-(2-cyanopyrimidin-4-yl)cyclohexyl)ureido)-[1,1'-biphenyl]-4-carboxamide;

N-(2-(1H-imidazol-1-yl)ethyl)-4'-(3-(1-(2-cyanopyrimidin-4-yl)cyclohexyl)ureido)-[1,1'-biphenyl]-4-carboxamide;

N-(2-(1H-imidazol-1-yl)ethyl)-4'-(3-(1-(2-cyanopyrimidin-4-yl)cyclohexyl)ureido)-2'-fluoro-[1,1'-biphenyl]-4-carboxamide;

N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;

N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;

N-(2-(1H-imidazol-4-yl)ethyl)-4'-(3-(1-(2-cyanopyrimidin-4-yl)cyclohexyl)ureido)-2'-(trifluoromethyl)-[1,1'-biphenyl]-4-carboxamide;

1-(4'-(2-aminoethoxy)-[1,1'-biphenyl]-4-yl)-3-(1-(2-cyanopyrimidin-4-yl)cyclohexyl)urea;

1-(1-(2-cyanopyrimidin-4-yl)cyclohexyl)-3-(4'-(2-(methylamino)ethoxy)-[1,1'-biphenyl]-4-yl)urea.

In the compound of the present invention, still more preferable compounds or pharmaceutically acceptable salt thereof include the following compounds:

1-(1-(2-cyanopyrimidin-4-yl)cyclohexyl)-3-(4'-(4-isopropylpiperazin-1-yl)-[1,1'-biphenyl]-4-yl)urea;

1-(4'-(4-acetylpiperazin-1-yl)-[1,1'-biphenyl]-4-yl)-3-(1-(2-cyanopyrimidin-4-yl)cyclohexyl)urea;

1-(1-(2-cyanopyrimidin-4-yl)cyclohexyl)-3-(4'-(4-ethylpiperazin-1-yl)-[1,1'-biphenyl]-4-yl)urea;

1-(1-(2-cyanopyrimidin-4-yl)cyclohexyl)-3-(2-fluoro-4'-(4-isopropylpiperazin-1-yl)-[1,1'-biphenyl]-4-yl)urea.

In the compound of the present invention, especially preferable compounds or pharmaceutically acceptable salt thereof include the following compounds:

1-(1-(2-cyanopyrimidin-4-yl)cyclohexyl)-3-(4'-(4-isopropylpiperazin-1-yl)-[1,1'-biphenyl]-4-yl)urea;

1-(1-(2-cyanopyrimidin-4-yl)cyclohexyl)-3-(2-fluoro-4'-(4-isopropylpiperazin-1-yl)-[1,1'-biphenyl]-4-yl)urea.

The compound of Formula 1 of the present invention may be in a pharmaceutically acceptable salt form. The salt may be a conventional acid addition salt form, which includes e.g., salts derived from an inorganic acid such as hydrochloric acid, hydrobromic acid, sulfuric acid, or phosphoric acid; and salts derived from an organic acid such as citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid or aspartic acid. And also, the salt may be in a conventional metal salt form, which includes e.g., salts derived from an alkali metal such as lithium, sodium, or potassium; or an alkali earth metal such as calcium or magnesium. The metal salt form also includes a chromium salt. In addition, the salt may be an organic ligand-derived salt, e.g., quaternary ammonium salt; an amine salt, e.g., dicyclohexylamine salt or N-methyl-D-glucamine salt; or an amino acid salt derived from arginine, lysine, etc.

The present invention also provides a process for preparing a compound of Formula 1 or pharmaceutically acceptable salt thereof. For example, the compound of Formula 1 or pharmaceutically acceptable salt thereof may be prepared according to the following Reaction Scheme 1.

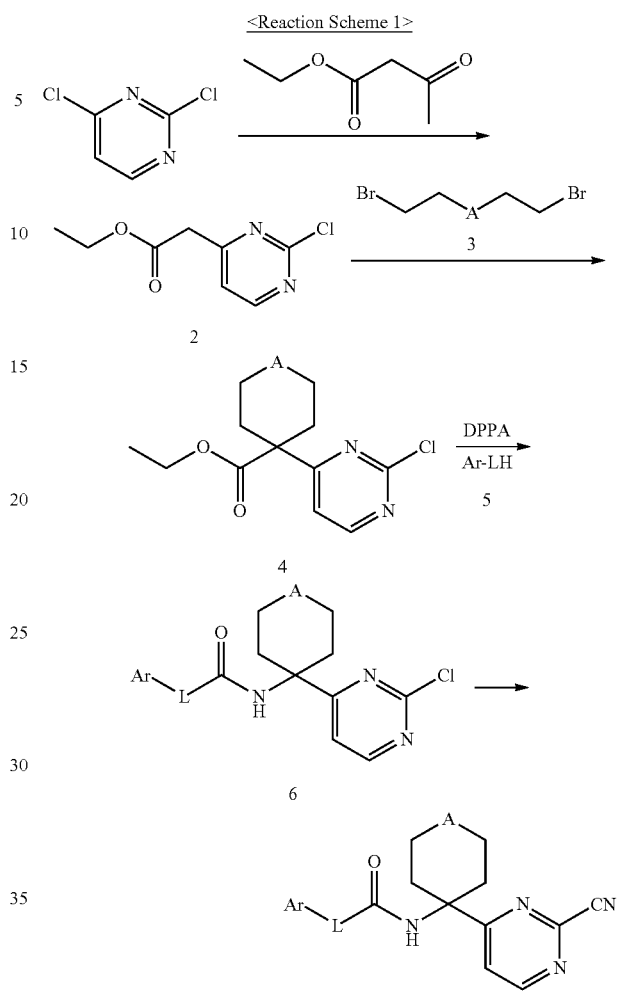

In the Reaction Scheme 1, A, L, and Ar are the same as defined in the above.

In the Reaction Scheme 1, the stating materials, 2,4-dichloropyrimidine and ethyl acetoacetate, are commercially available. The reaction between 2,4-dichloropyrimidine and ethyl acetoacetate for preparing a compound of Formula 2 may be carried out in the presence of a base such as sodium hydride. And, the reaction may be carried out in one or more solvents selected from the group consisting of tetrahydrofuran and toluene. The reaction may be carried out e.g., at a reflux temperature of the solvent used, but is not limited thereto.

The compound of Formula 2 may be reacted with a compound of Formula 3 to obtain a compound of Formula 4. The reaction between the compound of Formula 2 and the compound of Formula 3 may be carried out in the presence of a base such as sodium hydride. And, the reaction may be carried out in one or more solvents selected from the group consisting of dimethylformamide, tetrahydrofuran, and toluene. The reaction may be carried out at a temperature ranging from 20° C. to 80° C., preferably at a temperature ranging from 50° C. to 70° C.

The compound of Formula 4 may be hydrolyzed and then reacted with a compound of Formula 5 to obtain a compound of Formula 6. The hydrolysis may be carried out by reacting the compound of Formula 4 with sodium hydroxide, potassium hydroxide, or the like. The hydrolysis may be also carried out in alcohol (such 2-propanol) and water. The reaction between the product of hydrolysis and the compound of Formula 5 may be carried out in the presence of a base such as diphenyl phosphorazidate (DPPA) and triethylamine. The reaction may be carried out in a solvent such as toluene, at a temperature ranging from 80° C. to 130° C., preferably at a temperature ranging from 100° C. to 120° C.

The compound of Formula 6 may be reacted with alkali metal cyanide such as sodium cyanide to obtain a compound of Formula 1. The reaction may be carried out in the presence of a base such as 1,4-diazabicyclo[2.2.2]octane (DABCO). The reaction may be also carried out in a solvent such as dimethyl sulfoxide, at a temperature ranging from 50° C. to 150° C., preferably at a temperature ranging from 50° C. to 100° C.

If necessary, a Suzuki reaction, a Sonogashira reaction, an amide coupling reaction, and/or a Mitsunobu reaction may be additionally carried out in the Reaction Scheme 1.

In addition, the compound of Formula 1 or pharmaceutically acceptable salt thereof may be prepared according to the following Reaction Scheme 2.

<Reaction Scheme 2>

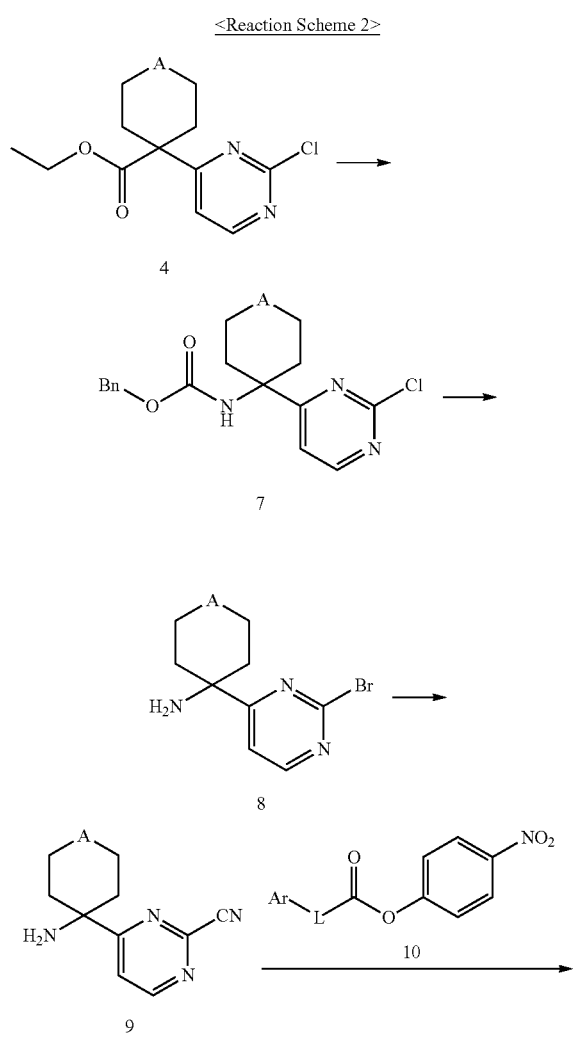

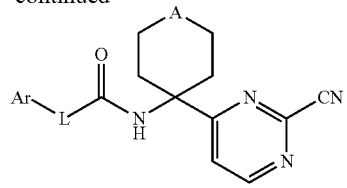

In the Reaction Scheme 2, A, L, and Ar are the same as defined in the above, and Bn is benzyl.

The compound of Formula 4 may be prepared by the same method as in the Reaction Scheme 1.

The compound of Formula 4 may be hydrolyzed and then reacted with phenylmethanol and diphenyl phosphorazidate to obtain a compound of Formula 7. The hydrolysis may be carried out by reacting the compound of Formula 4 with sodium hydroxide, potassium hydroxide, or the like. The hydrolysis may be also carried out in alcohol (such 2-propanol) and water. The reaction of the product of hydrolysis, phenylmethanol and diphenyl phosphorazidate may be carried out in the presence of a base such as diphenyl phosphorazidate (DPPA) and triethylamine.

The reaction may be carried out in a solvent such as toluene, at a temperature ranging from 80° C. to 130° C., preferably at a temperature ranging from 100° C. to 120° C.

The compound of Formula 7 may be reacted with hydrobromic acid to obtain a compound of Formula 8. The reaction may be carried out in a solvent such as acetic acid, at a temperature ranging from 0° C. to 80° C., preferably at a temperature ranging from 0° C. to 50° C.

The compound of Formula 8 may be reacted with alkali metal cyanide such as sodium cyanide to obtain a compound of Formula 9. The reaction may be carried out in the presence of a base such as 1,4-diazabicyclo[2.2.2]octane (DABCO). The reaction may be also carried out in a solvent such as dimethyl sulfoxide, at a temperature ranging from 50° C. to 150° C., preferably at a temperature ranging from 50° C. to 100° C.

The compound of Formula 9 may be reacted with a compound of Formula 10 to obtain a compound of Formula 1. The reaction between the compound of Formula 9 and the compound of Formula 10 may be carried out in a solvent such as pyridine, dichloromethane and the like, at a temperature ranging from 0° C. to 100° C., preferably at a temperature ranging from 0° C. to 50° C.

If necessary, a Suzuki reaction, a Sonogashira reaction, an amide coupling reaction, and/or a Mitsunobu reaction may be additionally carried out in the Reaction Scheme 2.

The present invention provides a pharmaceutical composition for preventing or treating osteoporosis comprising a therapeutically effective amount of the compound of Formula 1 or pharmaceutically acceptable salt thereof as an active ingredient. The therapeutically effective amount refers to an amount sufficient for accomplishing the prevention or treatment of osteoporosis. For example, the therapeutically effective amount may be from about 1 mg/kg to about 300 mg/kg per day. However, the therapeutically effective amount may be changed according to the patient's age, weight, susceptibility, symptom, or activity of the compound.

The pharmaceutical composition may comprise a pharmaceutically acceptable carrier, such as diluents, disintegrants, sweeteners, lubricants, or flavoring agents conventionally used in the field of art. The pharmaceutical composition may be formulated to an oral dosage form such as tablets, capsules, powders, granules, suspensions, emulsions, or syrups; or a parenteral dosage form such as injection, according to conventional methods. The dosage form may be various forms, e.g., dosage forms for single administration or for multiple administrations.

The pharmaceutical composition of the present invention may comprise, for example, a diluent (e.g., lactose, corn starch, etc.); a lubricant (e.g., magnesium stearate, etc.); an emulsifying agent; a suspending agent; a stabilizer; and/or an isotonic agent. If necessary, the composition further comprises sweeteners and/or flavoring agents.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The compound of Formula 1 or salt thereof may be also used as a reagent for inhibiting an activity of cathepsin K. Therefore, the present invention also provides a reagent for inhibiting cathepsin K comprising said compound of Formula 1 or salt thereof.

The following examples and experimental examples are provided for illustration purposes only, and are not intended to limit the scope of the invention.

The analyses of the compounds prepared in the following Examples were carried out as follows: Nuclear magnetic resonance (NMR) spectrum analysis was carried out using the Bruker 400 MHz spectrometer and chemical shifts thereof were analyzed in ppm. LCMS analysis was carried out using the Shimadzu 2020 system. Column chromatography was carried out using the CombiFlash Rf system. The starting materials in each Example are known compounds, which were synthesized according literatures or obtained from Sigma-Aldrich, Alfa Aesar, or TCI.

Example 1: Benzyl (1-(2-cyanopyrimidin-4-yl)cyclopentyl)carbamate

Step 1: Ethyl 2-(2-chloropyrimidin-4-yl)acetate

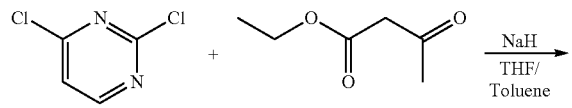

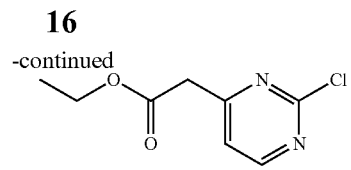

NaH (4.04 g, 100.68 mmol) was added to tetrahydrofuran (THF, 200 ml) and then stirred at 0° C. And then, ethyl acetoacetate (13.1 g, 100.68 mmol) was added dropwise thereto. The reaction mixture was stirred at room temperature additionally for 30 minutes and then concentrated under reduced pressure. 2,4-Dichloropyrimidine (10 g, 67.12 mmol) and toluene (200 ml) were added to the resulting residue under stirring. The reaction mixture was refluxed for about 12 hours. The reaction mixture was extracted with ethyl acetate and brine two times. The combined organic layer was dried on magnesium sulfate and then distilled under reduced pressure. The resulting residue was purified by MPLC to give 5.28 g of the titled compound (Yield: 39%). [M+1]$^+$=200.45

Step 2: Ethyl 1-(2-chloropyrimidin-4-yl)cyclopentanecarboxylate

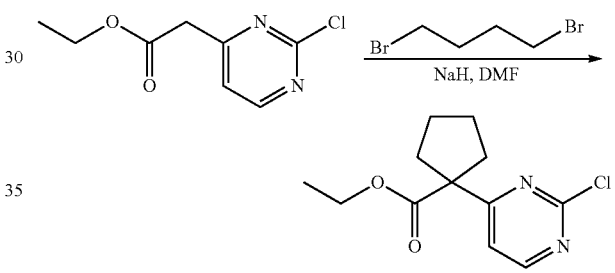

Ethyl 2-(2-chloropyrimidin-4-yl)acetate (4.9 g, 24.4 mmol) prepared in Step 1 was added to dimethylformamide (500 ml) and the resulting mixture was cooled to below 0° C. While maintaining the temperature below 0° C., 60% NaH (2.149 g, 53.7 mmol) and 1,4-dibromobutane (3.21 ml, 26.9 mmol) were added thereto. The reaction mixture was stirred at 60° C. for 2 hours and then water was added thereto to quench the reaction. The reaction mixture was extracted with ethyl acetate. The organic layer was washed with brine, dried on magnesium sulfate, and then distilled under reduced pressure. The resulting residue was purified by MPLC (100% hexane—8:2=hexane:ethyl acetate) to give 4.3 g of the titled compound (Yield: 70%). [M+1]$^+$=255.

Step 3: 1-(2-chloropyrimidin-4-yl)cyclopentanecarboxylic acid

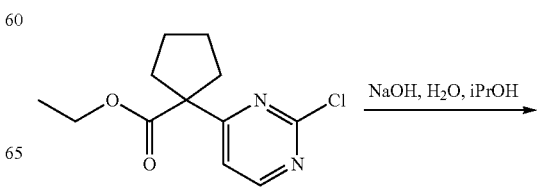

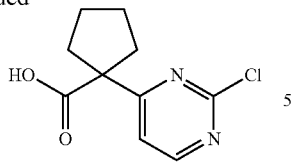

Ethyl 1-(2-chloropyrimidin-4-yl)cyclopentanecarboxylate (1.24 g, 4.87 mmol) prepared in Step 2 was dissolved in 2-propanol (25 ml) and then a 1M NaOH solution (25 ml) was added thereto. The reaction mixture was stirred for 100 minutes and then distilled under reduced pressure. The resulting residue was added to a 10% citric acid solution (5 ml) and the resulting mixture was extracted with dichloromethane. The organic layer was dried on magnesium sulfate and then distilled under reduced pressure. The resulting residue was used in the subsequent reaction without the purification thereof.

Step 4: Benzyl (1-(2-chloropyrimidin-4-yl)cyclopentyl)carbamate

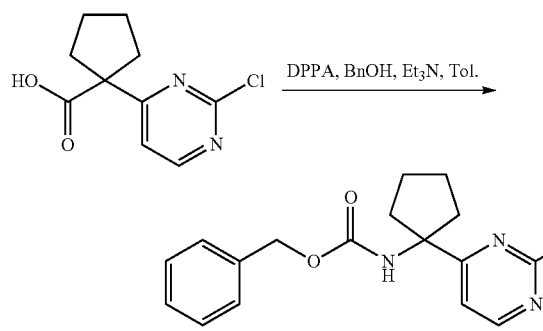

1-(2-Chloropyrimidin-4-yl)cyclopentanecarboxylic acid (0.85 g, 3.75 mmol) prepared in Step 3, phenylmethanol (2.48 g, 22.5 mmol), and triethylamine (0.862 g, 1.18 mmol) were sequentially added to toluene (37.5 ml) and then diphenyl phosphorazidate (1.39 g, 4.88 mmol) was slowly added thereto. The reaction mixture was stirred at 100° C. for 2 hours. The reaction mixture was cooled to room temperature and then ice water was added thereto to quench the reaction. The reaction mixture was extracted with ethyl acetate. The organic layer was washed with a sodium bicarbonate solution and brine, dried on magnesium sulfate, and then distilled under reduced pressure. The resulting residue was purified by MPLC to give 0.56 g of the titled compound (Yield: 45%).

Step 5: Benzyl (1-(2-cyanopyrimidin-4-yl)cyclopentyl)carbamate

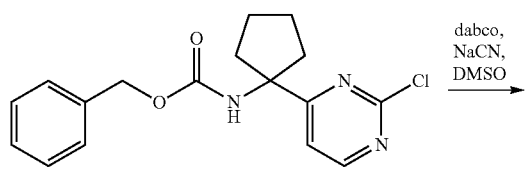

Benzyl (1-(2-chloropyrimidin-4-yl)cyclopentyl)carbamate (117 mg, 0.354 mmol) prepared in Step 4 and NaCN (27 mg, 0.531 mmol) were dissolved in dimethyl sulfoxide (1 mL). DABCO (8 mg, 0.071 mmol) was added at room temperature to the resulting solution, which was then stirred at 50° C. for about 12 hours. Water was added thereto to quench the reaction and then the reaction mixture was extracted with ethyl acetate. The organic layer was washed with a 1N NaOH solution and brine, dried on anhydrous Na$_2$SO$_4$ to remove the moisture, and then distilled under reduced pressure to give 86.58 mg of the titled compound (white solid, Yield: 76%).

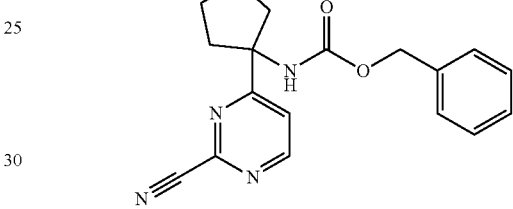

$^1$H NMR (500 MHz, CDCl$_3$): δ 8.70 (s, 1H), 7.53 (s, 1H), 7.35 (s, 5H), 5.25 (s, 1H), 5.04 (s, 2H), 2.38-2.30 (m, 2H), 2.19-2.13 (m, 2H), 1.97-1.93 (m, 4H)

HPLC purity=99%

LRMS(ESI): m/z=323 [M+H]+

The compounds of Examples 2 to 9 were prepared in accordance with the same procedures as in Example 1, using the corresponding substituted alcohol or substituted phenol derivatives, instead of phenylmethanol used in Step 4 of Example 1.

Example 2: 4-bromobenzyl (1-(2-cyanopyrimidin-4-yl)cyclopentyl)carbamate

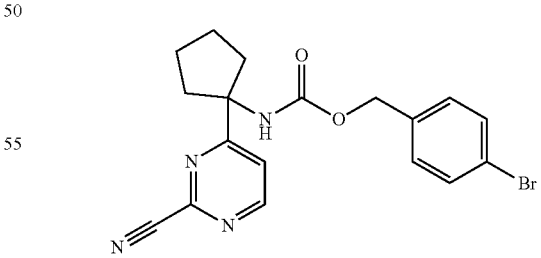

$^1$H NMR (400 MHz, CDCl$_3$): δ 8.72 (d, 1H, J=4.4 Hz), 7.54-7.49 (m, 3H), 7.22 (d, 2H, J=7.2 Hz), 5.27 (s, 1H), 4.99 (s, 2H), 2.38-2.3 (m, 2H), 2.19-2.13 (m, 2H), 1.97-1.93 (m, 4H)

HPLC purity=98%

LRMS(ESI): m/z=402 [M+H]+

Example 3: 3-bromobenzyl (1-(2-cyanopyrimidin-4-yl)cyclopentyl)carbamate

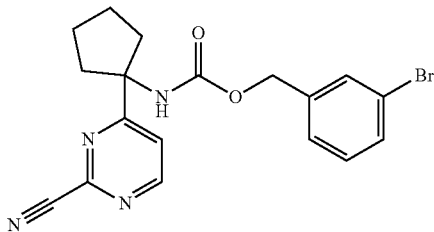 [SMILES: N#Cc1nccc(C2(NC(=O)OCc3cccc(Br)c3)CCCC2)n1]

¹H NMR (400 MHz, CDCl₃) δ 8.72 (d, J=4.8 Hz, 1H), 7.53 (d, J=5.2 Hz, 1H), 7.49-7.46 (m, 2H), 7.26-7.25 (m, 2H), 5.22 (s, 1H), 4.99 (s, 2H), 2.38-2.3 (m, 2H), 2.19-2.13 (m, 2H), 1.97-1.93 (m, 4H)
HPLC purity=99%
LRMS(ESI): m/z=402 [M+H]+

Example 4: phenethyl (1-(2-cyanopyrimidin-4-yl)cyclopentyl)carbamate

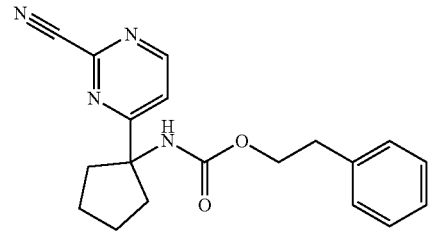 [SMILES: N#Cc1nccc(C2(NC(=O)OCCc3ccccc3)CCCC2)n1]

¹H NMR (400 MHz, CDCl₃): δ 8.68 (s, 1H), 7.42 (d, J=5.2 Hz, 1H), 7.31 (m, 2H), 7.25-7.23 (m, 2H), 5.12 (s, 1H), 4.27 (t, J=6.8 Hz, 2H), 2.95-2.92 (m, 2H), 2.38-2.3 (m, 2H), 2.19-2.13 (m, 2H), 1.97-1.93 (m, 4H)
HPLC purity=98%
LRMS(ESI): m/z=337 [M+H]+

Example 5: 3-methylbenzyl (1-(2-cyanopyrimidin-4-yl)cyclopentyl)carbamate

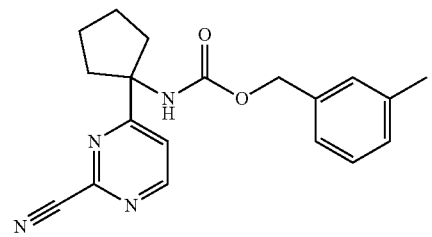 [SMILES: Cc1cccc(COC(=O)NC2(c3ccnc(C#N)n3)CCCC2)c1]

¹H NMR (400 MHz, CDCl₃) δ 8.68 (s, 1H), 7.52 (d, J=3.2 Hz, 1H), 7.24 (s, 1H), 7.14-7.12 (m, 3H), 5.25 (s, 1H), 4.99 (s, 2H), 2.34 (s, 3H), 2.38-2.3 (m, 2H), 2.19-2.13 (m, 2H), 1.97-1.93 (m, 4H)
HPLC purity=98%
LRMS(ESI): m/z=337 [M+H]+

Example 6: 3-methoxybenzyl (1-(2-cyanopyrimidin-4-yl)cyclopentyl)carbamate

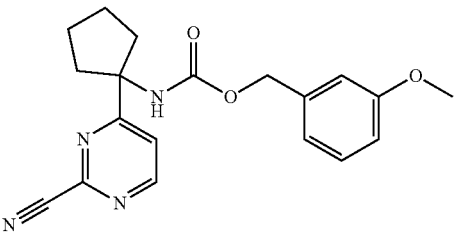 [SMILES: COc1cccc(COC(=O)NC2(c3ccnc(C#N)n3)CCCC2)c1]

¹H NMR (400 MHz, CDCl₃) δ 8.68 (s, 1H), 7.53 (d, J=4 Hz, 1H), 7.26 (s, 1H), 6.89-6.84 (m, 3H), 5.27 (s, 1H), 4.99 (s, 2H), 3.79 (s, 3H), 2.38-2.3 (m, 2H), 2.19-2.13 (m, 2H), 1.97-1.93 (m, 4H)
HPLC purity=99%
LRMS(ESI): m/z=353 [M+H]+

Example 7: 3-fluorobenzyl (1-(2-cyanopyrimidin-4-yl)cyclopentyl)carbamate

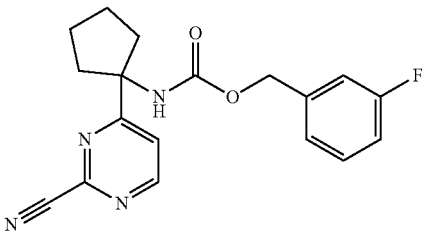 [SMILES: N#Cc1nccc(C2(NC(=O)OCc3cccc(F)c3)CCCC2)n1]

¹H NMR (400 MHz, CDCl₃) δ 8.69 (s, 1H), 7.53 (d, J=5.2 Hz, 1H), 7.32-7.31 (m, 1H), 7.09-6.98 (m, 3H), 5.29 (s, 1H), 5.01 (s, 2H), 2.38-2.3 (m, 2H), 2.19-2.13 (m, 2H), 1.97-1.93 (m, 4H)
HPLC purity=99%
LRMS(ESI): m/z=341 [M+H]+

Example 8: 3-chlorobenzyl (1-(2-cyanopyrimidin-4-yl)cyclopentyl)carbamate

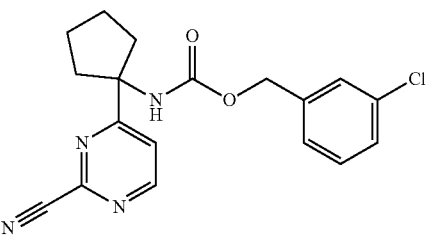 [SMILES: N#Cc1nccc(C2(NC(=O)OCc3cccc(Cl)c3)CCCC2)n1]

¹H NMR (400 MHz, CDCl₃) δ 8.69 (bs, 1H), 7.52 (d, J=5.2 Hz, 1H), 7.31-7.28 (m, 3H), 7.19 (s, 1H), 5.28 (s, 1H), 4.99 (s, 2H), 2.38-2.3 (m, 2H), 2.19-2.13 (m, 2H), 1.97-1.93 (m, 4H)
HPLC purity=99%
LRMS(ESI): m/z=357 [M+H]+

Example 9: 3-cyanobenzyl (1-(2-cyanopyrimidin-4-yl)cyclopentyl)carbamate

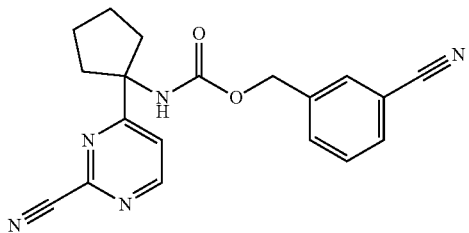 [SMILES: N#Cc1cccc(COC(=O)NC2(c3ccnc(C#N)n3)CCCC2)c1]

$^1$H NMR (400 MHz, CDCl$_3$) δ 8.71 (d, J=5 Hz, 1H), 7.6 (d, J=7.8 Hz, 2H), 7.53 (d, J=5.4 Hz, 2H), 7.49-7.45 (m, 1H), 5.32 (s, 1H), 5.04 (s, 2H), 2.38-2.3 (m, 2H), 2.19-2.13 (m, 2H), 1.97-1.93 (m, 4H)

HPLC purity=99%

LRMS(ESI): m/z=348 [M+H]+

Example 10: Benzyl (1-(2-cyanopyrimidin-4-yl)cyclohexyl)carbamate

Step 1: Ethyl 2-(2-chloropyrimidin-4-yl)acetate

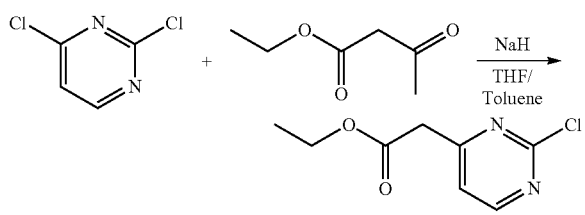

NaH (4.04 g, 100.68 mmol) was added to tetrahydrofuran (THF, 200 ml) and then stirred at 0° C. And then, ethyl acetoacetate (13.1 g, 100.68 mmol) was added dropwise thereto. The reaction mixture was stirred at room temperature additionally for 30 minutes and then concentrated under reduced pressure. 2,4-Dichloropyrimidine (10 g, 67.12 mmol) and toluene (200 ml) were added to the resulting residue under stirring. The reaction mixture was refluxed for about 12 hours. The reaction mixture was extracted with ethyl acetate and brine two times. The combined organic layer was dried on magnesium sulfate and then distilled under reduced pressure. The resulting residue was purified by MPLC to give 5.28 g of the titled compound (Yield: 39%). [M+1]$^+$=200.45

Step 2: Ethyl 1-(2-chloropyrimidin-4-yl)cyclohexanecarboxylate

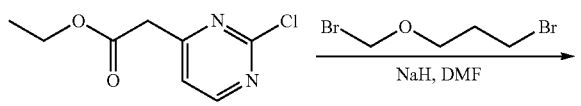

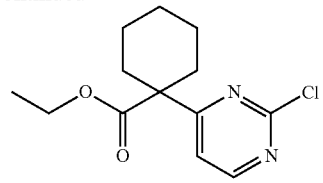

Ethyl 2-(2-chloropyrimidin-4-yl)acetate (4.9 g, 24.4 mmol) prepared in Step 1 was added to dimethylformamide (488 ml) and the resulting mixture was cooled to below 0° C. While maintaining the temperature below 0° C., 60% NaH (2.149 g, 53.7 mmol) and 1,5-dibromopentane (3.73 ml, 26.9 mmol) were added thereto. The reaction mixture was stirred at 60° C. for 2 hours and then cooled to room temperature. Water was added to the reaction mixture to quench the reaction. The reaction mixture was extracted with ethyl acetate. The organic layer was washed with brine, dried on magnesium sulfate, and then distilled under reduced pressure. The resulting residue was purified by MPLC to give 3.8 g of the titled compound (Yield: 60%). [M+1]$^+$=269.

Step 3: 1-(2-chloropyrimidin-4-yl)cyclohexanecarboxylic acid

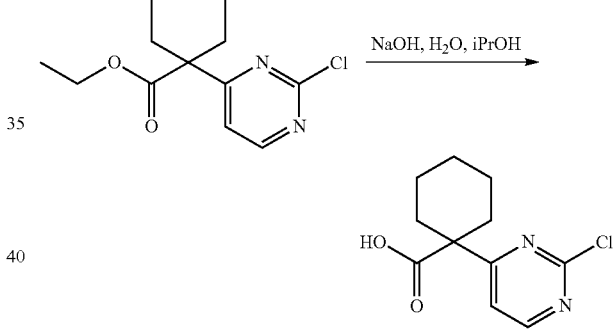

Ethyl 1-(2-chloropyrimidin-4-yl)cyclohexanecarboxylate (3.8 g 14.14 mmol) was dissolved in 2-propanol (70.7 ml) and then a 1M NaOH solution (70.7 ml) was added thereto. The reaction mixture was stirred for 100 minutes and then distilled under reduced pressure. The resulting residue was added to a 10% citric acid solution (15 ml) and the resulting mixture was extracted with dichloromethane. The organic layer was dried on magnesium sulfate and then distilled under reduced pressure. The resulting residue was used in the subsequent reaction without the purification thereof.

Step 4: Benzyl (1-(2-chloropyrimidin-4-yl)cyclohexyl)carbamate

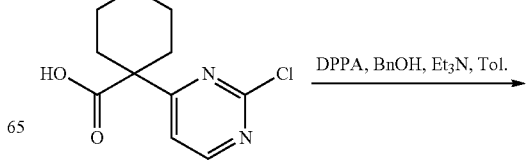

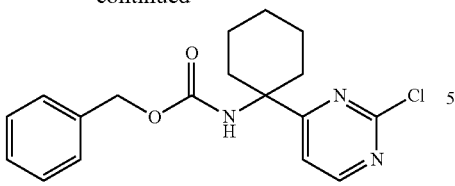

1-(2-Chloropyrimidin-4-yl)cyclohexanecarboxylic acid (3.40 g, 14.14 mmol) prepared in Step 3, phenylmethanol (9.17 g, 85 mmol), and triethylamine (1.860 g, 18.38 mmol) were sequentially added to toluene (141 ml) and then diphenyl phosphorazidate (7.74 g, 31.8 mmol) was slowly added thereto. The reaction mixture was stirred at 100° C. for 2 hours. The reaction mixture was cooled to room temperature and then ice water was added thereto to quench the reaction. The reaction mixture was extracted with ethyl acetate. The organic layer was washed with a sodium bicarbonate solution and brine, dried on magnesium sulfate, and then distilled under reduced pressure. The resulting residue was purified by MPLC to give 3.6 g of the titled compound (Yield: 74%). [M+1]⁺=345.70.

Step 5: Benzyl (1-(2-cyanopyrimidin-4-yl)cyclohexyl)carbamate

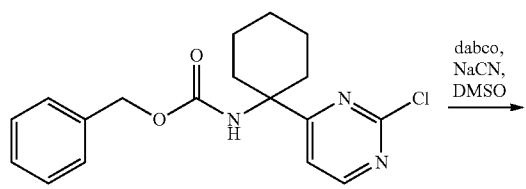

Benzyl (1-(2-chloropyrimidin-4-yl)cyclohexyl)carbamate (37 mg, 0.108 mmol) prepared in Step 4 and NaCN (8 mg, 0.162 mmol) were dissolved in dimethyl sulfoxide (1 mL). DABCO (2.5 mg, 0.022 mmol) was added at room temperature to the resulting solution, which was then stirred at 50° C. for about 12 hours. Water was added thereto to quench the reaction and then the reaction mixture was extracted with ethyl acetate. The organic layer was washed with a 1N NaOH solution and brine, dried on anhydrous Na₂SO₄ to remove the moisture, and then distilled under reduced pressure. The resulting residue was purified by MPLC (100% hexane—6:4=hexane:ethyl acetate) to give 19.6 mg of the titled compound (white solid, Yield: 54%).

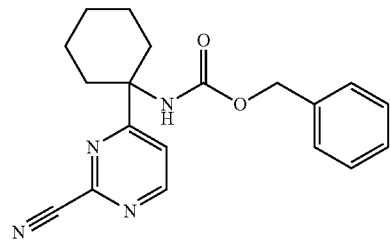 [SMILES: N#Cc1nccc(C2(NC(=O)OCc3ccccc3)CCCCC2)n1]

¹H NMR (400 MHz, CDCl₃) δ 8.71 (s, 1H), 7.54 (s, 1H), 7.40-7.30 (m, 5H), 5.20 (s, 1H), 5.02 (s, 2H), 2.12-2.08 (m, 2H), 2.00-1.90 (m, 2H), 1.75-1.57 (m, 4H), 1.32-1.24 (m, 2H)

HPLC purity=98%
LRMS(ESI): m/z=337 [M+H]+

The compounds of Examples 11 to 28 were prepared in accordance with the same procedures as in Example 10, using the corresponding substituted alcohol or substituted phenol derivatives instead of phenylmethanol used in Step 4 of Example 10.

Example 11: 4-bromobenzyl (1-(2-cyanopyrimidin-4-yl)cyclohexyl)carbamate

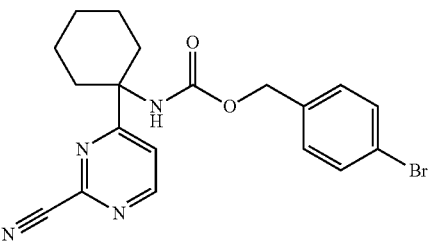 [SMILES: N#Cc1nccc(C2(NC(=O)OCc3ccc(Br)cc3)CCCCC2)n1]

22.69 mg of the titled compound (white solid, Yield: 63%)
¹H NMR (400 MHz, CDCl₃) δ 8.72 (d, J=3.4 Hz, 1H), 7.53 (d, J=5.2 Hz, 1H), 7.49 (d, J=8 Hz, 2H), 7.21 (bs, 2H), 5.22 (s, 1H), 4.97 (s, 2H), 2.12-2.08 (m, 2H), 1.91-1.84 (m, 2H), 1.67-1.57 (m, 4H), 1.35-1.25 (m, 2H)
HPLC purity=99%
LRMS(ESI): m/z=416 [M+H]+

Example 12: 3-bromobenzyl (1-(2-cyanopyrimidin-4-yl)cyclohexyl)carbamate

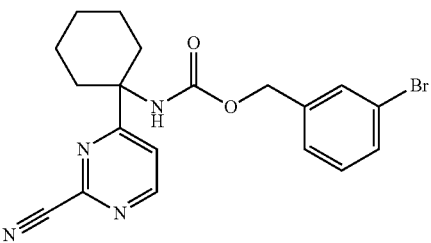 [SMILES: N#Cc1nccc(C2(NC(=O)OCc3cccc(Br)c3)CCCCC2)n1]

20.37 mg of the titled compound (white solid, Yield: 46%)
¹H NMR (400 MHz, CDCl₃) δ 8.73 (d, J=4 Hz, 1H), 7.54 (d, J=5.3 Hz, 1H), 7.47-7.45 (m, 2H), 7.26-7.25 (m, 2H), 5.22 (s, 1H), 4.99 (s, 2H), 2.12-2.08 (m, 2H), 1.91-1.84 (m, 2H), 1.67-1.57 (m, 4H), 1.35-1.25 (m, 2H)

HPLC purity=97%
LRMS(ESI): m/z=416 [M+H]+

Example 13: 3-methylbenzyl (1-(2-cyanopyrimidin-4-yl)cyclohexyl)carbamate

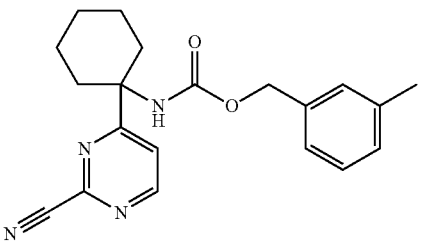 [SMILES: Cc1cccc(COC(=O)NC2(c3ccnc(C#N)n3)CCCCC2)c1]

19.53 mg of the titled compound (white solid, Yield: 53%)
$^1$H NMR (400 MHz, CDCl$_3$) δ 8.71 (s, 1H), 7.54 (s, 1H), 7.26 (s, 2H), 7.15-7.14 (m, 2H), 5.18 (s, 1H), 4.98 (s, 2H), 2.36 (s, 3H), 2.12-2.08 (m, 2H), 1.91-1.84 (m, 2H), 1.67-1.57 (m, 4H), 1.35-1.25 (m, 2H)
HPLC purity=94%
LRMS(ESI): m/z=351 [M+H]+

Example 14: 3-(trifluoromethyl)benzyl (1-(2-cyanopyrimidin-4-yl)cyclohexyl)carbamate

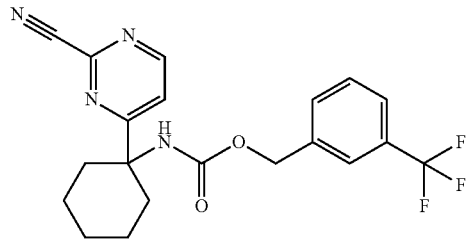 [SMILES: N#Cc1nccc(C2(NC(=O)OCc3cccc(C(F)(F)F)c3)CCCCC2)n1]

18.04 mg of the titled compound (white solid, Yield: 42%)
$^1$H NMR (400 MHz, CDCl$_3$) δ 8.69 (s, 1H), 7.57-7.56 (m, 2H), 7.54-2.49 (m, 3H), 5.22 (s, 1H), 5.06 (s, 2H), 2.12-2.08 (m, 2H), 1.91-1.84 (m, 2H), 1.67-1.57 (m, 4H), 1.35-1.25 (m, 2H)
HPLC purity=98%
LRMS(ESI): m/z=405 [M+H]+

Example 15: 3-fluorobenzyl (1-(2-cyanopyrimidin-4-yl)cyclohexyl)carbamate

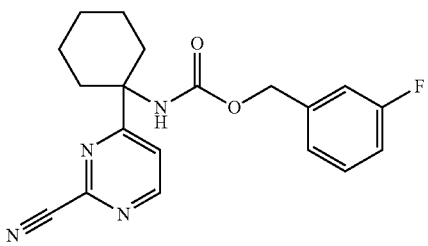 [SMILES: N#Cc1nccc(C2(NC(=O)OCc3cccc(F)c3)CCCCC2)n1]

9.16 mg of the titled compound (white solid, Yield: 26%)
$^1$H NMR (400 MHz, CDCl$_3$) δ 8.72 (s, 1H), 7.54 (d, J=5.3 Hz, 1H), 7.36-7.31 (m, 1H), 7.1-7.09 (m, 1H), 7.04-7.00 (m, 2H), 5.22 (s, 1H), 5.01 (s, 2H), 2.12-2.08 (m, 2H), 1.91-1.84 (m, 2H), 1.67-1.57 (m, 4H), 1.35-1.25 (m, 2H)
HPLC purity=94%
LRMS(ESI): m/z=355 [M+H]+

Example 16: 3-chlorobenzyl (1-(2-cyanopyrimidin-4-yl)cyclohexyl)carbamate

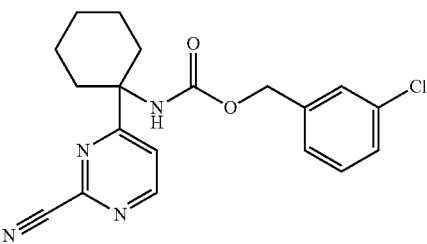 [SMILES: N#Cc1nccc(C2(NC(=O)OCc3cccc(Cl)c3)CCCCC2)n1]

23.1 mg of the titled compound (white solid, Yield: 59%)
$^1$H NMR (400 MHz, CDCl$_3$) δ 8.72 (d, J=3.5 Hz, 1H), 7.54 (d, J=5.2 Hz, 1H), 7.3 (d, J=4.1 Hz, 3H), 7.2 (bs, 1H), 5.22 (s, 1H), 5.00 (s, 2H), 2.12-2.08 (m, 2H), 1.91-1.84 (m, 2H), 1.67-1.57 (m, 4H), 1.35-1.25 (m, 2H)
HPLC purity=96%
LRMS(ESI): m/z=371 [M+H]+

Example 17: 2-methylbenzyl (1-(2-cyanopyrimidin-4-yl)cyclohexyl)carbamate

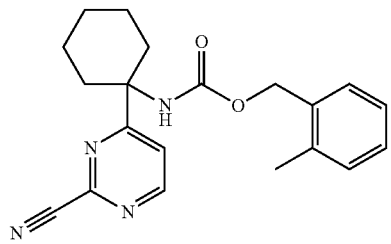 [SMILES: Cc1ccccc1COC(=O)NC1(c2ccnc(C#N)n2)CCCCC1]

21.28 mg of the titled compound (white solid, Yield: 61%)
$^1$H NMR (400 MHz, CDCl$_3$) δ 8.71 (s, 1H), 7.54 (s, 1H), 7.27-7.2 (m, 4H), 5.2 (s, 1H), 5.05 (s, 2H), 2.34 (s, 3H), 2.12-2.08 (m, 2H), 1.91-1.84 (m, 2H), 1.67-1.57 (m, 4H), 1.35-1.25 (m, 2H)
HPLC purity=99%
LRMS(ESI): m/z=351 [M+H]+

Example 18: 2-fluorobenzyl (1-(2-cyanopyrimidin-4-yl)cyclohexyl)carbamate

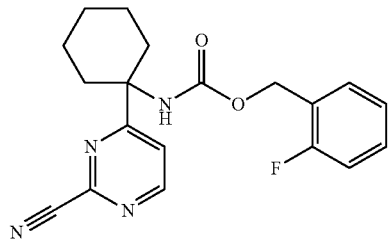

19.29 mg of the titled compound (white solid, Yield: 54%)

¹H NMR (400 MHz, CDCl₃) δ 8.71 (s, 1H), 7.54 (d, J=4.7 Hz, 1H), 7.36-7.3 (m, 2H), 7.15 (t, J=7.26 Hz, 1H), 7.07 (t, J=8.84 Hz, 1H), 5.19 (s, 1H), 5.1 (s, 2H), 2.12-2.08 (m, 2H), 1.91-1.84 (m, 2H), 1.67-1.57 (m, 4H), 1.35-1.25 (m, 2H)

HPLC purity=99%

LRMS(ESI): m/z=355 [M+H]+

Example 19: 2-bromobenzyl (1-(2-cyanopyrimidin-4-yl)cyclohexyl)carbamate

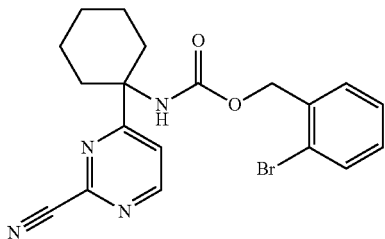

25.77 mg of the titled compound (white solid, Yield: 68%)

¹H NMR (400 MHz, CDCl₃) δ 8.72 (s, 1H), 7.58-7.56 (m, 2H), 7.36-7.34 (m, 2H), 7.22-7.18 (m, 1H), 5.25 (s, 1H), 5.12 (s, 2H), 2.12-2.08 (m, 2H), 1.91-1.84 (m, 2H), 1.67-1.57 (m, 4H), 1.35-1.25 (m, 2H)

HPLC purity=95%

LRMS(ESI): m/z=416 [M+H]+

Example 20: 2-(trifluoromethyl)benzyl (1-(2-cyano-pyrimidin-4-yl)cyclohexyl)carbamate

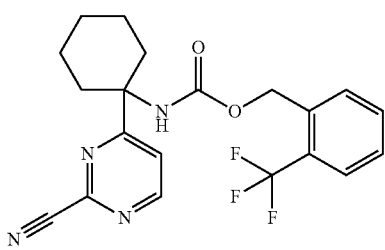 [SMILES: N#Cc1nccc(C2(NC(=O)OCc3ccccc3C(F)(F)F)CCCCC2)n1]

20.16 mg of the titled compound (white solid, Yield: 65%)

¹H NMR (400 MHz, CDCl₃) δ 8.73 (s, 1H), 7.68 (d, J=7.7 Hz, 1H), 7.59-7.52 (m, 3H), 7.44 (t, J=7.7 Hz, 1H), 5.23 (s, 2H), 2.12-2.08 (m, 2H), 1.91-1.84 (m, 2H), 1.67-1.57 (m, 4H), 1.35-1.25 (m, 2H)

HPLC purity=99%

LRMS(ESI): m/z=405 [M+H]+

Example 21: 2-methoxybenzyl (1-(2-cyanopyrimidin-4-yl)cyclohexyl)carbamate

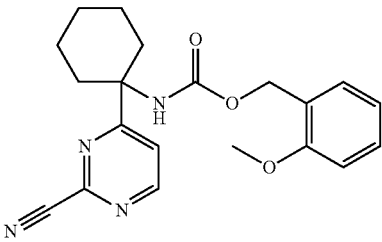 [SMILES: COc1ccccc1COC(=O)NC1(c2ccnc(C#N)n2)CCCCC1]

17.00 mg of the titled compound (white solid, Yield: 62%)

¹H NMR (400 MHz, CDCl₃) δ 8.7 (s, 1H), 7.55 (s, 1H), 7.34-7.29 (m, 2H), 6.97-6.88 (m, 2H), 5.18 (s, 1H), 5.09 (s, 2H), 3.83 (s, 3H), 2.12-2.08 (m, 2H), 1.91-1.84 (m, 2H), 1.67-1.57 (m, 4H), 1.35-1.25 (m, 2H)

HPLC purity=99%

LRMS(ESI): m/z=367 [M+H]+

Example 22: 4-methylbenzyl (1-(2-cyanopyrimidin-4-yl)cyclohexyl)carbamate

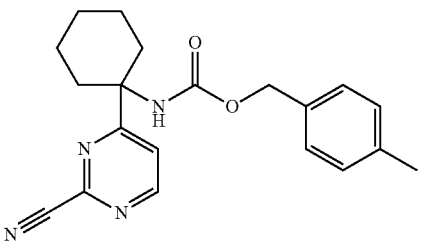 [SMILES: Cc1ccc(COC(=O)NC2(c3ccnc(C#N)n3)CCCCC2)cc1]

19.53 mg of the titled compound (white solid, Yield: 74%)

¹H NMR (400 MHz, CDCl₃) δ 8.7 (s, 1H), 7.53 (d, J=4.4 Hz, 1H), 7.21-7.18 (m, 4H), 5.16 (s, 1H), 4.98 (s, 2H), 2.36 (s, 3H), 2.12-2.08 (m, 2H), 1.91-1.84 (m, 2H), 1.67-1.57 (m, 4H), 1.35-1.25 (m, 2H)

HPLC purity=96%

LRMS(ESI): m/z=351 [M+H]+

Example 23: 4-chlorobenzyl (1-(2-cyanopyrimidin-4-yl)cyclohexyl)carbamate

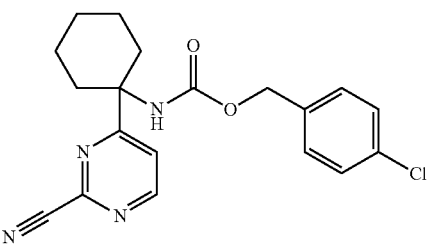 [SMILES: N#Cc1nccc(C2(NC(=O)OCc3ccc(Cl)cc3)CCCCC2)n1]

23.47 mg of the titled compound (white solid, Yield: 55%)

¹H NMR (400 MHz, CDCl₃) δ 8.71 (s, 1H), 7.53 (d, J=5.1 Hz, 1H), 7.39-7.30 (m, 2H), 7.30-7.19 (m, 2H), 5.20 (s, 1H), 4.98 (s, 2H), 2.12-2.08 (m, 2H), 1.91-1.84 (m, 2H), 1.67-1.57 (m, 4H), 1.35-1.25 (m, 2H)

HPLC purity=98%
LRMS(ESI): m/z=371 [M+H]+

Example 24: 4-(trifluoromethyl)benzyl (1-(2-cyano-pyrimidin-4-yl)cyclohexyl)carbamate

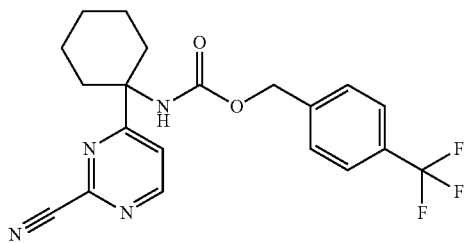 [SMILES: N#Cc1nccc(C2(NC(=O)OCc3ccc(C(F)(F)F)cc3)CCCCC2)n1]

18.60 mg of the titled compound (white solid, Yield: 51%)
¹H NMR (400 MHz, CDCl₃) δ 8.72 (d, J=3.9 Hz, 1H), 7.63 (d, J=7.8 Hz, 2H), 7.54 (d, J=5.3 Hz, 1H), 7.45 (bs, 2H), 5.24 (s, 1H), 5.08 (s, 2H), 2.12-2.08 (m, 2H), 1.91-1.84 (m, 2H), 1.67-1.57 (m, 4H), 1.35-1.25 (m, 2H)
HPLC purity=99%
LRMS(ESI): m/z=405 [M+H]+

Example 25: 4-methoxybenzyl (1-(2-cyanopyrimidin-4-yl)cyclohexyl)carbamate

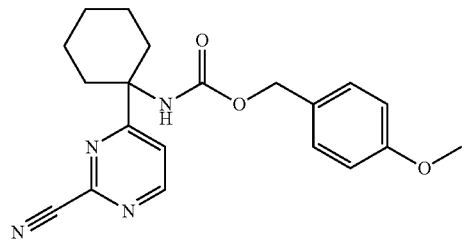 [SMILES: COc1ccc(COC(=O)NC2(c3ccnc(C#N)n3)CCCCC2)cc1]

15.60 mg of the titled compound (white solid, Yield: 43%)
¹H NMR (400 MHz, CDCl₃) δ 8.7 (bs, 1H), 7.52 (bs, 1H), 7.31-7.29 (m, 2H), 6.91-6.9 (m, 2H), 5.14 (s, 1H), 4.95 (s, 2H), 3.81 (s, 3H), 2.12-2.08 (m, 2H), 1.91-1.84 (m, 2H), 1.67-1.57 (m, 4H), 1.35-1.25 (m, 2H)
HPLC purity=99%
LRMS(ESI): m/z=367 [M+H]+

Example 26: naphthalen-1-ylmethyl (1-(2-cyanopyrimidin-4-yl)cyclohexyl)carbamate

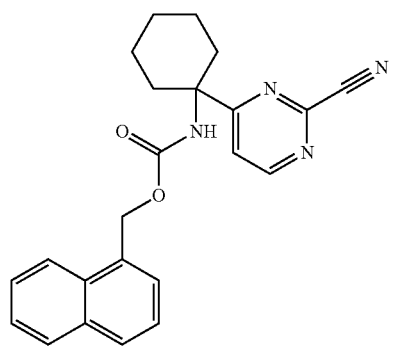 [SMILES: N#Cc1nccc(C2(NC(=O)OCc3cccc4ccccc34)CCCCC2)n1]

26.53 mg of the titled compound (white solid, Yield: 74%)
¹H NMR (400 MHz, CDCl₃) δ 8.71 (bs, 1H), 8.00 (bs, 1H), 7.91-7.85 (m, 3H), 7.91-7.85 (m, 2H), 7.5 (d, J=41.7 Hz, 5H), 5.50 (s, 2H), 5.18 (s, 1H), 2.12-2.08 (m, 2H), 1.91-1.84 (m, 2H), 1.67-1.57 (m, 4H), 1.35-1.25 (m, 2H)
HPLC purity=99%
LRMS(ESI): m/z=387 [M+H]+

Example 27: 4-fluorobenzyl (1-(2-cyanopyrimidin-4-yl)cyclohexyl)carbamate

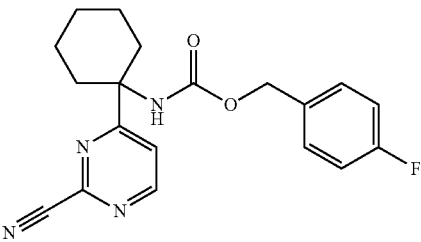 [SMILES: N#Cc1nccc(C2(NC(=O)OCc3ccc(F)cc3)CCCCC2)n1]

12.05 mg of the titled compound (white solid, Yield: 33%)
¹H NMR (400 MHz, CDCl₃) δ 8.71 (s, 1H), 7.53 (d, J=5.1 Hz, 1H), 7.31 (s, 2H), 7.05 (t, J=8.4 Hz, 2H), 5.18 (s, 1H), 4.98 (s, 2H), 2.12-2.08 (m, 2H), 1.91-1.84 (m, 2H), 1.67-1.57 (m, 4H), 1.35-1.25 (m, 2H)
HPLC purity=99%
LRMS(ESI): m/z=355 [M+H]+

Example 28: 2-chlorobenzyl (1-(2-cyanopyrimidin-4-yl)cyclohexyl)carbamate

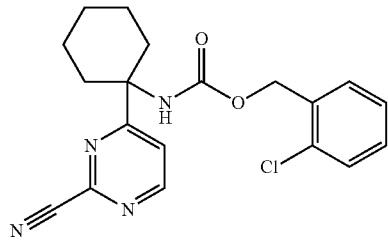 [SMILES: N#Cc1nccc(C2(NC(=O)OCc3ccccc3Cl)CCCCC2)n1]

4.67 mg of the titled compound (white solid, Yield: 9%)
¹H NMR (400 MHz, CDCl₃) δ 8.72 (s, 1H), 7.56 (s, 1H), 7.38 (s, 2H), 7.34-7.27 (m, 2H), 5.24 (s, 1H), 5.14 (s, 2H), 2.12-2.08 (m, 2H), 1.91-1.84 (m, 2H), 1.67-1.57 (m, 4H), 1.35-1.25 (m, 2H)
HPLC purity=97%
LRMS(ESI): m/z=371 [M+H]+

Example 29: (4'-(methylsulfonyl)-[1,1'-biphenyl]-4-yl)methyl (1-(2-cyanopyrimidin-4-yl)cyclopentyl)carbamate

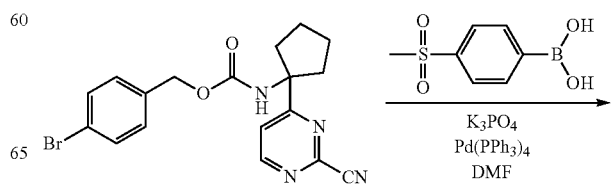

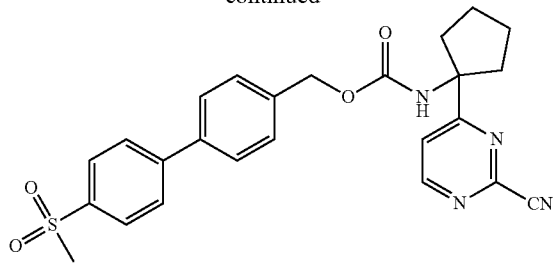

4-Bromobenzyl (1-(2-cyanopyrimidin-4-yl)cyclopentyl) carbamate (18.66 mg, 0.047 mmol) prepared in Example 2 was dissolved in a mixed solvent of dimethylformamide and water (1:0.02). Potassium phosphate (29.6 mg, 0.140 mmol), (4-(methylsulfonyl)phenyl)boronic acid (27.9 mg, 0.140 mmol), and Pd(PPh$_3$)$_4$ (1.343 mg, 0.00465 mmol) were sequentially added to the solution, and the reaction was carried out at 75° C. overnight. After the reaction mixture was cooled to room temperature, water and ethyl acetate were added thereto to quench the reaction and then extracted with ethyl acetate. The organic layer was washed with brine, dried on magnesium sulfate, and then distilled under reduced pressure. The resulting residue was purified by column chromatography (methylene chloride/pentanol) and Prep-HPLC to give 4.82 mg of the titled compound (white solid, Yield: 22%).

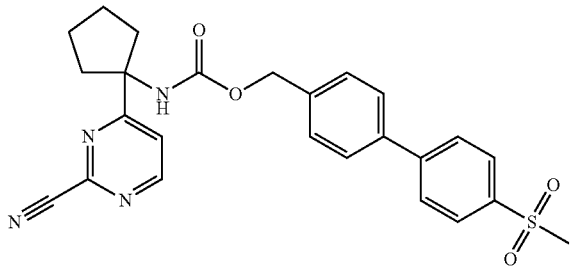 [SMILES: CS(=O)(=O)c1ccc(-c2ccc(COC(=O)NC3(c4ccnc(C#N)n4)CCCC3)cc2)cc1]

$^1$H NMR (400 MHz, CDCl$_3$) δ 8.72 (d, J=4.8 Hz, 1H), 8.02 (d, J=8.4 Hz, 2H), 7.78 (d, J=8.4 Hz, 2H), 7.63 (d, J=7.2 Hz, 2H), 7.57 (d, J=4.8 Hz, 1H), 7.47 (d, J=6.8 Hz, 2H), 5.34 (s, 1H), 5.11 (s, 2H), 3.11 (s, 3H), 2.38-2.3 (m, 2H), 2.19-2.13 (m, 2H), 1.97-1.93 (m, 4H)

HPLC purity=96%
LRMS(ESI): m/z=477 [M+H]+

Example 30: (4'-(methylsulfonyl)-[1,1'-biphenyl]-3-yl)methyl (1-(2-cyanopyrimidin-4-yl)cyclopentyl) carbamate

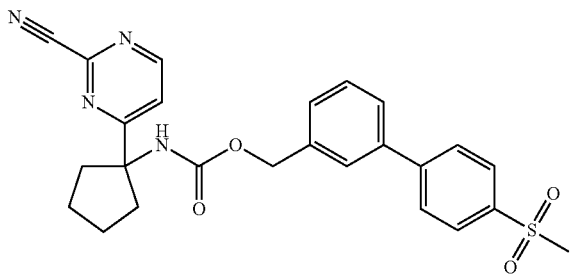 [SMILES: CS(=O)(=O)c1ccc(-c2cccc(COC(=O)NC3(c4ccnc(C#N)n4)CCCC3)c2)cc1]

The titled compound (2.001 mg) was prepared in accordance with the same procedures as in Example 29, using 3-bromobenzyl (1-(2-cyanopyrimidin-4-yl)cyclopentyl)carbamate prepared in Example 3 as a starting material. (white solid, Yield: 9%)

$^1$H NMR (400 MHz, CDCl$_3$) δ 8.69 (s, 1H), 8.02 (d, J=6.6 Hz, 2H), 7.76 (d, J=6.08 Hz, 2H), 7.59-7.51 (m, 4H), 7.42 (m, 1H), 5.31 (s, 1H), 5.12 (s, 2H), 3.11 (s, 3H), 2.29-2.27 (m, 2H), 2.18-2.17 (m, 2H), 1.90-1.89 (m, 4H)

HPLC purity=99%
LRMS(ESI): m/z=477 [M+H]+

Example 31: (4'-morpholino-[1,1'-biphenyl]-4-yl) methyl (1-(2-cyanopyrimidin-4-yl)cyclopentyl)carbamate

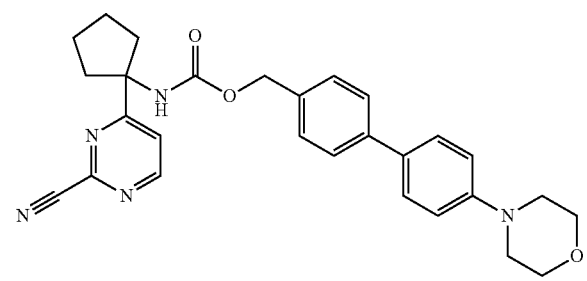 [SMILES: N#Cc1nccc(C2(NC(=O)OCc3ccc(-c4ccc(N5CCOCC5)cc4)cc3)CCCC2)n1]

The titled compound (5.58 mg) was prepared in accordance with the same procedures as in Example 29, using PdCl$_2$(dppf)-CH$_2$Cl$_2$ and (4-morpholinophenyl)boronic acid instead of Pd(PPh$_3$)$_4$ and (4-(methylsulfonyl)phenyl)boronic acid, respectively. (white solid, Yield: 28%)

$^1$H NMR (400 MHz, CDCl$_3$) δ 8.69 (bs, 1H), 7.56-7.52 (m, 5H), 7.39 (bs, 2H), 6.99 (d, J=6.96 Hz, 2H), 5.27 (s, 1H), 5.07 (s, 2H), 3.89 (t, J=3.8 Hz, 4H), 3.22 (t, J=3.8 Hz, 4H), 2.29-2.27 (m, 2H), 2.18-2.17 (m, 2H), 1.90-1.89 (m, 4H)

HPLC purity=96%
LRMS(ESI): m/z=484 [M+H]+

Example 32: (4'-morpholino-[1,1'-biphenyl]-3-yl) methyl (1-(2-cyanopyrimidin-4-yl)cyclopentyl)carbamate

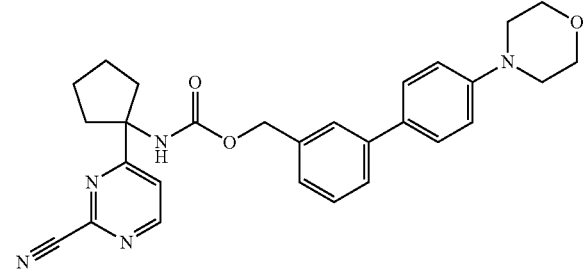 [SMILES: N#Cc1nccc(C2(NC(=O)OCc3cccc(-c4ccc(N5CCOCC5)cc4)c3)CCCC2)n1]

The titled compound (3.99 mg) was prepared in accordance with the same procedures as in Example 29, using 3-bromobenzyl (1-(2-cyanopyrimidin-4-yl)cyclopentyl)carbamate prepared in Example 3 as a starting material; and using PdCl$_2$(dppf)-CH$_2$C$_2$ and (4-morpholinophenyl)boronic acid instead of Pd(PPh$_3$)$_4$ and (4-(methylsulfonyl)phenyl)boronic acid, respectively. (brown oil, Yield: 21%)

¹H NMR (400 MHz, CDCl₃) δ 8.75 (s, 1H), 7.52-7.51 (m, 5H), 7.4 (s, 1H), 6.99-6.95 (m, 3H), 5.36 (s, 1H), 5.09 (s, 2H), 4.02 (s, 3H), 3.89 (t, J=3.84 Hz, 4H), 3.22 (t, J=3.86 Hz, 4H), 2.29-2.27 (m, 2H), 2.18-2.17 (m, 2H), 1.90-1.89 (m, 4H)

HPLC purity=95%

LRMS(ESI): m/z=484 [M+H]+

Example 33: 4-(6-fluoropyridin-3-yl)benzyl (1-(2-cyanopyrimidin-4-yl)cyclopentyl)carbamate

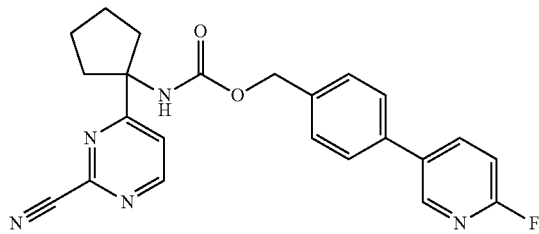 [SMILES: N#Cc1nccc(C2(NC(=O)OCc3ccc(-c4ccc(F)nc4)cc3)CCCC2)n1]

The titled compound (6.25 mg) was prepared in accordance with the same procedures as in Example 29, using 4-bromobenzyl (1-(2-cyanopyrimidin-4-yl)cyclopentyl)carbamate prepared in Example 2 as a starting material; and using (6-fluoropyridin-3-yl)boronic acid instead of (4-(methylsulfonyl)phenyl)boronic acid. (white solid, Yield: 38%)

¹H NMR (400 MHz, CDCl₃) δ 8.72 (m, 1H), 8.42 (d, J=2.4 Hz, 1H), 7.98 (td, J=2.4 Hz, 4 Hz, 1H), 7.58-7.54 (m, 3H), 7.46-7.45 (m, 2H), 7.02 (dd, J=2.8 Hz, 8.4 Hz, 1H), 5.33 (s, 1H), 5.10 (s, 2H), 2.29-2.27 (m, 2H), 2.18-2.17 (m, 2H), 1.90-1.89 (m, 4H)

HPLC purity=99%

LRMS(ESI): m/z=418 [M+H]+

Example 34: 4-(1-methyl-1H-indazol-6-yl)benzyl (1-(2-cyanopyrimidin-4-yl)cyclopentyl)carbamate

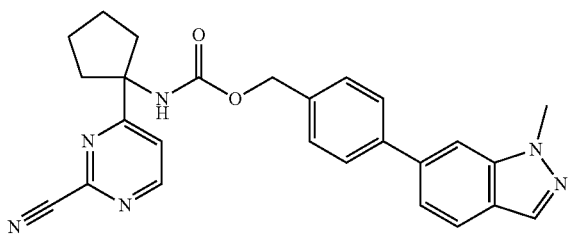 [SMILES: Cn1ncc2ccc(-c3ccc(COC(=O)NC4(c5ccnc(C#N)n5)CCCC4)cc3)cc21]

The titled compound (5.99 mg) was prepared in accordance with the same procedures as in Example 29, using 4-bromobenzyl (1-(2-cyanopyrimidin-4-yl)cyclopentyl)carbamate prepared in Example 2 as a starting material; and using (1-methyl-1H-indazol-6-yl)boronic acid instead of (4-(methylsulfonyl)phenyl)boronic acid. (Yield: 36%)

¹H NMR (400 MHz, CDCl₃) δ 8.71 (m, 1H), 8.01 (s, 1H), 7.79 (d, J=8.8 Hz, 1H), 7.69 (d, J=7.2 Hz, 2H), 7.56 (s, 1H), 7.46-7.45 (m, 1H), 7.4 (dd, J=1.2 Hz, J=8.4 Hz, 1H), 7.26 (s, 1H), 5.32 (s, 1H), 5.11 (s, 1H), 4.13 (s, 3H), 2.29-2.27 (m, 2H), 2.18-2.17 (m, 2H), 1.90-1.89 (m, 4H)

HPLC purity=99%

LRMS(ESI): m/z=453 [M+H]+

Example 35: 3-(6-fluoropyridin-3-yl)benzyl (1-(2-cyanopyrimidin-4-yl)cyclopentyl)carbamate

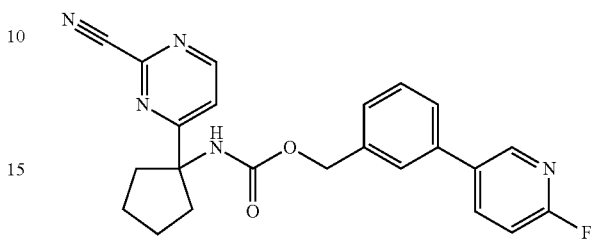

The titled compound (6.63 mg) was prepared in accordance with the same procedures as in Example 29, using 3-bromobenzyl (1-(2-cyanopyrimidin-4-yl)cyclopentyl)carbamate prepared in Example 3 as a starting material; and using (6-fluoropyridin-3-yl)boronic acid instead of (4-(methylsulfonyl)phenyl)boronic acid. (Yield: 44%)

¹H NMR (400 MHz, CDCl₃) δ 8.71-8.7 (m, 1H), 8.42 (s, 1H), 7.99-7.95 (m, 1H), 7.57 (d, J=5.2 Hz, 1H), 7.51 (s, 3H), 7.4 (s, 1H), 7.03 (dd, J=3.2 Hz, J=8.4 Hz, 1H), 5.33 (s, 1H), 5.11 (s, 1H), 2.29-2.27 (m, 2H), 2.18-2.17 (m, 2H), 1.90-1.89 (m, 4H)

HPLC purity=99%

LRMS(ESI): m/z=418 [M+H]+

Example 36: 3-(1-methyl-1H-indazol-6-yl)benzyl (1-(2-cyanopyrimidin-4-yl)cyclopentyl)carbamate

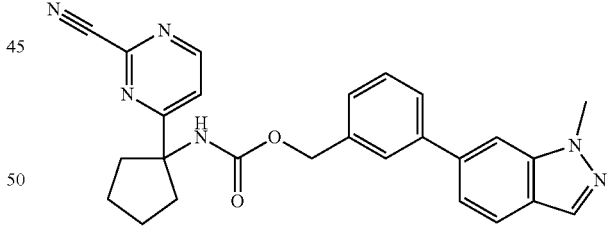

The titled compound (6.22 mg) was prepared in accordance with the same procedures as in Example 29, using 3-bromobenzyl (1-(2-cyanopyrimidin-4-yl)cyclopentyl)carbamate prepared in Example 3 as a starting material, and using (1-methyl-1H-indazol-6-yl)boronic acid instead of (4-(methylsulfonyl)phenyl)boronic acid. (Yield: 38%)

¹H NMR (400 MHz, CDCl₃) δ 8.66 (m, 1H), 8.01 (d, J=0.8 Hz, 1H), 7.79 (d, J=8.4 Hz, 1H), 7.66-7.64 (m, 2H), 7.54 (m, 2H), 7.51-7.48 (m, 1H), 7.39-7.37 (m, 2H), 5.33 (s, 1H), 5.14 (s, 2H), 4.13 (s, 3H), 2.29-2.27 (m, 2H), 2.18-2.17 (m, 2H), 1.90-1.89 (m, 4H)

HPLC purity=99%

LRMS(ESI): m/z=453 [M+H]+

Example 37: 1-(1-(2-cyanopyrimidin-4-yl)cyclopentyl)-3-(ortho-tolyl)urea

Step 1: Ethyl 2-(2-chloropyrimidin-4-yl)acetate

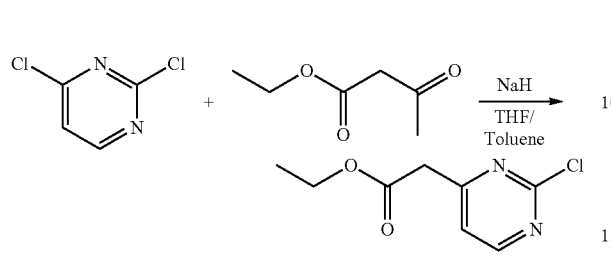

NaH (4.04 g, 100.68 mmol) was added to tetrahydrofuran (THF, 200 ml) and then stirred at 0° C. And then, ethyl acetoacetate (13.1 g, 100.68 mmol) was added dropwise thereto. The reaction mixture was stirred at room temperature additionally for 30 minutes and then concentrated under reduced pressure. 2,4-Dichloropyrimidine (10 g, 67.12 mmol) and toluene (200 ml) were added to the resulting residue under stirring. The reaction mixture was refluxed for about 12 hours. The reaction mixture was extracted with ethyl acetate and brine two times. The combined organic layer was dried on magnesium sulfate and then distilled under reduced pressure. The resulting residue was purified by MPLC to give 5.28 g of the titled compound (Yield: 39%). [M+1]$^+$=200.45

Step 2: Ethyl 1-(2-chloropyrimidin-4-yl)cyclopentanecarboxylate

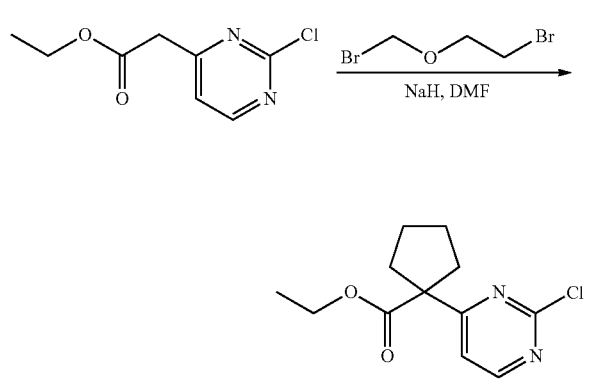

Ethyl 2-(2-chloropyrimidin-4-yl)acetate (4.9 g, 24.4 mmol) prepared in Step 1 was added to dimethylformamide (500 ml) and the resulting mixture was cooled to below 0° C. While maintaining the temperature below 0° C., 60% NaH (2.149 g, 53.7 mmol) and 1,4-dibromobutane (3.21 ml, 26.9 mmol) were added thereto. The reaction mixture was stirred at 60° C. for 2 hours and then water was added thereto to quench the reaction. The reaction mixture was extracted with ethyl acetate. The organic layer was washed with brine, dried on magnesium sulfate, and then distilled under reduced pressure. The resulting residue was purified by MPLC (100% hexane—8:2=hexane:ethyl acetate) to give 4.3 g of the titled compound (Yield: 70%). [M+1]$^+$=255.

Step 3: (1-(2-chloropyrimidin-4-yl)cyclopentyl)carboxylic acid

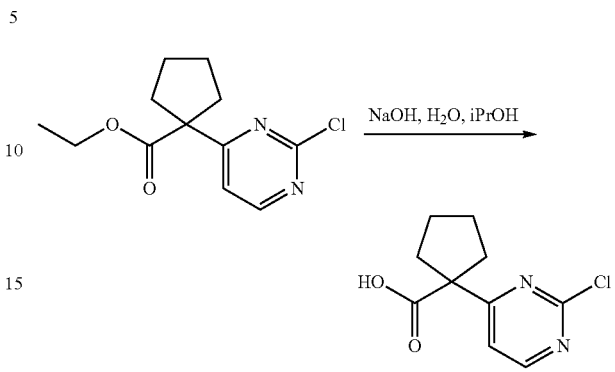

Ethyl 1-(2-chloropyrimidin-4-yl)cyclopentanecarboxylate (1.24 g, 4.87 mmol) prepared in Step 2 was dissolved in 2-propanol (25 ml) and then a 1M NaOH solution (25 ml) was added thereto. The reaction mixture was stirred for 100 minutes and then distilled under reduced pressure. The resulting residue was added to a 10% citric acid solution (5 ml) and the resulting mixture was extracted with dichloromethane. The organic layer was dried on magnesium sulfate and then distilled under reduced pressure. The resulting residue was used in the subsequent reaction without the purification thereof.

Step 4: 1-(1-(2-chloropyrimidin-4-yl)cyclopentyl)-3-(ortho-tolyl)urea

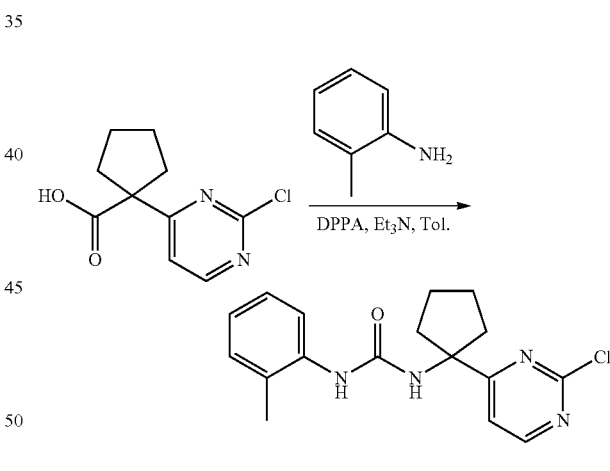

(1-(2-Chloropyrimidin-4-yl)cyclopentyl)carboxylic acid (0.20 g, 0.882 mmol) prepared in Step 3 and triethylamine (0.201 g, 1.98 mmol) were dissolved in toluene (2 ml) under stirring and then diphenylphosphoryl azide (0.316 g, 1.15 mmol) was slowly added thereto. The reaction mixture was reacted at 100° C. for 2 hours. While the reaction mixture was cooled, o-toluidine (0.095 g, 0.882 mmol) was added thereto. The reaction mixture was stirred at room temperature. After the reaction was completed, ice water was added thereto to quench the reaction. The reaction mixture was extracted with ethyl acetate. The organic layer was washed with a sodium bicarbonate solution and brine, dried on magnesium sulfate, and then distilled under reduced pressure. The resulting residue was purified by MPLC to give 88 mg of the titled compound (Yield: 30%). [M+1]$^+$=331

Step 5: 1-(1-(2-cyanopyrimidin-4-yl)cyclopentyl)-3-(ortho-tolyl)urea

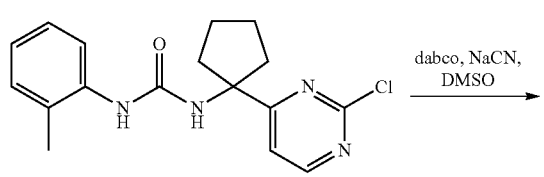

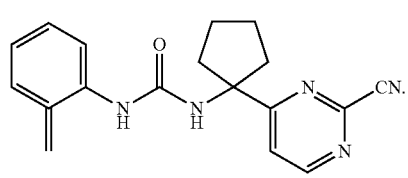

1-(1-(2-Chloropyrimidin-4-yl)cyclopentyl)-3-(ortho-tolyl)urea (84 mg, 0.254 mmol) prepared in Step 4 and NaCN (25 mg, 0.508 mmol) were dissolved in dimethyl sulfoxide (2 mL). DABCO (11 mg, 0.102 mmol) was added at room temperature to the resulting solution, which was then stirred at 50° C. for about 12 hours. Water was added thereto to quench the reaction and then the reaction mixture was extracted with ethyl acetate. The organic layer was washed with a 1N NaOH solution and brine, dried on anhydrous $Na_2SO_4$ to remove the moisture, and then distilled under reduced pressure. The resulting residue was purified by MPLC (100% hexane–6:4=hexane:ethyl acetate) to give 37 mg of the titled compound (white solid, Yield: 45%).

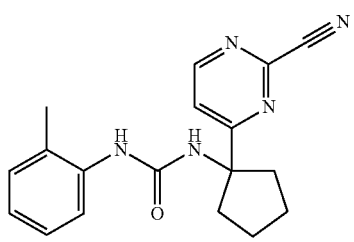 [SMILES: Cc1ccccc1NC(=O)NC1(c2ccnc(C#N)n2)CCCC1]

$^1$H NMR (400 MHz, $CDCl_3$) δ 8.73 (d, J=5.2 Hz, 1H), 7.63 (d, J=5.2 Hz, 1H), 7.39-7.32 (m, 2H), 7.24-7.17 (m, 2H), 5.93 (s, 1H), 4.99 (s, 1H) 2.27 (s, 3H), 2.26-2.22 (m, 2H), 2.16-2.11 (m, 2H), 1.89-1.80 (m, 4H)

HPLC purity=93.6%

LRMS(ESI): m/z=322 [M+H]+

The compounds of Examples 38 to 83 were prepared in accordance with the same procedures as in Example 37, using the corresponding amines instead of o-toluidine used in Step 4 of Example 37.

Example 38: 1-(1-(2-cyanopyrimidin-4-yl)cyclopentyl)-3-(meta-tolyl)urea

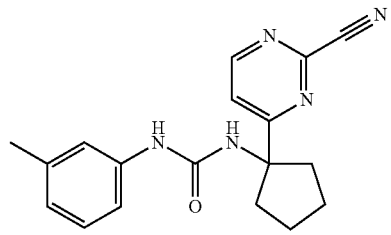 [SMILES: Cc1cccc(NC(=O)NC2(c3ccnc(C#N)n3)CCCC2)c1]

$^1$H NMR (400 MHz, $CDCl_3$) δ 8.71 (d, J=5.2 Hz, 1H), 7.64 (d, J=5.2 Hz, 1H), 7.23-7.19 (m, 2H), 7.02-6.93 (m, 2H), 6.32 (s, 1H), 5.22 (s, 1H), 2.27 (s, 3H), 2.26-2.22 (m, 2H), 2.18-2.11 (m, 2H), 1.90-1.80 (m, 4H) 15.3 mg (white solid, Yield: 44%)

HPLC purity=100%

LRMS(ESI): m/z=322 [M+H]+

Example 39: 1-(1-(2-cyanopyrimidin-4-yl)cyclopentyl)-3-(para-tolyl)urea

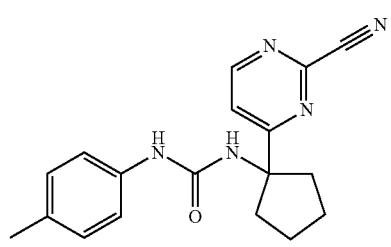 [SMILES: Cc1ccc(NC(=O)NC2(c3ccnc(C#N)n3)CCCC2)cc1]

21.6 mg (white solid, Yield: 26.8%)

$^1$H NMR (400 MHz, $CDCl_3$) δ 8.72 (d, J=5.2 Hz, 1H), 7.64 (d, J=5.2 Hz, 1H), 7.15-7.10 (m, 4H), 6.21 (s, 1H), 5.13 (s, 1H), 2.30 (s, 3H), 2.28-2.24 (m, 2H), 2.18-2.13 (m, 2H), 1.89-1.83 (m, 4H)

HPLC purity=85%

LRMS(ESI): m/z=322 [M+H]+

Example 40: 1-(1-(2-cyanopyrimidin-4-yl)cyclopentyl)-3-(2-fluorobenzyl)urea

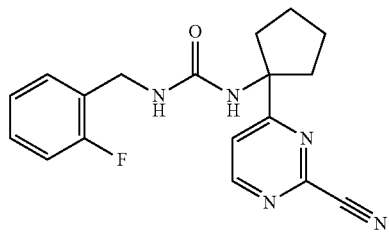 [SMILES: N#Cc1nccc(C2(NC(=O)NCc3ccccc3F)CCCC2)n1]

19.6 mg (white solid, Yield: 69.7%)

$^1$H NMR (400 MHz, $CDCl_3$) δ 8.68 (d, J=5.6 Hz, 1H), 7.56 (d, J=5.6 Hz, 1H), 7.14-7.02 (m, 4H), 4.81 (s, 1H), 4.74 (s, 1H), 4.37 (s, 2H), 2.27-2.24 (m, 2H), 2.15-2.10 (m, 2H), 1.89-1.83 (m, 4H)

HPLC purity=92%

LRMS(ESI): m/z=340 [M+H]+

Example 41: 1-(1-(2-cyanopyrimidin-4-yl)cyclopentyl)-3-phenylurea

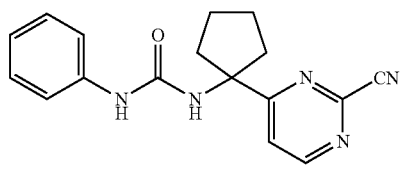 [SMILES: N#Cc1nccc(C2(NC(=O)Nc3ccccc3)CCCC2)n1]

¹H NMR (500 MHz, DMSO) δ 8.89 (d, J=5.4 Hz, 1H), 8.54 (s, 1H), 7.85 (d, J=5.4 Hz, 1H), 7.30 (d, J=8.0 Hz, 2H), 7.19 (t, J=7.4 Hz, 2H), 6.97 (s, 1H), 6.88 (t, J=7.3 Hz, 1H), 2.19-2.15 (m, 2H), 2.08-2.05 (m, 2H), 1.89-1.78 (m, 4H). LRMS(ESI): m/z=308.1 [M+H]+

Example 42: 1-benzyl-3-(1-(2-cyanopyrimidin-4-yl)cyclopentyl)urea

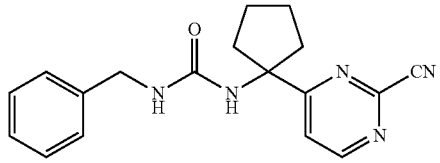 [SMILES: N#Cc1nccc(C2(NC(=O)NCc3ccccc3)CCCC2)n1]

¹H NMR (500 MHz, DMSO) δ 8.87 (d, J=5.4 Hz, 1H), 7.76 (d, J=5.4 Hz, 1H), 7.33-7.29 (m, 2H), 7.23-7.20 (m, 3H), 6.76 (s, 1H), 6.88 (m, 1H), 4.15 (d, J=6.0 Hz, 1H), 2.14-2.09 (m, 2H), 2.04-2.00 (m, 2H), 1.80-1.74 (m, 4H). LRMS(ESI) m/z=322.2 [M+H]+

Example 43: 1-(benzo[d][1,3]dioxol-5-ylmethyl)-3-(1-(2-cyanopyrimidin-4-yl)cyclopentyl)urea

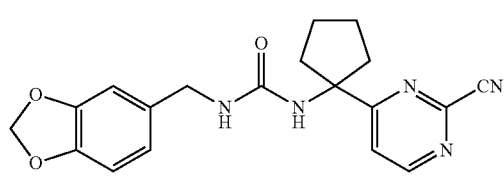 [SMILES: N#Cc1nccc(C2(NC(=O)NCc3ccc4c(c3)OCO4)CCCC2)n1]

¹H NMR (500 MHz, DMSO) δ 8.86 (d, J=5.4 Hz, 1H), 7.75 (d, J=5.4 Hz, 1H), 6.84 (d, J=7.9 Hz, 1H), 6.75 (m, 2H), 6.68 (m, 1H), 6.35 (m, 1H), 5.97 (s, 2H), 4.04 (d, J=6.0 Hz, 1H), 2.14-2.09 (m, 2H), 2.04-2.00 (m, 2H), 1.80-1.74 (m, 4H).
LRMS(ESI): m/z=366.2 [M+H]+

Example 44: 1-(1-(2-cyanopyrimidin-4-yl)cyclopentyl)-3-(4-phenoxyphenyl)urea

¹H NMR (500 MHz, DMSO) δ 8.89 (d, J=5.4 Hz, 1H), 8.87 (s, 1H), 7.85 (d, J=5.4 Hz, 1H), 7.31-7.36 (m, 4H), 7.13 (s, 1H), 7.05 (m, 1H), 6.91-6.88 (m, 4H), 2.20-2.14 (m, 2H), 2.09-2.05 (m, 2H), 1.85-1.77 (m, 4H). LRMS(ESI): m/z=400.2 [M+H]+

Example 45: 4-(2-(3-(1-(2-cyanopyrimidin-4-yl)cyclopentyl)ureido)ethyl)benzenesulfonamide

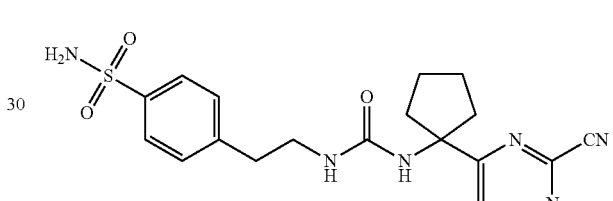

¹H NMR (500 MHz, DMSO) δ 8.86 (d, J=5.4 Hz, 1H), 7.74 (d, J=8.3 Hz, 2H), 7.63 (d, J=5.4 Hz, 1H), 7.37 (d, J=8.3 Hz, 2H), 7.32 (s, 2H), 6.72 (s, 1H), 6.01 (m, 1H), 3.22-3.18 (m, 2H), 2.72 (t, J=6.9 Hz, 2H), 2.09-2.06 (m, 2H), 1.98-1.76 (m, 2H), 1.76-1.74 (m, 4H). LRMS(ESI): m/z=415.2 [M+H]+

Example 46: 1-(1-(2-cyanopyrimidin-4-yl)cyclopentyl)-3-(2-methylbenzyl)urea

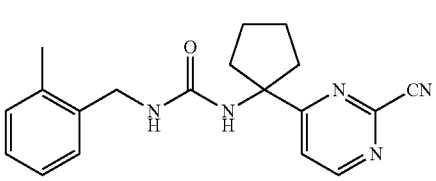 [SMILES: Cc1ccccc1CNC(=O)NC1(c2ccnc(C#N)n2)CCCC1]

¹H NMR (400 MHz, chloroform-d) δ 8.70 (d, J=5.3 Hz, 1H), 7.60 (d, J=5.3 Hz, 1H), 7.24-7.12 (m, 5H), 4.83 (s, 1H), 4.55 (t, J=5.7 Hz, 1H), 4.30 (d, J=5.5 Hz, 2H), 2.30 (s, 3H), 2.28-2.18 (m, 2H), 2.18-2.07 (m, 2H), 1.89-1.78 (m, 4H). LRMS(ESI): m/z=336.2 [M+H]+

Example 47: 1-(1-(2-cyanopyrimidin-4-yl)cyclopentyl)-3-(3-methylbenzyl)urea

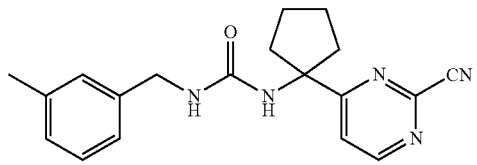 [SMILES: Cc1cccc(CNC(=O)NC2(c3ccnc(C#N)n3)CCCC2)c1]

¹H NMR (400 MHz, chloroform-d) δ 8.68 (d, J=5.4 Hz, 1H), 7.57 (d, J=5.3 Hz, 1H), 7.23 (d, J=7.6 Hz, 1H), 7.07 (q, J=7.9 Hz, 3H), 4.90 (s, 1H), 4.78 (t, J=5.8 Hz, 1H), 4.26 (d, J=5.7 Hz, 2H), 2.34 (s, 3H), 2.29-2.17 (m, 2H), 2.17-2.04 (m, 2H), 1.92-1.70 (m, 4H). LRMS(ESI): m/z=336.2 [M+H]+

Example 48: 1-(1-(2-cyanopyrimidin-4-yl)cyclopentyl)-3-(4-methylbenzyl)urea

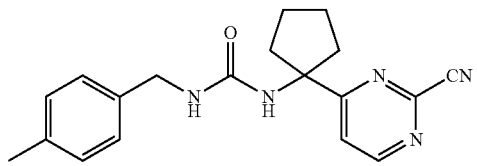 [SMILES: Cc1ccc(CNC(=O)NC2(c3ccnc(C#N)n3)CCCC2)cc1]

¹H NMR (400 MHz, chloroform-d) δ 8.69 (d, J=5.4 Hz, 1H), 7.58 (d, J=5.4 Hz, 1H), 7.16 (s, 4H), 4.80 (s, 1H), 4.68 (t, J=5.8 Hz, 1H), 4.26 (d, J=5.7 Hz, 2H), 2.34 (s, 3H), 2.23 (q, J=7.7, 7.1 Hz, 2H), 2.16-2.05 (m, 3H), 1.91-1.74 (m, 4H). LRMS(ESI): m/z=336.2 [M+H]+

Example 49: 1-(1-(2-cyanopyrimidin-4-yl)cyclopentyl)-3-(3,4-dimethoxybenzyl)urea

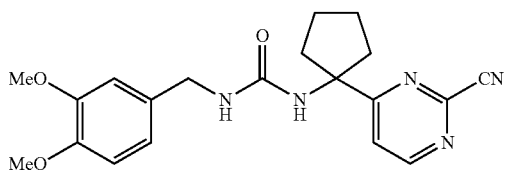 [SMILES: COc1ccc(CNC(=O)NC2(c3ccnc(C#N)n3)CCCC2)cc1OC]

¹H NMR (400 MHz, chloroform-d) δ 8.69 (d, J=5.4 Hz, 1H), 7.59 (d, J=5.4 Hz, 1H), 6.88-6.75 (m, 3H), 4.90 (s, 1H), 4.75 (t, J=5.7 Hz, 1H), 4.23 (d, J=5.7 Hz, 2H), 3.88 (s, 3H), 3.86 (s, 3H), 2.31-2.16 (m, 2H), 2.11 (dq, J=12.6, 4.8, 3.6 Hz, 2H), 1.91-1.70 (m, 4H). LRMS(ESI): m/z=382.2 [M+H]+

Example 50: 1-(1-(2-cyanopyrimidin-4-yl)cyclopentyl)-3-(2,5-dimethylphenyl)urea

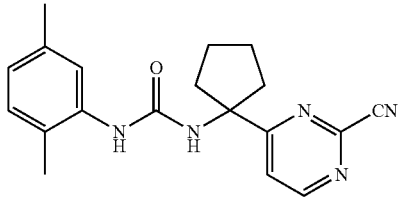 [SMILES: Cc1ccc(C)c(NC(=O)NC2(c3ccnc(C#N)n3)CCCC2)c1]

¹H NMR (400 MHz, chloroform-d) δ 8.73 (d, J=5.3 Hz, 1H), 7.63 (d, J=5.3 Hz, 1H), 7.19 (s, 1H), 7.16 (d, J=7.7 Hz, 1H), 7.00 (d, J=7.5 Hz, 1H), 5.87 (s, 1H), 4.97 (s, 1H), 2.31 (d, J=26.2 Hz, 7H), 2.19-2.08 (m, 2H), 1.94-1.77 (m, 4H). LRMS(ESI): m/z=336.2 [M+H]+

Example 51: 1-(1-(2-cyanopyrimidin-4-yl)cyclopentyl)-3-(1-phenylethyl)urea

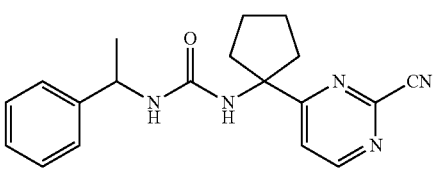 [SMILES: CC(NC(=O)NC1(c2ccnc(C#N)n2)CCCC1)c1ccccc1]

¹H NMR (400 MHz, chloroform-d) 8.64 (d, J=5.4 Hz, 1H), 7.46 (d, J=5.4 Hz, 1H), 7.42-7.35 (m, 2H), 7.35-7.28 (m, 3H), 4.76-4.61 (m, 3H), 2.25-2.10 (m, 2H), 2.08-1.91 (m, 3H), 1.85-1.71 (m, 2H), 1.71-1.51 (m, 3H), 1.46 (d, J=6.6 Hz, 3H). LRMS(ESI): m/z=336.2 [M+H]+

Example 52: 1-(1-(2-cyanopyrimidin-4-yl)cyclopentyl)-3-(4-(piperazin-1-yl)phenyl)urea

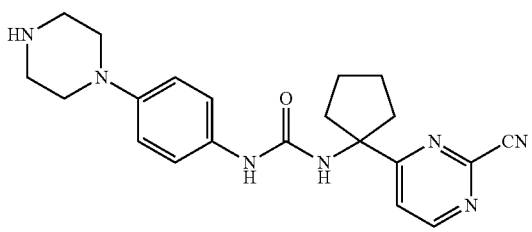 [SMILES: N#Cc1nccc(C2(NC(=O)Nc3ccc(N4CCNCC4)cc3)CCCC2)n1]

¹H NMR (400 MHz, chloroform-d) δ 8.71 (d, J=5.3 Hz, 1H), 7.59 (d, J=5.4 Hz, 1H), 6.81 (d, 2H), 6.66 (d, 2H), 5.01 (s, 1H), 3.51 (t, 4H), 3.02 (t, J=5.1 Hz, 4H), 2.37-2.22 (m, 2H), 2.22-2.08 (m, 3H), 1.98-1.77 (m, 5H). LRMS(ESI): m/z=392.2 [M+H]+

Example 53: 1-(1-(2-cyanopyrimidin-4-yl)cyclopentyl)-3-(furan-3-ylmethyl)urea

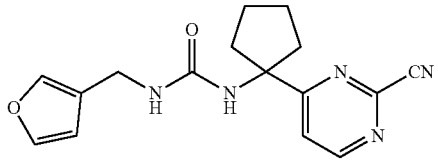 [SMILES: N#Cc1nccc(C2(NC(=O)NCc3ccoc3)CCCC2)n1]

$^1$H NMR (400 MHz, chloroform-d) δ 8.70 (d, J=5.4 Hz, 1H), 7.59 (d, J=5.4 Hz, 1H), 7.36 (dd, J=1.8, 0.9 Hz, 1H), 6.33 (dd, J=3.2, 1.9 Hz, 1H), 6.23-6.11 (m, 1H), 4.90 (s, 1H), 4.71 (t, J=5.6 Hz, 1H), 4.30 (d, J=5.7 Hz, 2H), 2.34-2.19 (m, 2H), 2.19-2.05 (m, 2H), 1.92-1.78 (m, 4H). LRMS(ESI): m/z=312.1 [M+H]+

Example 54: 1-(1-(2-cyanopyrimidin-4-yl)cyclopentyl)-3-(4-fluorobenzyl)urea

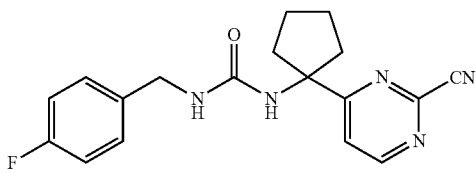 [SMILES: N#Cc1nccc(C2(NC(=O)NCc3ccc(F)cc3)CCCC2)n1]

$^1$H NMR (400 MHz, chloroform-d) δ 8.71 (d, J=5.4 Hz, 1H), 7.59 (d, J=5.4 Hz, 1H), 7.25-7.20 (m, 2H), 7.10-6.92 (m, 2H), 4.81 (s, 1H), 4.67 (d, J=6.2 Hz, 1H), 4.28 (d, J=5.8 Hz, 2H), 2.31-2.20 (m, 2H), 2.20-2.08 (m, 2H), 1.91-1.78 (m, 4H). LRMS(ESI): m/z=340.2 [M+H]+

Example 55: 1-(1-(2-cyanopyrimidin-4-yl)cyclopentyl)-3-(naphthalen-1-ylmethyl)urea

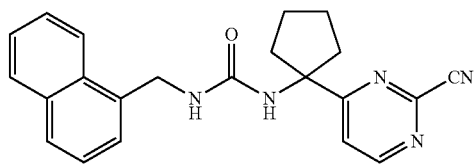 [SMILES: N#Cc1nccc(C2(NC(=O)NCc3cccc4ccccc34)CCCC2)n1]

$^1$H NMR (400 MHz, chloroform-d) δ 8.67 (d, J=5.3 Hz, 1H), 8.00-7.93 (m, 1H), 7.92-7.86 (m, 1H), 7.86-7.78 (m, 1H), 7.58 (d, J=5.3 Hz, 1H), 7.56-7.49 (m, 2H), 7.48-7.39 (m, 2H), 4.77 (d, J=5.6 Hz, 3H), 4.63 (d, J=5.9 Hz, 1H), 2.33-2.20 (m, 2H), 2.16-2.05 (m, 2H), 1.91-1.70 (m, 4H). LRMS(ESI): m/z=372.2 [M+H]+

Example 56: 1-(1-(2-cyanopyrimidin-4-yl)cyclopentyl)-3-(2-(trifluoromethyl)benzyl)urea

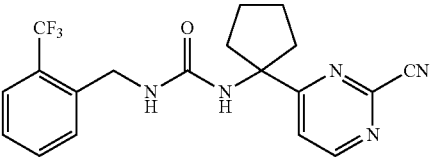 [SMILES: N#Cc1nccc(C2(NC(=O)NCc3ccccc3C(F)(F)F)CCCC2)n1]

$^1$H NMR (400 MHz, chloroform-d) δ 8.68 (d, J=5.4 Hz, 1H), 7.64 (d, J=7.8 Hz, 1H), 7.60-7.48 (m, 3H), 7.39 (t, J=7.5 Hz, 1H), 4.88 (s, 1H), 4.83 (t, J=6.2 Hz, 1H), 4.53-4.44 (m, 2H), 2.31-2.19 (m, 2H), 2.17-2.06 (m, 2H), 1.90-1.78 (m, 4H). LRMS(ESI): m/z=390.1 [M+H]+

Example 57: 1-(1-(2-cyanopyrimidin-4-yl)cyclopentyl)-3-(3-(trifluoromethyl)benzyl)urea

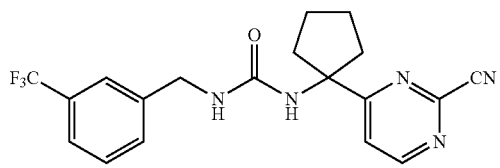 [SMILES: N#Cc1nccc(C2(NC(=O)NCc3cccc(C(F)(F)F)c3)CCCC2)n1]

$^1$H NMR (400 MHz, chloroform-d) δ 8.69 (d, J=5.4 Hz, 1H), 7.59 (d, J=5.3 Hz, 1H), 7.53 (dd, J=7.5, 2.0 Hz, 1H), 7.50-7.39 (m, 3H), 5.01 (s, 1H), 4.93 (t, J=6.0 Hz, 1H), 4.36 (d, J=5.9 Hz, 2H), 2.31-2.18 (m, 2H), 2.18-2.04 (m, 2H), 1.95-1.75 (m, 4H). LRMS(ESI): m/z=390.1 [M+H]+

Example 58: 1-(1-(2-cyanopyrimidin-4-yl)cyclopentyl)-3-(4-(trifluoromethyl)benzyl)urea

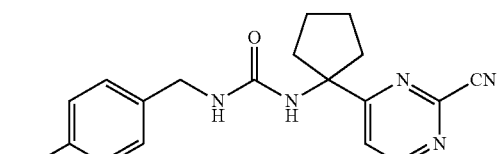

$^1$H NMR (400 MHz, chloroform-d) δ 8.72 (d, J=5.4 Hz, 1H), 7.64-7.56 (m, 3H), 7.37 (d, J=8.0 Hz, 2H), 4.85 (s, 1H), 4.75 (d, J=5.6 Hz, 1H), 4.38 (d, J=6.0 Hz, 2H), 2.29-2.20 (m, 2H), 2.16 (d, J=13.4 Hz, 2H), 1.87 (d, J=7.7 Hz, 4H). LRMS(ESI): m/z=390.1 [M+H]+

Example 59: 1-(1-(2-cyanopyrimidin-4-yl)cyclopentyl)-3-(2-(trifluoromethyl)phenyl)urea

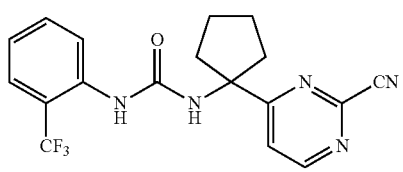 [SMILES: N#Cc1nccc(C2(NC(=O)Nc3ccccc3C(F)(F)F)CCCC2)n1]

¹H NMR (400 MHz, chloroform-d) δ 8.72 (d, J=5.4 Hz, 1H), 7.82 (d, J=8.2 Hz, 1H), 7.67-7.57 (m, 2H), 7.52 (t, J=8.0 Hz, 1H), 7.22 (t, J=7.7 Hz, 1H), 6.53 (s, 1H), 5.26 (s, 1H), 2.38-2.25 (m, 2H), 2.25-2.11 (m, 2H), 1.98-1.80 (m, 4H). LRMS(ESI): m/z=376.1 [M+H]+

Example 60: 1-(1-(2-cyanopyrimidin-4-yl)cyclopentyl)-3-(3-(trifluoromethyl)phenyl)urea

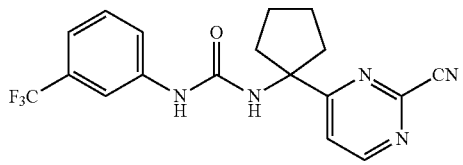 [SMILES: N#Cc1nccc(C2(NC(=O)Nc3cccc(C(F)(F)F)c3)CCCC2)n1]

¹H NMR (400 MHz, chloroform-d) δ 8.75 (d, J=5.3 Hz, 1H), 7.66 (d, J=5.4 Hz, 1H), 7.60 (s, 1H), 7.46 (d, J=8.3 Hz, 1H), 7.39 (t, J=7.9 Hz, 1H), 7.30 (d, J=7.7 Hz, 1H), 6.57 (s, 1H), 5.23 (s, 1H), 2.37-2.16 (m, 4H), 1.97-1.84 (m, 4H). LRMS(ESI): m/z=376.1 [M+H]+

Example 61: 1-(1-(2-cyanopyrimidin-4-yl)cyclopentyl)-3-(4-(trifluoromethyl)phenyl)urea

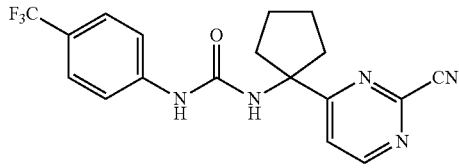 [SMILES: N#Cc1nccc(C2(NC(=O)Nc3ccc(C(F)(F)F)cc3)CCCC2)n1]

¹H NMR (400 MHz, chloroform-d) δ 8.75 (d, J=5.4 Hz, 1H), 7.66 (d, J=5.4 Hz, 1H), 7.53 (d, J=8.6 Hz, 2H), 7.41 (d, J=8.4 Hz, 2H), 6.65 (s, 1H), 5.29 (s, 1H), 2.39-2.19 (m, 4H), 2.01-1.80 (m, 4H). LRMS(ESI): m/z=376.1 [M+H]+

Example 62: 1-(1-(2-cyanopyrimidin-4-yl)cyclopentyl)-3-(3,4-dimethylphenyl)urea

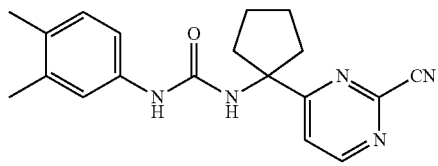 [SMILES: Cc1ccc(NC(=O)NC2(c3ccnc(C#N)n3)CCCC2)cc1C]

¹H NMR (400 MHz, chloroform-d) δ 8.70 (d, J=5.4 Hz, 1H), 7.63 (d, J=5.3 Hz, 1H), 7.09 (d, J=8.0 Hz, 1H), 7.05 (d, J=2.2 Hz, 1H), 6.95 (dd, J=8.1, 2.3 Hz, 1H), 6.30 (s, 1H), 5.24 (s, 1H), 2.32-2.19 (m, 8H), 2.19-2.10 (m, 2H), 1.95-1.79 (m, 4H). LRMS(ESI): m/z=336.2 [M+H]+

Example 63: 1-(1-(2-cyanopyrimidin-4-yl)cyclopentyl)-3-(3,5-dimethylphenyl)urea

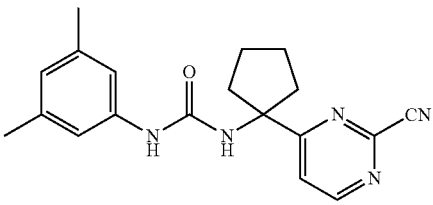 [SMILES: Cc1cc(C)cc(NC(=O)NC2(c3ccnc(C#N)n3)CCCC2)c1]

¹H NMR (400 MHz, chloroform-d) δ 8.71 (d, J=5.3 Hz, 1H), 7.64 (d, J=5.4 Hz, 1H), 6.87 (s, 2H), 6.77 (s, 1H), 6.31 (s, 1H), 5.25 (s, 1H), 2.29 (m, 8H), 2.21-2.12 (m, 2H), 1.95-1.79 (m, 4H). LRMS(ESI): m/z=336.2 [M+H]+

Example 64: 1-(1-(2-cyanopyrimidin-4-yl)cyclopentyl)-3-(2,3-dimethylphenyl)urea

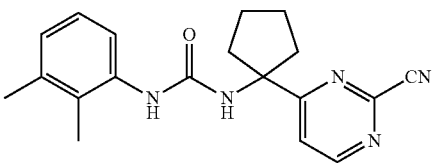 [SMILES: Cc1cccc(NC(=O)NC2(c3ccnc(C#N)n3)CCCC2)c1C]

¹H NMR (400 MHz, chloroform-d) δ 8.70 (d, J=5.3 Hz, 1H), 7.61 (d, J=5.3 Hz, 1H), 7.20-7.08 (m, 3H), 6.03 (s, 1H), 4.99 (s, 1H), 2.34 (s, 3H), 2.23 (s, 5H), 2.15-2.04 (m, 2H), 1.92-1.82 (m, 2H), 1.82-1.73 (m, 2H). LRMS(ESI): m/z=336.2 [M+H]+

Example 65: 1-(1-(2-cyanopyrimidin-4-yl)cyclopentyl)-3-(2,5-difluorophenyl)urea

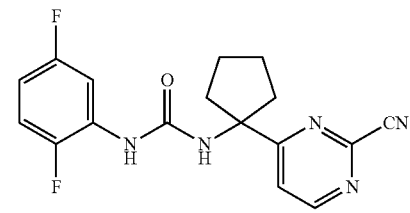 [SMILES: N#Cc1nccc(C2(NC(=O)Nc3cc(F)ccc3F)CCCC2)n1]

¹H NMR (400 MHz, chloroform-d) δ 8.75 (d, J=5.3 Hz, 1H), 7.85-7.76 (m, 1H), 7.66 (d, J=5.4 Hz, 1H), 7.05-6.92 (m, 1H), 6.69-6.55 (m, 2H), 5.25 (s, 1H), 2.38-2.27 (m, 2H), 2.27-2.18 (m, 2H), 1.96-1.89 (m, 4H). LRMS(ESI): m/z=344.1 [M+H]+

Example 66: 1-(1-(2-cyanopyrimidin-4-yl)cyclopentyl)-3-(2-methyl-5-(trifluoromethyl)phenyl)urea

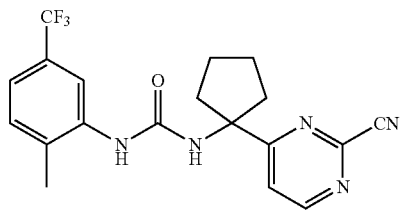 [SMILES: Cc1ccc(C(F)(F)F)cc1NC(=O)NC1(c2ccnc(C#N)n2)CCCC1]

$^1$H NMR (400 MHz, chloroform-d) δ 8.75 (d, J=5.3 Hz, 1H), 7.83 (s, 1H), 7.64 (d, J=5.4 Hz, 1H), 7.34 (d, J=1.4 Hz, 2H), 6.09 (s, 1H), 5.12 (s, 1H), 2.34 (s, 3H), 2.32-2.16 (m, 4H), 1.91 (q, J=3.5 Hz, 4H). LRMS(ESI): m/z=390.1 [M+H]+

Example 67: 1-(1-(2-cyanopyrimidin-4-yl)cyclopentyl)-3-(5-fluoro-2-(trifluoromethyl)phenyl)urea

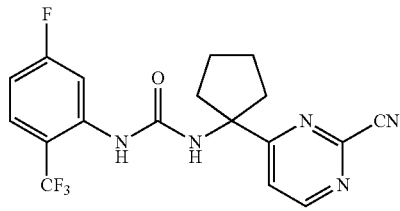 [SMILES: N#Cc1nccc(C2(NC(=O)Nc3cc(F)ccc3C(F)(F)F)CCCC2)n1]

$^1$H NMR (400 MHz, chloroform-d) δ 8.75 (d, J=5.4 Hz, 1H), 7.82 (dd, J=10.9, 2.4 Hz, 1H), 7.63 (d, J=5.4 Hz, 1H), 7.59-7.50 (m, 1H), 6.83 (t, J=8.2 Hz, 1H), 6.68 (s, 1H), 5.34 (s, 1H), 2.41-2.28 (m, 2H), 2.28-2.16 (m, 2H), 2.00-1.87 (m, 4H). LRMS(ESI): m/z=394.1 [M+H]+

Example 68: 1-(1-(2-cyanopyrimidin-4-yl)cyclopentyl)-3-(2-methoxybenzyl)urea

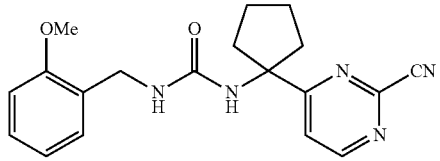 [SMILES: COc1ccccc1CNC(=O)NC1(c2ccnc(C#N)n2)CCCC1]

$^1$H NMR (400 MHz, chloroform-d) δ 8.62 (d, J=5.4 Hz, 1H), 7.51 (d, J=5.4 Hz, 1H), 7.31-7.19 (m, 2H), 6.98-6.86 (m, 2H), 4.95 (s, 1H), 4.92 (t, J=7.2 Hz, 1H), 4.28 (d, J=5.7 Hz, 2H), 3.86 (s, 3H), 2.31-2.20 (m, 2H), 2.14-2.04 (m, 2H), 1.91-1.72 (m, 4H). LRMS(ESI): m/z=356.2 [M+H]+

Example 69: 1-(1-(2-cyanopyrimidin-4-yl)cyclopentyl)-3-(3-methoxybenzyl)urea

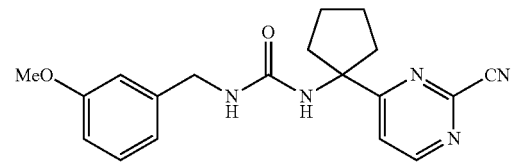 [SMILES: COc1cccc(CNC(=O)NC2(c3ccnc(C#N)n3)CCCC2)c1]

$^1$H NMR (400 MHz, chloroform-d) δ 8.69 (d, J=5.4 Hz, 1H), 7.58 (d, J=5.4 Hz, 1H), 7.31-7.21 (m, 3H), 6.88-6.75 (m, 3H), 4.87 (s, 1H), 4.76 (t, J=5.9 Hz, 1H), 4.28 (d, J=5.5 Hz, 2H), 3.80 (s, 3H), 2.31-2.19 (m, 2H), 2.15-2.05 (m, 2H), 1.92-1.71 (m, 4H). LRMS(ESI): m/z=356.2 [M+H]+

Example 70: 1-(1-(2-cyanopyrimidin-4-yl)cyclopentyl)-3-(4-methoxybenzyl)urea

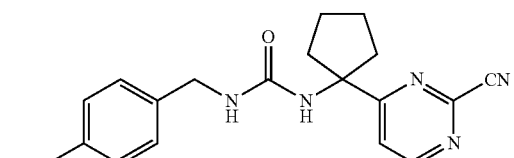

$^1$H NMR (400 MHz, chloroform-d) δ 8.68 (d, J=5.3 Hz, 1H), 7.57 (d, J=5.3 Hz, 1H), 7.18 (d, 2H), 6.88 (d, 2H), 4.89 (s, 1H), 4.75 (t, J=5.6 Hz, 1H), 4.23 (d, J=5.4 Hz, 2H), 3.81 (s, 3H), 2.30-2.18 (m, 2H), 2.15-2.03 (m, 2H), 1.91-1.73 (m, 4H). LRMS(ESI): m/z=356.2 [M+H]+

Example 71: 1-(1-(2-cyanopyrimidin-4-yl)cyclopentyl)-3-(3-hydroxyphenyl)urea

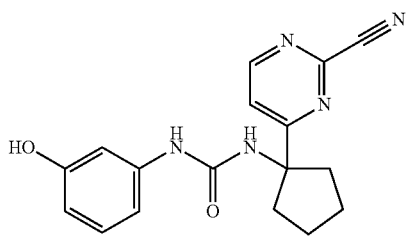 [SMILES: N#Cc1nccc(C2(NC(=O)Nc3cccc(O)c3)CCCC2)n1]

2.21 mg of the titled compound (white solid, Yield: 46%)

$^1$H NMR (400 MHz, MeOD) δ 8.79 (d, J=5.4 Hz, 1H), 7.82 (d, J=5.4 Hz, 1H), 7.04 (t, J=8.08 Hz, 1H), 6.87 (t, J=2.18 Hz, 1H), 6.72-6.7 (m, 1H), 6.44-6.41 (m, 1H), 2.38-2.3 (m, 2H), 2.19-2.13 (m, 2H), 1.97-1.93 (m, 4H)

HPLC purity=94%

LRMS(ESI): m/z=324 [M+H]+

Example 72: 4-(3-(1-(2-cyanopyrimidin-4-yl)cyclopentyl)ureido)benzenesulfonamide

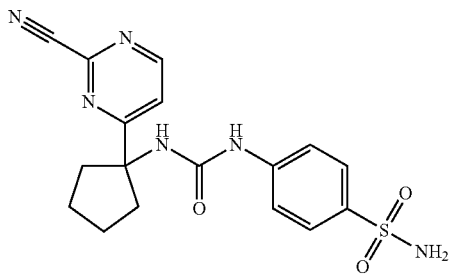 [SMILES: N#Cc1nccc(C2(NC(=O)Nc3ccc(S(N)(=O)=O)cc3)CCCC2)n1]

21.60 mg of the titled compound (white solid, Yield: 47%)
$^1$H NMR (400 MHz, MeOD) δ 8.80 (d, J=5.4 Hz, 1H), 7.83 (d, J=5.4 Hz, 1H), 7.80-7.75 (m, 2H), 7.51-7.45 (m, 2H), 2.40-2.29 (m, 2H), 2.24-2.14 (m, 2H), 2.00-1.91 (m, 4H)
HPLC purity=100%
LRMS(ESI): m/z=387 [M+H]+

Example 73: 1-(1-(2-cyanopyrimidin-4-yl)cyclopentyl)-3-(2-hydroxyphenyl)urea

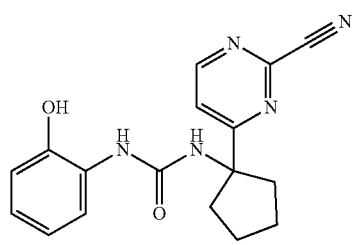 [SMILES: N#Cc1nccc(C2(NC(=O)Nc3ccccc3O)CCCC2)n1]

4.03 mg of the titled compound (white solid, Yield: 13%)
$^1$H NMR (400 MHz, DMSO-d$_6$) δ 9.79 (s, 1H), 8.82 (d, J=5.4 Hz, 1H), 8.00 (s, 1H), 7.77-7.72 (m, 2H), 7.56 (s, 1H), 6.72 (dd, J=7.9, 1.5 Hz, 1H), 6.64 (td, J=7.6, 1.7 Hz, 1H), 6.55 (td, J=7.7, 1.5 Hz, 1H), 2.15-2.04 (m, 2H), 2.02-1.94 (m, 2H), 1.80-1.67 (m, 4H)
HPLC purity=99%
LRMS(ESI): m/z=324 [M+H]+

Example 74: 1-(1-(2-cyanopyrimidin-4-yl)cyclopentyl)-3-(naphthalen-1-yl)urea

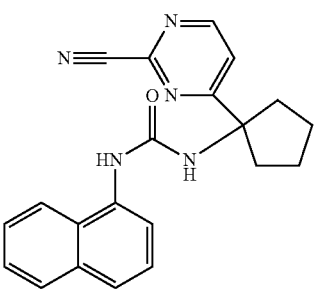 [SMILES: N#Cc1nccc(C2(NC(=O)Nc3cccc4ccccc34)CCCC2)n1]

$^1$H NMR (400 MHz, DMSO-d$_6$) δ 8.91 (d, J=5.4 Hz, 1H), 8.70 (s, 1H), 8.12 (d, J=8.4 Hz, 1H), 7.95-7.84 (m, 3H), 7.64-7.49 (m, 3H), 7.43 (s, 1H), 7.37 (t, J=7.9 Hz, 1H), 2.31-2.19 (m, 2H), 2.19-2.08 (m, 2H), 1.98-1.79 (m, 4H). 358 [M+H]+

Example 75: 1-(1-(2-cyanopyrimidin-4-yl)cyclopentyl)-3-(naphthalen-2-yl)urea

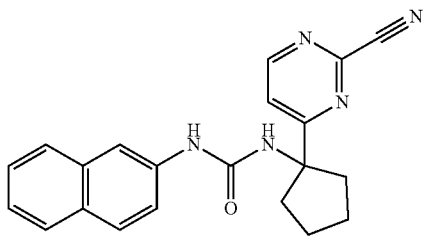 [SMILES: N#Cc1nccc(C2(NC(=O)Nc3ccc4ccccc4c3)CCCC2)n1]

$^1$H NMR (400 MHz, DMSO-d$_6$) δ 8.91 (d, J=5.4 Hz, 1H), 8.82 (s, 1H), 7.97 (d, J=2.1 Hz, 1H), 7.90 (d, J=5.4 Hz, 1H), 7.77 (d, J=8.6 Hz, 2H), 7.70 (d, J=8.2 Hz, 1H), 7.44-7.28 (m, 3H), 7.12 (s, 1H), 2.29-2.16 (m, 2H), 2.16-2.06 (m, 2H), 1.92-1.77 (m, 4H). 358 [M+H]+

Example 76: 1-(1-(2-cyanopyrimidin-4-yl)cyclopentyl)-3-(1-methyl-1H-indazol-5-yl)urea

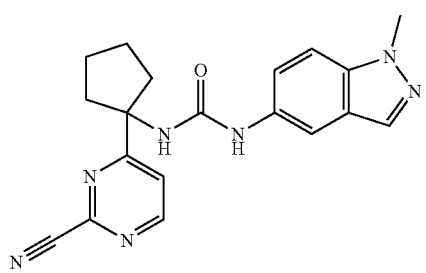 [SMILES: Cn1ncc2cc(NC(=O)NC3(c4ccnc(C#N)n4)CCCC3)ccc21]

$^1$H NMR (400 MHz, chloroform-d) δ 8.72 (d, J=5.6 Hz, 1H), 7.95 (s, 1H), 7.65 (s, 2H), 7.48-7.33 (m, 2H), 6.44 (s, 1H), 5.16 (s, 1H), 4.07 (s, 3H), 2.40-2.11 (m, 3H), 2.06-1.94 (m, 1H), 1.94-1.76 (m, 4H). 362 [M+H]+

Example 77: 1-(1-(2-cyanopyrimidin-4-yl)cyclopentyl)-3-(quinoxalin-6-yl)urea

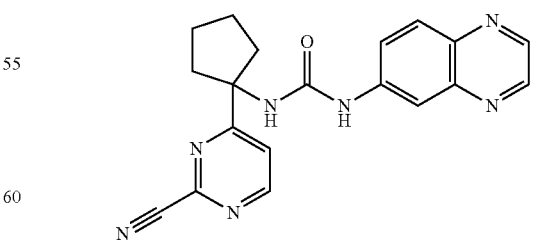

$^1$H NMR (400 MHz, chloroform-d) δ 8.80-8.73 (m, 3H), 8.03 (d, J=9.6 Hz, 1H), 7.98-7.86 (m, 2H), 7.73 (d, J=5.3 Hz, 1H), 7.26 (s, 1H), 5.78 (s, 1H), 2.44-2.22 (m, 4H), 2.02-1.87 (m, 4H). 360 [M+H]+

Example 78: 1-(benzo[d][1,3]dioxol-5-yl)-3-(1-(2-cyanopyrimidin-4-yl)cyclopentyl)urea

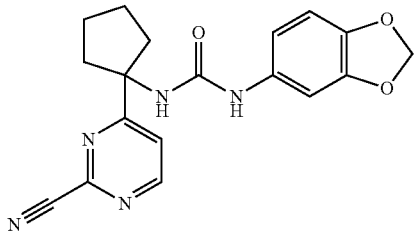 [SMILES: N#Cc1nccc(C2(NC(=O)Nc3ccc4c(c3)OCO4)CCCC2)n1]

¹H NMR (400 MHz, chloroform-d) δ 8.73 (d, J=5.3 Hz, 1H), 7.65 (d, J=5.3 Hz, 1H), 6.86 (d, J=2.2 Hz, 1H), 6.78 (d, J=8.2 Hz, 1H), 6.67 (dd, J=8.3, 2.2 Hz, 1H), 6.37 (s, 1H), 5.99 (s, 2H), 5.25 (s, 1H), 2.34-2.24 (m, 2H), 2.22-2.12 (m, 2H), 1.94-1.76 (m, 4H). 352 [M+H]+

Example 79: 1-(1-(2-cyanopyrimidin-4-yl)cyclopentyl)-3-(2-methoxyphenyl)urea

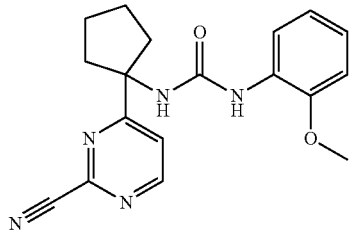 [SMILES: COc1ccccc1NC(=O)NC1(c2ccnc(C#N)n2)CCCC1]

¹H NMR (400 MHz, DMSO-d₆) δ 8.88 (d, J=5.6 Hz, 1H), 8.11 (s, 1H), 7.93 (d, J=8.0 Hz, 1H), 7.83 (d, J=5.5 Hz, 1H), 7.64 (s, 1H), 6.97 (d, J=8.0 Hz, 1H), 6.87 (t, J=7.7 Hz, 1H), 6.77 (t, J=7.7 Hz, 1H), 3.87 (s, 3H), 2.26-2.13 (m, 2H), 2.11-2.02 (m, 2H), 1.92-1.75 (m, 4H). 338 [M+H]+

Example 80: 1-(1-(2-cyanopyrimidin-4-yl)cyclopentyl)-3-(3-methoxyphenyl)urea

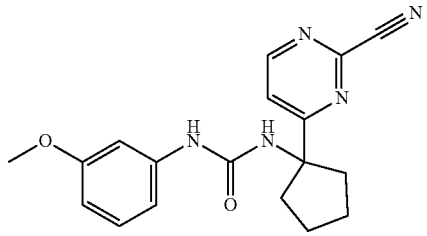 [SMILES: COc1cccc(NC(=O)NC2(c3ccnc(C#N)n3)CCCC2)c1]

¹H NMR (400 MHz, DMSO-d₆) δ 8.90 (d, J=5.4 Hz, 1H), 8.62 (s, 1H), 7.85 (d, J=5.4 Hz, 1H), 7.10 (t, J=8.1 Hz, 1H), 7.06-7.00 (m, 2H), 6.87-6.74 (m, 1H), 6.47 (dd, J=8.2, 2.5 Hz, 1H), 3.68 (s, 3H), 2.24-2.14 (m, 2H), 2.13-2.02 (m, 2H), 1.89-1.75 (m, 4H). 338 [M+H]+

Example 81: 1-(1-(2-cyanopyrimidin-4-yl)cyclopentyl)-3-(4-methoxyphenyl)urea

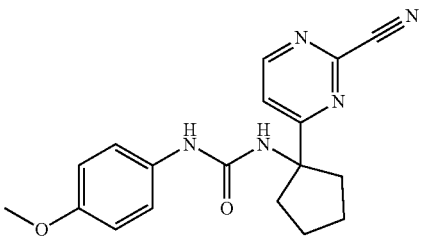 [SMILES: COc1ccc(NC(=O)NC2(c3ccnc(C#N)n3)CCCC2)cc1]

¹H NMR (400 MHz, methanol-d₄) δ 8.78 (d, J=5.4 Hz, 1H), 7.82 (d, J=5.4 Hz, 1H), 7.38 (t, J=7.9 Hz, 1H), 7.26 (d, J=8.1 Hz, 1H), 7.23-7.14 (m, 2H), 6.87-6.78 (m, 2H), 3.76 (s, 3H), 2.43-2.26 (m, 2H), 2.25-2.11 (m, 2H), 2.04-1.86 (m, 4H). 338 [M+H]+

Example 82: 1-(1-(2-cyanopyrimidin-4-yl)cyclopentyl)-3-(2,3-dihydro-1H-inden-5-yl)urea

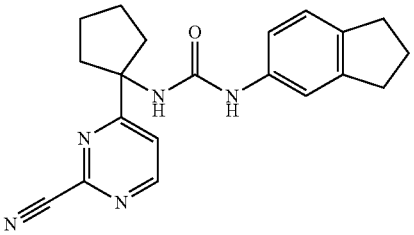

¹H NMR (400 MHz, DMSO-d₆) δ 8.89 (d, J=5.4 Hz, 1H), 8.47 (s, 1H), 7.84 (d, J=5.4 Hz, 1H), 7.27 (d, J=1.9 Hz, 1H), 7.03 (d, J=8.1 Hz, 1H), 7.00-6.92 (m, 2H), 2.76 (q, J=7.0 Hz, 4H), 2.24-2.13 (m, 2H), 2.12-2.02 (m, 2H), 1.96 (quintet, J=7.4 Hz, 2H), 1.82-1.75 (m, 4H). 348 [M+H]⁺

Example 83: 1-(1-(2-cyanopyrimidin-4-yl)cyclopentyl)-3-(2-fluoro-5-(trifluoromethyl)phenyl)urea

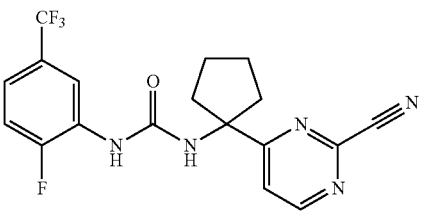 [SMILES: N#Cc1nccc(C2(NC(=O)Nc3cc(C(F)(F)F)ccc3F)CCCC2)n1]

¹H NMR (400 MHz, methanol-d₄) δ 8.66 (d, J=5.2 Hz, 1H), 8.25 (d, J=7.9 Hz, 1H), 7.69 (d, J=5.2 Hz, 1H), 7.25 (s, 1H), 7.22-7.09 (m, 1H), 2.40-2.29 (m, 2H), 2.24-2.14 (m, 2H), 2.00-1.91 (m, 4H) ppm. HPLC purity=99%, LRMS (ESI) m/z 394 [M+H]+

Example 84: 1-(1-(2-cyanopyrimidin-4-yl)-4,4-dimethylcyclohexyl)-3-(2,5-dimethylphenyl)urea

Step 1: Ethyl 2-(2-chloropyrimidin-4-yl)acetate

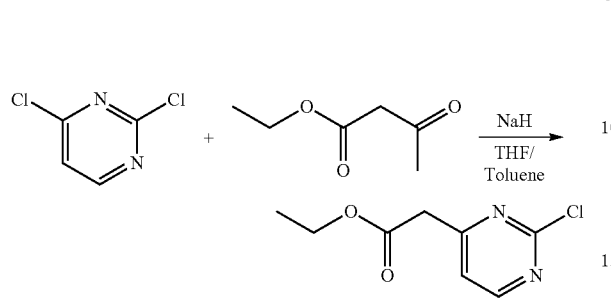

NaH (4.04 g, 100.68 mmol) was added to tetrahydrofuran (THF, 200 ml) and then stirred at 0° C. And then, ethyl acetoacetate (13.1 g, 100.68 mmol) was added dropwise thereto. The reaction mixture was stirred at room temperature additionally for 30 minutes and then concentrated under reduced pressure. 2,4-Dichloropyrimidine (10 g, 67.12 mmol) and toluene (200 ml) were added to the resulting residue under stirring. The reaction mixture was refluxed for about 12 hours. The reaction mixture was extracted with ethyl acetate and brine two times. The combined organic layer was dried on magnesium sulfate and then distilled under reduced pressure. The resulting residue was purified by MPLC to give 5.28 g of the titled compound (Yield: 39%). [M+1]$^+$=200.45

Step 2: Ethyl 1-(2-chloropyrimidin-4-yl)-4,4-dimethylcyclohexanecarboxylate

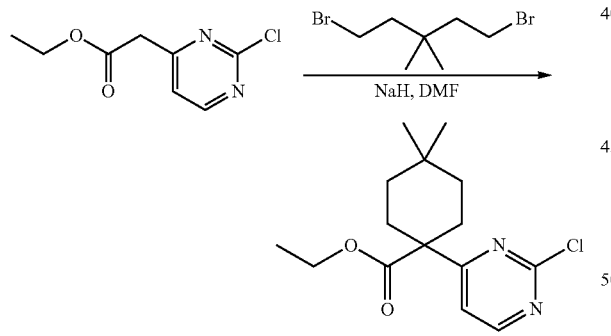

Ethyl 2-(2-chloropyrimidin-4-yl)acetate (448 mg, 2.24 mmol) prepared in Step 1 was added to dimethylformamide (15 ml) and the resulting mixture was cooled to below 0° C. While maintaining the temperature below 0° C., 60% NaH (179 mg, 4.48 mmol) and 1,5-dibromo-3,3-dimethylpentane (607 mg, 2.35 mmol) were added thereto. The reaction mixture was stirred at room temperature for 15 hours and then water was added thereto to quench the reaction. The reaction mixture was extracted with ethyl acetate. The organic layer was washed with brine, dried on magnesium sulfate, and then distilled under reduced pressure. The resulting residue was purified by MPLC to give 46 mg of the titled compound (Yield: 7%). [M+1]$^+$=296.

Step 3: 1-(2-chloropyrimidin-4-yl)-4,4-dimethylcyclohexanecarboxylic acid

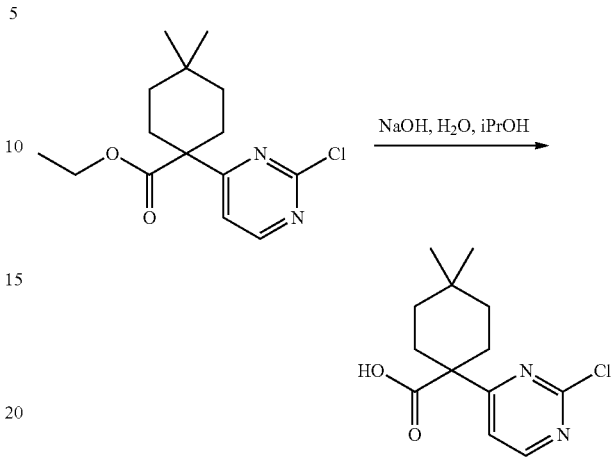

Ethyl 1-(2-chloropyrimidin-4-yl)-4,4-dimethylcyclohexanecarboxylate (53 mg, 0.18 mmol) prepared in Step 2 was dissolved in 2-propanol (2 ml) and then a 2M NaOH solution (0.45 ml) was added thereto. The reaction mixture was stirred at room temperature for 3 hours and then water (2 ml) was added thereto. The reaction mixture was acidified by adding a 10% citric acid solution (15 ml) and then extracted with dichloromethane. The organic layer was dried on magnesium sulfate and then distilled under reduced pressure. The resulting residue was used in the subsequent reaction without the purification thereof.

Step 4: 1-(1-(2-chloropyrimidin-4-yl)-4,4-dimethylcyclohexyl)-3-(2,5-dimethylphenyl)urea

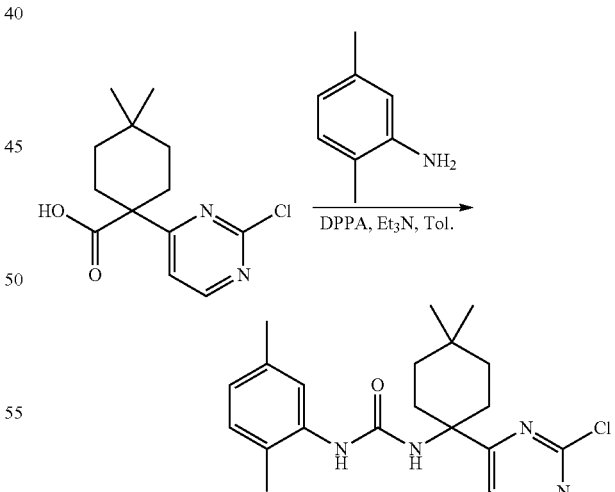

1-(2-Chloropyrimidin-4-yl)-4,4-dimethylcyclohexanecarboxylic acid (46 mg, 0.17 mmol) prepared in Step 3 and triethylamine (38 mg, 0.38 mmol) were dissolved in toluene (1.5 ml) under stirring and then diphenylphosphoryl azide (60 mg, 0.22 mmol) was slowly added thereto. The reaction mixture was reacted at 100° C. for 2 hours. While the reaction mixture was cooled, 2,5-dimethylaniline (100 mg, 0.85 mmol) was added thereto. The reaction mixture was reacted under stirring at room temperature. After the reaction was completed, ice water was added thereto to quench the reaction. The reaction mixture was extracted with ethyl acetate. The organic layer was washed with a sodium bicarbonate solution and brine, dried on magnesium sulfate to remove the moisture, and then distilled under reduced pressure. The resulting residue was purified by MPLC to give 6 mg of the titled compound (Yield: 10%). [M+1]$^+$=387

Step 5: 1-(1-(2-cyanopyrimidin-4-yl)-4,4-dimethyl-cyclohexyl)-3-(2,5-dimethylphenyl)urea

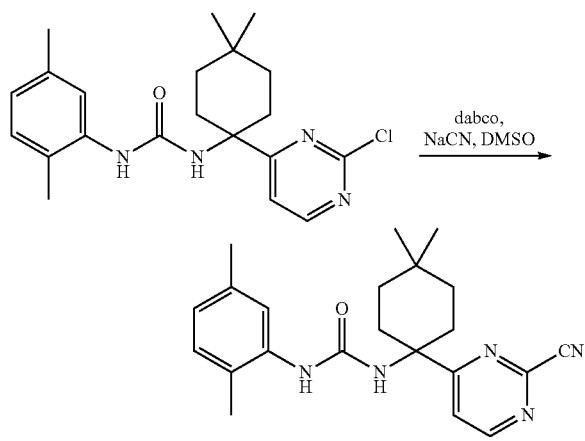

1-(1-(2-Chloropyrimidin-4-yl)-4,4-dimethylcyclohexyl)-3-(2,5-dimethylphenyl)urea (6 mg, 0.015 mmol) prepared in Step 4 and NaCN (1.5 mg, 0.031 mmol) were dissolved in dimethyl sulfoxide (1 mL). DABCO (0.7 mg, 0.0062 mmol) was added at room temperature to the resulting solution, which was then stirred at 50° C. for about 15 hours. Water was added thereto to quench the reaction and then the reaction mixture was extracted with ethyl acetate. The organic layer was washed with a 1N NaOH solution and brine, dried on anhydrous Na$_2$SO$_4$ to remove the moisture, and then distilled under reduced pressure. The resulting residue was purified by MPLC to give 5.4 mg of the titled compound (white solid, Yield: 83%).

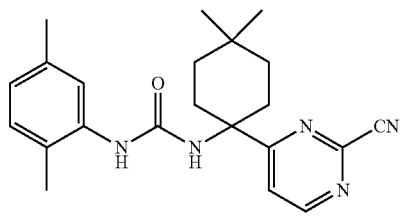 [SMILES: Cc1ccc(C)c(NC(=O)NC2(c3ccnc(C#N)n3)CCC(C)(C)CC2)c1]

$^1$H NMR (400 MHz, DMSO-d$_6$) 8.83 (d, J=5.4 Hz, 1H), 7.79 (s, 1H), 7.78 (d, J=5.5 Hz, 1H), 7.50-7.41 (m, 1H), 7.07 (s, 1H), 6.91 (d, J=7.7 Hz, 1H), 6.68-6.55 (m, 1H), 2.26 (s, 3H), 2.19 (s, 3H), 2.08-2.03 (m, 2H), 1.83-1.68 (m, 2H), 1.68-1.46 (m, 4H), 0.87 (s, 6H), MS m/z: 378 [M+H]+

Example 85: 1-(4-(2-cyanopyrimidin-4-yl)tetra-hydro-2H-pyran-4-yl)-3-(4-fluoro-3-(trifluorom-ethyl)phenyl)urea Step 1: Ethyl 2-(2-chloropyrimidin-4-yl)acetate

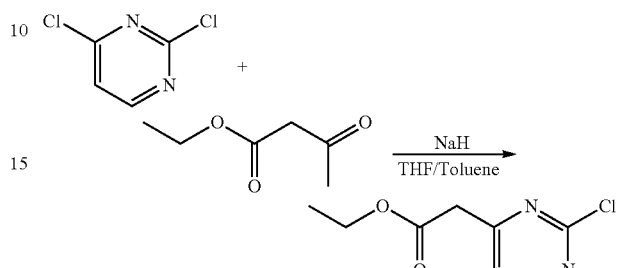

NaH (4.04 g, 100.68 mmol) was added to tetrahydrofuran (THF, 200 ml) and then stirred at 0° C. And then, ethyl acetoacetate (13.1 g, 100.68 mmol) was added dropwise thereto. The reaction mixture was stirred at room temperature additionally for 30 minutes and then concentrated under reduced pressure. 2,4-Dichloropyrimidine (10 g, 67.12 mmol) and toluene (200 ml) were added to the resulting residue under stirring. The reaction mixture was refluxed for about 12 hours. The reaction mixture was extracted with ethyl acetate and brine two times. The combined organic layer was dried on magnesium sulfate and then distilled under reduced pressure. The resulting residue was purified by MPLC to give 5.28 g of the titled compound (Yield: 39%). [M+1]$^+$=200.45

Step 2: Ethyl 4-(2-chloropyrimidin-4-yl)-tetrahydro-2H-pyran-4-carboxylate

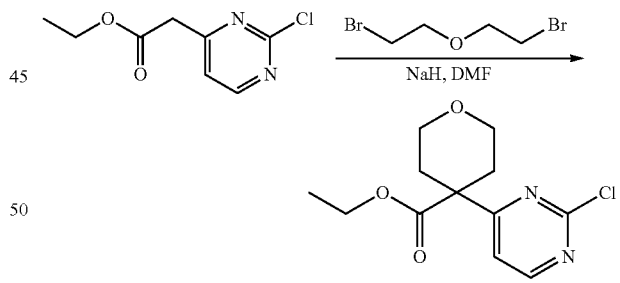

Ethyl 2-(2-chloropyrimidin-4-yl)acetate (200 mg, 0.997 mmol) prepared in Step 1 was added to dimethylformamide (10 ml) and the resulting mixture was cooled to below 0° C. While maintaining the temperature below 0° C., 60% NaH (88 mg, 2.19 mmol) and 1-bromo-2-(2-bromoethoxy)ethane (254 mg, 1.09 mmol) were added thereto. The reaction mixture was stirred at 60° C. for 2 hours and then water was added thereto to quench the reaction. The reaction mixture was extracted with ethyl acetate. The organic layer was washed with brine, dried on magnesium sulfate, and then distilled under reduced pressure. The resulting residue was purified by MPLC to give 200 mg of the titled compound (Yield: 72%). [M+1]$^+$=271

Step 3: 4-(2-chloropyrimidin-4-yl)-tetrahydro-2H-pyran-4-carboxylic acid

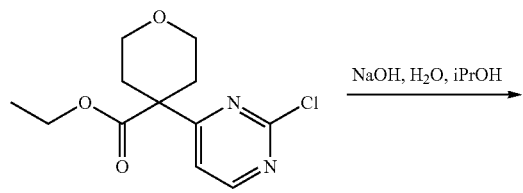

Ethyl 4-(2-chloropyrimidin-4-yl)-tetrahydro-2H-pyran-4-carboxylate (200 mg, 0.718 mmol) prepared in Step 2 was dissolved in 2-propanol (4 ml) and then a 1M NaOH solution (4 ml) was added thereto. The reaction mixture was stirred at room temperature for 15 hours and then water (2 ml) was added thereto. The reaction mixture was acidified by adding a 10% citric acid solution (20 ml) and then extracted with dichloromethane. The organic layer was dried on magnesium sulfate and then distilled under reduced pressure. The resulting residue was used in the subsequent reaction without the purification thereof.

Step 4: 1-(4-(2-chloropyrimidin-4-yl)-tetrahydro-2H-pyran-4-yl)-3-(4-fluoro-3-(trifluoromethyl)phenyl)urea

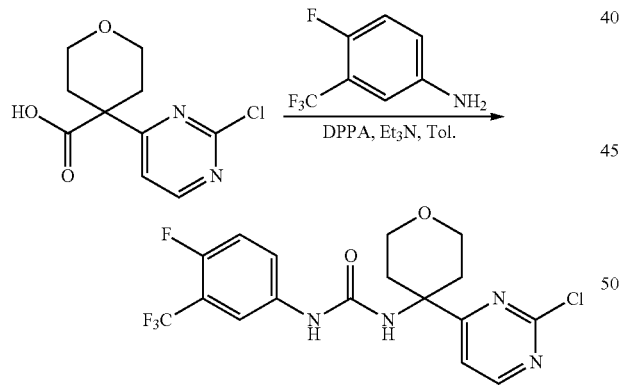

4-(2-Chloropyrimidin-4-yl)-tetrahydro-2H-pyran-4-carboxylic acid (174 mg, 0.718 mmol) prepared in Step 3 and triethylamine (165 mg, 1.61 mmol) were dissolved in toluene (4 ml) under stirring and then diphenylphosphoryl azide (268 mg, 0.933 mmol) was slowly added thereto. The reaction mixture was reacted at 50° C. for 10 minutes. While the reaction mixture was slowly cooled, 4-fluoro-3-(trifluoromethyl)aniline (193 mg, 1.08 mmol) was added thereto. The reaction mixture was reacted at 110° C. for 5 hours. After the reaction was completed, ice water was added thereto to quench the reaction. The reaction mixture was extracted with ethyl acetate. The organic layer was washed with a sodium bicarbonate solution and brine, dried on magnesium sulfate to remove the moisture, and then distilled under reduced pressure. The resulting residue was purified by MPLC to give 20 mg of the titled compound (Yield: 7%). [M+1]$^+$=419

Step 5: 1-(4-(2-cyanopyrimidin-4-yl)tetrahydro-2H-pyran-4-yl)-3-(4-fluoro-3-(trifluoromethyl)phenyl)urea

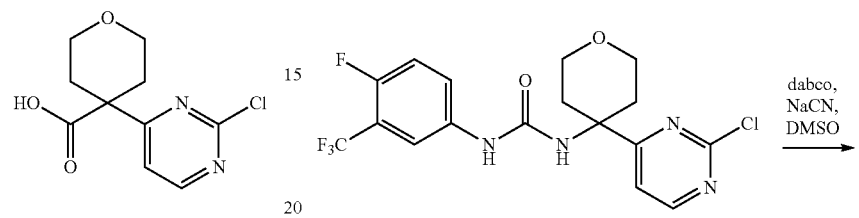

1-(4-(2-Chloropyrimidin-4-yl)-tetrahydro-2H-pyran-4-yl)-3-(4-fluoro-3-(trifluoromethyl)phenyl)urea (20 mg, 0.047 mmol) prepared in Step 4 and NaCN (4.5 mg, 0.093 mmol) were dissolved in dimethyl sulfoxide (2 mL). DABCO (21 mg, 0.018 mmol) was added at room temperature to the resulting solution, which was then stirred at 50° C. for about 15 hours. Water was added thereto to quench the reaction and then the reaction mixture was extracted with ethyl acetate. The organic layer was washed with a 1N NaOH solution and brine, dried on anhydrous Na$_2$SO$_4$ to remove the moisture, and then distilled under reduced pressure. The resulting residue was purified by MPLC to give 3.20 mg of the titled compound (white solid, Yield: 16%).

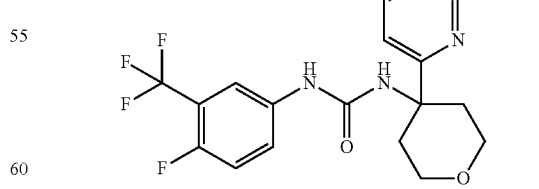

$^1$H NMR (400 MHz, MeOD) δ 8.85 (d, J=5.4 Hz, 1H), 7.85 (d, J=5.4 Hz, 1H), 7.77-7.72 (m, 1H), 7.54-7.46 (m, 1H), 7.22 (t, J=9.6 Hz, 1H), 3.98-3.89 (m, 2H), 3.85 (td, J=11.8, 1.9 Hz, 2H), 2.38-2.28 (m, 2H), 2.21-2.12 (m, 2H). HPLC purity=97%, LRMS(ESI): m/z=410 [M+H]+

Example 86: 1-(1-(2-cyanopyrimidin-4-yl)cyclohexyl)-3-phenylurea

Step 1: Ethyl 2-(2-chloropyrimidin-4-yl)acetate

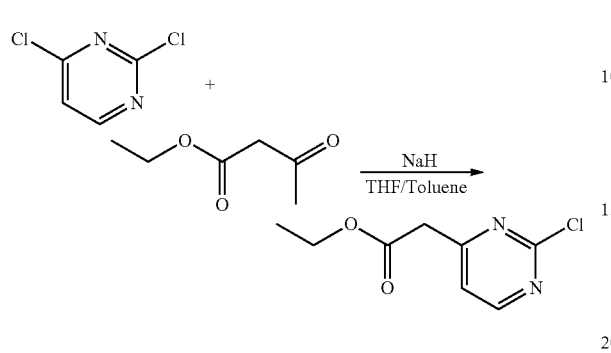

NaH (4.04 g, 100.68 mmol) was added to tetrahydrofuran (THF, 200 ml) and then stirred at 0° C. And then, ethyl acetoacetate (13.1 g, 100.68 mmol) was added dropwise thereto. The reaction mixture was stirred at room temperature additionally for 30 minutes and then concentrated under reduced pressure. 2,4-Dichloropyrimidine (10 g, 67.12 mmol) and toluene (200 ml) were added to the resulting residue under stirring. The reaction mixture was refluxed for about 12 hours. The reaction mixture was extracted with ethyl acetate and brine two times. The combined organic layer was dried on magnesium sulfate and then distilled under reduced pressure. The resulting residue was purified by MPLC to give 5.28 g of the titled compound (Yield: 39%). $[M+1]^+$=200.45

Step 2: Ethyl 1-(2-chloropyrimidin-4-yl)cyclohexanecarboxylate

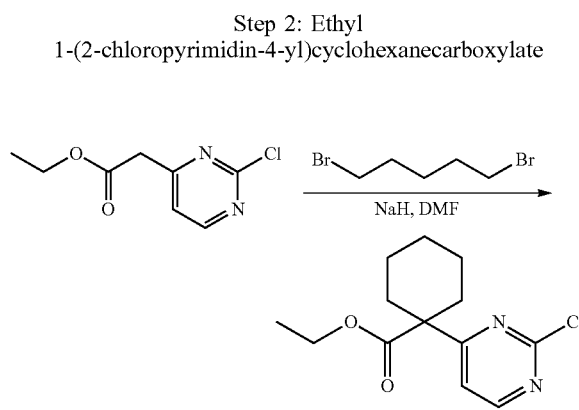

Ethyl 2-(2-chloropyrimidin-4-yl)acetate (4.9 g, 24.42 mmol) prepared in Step 1 was added to dimethylformamide (488 ml) and the resulting mixture was cooled to below 0° C. While maintaining the temperature below 0° C., 60% NaH (2.149 g, 53.7 mmol) and 1,5-dibromopentane (3.73 ml, 26.9 mmol) were added thereto. The reaction mixture was stirred at 60° C. for 2 hours and then cooled to room temperature. Water was added to the reaction mixture to quench the reaction. The reaction mixture was extracted with ethyl acetate. The organic layer was washed with brine, dried on magnesium sulfate, and then distilled under reduced pressure. The resulting residue was purified by MPLC to give 3.8 g of the titled compound (Yield: 60%). $[M+1]^+$=269.

Step 3: 1-(2-chloropyrimidin-4-yl)cyclohexanecarboxylic acid

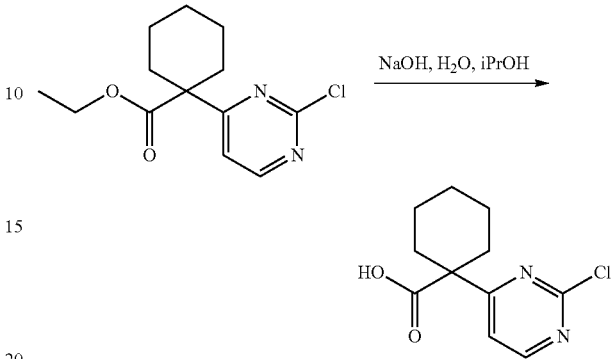

Ethyl 1-(2-chloropyrimidin-4-yl)cyclohexanecarboxylate (3.8 g, 14.14 mmol) prepared in Step 2 was dissolved in 2-propanol (70.7 ml) and then a 1M NaOH solution (70.7 ml) was added thereto. The reaction mixture was stirred for 100 minutes and then distilled under reduced pressure. The resulting residue was added to a 10% citric acid solution (15 ml) and then extracted with dichloromethane. The organic layer was dried on magnesium sulfate and then distilled under reduced pressure. The resulting residue was used in the subsequent reaction without the purification thereof.

Step 4: 1-(1-(2-chloropyrimidin-4-yl)cyclohexyl)-3-phenylurea

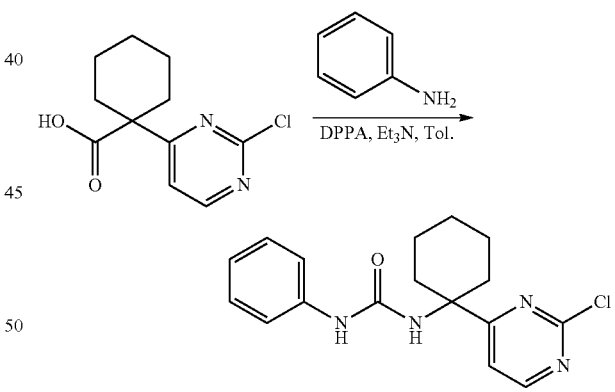

1-(2-Chloropyrimidin-4-yl)cyclohexanecarboxylic acid (61 mg, 0.253 mmol) prepared in Step 3 and triethylamine (57 mg, 0.57 mmol) were dissolved in toluene (2 ml) under stirring and then diphenylphosphoryl azide (90 mg, 0.329 mmol) was slowly added thereto. The reaction mixture was reacted at 100° C. for 2 hours. While the reaction mixture was cooled, aniline (142 mg, 1.524 mmol) was added thereto. The reaction mixture was reacted under stirring at room temperature. After the reaction was completed, ice water was added thereto to quench the reaction. The reaction mixture was extracted with ethyl acetate. The organic layer was washed with a sodium bicarbonate solution and brine, dried on magnesium sulfate to remove the moisture, and then distilled under reduced pressure. The resulting residue was purified by MPLC to give 32 mg of the titled compound (Yield: 38%). [M+1]⁺=331

Step 5: 1-(1-(2-cyanopyrimidin-4-yl)cyclohexyl)-3-phenylurea

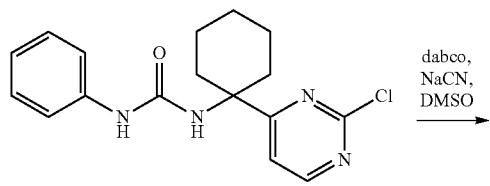

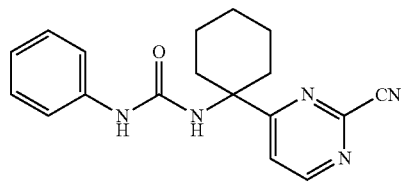

1-(1-(2-Chloropyrimidin-4-yl)cyclohexyl)-3-phenylurea (32 mg, 0.097 mmol) prepared in Step 4 and NaCN (9.5 mg, 0.193 mmol) were dissolved in dimethyl sulfoxide (1 mL). DABCO (4.3 mg, 0.039 mmol) was added at room temperature to the resulting solution, which was then stirred at 50° C. for about 12 hours. Water was added thereto to quench the reaction and then the reaction mixture was extracted with ethyl acetate. The organic layer was washed with a 1N NaOH solution and brine, dried on anhydrous Na₂SO₄ to remove the moisture, and then distilled under reduced pressure. The resulting residue was purified by MPLC to give 17.7 mg of the titled compound (white solid, Yield: 56%).

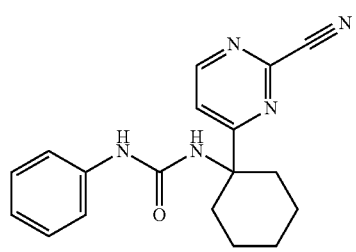 [SMILES: N#Cc1nccc(C2(NC(=O)Nc3ccccc3)CCCCC2)n1]

¹H NMR (400 MHz, DMSO-d₆) δ 8.83 (d, J=5.4 Hz, 1H), 8.60 (s, 1H), 7.79 (d, J=5.4 Hz, 1H), 7.25-7.19 (m, 2H), 7.17-7.07 (m, 2H), 6.81 (tt, J=7.3, 1.2 Hz, 1H), 6.71 (s, 1H), 2.02 (d, J=13.2 Hz, 2H), 1.77 (td, J=12.9, 4.4 Hz, 2H), 1.67-1.41 (m, 5H), 1.28-1.18 (m, 1H). [M+H]⁺=322.

The compounds of Examples 87 to 110 were prepared in accordance with the same procedures as in Example 86, using the corresponding amines, instead of aniline used in Step 4 of Example 86.

Example 87: 1-(1-(2-cyanopyrimidin-4-yl)cyclohexyl)-3-(2,5-dimethylphenyl)urea

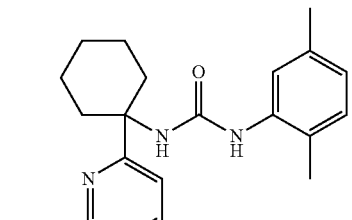

¹H NMR (400 MHz, DMSO-d₆) δ 8.83 (d, J=5.4 Hz, 1H), 7.79 (s, 1H), 7.78 (d, J=5.5 Hz, 1H), 7.50-7.41 (m, 1H), 7.07 (s, 1H), 6.91 (d, J=7.7 Hz, 1H), 6.68-6.55 (m, 1H), 2.09 (d, J=4.6 Hz, 6H), 2.03 (d, J=13.3 Hz, 2H), 1.83-1.68 (m, 2H), 1.68-1.46 (m, 5H), 1.28-1.20 (m, 1H); MS m/z: 350 [M+H]⁺

Example 88: 1-benzyl-3-(1-(2-cyanopyrimidin-4-yl)cyclohexyl)urea

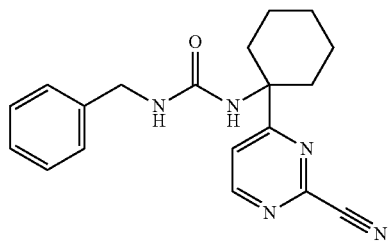 [SMILES: N#Cc1nccc(C2(NC(=O)NCc3ccccc3)CCCCC2)n1]

¹H NMR (400 MHz, chloroform-d) δ 8.70 (d, J=5.4 Hz, 1H), 7.57 (d, J=5.4 Hz, 1H), 7.41-7.33 (m, 2H), 7.32-7.27 (m, 3H), 4.82 (t, J=5.6 Hz, 1H), 4.75 (s, 1H), 4.31 (d, J=5.5 Hz, 2H), 2.17 (d, J=13.5 Hz, 2H), 1.88 (td, J=13.1, 3.8 Hz, 3H), 1.75-1.60 (m, 3H), 1.51-1.37 (m, 2H). 336 [M+H]⁺

Example 89: 1-(1-(2-cyanopyrimidin-4-yl)cyclohexyl)-3-(3-(trifluoromethyl)phenyl)urea

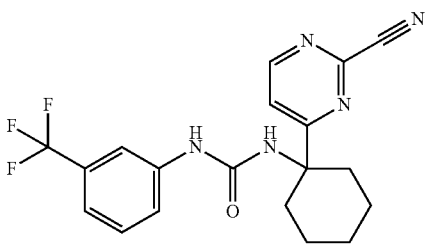 [SMILES: N#Cc1nccc(C2(NC(=O)Nc3cccc(C(F)(F)F)c3)CCCCC2)n1]

¹H NMR (400 MHz, chloroform-d) δ 8.77 (d, J=5.4 Hz, 1H), 7.67 (d, J=5.4 Hz, 1H), 7.60 (s, 1H), 7.49 (d, J=8.2 Hz, 1H), 7.40 (t, J=7.9 Hz, 1H), 7.31 (s, 1H), 6.93 (s, 1H), 5.29 (s, 1H), 2.31 (d, J=13.5 Hz, 2H), 1.97 (td, J=13.1, 3.7 Hz, 2H), 1.85-1.70 (m, 4H), 1.69-1.64 (m, 1H), 1.45-1.34 (m, 1H). 390 [M+H]⁺

Example 90: 1-(1-(2-cyanopyrimidin-4-yl)cyclohexyl)-3-(4-(trifluoromethyl)phenyl)urea

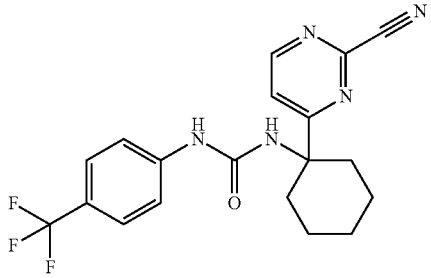 [SMILES: N#Cc1nccc(C2(NC(=O)Nc3ccc(C(F)(F)F)cc3)CCCCC2)n1]

$^1$H NMR (400 MHz, chloroform-d) δ 8.78 (d, J=5.4 Hz, 1H), 7.67 (d, J=5.4 Hz, 1H), 7.55 (d, J=8.2 Hz, 2H), 7.42 (d, J=8.5 Hz, 2H), 6.56 (s, 1H), 5.07 (s, 1H), 2.32 (d, J=13.5 Hz, 2H), 1.98 (td, J=13.3, 3.5 Hz, 2H), 1.85-1.70 (m, 4H), 1.72-1.61 (m, 1H), 1.47-1.36 (m, 1H). 390 [M+H]$^+$ Example 91: 1-(1-(2-cyanopyrimidin-4-yl)cyclohexyl)-3-(2-(trifluoromethyl)benzyl)urea

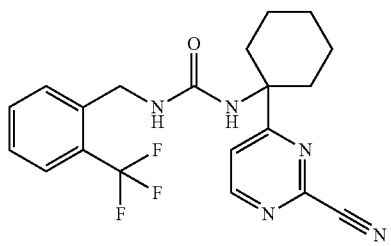 [SMILES: N#Cc1nccc(C2(NC(=O)NCc3ccccc3C(F)(F)F)CCCCC2)n1]

$^1$H NMR (400 MHz, chloroform-d) δ 8.73 (d, J=5.4 Hz, 1H), 7.67 (d, J=7.9 Hz, 1H), 7.63-7.57 (m, 2H), 7.53 (d, J=7.8 Hz, 1H), 7.41 (t, J=7.7 Hz, 1H), 4.84 (t, J=6.2 Hz, 1H), 4.74 (s, 1H), 4.52 (d, J=5.9 Hz, 2H), 2.22 (d, J=13.5 Hz, 2H), 1.91 (td, J=13.1, 3.8 Hz, 2H), 1.80-1.64 (m, 4H), 1.54-1.46 (m, 1H), 1.40-1.31 (m, 1H). 404 [M+H]$^+$ Example 92: 1-(1-(2-cyanopyrimidin-4-yl)cyclohexyl)-3-(2-(trifluoromethyl)phenyl)urea

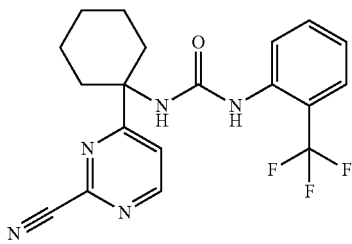 [SMILES: N#Cc1nccc(C2(NC(=O)Nc3ccccc3C(F)(F)F)CCCCC2)n1]

$^1$H NMR (400 MHz, chloroform-d) δ 8.74 (d, J=5.4 Hz, 1H), 7.83 (d, J=8.2 Hz, 1H), 7.66-7.58 (m, 3H), 7.52 (t, J=7.9 Hz, 1H), 7.21 (t, J=7.7 Hz, 1H), 5.63 (s, 1H), 2.26 (d, J=13.6 Hz, 2H), 1.97 (td, J=13.2, 3.8 Hz, 2H), 1.82-1.69 (m, 4H), 1.63-1.53 (m, 1H), 1.47-1.33 (m, 1H). 390 [M+H]$^+$ Example 93: 1-(4-chloro-3-(trifluoromethyl)phenyl)-3-(1-(2-cyanopyrimidin-4-yl)cyclohexyl)urea

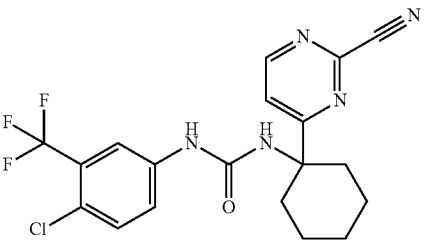 [SMILES: N#Cc1nccc(C2(NC(=O)Nc3ccc(Cl)c(C(F)(F)F)c3)CCCCC2)n1]

$^1$H NMR (400 MHz, DMSO-d$_6$) δ 8.83 (d, J=5.4 Hz, 1H), 7.79 (s, 1H), 7.78 (d, J=5.5 Hz, 1H), 7.50-7.41 (m, 1H), 7.07 (s, 1H), 6.91 (d, J=7.7 Hz, 1H), 6.68-6.55 (m, 1H), 2.09 (d, J=4.6 Hz, 6H), 2.03 (d, J=13.3 Hz, 2H), 1.83-1.68 (m, 2H), 1.68-1.46 (m, 5H), 1.28-1.20 (m, 1H). 424 [M+H]$^+$

Example 94: 1-(1-(2-cyanopyrimidin-4-yl)cyclohexyl)-3-(2-fluoro-5-methylphenyl)urea

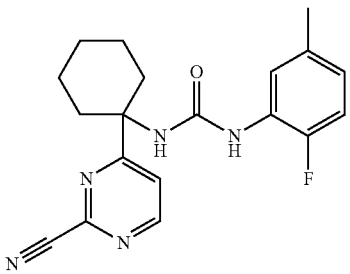 [SMILES: Cc1ccc(F)c(NC(=O)NC2(c3ccnc(C#N)n3)CCCCC2)c1]

$^1$H NMR (400 MHz, DMSO-d$_6$) δ 8.91 (d, J=5.4 Hz, 1H), 8.60 (d, J=2.7 Hz, 1H), 7.87 (d, J=5.5 Hz, 1H), 7.82 (dd, J=7.9, 2.1 Hz, 1H), 7.28 (s, 1H), 7.05 (dd, J=11.6, 8.3 Hz, 1H), 6.74-6.63 (m, 1H), 2.17 (s, 3H), 2.08 (d, J=13.3 Hz, 2H), 1.83 (td, J=12.9, 4.2 Hz, 2H), 1.73-1.51 (m, 5H), 1.35-1.20 (m, 1H). 354 [M+H]$^+$

Example 95: 1-(3,5-bis(trifluoromethyl)phenyl)-3-(1-(2-cyanopyrimidin-4-yl)cyclohexyl)urea

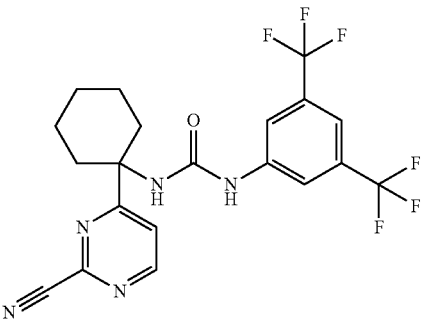 [SMILES: N#Cc1nccc(C2(NC(=O)Nc3cc(C(F)(F)F)cc(C(F)(F)F)c3)CCCCC2)n1]

$^1$H NMR (400 MHz, chloroform-d) δ 8.78 (d, J=5.4 Hz, 1H), 7.94-7.75 (m, 3H), 7.67 (d, J=5.4 Hz, 1H), 7.45 (s, 1H), 5.76 (s, 1H), 2.30 (d, J=13.5 Hz, 2H), 1.92 (td, J=13.1, 3.7 Hz, 2H), 1.81-1.74 (m, 4H), 1.67-1.52 (m, 1H), 1.44-1.32 (m, 1H). 458 [M+H]⁺

Example 96: 1-(1-(2-cyanopyrimidin-4-yl)cyclohexyl)-3-(4-fluoro-3-(trifluoromethyl)phenyl)urea

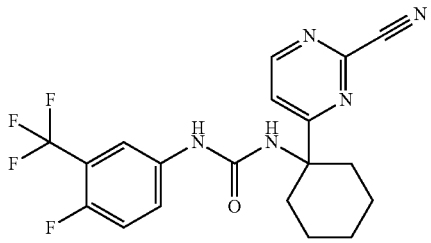

¹H NMR (400 MHz, DMSO-d₆) δ 9.03 (s, 1H), 8.91 (d, J=5.4 Hz, 1H), 7.91-7.82 (m, 2H), 7.49-7.41 (m, 1H), 7.40-7.32 (m, 1H), 6.91 (s, 1H), 2.14-2.03 (m, 2H), 1.89-1.78 (m, 2H), 1.73-1.50 (m, 5H), 1.34-1.25 (m, 1H). HPLC purity=99%, LRMS(ESI): m/z=408 [M+H]⁺

Example 97: 1-(1-(2-cyanopyrimidin-4-yl)cyclohexyl)-3-(2-fluoro-5-(trifluoromethyl)phenyl)urea

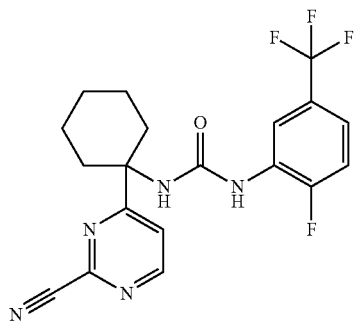 [SMILES: N#Cc1nccc(C2(NC(=O)Nc3cc(C(F)(F)F)ccc3F)CCCCC2)n1]

¹H NMR (400 MHz, DMSO-d₆) δ 9.01 (s, 1H), 8.92 (d, J=5.5 Hz, 1H), 8.41 (dd, J=7.5, 2.4 Hz, 1H), 7.90 (d, J=5.5 Hz, 1H), 7.51-7.37 (m, 2H), 7.35-7.25 (m, 1H), 2.10 (d, J=13.3 Hz, 2H), 1.85 (td, J=13.0, 4.1 Hz, 2H), 1.62 (dq, J=26.2, 13.2 Hz, 5H), 1.37-1.17 (m, 1H). 408 [M+H]⁺

Example 98: 2-(3-(1-(2-cyanopyrimidin-4-yl)cyclohexyl)ureido)-4-(trifluoromethyl)benzoic acid

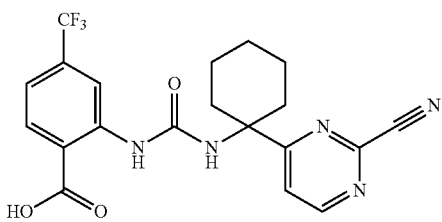 [SMILES: N#Cc1nccc(C2(NC(=O)Nc3cc(C(F)(F)F)ccc3C(=O)O)CCCCC2)n1]

¹H NMR (400 MHz, methanol-d₄) δ 8.69 (d, J=5.5 Hz, 1H), 8.42 (s, 1H), 8.06 (d, J=8.3 Hz, 1H), 7.69 (d, J=5.4 Hz, 1H), 7.12 (dd, J=8.3, 1.9 Hz, 1H), 2.12-2.08 (m, 2H), 1.91-1.84 (m, 2H), 1.67-1.57 (m, 4H), 1.35-1.25 (m, 2H) ppm. HPLC purity=98%, LRMS(ESI): m/z 434 [M+H]⁺

Example 99: 1-(1-(2-cyanopyrimidin-4-yl)cyclohexyl)-3-(2-methyl-5-(trifluoromethyl)phenyl)urea

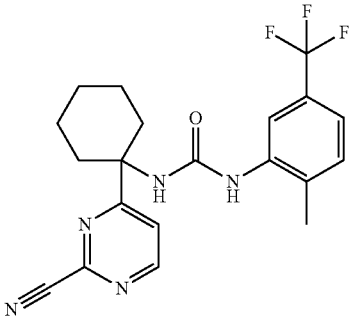

¹H NMR (400 MHz, DMSO-d₆) δ 8.92 (d, J=5.5 Hz, 1H), 8.23 (s, 1H), 8.19 (d, J=1.9 Hz, 1H), 7.88 (d, J=5.5 Hz, 1H), 7.43 (s, 1H), 7.36 (d, J=7.9 Hz, 1H), 7.18 (dt, J=7.7, 1.6 Hz, 1H), 2.31 (s, 3H), 2.11 (d, J=13.3 Hz, 2H), 1.86 (td, J=12.7, 4.6 Hz, 2H), 1.65 (q, J=20.1, 17.3 Hz, 5H), 1.37-1.22 (m, 1H). 404 [M+H]⁺

Example 100: 1-(4-benzylphenyl)-3-(1-(2-cyanopyrimidin-4-yl)cyclohexyl)urea

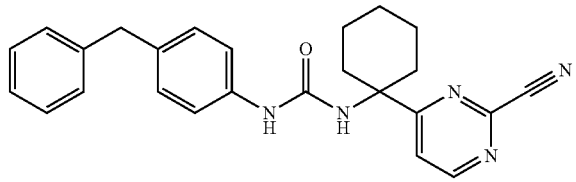 [SMILES: N#Cc1nccc(C2(NC(=O)Nc3ccc(Cc4ccccc4)cc3)CCCCC2)n1]

¹H NMR (400 MHz, methanol-d₄) δ 8.78 (d, J=5.4 Hz, 1H), 7.81 (d, J=5.5 Hz, 1H), 7.28-7.13 (m, 7H), 7.08 (d, J=8.5 Hz, 2H), 3.90 (s, 2H), 2.12-2.08 (m, 2H), 1.91-1.84 (m, 2H), 1.67-1.57 (m, 4H), 1.35-1.25 (m, 2H) ppm. HPLC purity=98%, LRMS(ESI): m/z 412 [M+H]⁺

Example 101: 1-(1-(2-cyanopyrimidin-4-yl)cyclohexyl)-3-(4-(phenylamino)phenyl)urea

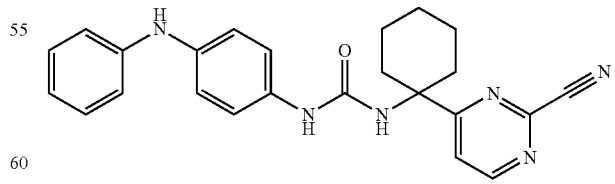

¹H NMR (400 MHz, methanol-d₄) δ 8.80 (d, J=5.4 Hz, 1H), 7.83 (d, J=5.5 Hz, 1H), 7.23-7.12 (m, 4H), 7.06-6.96 (m, 4H), 6.79 (tt, J=7.3, 1.2 Hz, 1H), 2.12-2.08 (m, 2H), 1.91-1.84 (m, 2H), 1.67-1.57 (m, 4H), 1.35-1.25 (m, 2H) ppm. HPLC purity=98%, LRMS(ESI): m/z 413 [M+H]⁺

Example 102: 1-(1-(2-cyanopyrimidin-4-yl)cyclohexyl)-3-(2-hydroxyphenyl)urea

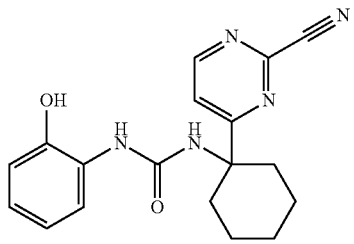 [SMILES: N#Cc1nccc(C2(NC(=O)Nc3ccccc3O)CCCCC2)n1]

¹H NMR (400 MHz, DMSO-d₆) δ 9.84 (s, 1H), 8.88 (d, J=5.48 Hz, 1H), 8.28 (s, 1H), 7.82 (d, J=5.48 Hz, 1H), 7.79 (dd, J=1.58 Hz, J=8.06 Hz, 1H), 7.44 (s, 1H), 6.78 (dd, J=1.5 Hz, J=7.9 Hz, 1H), 6.68 (td, J=3.81 Hz, J=13.6 Hz, 1H), 6.59 (td, J=3.89 Hz, J=13.84 Hz, 1H), 2.09-2.06 (m, 2H), 1.81 (d, J=29.92 Hz, 2H), 1.69-1.62 (m, 4H), 1.32-1.23 (m, 2H)

HPLC purity=98%

LRMS(ESI): m/z=338 [M+H]⁺

Example 103: 1-(2,5-bis(trifluoromethyl)phenyl)-3-(1-(2-cyanopyrimidin-4-yl)cyclohexyl)urea

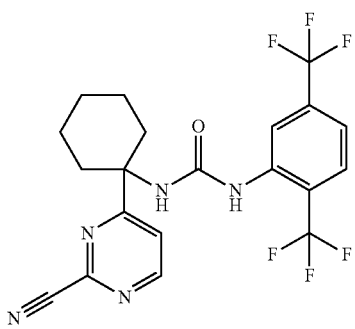 [SMILES: N#Cc1nccc(C2(NC(=O)Nc3cc(C(F)(F)F)ccc3C(F)(F)F)CCCCC2)n1]

¹H NMR (400 MHz, MeOD) δ 8.67 (d, J=5.4 Hz, 1H), 8.05-8.03 (m, 1H), 7.7 (d, J=8.28 Hz, 1H), 7.66 (d, J=5.44 Hz, 1H), 7.36 (d, J=8.28 Hz, 1H), 2.11-2.07 (m, 2H), 1.88-1.81 (m, 2H), 1.68-1.53 (m, 4H), 1.33-1.16 (m, 2H), HPLC purity=99%, LRMS(ESI): m/z=458 [M+H]⁺

Example 104: 3-(1-(2-cyanopyrimidin-4-yl)cyclohexyl)-1-methyl-1-phenylurea

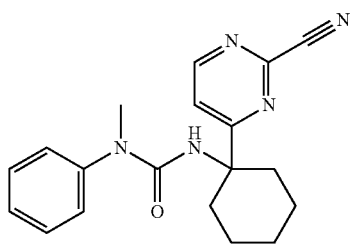 [SMILES: CN(C(=O)NC1(c2ccnc(C#N)n2)CCCCC1)c1ccccc1]

¹H NMR (400 MHz, MeOD) δ 8.8 (d, J=5.44 Hz, 1H), 7.77 (d, J=5.44 Hz, 1H), 7.57 (t, J=7.72 Hz, 2H), 7.48 (d, J=7.32 Hz, 2H), 7.43 (t, J=7.32 Hz, 1H), 5.32 (s, 1H), 3.21 (s, 3H), 2.11-2.08 (m, 2H), 1.91-1.85 (m, 2H), 1.7-1.64 (m, 4H), 1.36-1.31 (m, 2H)

HPLC purity=96%

LRMS(ESI): m/z=336 [M+H]⁺

Example 105: 3-(1-(2-cyanopyrimidin-4-yl)cyclohexyl)-1-(4-fluoro-3-(trifluoromethyl)phenyl)-1-methylurea

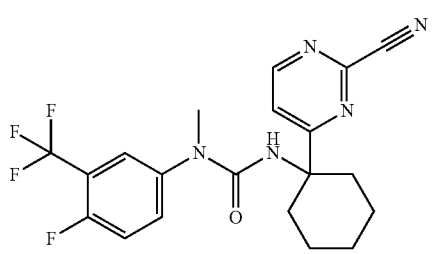 [SMILES: CN(C(=O)NC1(c2ccnc(C#N)n2)CCCCC1)c1ccc(F)c(C(F)(F)F)c1]

¹H NMR (400 MHz, MeOD) δ 8.8 (d, J=5.44 Hz, 1H), 7.78-7.75 (m, 2H), 7.72-7.69 (m, 1H), 7.36 (t, J=64.96 Hz, 1H), 3.27 (s, 3H), 2.23-2.2 (m, 2H), 1.95-1.88 (m, 2H), 1.77-1.68 (m, 4H), 1.57-1.47 (m, 2H)

HPLC purity=99%

LRMS(ESI): m/z=422 [M+H]⁺

Example 106: 1-(1-(2-cyanopyrimidin-4-yl)cyclohexyl)-3-(2,4-difluoro-5-(trifluoromethyl)phenyl)urea

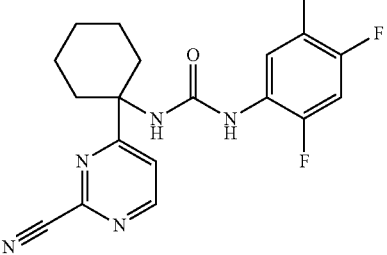

¹H NMR (400 MHz, MeOD) δ 8.69 (d, J=5.44 Hz, 1H), 8.22 (t, J=8.02 Hz, 1H), 7.7 (d, J=5.44 Hz, 1H), 7.18 (t, J=10.58 Hz, 1H), 2.18-2.08 (m, 2H), 1.91-1.84 (m, 2H), 1.67-1.57 (m, 4H), 1.35-1.25 (m, 2H), HPLC purity=99%, LRMS(ESI) m/z=426 [M+H]⁺

Example 107: 1-(1-(2-cyanopyrimidin-4-yl)cyclohexyl)-3-(2-(methoxymethyl)-5-(trifluoromethyl)phenyl)urea

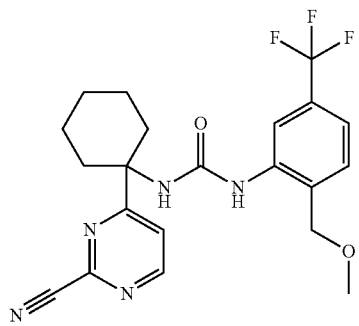 [SMILES: COCc1ccc(C(F)(F)F)cc1NC(=O)NC1(c2ccnc(C#N)n2)CCCCC1]

¹H NMR (400 MHz, MeOD) δ 8.79 (d, J=5.44 Hz, 1H), 8.02 (s, 1H), 7.8 (d, J=5.44 Hz, 1H), 7.45 (d, J=7.92 Hz, 1H), 7.28 (d, J=7.52 Hz, 1H), 4.55 (s, 2H), 3.42 (s, 3H), 2.24-2.21 (m, 2H), 2.01-1.94 (m, 2H), 1.8-1.71 (m, 4H), 1.43-1.38 (m, 2H), HPLC purity=99%, LRMS(ESI): m/z=434 [M+H]⁺

Example 108: 1-(1-(2-cyanopyrimidin-4-yl)cyclohexyl)-3-(2-(hydroxymethyl)-5-(trifluoromethyl)phenyl)urea

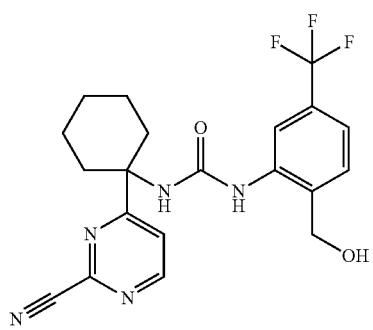 [SMILES: N#Cc1nccc(C2(NC(=O)Nc3cc(C(F)(F)F)ccc3CO)CCCCC2)n1]

¹H NMR (400 MHz, chloroform-d) δ 8.77 (d, J=5.3 Hz, 1H), 8.10 (s, 1H), 7.77 (s, 1H), 7.67 (d, J=5.4 Hz, 1H), 7.33-7.28 (m, 1H), 5.44-5.29 (m, 1H), 5.18 (s, 1H), 4.76 (s, 2H), 2.30 (d, J=13.4 Hz, 2H), 1.94 (td, J=13.9, 3.9 Hz, 2H), 1.82-1.70 (m, 4H), 1.69-1.60 (m, 1H), 1.44-1.32 (m, 1H). m/z=420 [M+H]+

Example 109: 1-(3-bromophenyl)-3-(1-(2-cyanopyrimidin-4-yl)cyclohexyl)urea

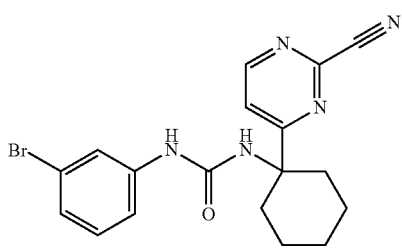 [SMILES: N#Cc1nccc(C2(NC(=O)Nc3cccc(Br)c3)CCCCC2)n1]

¹H NMR (400 MHz, MeOD) δ 8.67 (d, J=5.44 Hz, 1H), 7.69 (d, J=5.44 Hz, 1H), 7.51 (t, J=1.7 Hz, 1H), 7.07-6.96 (m, 3H), 2.09-2.06 (m, 2H), 1.9-1.82 (m, 2H), 1.68-1.55 (m, 4H), 1.33-1.18 (m, 2H)
HPLC purity=97%
LRMS(ESI): m/z=401 [M+H]+

Example 110: 1-(4-bromophenyl)-3-(1-(2-cyanopyrimidin-4-yl)cyclohexyl)urea

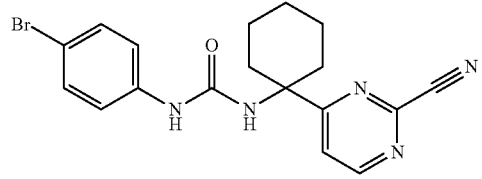 [SMILES: N#Cc1nccc(C2(NC(=O)Nc3ccc(Br)cc3)CCCCC2)n1]

¹H NMR (400 MHz, methanol-d₄) δ 8.80 (d, J=5.5 Hz, 1H), 7.82 (d, J=5.5 Hz, 1H), 7.37 (d, J=8.7 Hz, 2H), 7.25 (d, J=8.8 Hz, 2H), 2.12-2.08 (m, 2H), 1.91-1.84 (m, 2H), 1.67-1.57 (m, 4H), 1.35-1.25 (m, 2H) ppm. HPLC purity=98.1%, LRMS(ESI): m/z 401 [M+H]+

Example 111: 1-([1,1'-biphenyl]-3-yl)-3-(1-(2-cyanopyrimidin-4-yl)cyclohexyl)urea

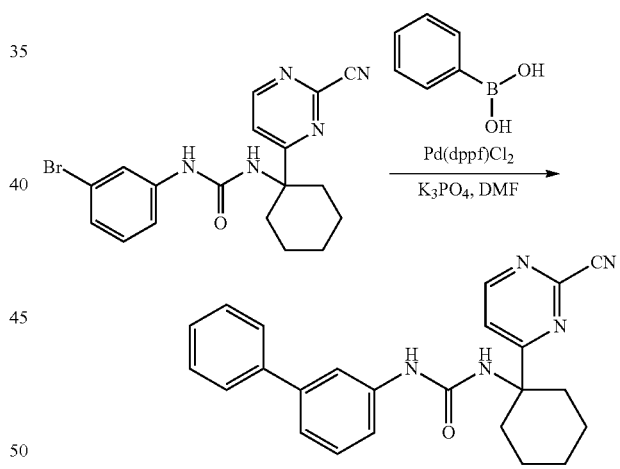

1-(3-Bromophenyl)-3-(1-(2-cyanopyrimidin-4-yl)cyclohexyl)urea (21 mg, 0.052 mmol) prepared in Example 109 was dissolved in 0.6 mL of a mixed solvent of dimethylformamide and water (5:1). Potassium phosphate (33 mg, 0.157 mmol), phenylboronic acid (9.60 mg, 0.079 mmol), and Pd(dppf)Cl₂CH₂Cl₂ (4.28 mg, 0.00525 mmol) were sequentially added to the solution, and the reaction was carried out at 80° C. using microwave. After the reaction was completed, water and ethyl acetate were added to the reaction mixture and then the organic layer was separated. The organic layer was washed with a sodium bicarbonate solution and brine, dried on magnesium sulfate, and then distilled under reduced pressure. The resulting residue was purified by Prep-HPLC to give 3.82 mg of the titled compound (white solid, Yield: 18%).

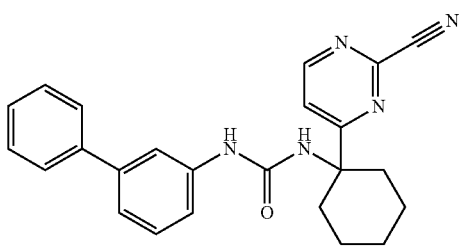 [SMILES: N#Cc1nccc(C2(NC(=O)Nc3cccc(-c4ccccc4)c3)CCCCC2)n1]

¹H NMR (400 MHz, CDCl₃) δ 8.71 (d, J=5.36 Hz, 2H), 7.63 (d, J=5.36 Hz, 2H), 7.52 (t, J=1.74 Hz, 1H), 7.45-7.33 (m, 5H), 7.24 (t, J=1.64 Hz, 1H), 6.59 (s, 1H), 5.21 (s, 1H), 2.12-2.08 (m, 2H), 1.91-1.84 (m, 2H), 1.67-1.57 (m, 4H), 1.35-1.25 (m, 2H)

HPLC purity=95%

LRMS(ESI): m/z=398 [M+H]+

Example 112: 1-(1-(2-cyanopyrimidin-4-yl)cyclohexyl)-3-(4'-(trifluoromethyl)-[1,1'-biphenyl]-3-yl)urea The compound of Example 112 was prepared in accordance with the same procedures as in Example 111, using 1-(3-bromophenyl)-3-(1-(2-cyanopyrimidin-4-yl)cyclohexyl)urea (14.7 mg, 0.037 mmol) prepared in Example 109 as a starting material and using (4-trifluoromethyl)phenyl boronic acid instead of phenylboronic acid used in Example 111.

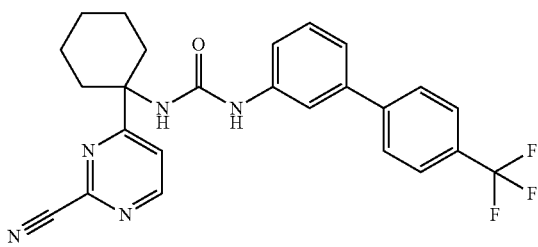 [SMILES: N#Cc1nccc(C2(NC(=O)Nc3cccc(-c4ccc(C(F)(F)F)cc4)c3)CCCCC2)n1]

¹H NMR (400 MHz, MeOD) δ 8.69 (d, J=5.44 Hz, 1H), 7.73 (d, J=5.44 Hz, 1H), 7.68-7.59 (m, 5H), 7.27-7.14 (m, 3H), 2.13-2.07 (m, 2H), 1.94-1.85 (m, 2H), 1.7-1.56 (m, 4H) 1.36-1.19 (m, 2H)

HPLC purity=97%

LRMS(ESI): m/z=466 [M+H]+

The compounds of Examples 113 to 131 were prepared in accordance with the same procedures as in Example 111, using 1-(4-bromophenyl)-3-(1-(2-cyanopyrimidin-4-yl)cyclohexyl)urea prepared in Example 110 as a starting material and using the corresponding boronic acids instead of phenylboronic acid used in Example 111.

Example 113: 1-([1,1'-biphenyl]-4-yl)-3-(1-(2-cyanopyrimidin-4-yl)cyclohexyl)urea

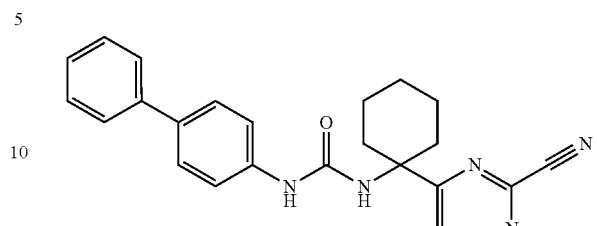

¹H NMR (400 MHz, DMSO-d₆) δ 8.91 (d, J=5.4 Hz, 1H), 8.87 (s, 1H), 7.88 (d, J=5.5 Hz, 1H), 7.59 (d, J=7.0 Hz, 1H), 7.52 (d, J=8.7 Hz, 2H), 7.41 (m, 4H), 7.29 (t, J=7.3 Hz, 1H), 6.90 (s, 1H), 2.14-2.03 (m, 2H), 1.89-1.78 (m, 2H), 1.73-1.50 (m, 5H), 1.34-1.25 (m, 1H) ppm. HPLC purity=94.3%, LRMS(ESI): m/z 398 [M+H]+

Example 114. 1-(1-(2-cyanopyrimidin-4-yl)cyclohexyl)-3-(4'-(trifluoromethyl)-[1,1'-biphenyl]-4-yl)urea

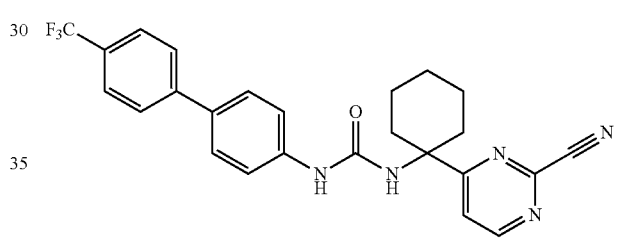

¹H NMR (400 MHz, methanol-d₄) δ 8.81 (d, J=5.5 Hz, 1H), 7.85 (d, J=5.5 Hz, 1H), 7.78 (d, J=8.2 Hz, 2H), 7.71 (d, J=8.3 Hz, 2H), 7.63-7.58 (m, 2H), 7.47-7.41 (m, 2H), 2.12-2.08 (m, 2H), 1.91-1.84 (m, 2H), 1.67-1.57 (m, 4H), 1.35-1.25 (m, 2H) ppm. HPLC purity=95%, LRMS(ESI): m/z 466 [M+H]+

Example 115: 1-(1-(2-cyanopyrimidin-4-yl)cyclohexyl)-3-(4'-hydroxy-[1,1'-biphenyl]-4-yl)urea

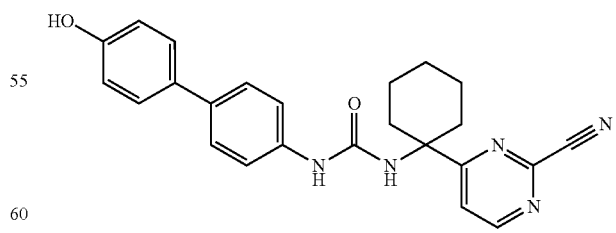

¹H NMR (400 MHz, methanol-d₄) δ 8.80 (d, J=5.4 Hz, 1H), 7.83 (d, J=5.4 Hz, 1H), 7.48-7.38 (m, 4H), 7.38-7.29 (m, 2H), 6.91-6.79 (m, 2H), 2.12-2.08 (m, 2H), 1.91-1.84 (m, 2H), 1.67-1.57 (m, 4H), 1.35-1.25 (m, 2H) ppm. HPLC purity=97%, LRMS(ESI): m/z 414 [M+H]+

Example 116: 1-(1-(2-cyanopyrimidin-4-yl)cyclohexyl)-3-(4'-(methylsulfonyl)-[1,1'-biphenyl]-4-yl)urea

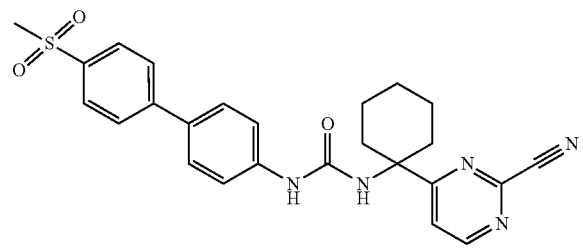 [SMILES: CS(=O)(=O)c1ccc(-c2ccc(NC(=O)NC3(c4ccnc(C#N)n4)CCCCC3)cc2)cc1]

¹H NMR (400 MHz, methanol-d₄) δ 8.82 (d, J=5.4 Hz, 1H), 7.99 (d, J=8.5 Hz, 2H), 7.90-7.80 (m, 3H), 7.64 (d, J=8.7 Hz, 2H), 7.46 (d, J=8.7 Hz, 2H), 3.16 (s, 3H), 2.12-2.08 (m, 2H), 1.91-1.84 (m, 2H), 1.67-1.57 (m, 4H), 1.35-1.25 (m, 2H) ppm. HPLC purity=98%, LRMS(ESI): m/z 476 [M+H]+

Example 117: 1-(1-(2-cyanopyrimidin-4-yl)cyclohexyl)-3-(4'-morpholino-[1,1'-biphenyl]-4-yl)urea

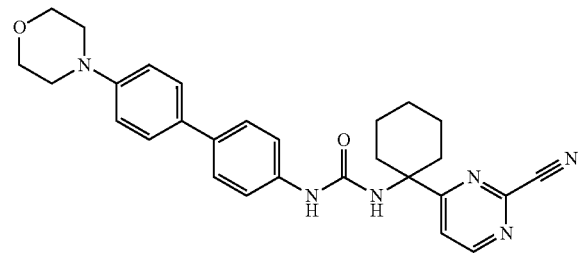 [SMILES: N#Cc1nccc(C2(NC(=O)Nc3ccc(-c4ccc(N5CCOCC5)cc4)cc3)CCCCC2)n1]

¹H NMR (400 MHz, methanol-d₄) δ 8.84 (d, J=5.4 Hz, 1H), 7.87 (d, J=5.5 Hz, 1H), 7.51 (t, J=8.6 Hz, 4H), 7.37 (d, J=8.6 Hz, 2H), 7.04 (d, J=8.7 Hz, 2H), 3.89-3.84 (m, 4H), 3.22-3.17 (m, 4H), 2.12-2.08 (m, 2H), 1.91-1.84 (m, 2H), 1.67-1.57 (m, 4H), 1.35-1.25 (m, 2H) ppm. HPLC purity=98%, LRMS(ESI): m/z 483 [M+H]+

Example 118: 1-(1-(2-cyanopyrimidin-4-yl)cyclohexyl)-3-(4-(1-methyl-1H-indazol-6-yl)phenyl)urea

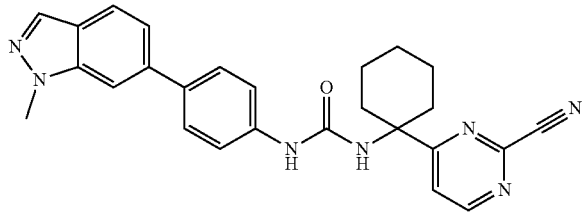 [SMILES: Cn1ncc2ccc(-c3ccc(NC(=O)NC4(c5ccnc(C#N)n5)CCCCC4)cc3)cc21]

¹H NMR (400 MHz, methanol-d₄) δ 8.85 (d, J=5.4 Hz, 1H), 8.02 (d, J=0.9 Hz, 1H), 7.89 (d, J=5.5 Hz, 1H), 7.81 (dd, J=8.4, 0.8 Hz, 1H), 7.76 (q, J=1.1 Hz, 1H), 7.68 (d, J=8.7 Hz, 2H), 7.46 (d, J=8.7 Hz, 3H), 4.13 (s, 3H), 2.12-2.08 (m, 2H), 1.91-1.84 (m, 2H), 1.67-1.57 (m, 4H), 1.35-1.25 (m, 2H) ppm. HPLC purity=99%, LRMS(ESI): m/z 452 [M+H]+

Example 119: 1-(1-(2-cyanopyrimidin-4-yl)cyclohexyl)-3-(4-(pyridin-4-yl)phenyl)urea

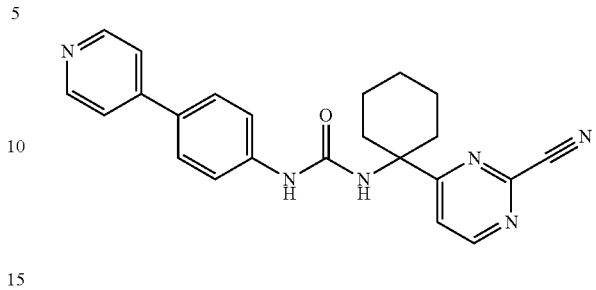

¹H NMR (400 MHz methanol-d₄) δ 8.81 (d, J=5.4 Hz, 1H), 8.54 (d, J=5.4 Hz, 2H), 7.85 (d, J=5.4 Hz, 1H), 7.75-7.66 (m, 4H), 7.48 (d, J=8.7 Hz, 2H), 6.76 (s, 1H), 2.12-2.08 (m, 2H), 1.91-1.84 (m, 2H), 1.67-1.57 (m, 4H), 1.35-1.25 (m, 2H) ppm. HPLC purity=98%, LRMS(ESI): m/z 399 [M+H]+

Example 120: 1-(1-(2-cyanopyrimidin-4-yl)cyclohexyl)-3-(4-(1-methyl-1H-pyrazol-4-yl)phenyl)urea

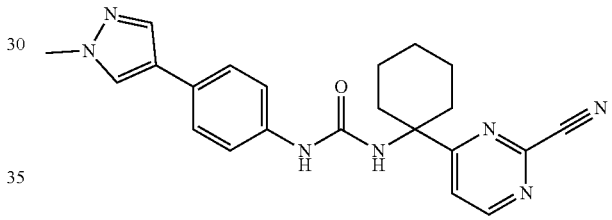

¹H NMR (400 MHz, methanol-d₄) δ 8.80 (d, J=5.4 Hz, 1H), 7.87 (s, 1H), 7.83 (d, J=5.4 Hz, 1H), 7.75 (s, 1H), 7.43 (d, J=8.6 Hz, 2H), 7.30 (d, J=8.6 Hz, 2H), 3.92 (s, 3H), 2.12-2.08 (m, 2H), 1.91-1.84 (m, 2H), 1.67-1.57 (m, 4H), 1.35-1.25 (m, 2H) ppm. HPLC purity=97%, LRMS(ESI): m/z 402 [M+H]+

Example 121: 1-(1-(2-cyanopyrimidin-4-yl)cyclohexyl)-3-(4'-fluoro-[1,1'-biphenyl]-4-yl)urea

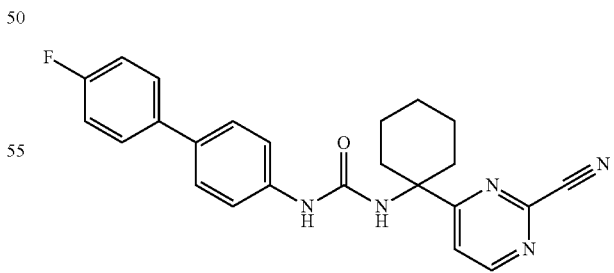

¹H NMR (400 MHz, methanol-d₄) δ 8.81 (d, J=5.5 Hz, 1H), 7.85 (d, J=5.4 Hz, 1H), 7.64-7.53 (m, 2H), 7.49 (d, J=8.7 Hz, 2H), 7.38 (d, J=8.8 Hz, 2H), 7.20-7.09 (m, 2H), 2.12-2.08 (m, 2H), 1.91-1.84 (m, 2H), 1.67-1.57 (m, 4H), 1.35-1.25 (m, 2H) ppm. HPLC purity=99%, LRMS(ESI): m/z 416 [M+H]+

Example 122: 1-(1-(2-cyanopyrimidin-4-yl)cyclohexyl)-3-(4'-ethynyl-[1,1'-biphenyl]-4-yl)urea

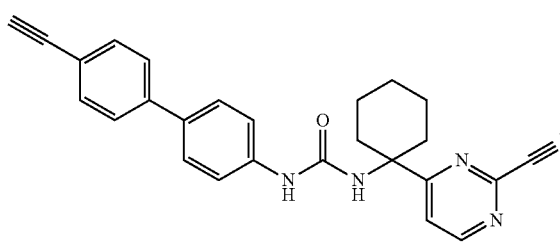

¹H NMR (400 MHz methanol-d₄) 8.81 (d, J=5.5 Hz, 1H), 7.85 (d, J=5.4 Hz, 1H), 7.83-7.73 (m, 4H), 7.61 (d, J=8.8 Hz, 2H), 7.45 (d, J=8.7 Hz, 2H), 2.12-2.08 (m, 2H), 1.91-1.84 (m, 2H), 1.67-1.57 (m, 4H), 1.35-1.25 (m, 2H) ppm. HPLC purity=97%, LRMS(ESI): m/z 423 [M+H]+

Example 123: 1-(1-(2-cyanopyrimidin-4-yl)cyclohexyl)-3-(3'-fluoro-[1,1'-biphenyl]-4-yl)urea

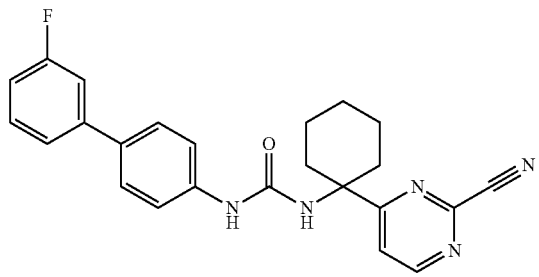 [SMILES: N#Cc1nccc(C2(NC(=O)Nc3ccc(-c4cccc(F)c4)cc3)CCCCC2)n1]

¹H NMR (400 MHz, chloroform-d) δ 8.75 (d, J=5.4 Hz, 1H), 7.66 (d, J=5.4 Hz, 1H), 7.58-7.50 (m, 2H), 7.44-7.29 (m, 4H), 7.25-7.22 (m, 1H), 7.07-6.98 (m, 1H), 6.37 (s, 1H), 2.27 (d, J=13.6 Hz, 2H), 1.95 (td, J=13.3, 3.8 Hz, 2H), 1.78-1.69 (m, 4H), 1.40-1.29 (m, 2H) ppm. HPLC purity=98%, LRMS(ESI): m/z 416 [M+H]+

Example 124: 1-(1-(2-cyanopyrimidin-4-yl)cyclohexyl)-3-(2'-fluoro-[1,1'-biphenyl]-4-yl)urea

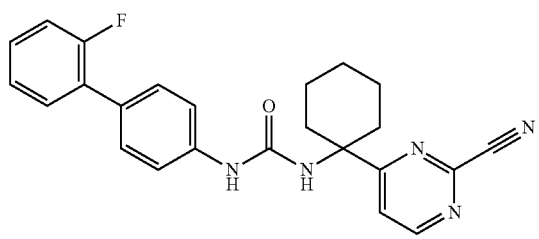 [SMILES: N#Cc1nccc(C2(NC(=O)Nc3ccc(-c4ccccc4F)cc3)CCCCC2)n1]

¹H NMR (400 MHz, chloroform-d) δ 8.75 (d, J=5.4 Hz, 1H), 7.65 (d, J=5.4 Hz, 1H), 7.57-7.49 (m, 2H), 7.46-7.26 (m, 4H), 7.25-7.09 (m, 2H), 6.40 (s, 1H), 2.27 (d, J=13.6 Hz, 2H), 1.95 (td, J=13.3, 3.8 Hz, 2H), 1.78-1.69 (m, 4H), 1.40-1.29 (m, 2H) ppm. HPLC purity=99%, LRMS(ESI): m/z 416 [M+H]+

Example 125: 1-(1-(2-cyanopyrimidin-4-yl)cyclohexyl)-3-(4-(6-fluoropyridin-3-yl)phenyl)urea

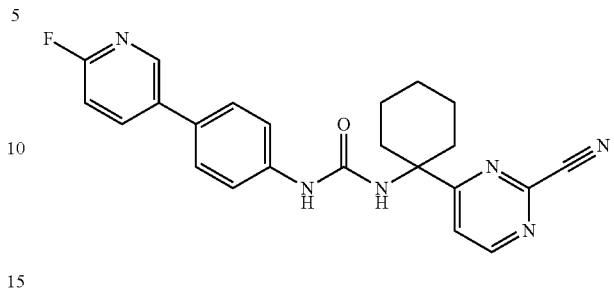

¹H NMR (400 MHz, methanol-d₄) δ 8.81 (d, J=5.4 Hz, 1H), 8.41 (dt, J=2.7, 0.8 Hz, 1H), 8.16 (m, 1H), 7.85 (d, J=5.4 Hz, 1H), 7.60-7.50 (m, 2H), 7.50-7.40 (m, 2H), 7.13 (m, 1H), 2.12-2.08 (m, 2H), 1.91-1.84 (m, 2H), 1.67-1.57 (m, 4H), 1.35-1.25 (m, 2H) ppm. HPLC purity=98%, LRMS (ESI): m/z 417 [M+H]+

Example 126: 1-(1-(2-cyanopyrimidin-4-yl)cyclohexyl)-3-(4-(6-(trifluoromethyl)pyridin-3-yl)phenyl) urea

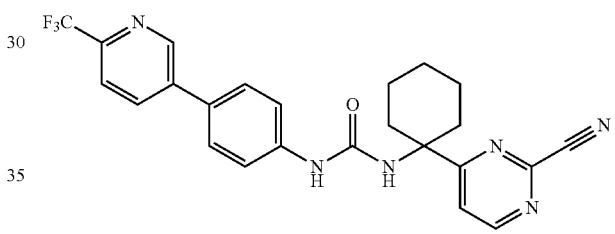

¹H NMR (400 MHz, methanol-d₄) δ 8.95 (d, J=2.2 Hz, 1H), 8.81 (d, J=5.5 Hz, 1H), 8.24 (dd, J=8.2, 2.3 Hz, 1H), 7.89-7.82 (m, 2H), 7.66 (d, J=8.7 Hz, 2H), 7.50 (d, J=8.7 Hz, 2H), 2.12-2.08 (m, 2H), 1.91-1.84 (m, 2H), 1.67-1.57 (m, 4H), 1.35-1.25 (m, 2H) ppm. HPLC purity=98%, LRMS (ESI): m/z 467 [M+H]+

Example 127: 1-(1-(2-cyanopyrimidin-4-yl)cyclohexyl)-3-(4-(6-methoxypyridin-3-yl)phenyl)urea

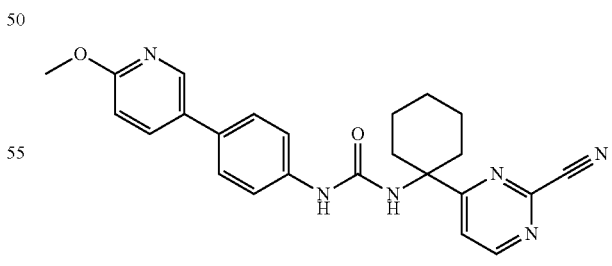

¹H NMR (400 MHz, methanol-d₄) δ 8.81 (d, J=5.4 Hz, 1H), 8.33 (d, J=2.6 Hz, 1H), 7.91 (dd, J=8.6, 2.6 Hz, 1H), 7.84 (d, J=5.5 Hz, 1H), 7.49 (d, J=8.6 Hz, 2H), 7.40 (d, J=8.6 Hz, 2H), 6.87 (d, J=8.6 Hz, 1H), 3.94 (s, 3H), 2.12-2.08 (m, 2H), 1.91-1.84 (m, 2H), 1.67-1.57 (m, 4H), 1.35-1.25 (m, 2H) ppm. HPLC purity=99%, LRMS(ESI): m/z 429 [M+H]+

Example 128: 1-(1-(2-cyanopyrimidin-4-yl)cyclohexyl)-3-(4-(pyridin-3-yl)phenyl)urea

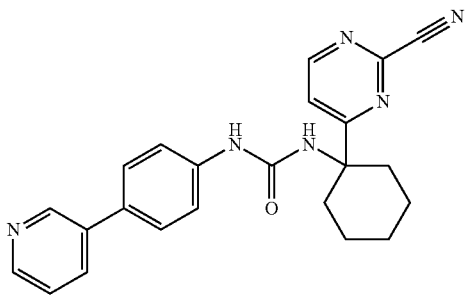 [SMILES: N#Cc1nccc(C2(NC(=O)Nc3ccc(-c4cccnc4)cc3)CCCCC2)n1]

¹H NMR (400 MHz, MeOD) δ 8.81 (d, J=5.44 Hz, 1H), 8.77 (d, J=1.88 Hz, 1H), 8.47 (dd, J=1.44 Hz, J=4.84 Hz, 1H), 8.05 (td, J=1.94 Hz, J=8.44 Hz, 1H), 7.85 (d, J=5.44 Hz, 1H), 7.6-7.57 (m, 2H), 7.5 (dd, J=5.18 Hz, J=7.82 Hz, 1H), 7.47-7.45 (m, 2H), 6.73 (s, 1H), 2.24-2.21 (m, 2H), 2.04-2 (m, 2H), 1.77-1.71 (m, 4H), 1.45-1.26 (m, 2H)
HPLC purity=96%
LRMS(ESI): m/z=399 [M+H]+

Example 129: N-(4'-(3-(1-(2-cyanopyrimidin-4-yl)cyclohexyl)ureido)-[1,1'-biphenyl]-4-yl)acetamide

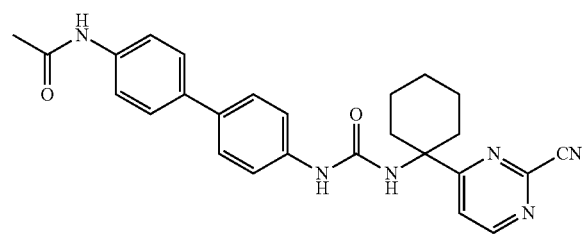 [SMILES: CC(=O)Nc1ccc(-c2ccc(NC(=O)NC3(c4ccnc(C#N)n4)CCCCC3)cc2)cc1]

¹H NMR (400 MHz, DMSO-d) δ 9.99 (s, 1H), 8.92 (d, J=5.4 Hz, 1H), 8.76 (s, 1H), 7.89 (d, J=5.4 Hz, 1H), 7.86 (d, J=5.4 Hz, 1H), 7.62 (d, J=8.5 Hz, 2H), 7.51 (m, 3H), 7.37 (d, J=8.6 Hz, 2H), 2.12-2.08 (m, 2H), 1.93-1.85 (m, 2H), 1.64-1.52 (m, 4H), 1.35-1.25 (m, 2H), [M+1]⁺=455.

Example 130: 4'-(3-(1-(2-cyanopyrimidin-4-yl)cyclohexyl)ureido)-N,N-dimethyl-[1,1'-biphenyl]-4-carboxamide

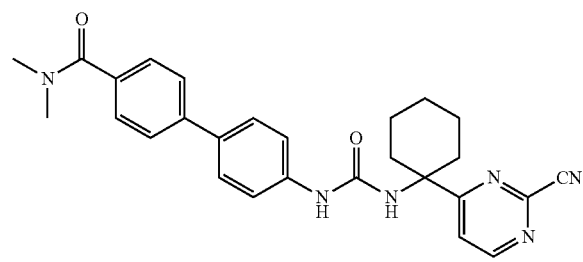 [SMILES: CN(C)C(=O)c1ccc(-c2ccc(NC(=O)NC3(c4ccnc(C#N)n4)CCCCC3)cc2)cc1]

¹H NMR (400 MHz, MeOD) δ 8.82 (d, J=5.4 Hz, 1H), 7.84 (m, 2H), 7.69 (d, J=8.6 Hz, 1H), 7.59 (m, 3H), 7.48 (m, 2H), 7.42 (d, J=8.7 Hz, 2H), 3.13 (s, 3H), 3.07 (s, 3H), 2.12-2.08 (m, 2H), 1.93-1.85 (m, 2H), 1.64-1.52 (m, 4H), 1.35-1.25 (m, 2H), [M+1]⁺=469.

Example 131: 3-(4'-(3-(1-(2-cyanopyrimidin-4-yl)cyclohexyl)ureido)-[1,1'-biphenyl]-4-yl)propanoic acid

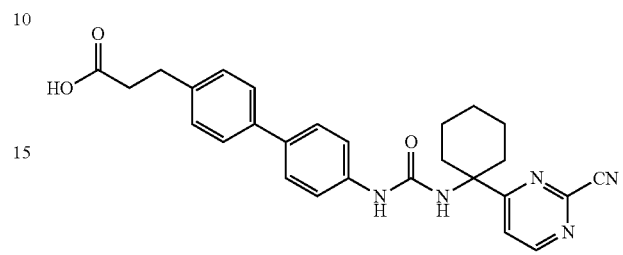

¹H NMR (400 MHz, MeOD) δ 8.81 (d, J=5.4 Hz, 1H), 7.84 (d, J=5.4 Hz, 1H), 7.50 (m, 4H), 7.37 (d, J=8.6 Hz, 2H), 7.29 (d, J=8.2 Hz, 2H), 2.95 (t, J=7.6 Hz, 2H), 2.64 (t, J=7.6 Hz, 2H), 2.12-2.08 (m, 2H), 1.93-1.85 (m, 2H), 1.64-1.52 (m, 4H), 1.35-1.25 (m, 2H), [M+1]⁺=470.

Example 132: 1-(1-(2-cyanopyrimidin-4-yl)cyclohexyl)-3-(4-iodophenyl)urea

Step 1: 1-(2-bromopyrimidin-4-yl)cyclohexanamine

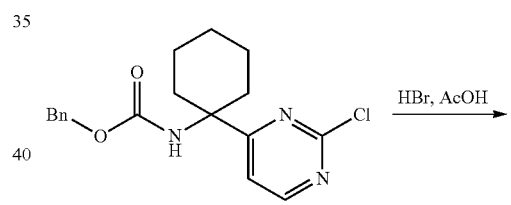

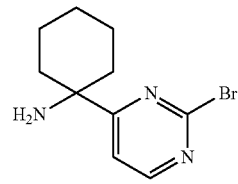

Benzyl (1-(2-chloropyrimidin-4-yl)cyclohexyl)carbamate (15.78 g, 45.6 mmol) prepared in Step 4 of Example 10 was dissolved in acetic acid (450 ml) and then a 33% HBr acetic acid solution (75 ml, 456 mmol) was added dropwise thereto. The reaction mixture was stirred at room temperature for 2 hours. Diethyl ether was added to the reaction mixture so as to generate a precipitate, followed by filtration. The resulting solid was washed with diethyl ether and then dissolved in water. The solution was basified with a 1N sodium hydroxide solution and then extracted with ethyl acetate. The extract was dried on magnesium sulfate and then distilled under reduced pressure to give 8.32 g of the titled compound (Yield: 72%). [M+1]⁺=257.50

Step 2: Intermediate, 4-(1-aminocyclohexyl)pyrimidine-2-carbonitrile

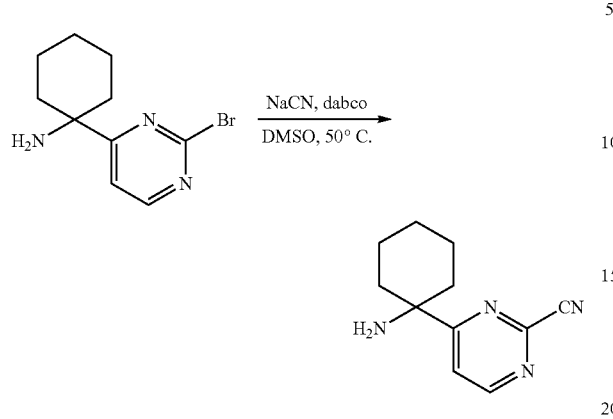

1-(2-Bromopyrimidin-4-yl)cyclohexanamine (1.53 g, 5.97 mmol) prepared in Step 1 and NaCN (0.453 g, 8.96 mmol) were dissolved in dimethyl sulfoxide (53.3 mL). DABCO (0.135 g, 1.195 mmol) was added at room temperature to the resulting solution, which was then stirred at 50° C. for about 12 hours. Water was added thereto to quench the reaction and then the reaction mixture was extracted with ethyl acetate. The organic layer was washed with a 1N NaOH solution and brine, dried on anhydrous $Na_2SO_4$ to remove the moisture, and then distilled under reduced pressure to give 1.1 g of the titled compound (Yield: 91%). $[M+1]^+=202.55$

Step 3: 4-nitrophenyl (4-iodophenyl)carbamate

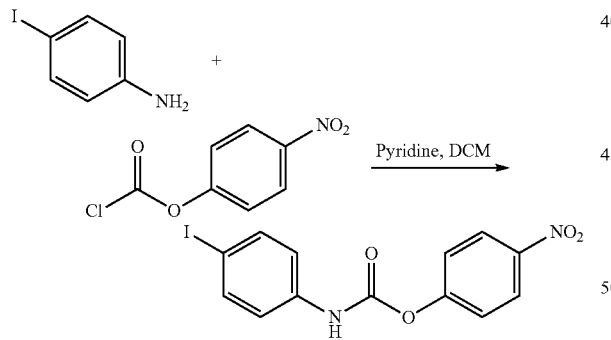

4-Iodoaniline (0.500 g, 2.283 mmol) was dissolved in dichloromethane (11.4 ml) and then the solution was cooled below 0° C. While maintaining the temperature, pyridine (0.923 ml, 11.41 mmol) was added to the reaction mixture, which was then stirred for 10 minutes. 4-Nitrophenyl carbonochloridate (506 g, 2.51 mmol) was slowly added to the reaction mixture, which was then stirred at room temperature for 1 hour. Water was added thereto to quench the reaction and then the reaction mixture was extracted with dichloromethane. The organic layer was dried on magnesium sulfate and then distilled under reduced pressure. The resulting residue was used in the subsequent reaction without the purification thereof.

Step 4: 1-(1-(2-cyanopyrimidin-4-yl)cyclohexyl)-3-(4-iodophenyl)urea

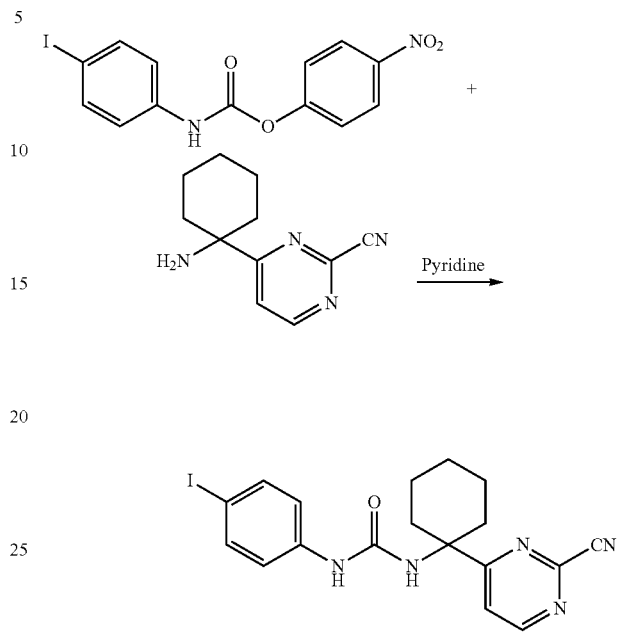

4-Nitrophenyl (4-iodophenyl)carbamate (0.877 g, 2.28 mmol) prepared in Step 3 and the intermediate prepared in Step 2, i.e., 4-(1-aminocyclohexyl)pyrimidine-2-carbonitrile (0.462 g, 2.28 mmol), were dissolved in pyridine (11.4 ml). The resulting solution was reacted at 60° C. for 1 hour. Ethyl acetate and brine were added to the reaction mixture. The organic layer was extracted with ethyl acetate. The extract was washed with a 10% $CuSO_4$ solution, dried on magnesium sulfate, and then distilled under reduced pressure. The resulting residue was purified by MPLC to give 540 mg of the titled compound (Yield: 52.9%).

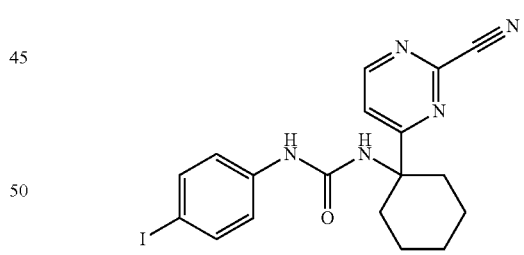

$^1$H NMR (400 MHz, DMSO-$d_6$) δ 8.9 (d, 1H, J=5.44 Hz), 8.78 (s, 1H), 7.86 (d, 1H, J=5.44 Hz), 7.5 (d, 2H, J=8.76 Hz), 7.15 (d, 2H, J=8.8 Hz), 6.82 (s, 1H), 2.09-2.06 (m, 2H), 1.86-1.79 (m, 2H), 1.69-1.55 (m, 4H), 1.29-1.23 (m, 2H) HPLC purity=94%, LRMS(ESI): m/z=448 [M+H]+

The compounds of Examples 133 to 146 were prepared in accordance with the same procedures as in Example 132, using the corresponding amines instead of 4-iodoaniline used in Step 3 of Example 132. 1-(4-Bromophenyl)-3-(1-(2-cyanopyrimidin-4-yl)cyclohexyl)urea of Example 110 can be also prepared in accordance with the same procedures, using 4-bromoaniline instead of 4-iodoaniline used in Step 3 of Example 132.

Example 133: 1-(4-bromo-3-(trifluoromethyl)phenyl)-3-(1-(2-cyanopyrimidin-4-yl)cyclohexyl)urea

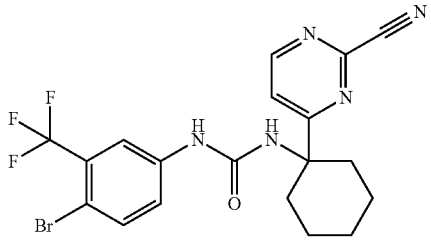 [SMILES: N#Cc1nccc(C2(NC(=O)Nc3ccc(Br)c(C(F)(F)F)c3)CCCCC2)n1]

¹H NMR (400 MHz, MeOD) δ 8.81 (d, J=5.44 Hz, 1H), 7.86 (d, J=1.96 Hz, 1H), 7.82 (d, J=5.44 Hz, 1H), 7.63 (d, J=8.72 Hz, 1H), 7.4 (dd, J=2 Hz, J=8.72 Hz, 1H), 2.23-2.19 (m, 2H), 2.03-1.95 (m, 2H), 1.78-1.65 (m, 4H), 1.45-1.26 (m, 2H)

HPLC purity=98%

LRMS(ESI): m/z=469 [M+H]+

Example 134: 1-(4-bromo-2-fluorophenyl)-3-(1-(2-cyanopyrimidin-4-yl)cyclohexyl)urea

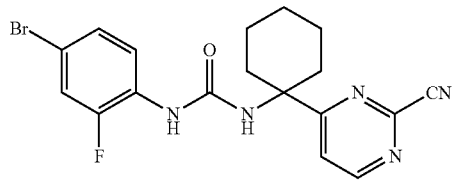 [SMILES: N#Cc1nccc(C2(NC(=O)Nc3ccc(Br)cc3F)CCCCC2)n1]

¹H NMR (400 MHz, DMSO-d₆) δ 8.88 (d, J=5.4 Hz, 1H), 8.72 (d, J=2.7 Hz, 1H), 7.93 (t, J=8.9 Hz, 1H), 7.85 (d, J=5.4 Hz, 1H), 7.51 (dd, J=11.1, 2.3 Hz, 1H), 7.27 (s, 1H), 7.19 (dt, J=8.9, 1.6 Hz, 1H), 2.10-2.02 (m, 2H), 1.82 (td, J=13.3, 3.7 Hz, 2H), 1.61 (p, J=12.9 Hz, 5H), 1.27 (s, 1H). [M+H]⁺=418.

Example 135: 4-(3-(1-(2-cyanopyrimidin-4-yl)cyclohexyl)ureido)benzoic acid

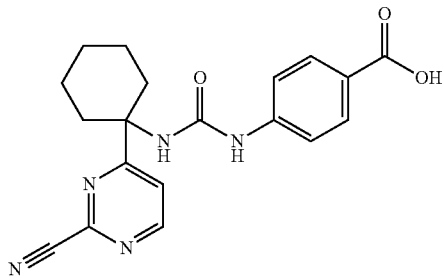 [SMILES: N#Cc1nccc(C2(NC(=O)Nc3ccc(C(=O)O)cc3)CCCCC2)n1]

¹H NMR (400 MHz, MeOD) δ 8.69 (d, J=5.44 Hz, 1H), 7.79 (d, J=8.84 Hz, 2H), 7.71 (d, J=5.44 Hz, 1H), 7.29 (d, J=8.8 Hz, 2H), 2.12-2.08 (m, 2H), 1.94-1.84 (m, 2H), 1.64-1.5 (m, 4H), 1.34-1.19 (m, 2H)

HPLC purity=99%, LRMS(ESI): m/z=366 [M+H]+

Example 136: 1-(1-(2-cyanopyrimidin-4-yl)cyclohexyl)-3-(4-iodo-3-(trifluoromethyl)phenyl)urea

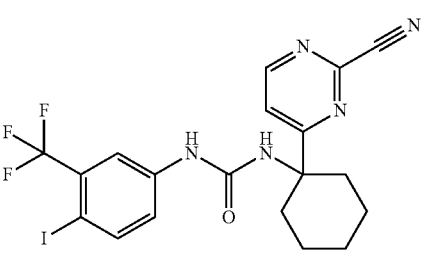 [SMILES: N#Cc1nccc(C2(NC(=O)Nc3ccc(I)c(C(F)(F)F)c3)CCCCC2)n1]

¹H NMR (400 MHz, MeOD) δ 8.81 (d, J=5.4 Hz, 1H), 7.91 (d, J=8.6 Hz, 1H), 7.85-7.79 (m, 2H), 7.23 (dd, J=8.6, 2.5 Hz, 1H), 2.12-2.08 (m, 2H), 1.91-1.84 (m, 2H), 1.67-1.57 (m, 4H), 1.35-1.25 (m, 2H)

HPLC purity=99%, LRMS(ESI): m/z=516 [M+H]+

Example 137: 1-(1-(2-cyanopyrimidin-4-yl)cyclohexyl)-3-(3-fluoro-4-iodophenyl)urea

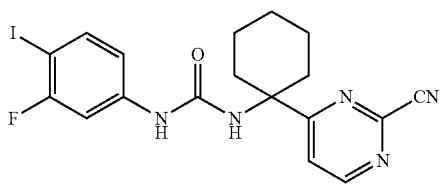 [SMILES: N#Cc1nccc(C2(NC(=O)Nc3ccc(I)c(F)c3)CCCCC2)n1]

¹H NMR (400 MHz, DMSO-d₆) δ 9.01 (s, 1H), 8.91 (d, J=5.6 Hz, 1H), 7.87 (d, J=5.5 Hz, 1H), 7.61 (dd, J=8.6, 7.5 Hz, 1H), 7.39 (dd, J=11.1, 2.3 Hz, 1H), 6.93 (s, 1H), 6.85 (dd, J=8.6, 2.3 Hz, 1H), 2.08 (d, J=13.2 Hz, 2H), 1.83 (td, J=13.1, 3.9 Hz, 2H), 1.58 (dt, J=26.0, 13.7 Hz, 5H), 1.28 (d, J=11.9 Hz, 1H). [M+H]⁺=465.9.

Example 138: 1-(1-(2-cyanopyrimidin-4-yl)cyclohexyl)-3-(4-(4-methylpiperazin-1-yl)phenyl)urea

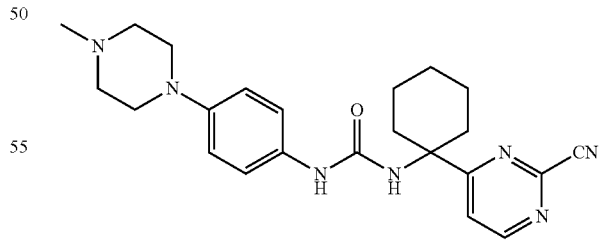

¹H NMR (400 MHz, DMSO-d₆) δ 8.89 (d, J=5.4 Hz, 1H), 8.41 (s, 1H), 7.85 (d, J=5.4 Hz, 1H), 7.14 (d, J=8.6 Hz, 2H), 6.79 (d, J=8.6 Hz, 2H), 6.65 (s, 1H), 2.99 (t, J=4.8 Hz, 4H), 2.42 (t, J=4.9 Hz, 4H), 2.20 (s, 3H), 2.06 (d, J=13.4 Hz, 2H), 1.82 (dt, J=14.5, 7.3 Hz, 2H), 1.71-1.51 (m, 5H), 1.27 (d, J=12.2 Hz, 1H). [M+H]⁺=420.1.

Example 139: 1-(1-(2-cyanopyrimidin-4-yl)cyclohexyl)-3-(4-morpholinophenyl)urea

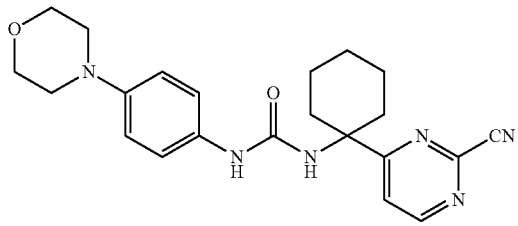 [SMILES: N#Cc1nccc(C2(NC(=O)Nc3ccc(N4CCOCC4)cc3)CCCCC2)n1]

¹H NMR (400 MHz, MeOD) δ 8.80 (d, J=5.44 Hz, 1H), 7.82 (d, J=5.44 Hz, 1H), 7.35 (d, J=7.72 Hz, 2H), 7.18 (s, 2H), 3.92 (s, 4H), 2.22 (d, J=13.20 Hz, 2H), 2.03 (m, 2H), 1.77 (m, 5H), 1.42 (m, 1H). [M+H]⁺=407.0.

Example 140: 1-(1-(2-cyanopyrimidin-4-yl)cyclohexyl)-3-(4-(piperazin-1-yl)phenyl)urea

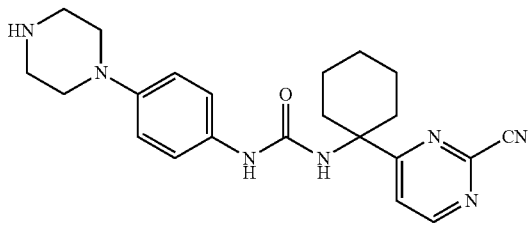 [SMILES: N#Cc1nccc(C2(NC(=O)Nc3ccc(N4CCNCC4)cc3)CCCCC2)n1]

¹H NMR (400 MHz, MeOD) δ 8.78 (d, J=5.44 Hz, 1H), 7.73 (d, J=5.44 Hz, 1H), 7.28 (d, J=8.96 Hz, 2H), 7.14 (d, J=9.0 Hz, 2H), 3.63 (m, 4H), 3.28 (m, 4H), 2.26 (d, J=13.16 Hz, 2H), 2.01 (m, 2H), 1.78 (m, 5H), 1.44 (m, 1H). [M+H]⁺=406.0.

Example 141: 1-(1-(2-cyanopyrimidin-4-yl)cyclohexyl)-3-(4-(4-(dimethylamino)piperidin-1-yl)phenyl)urea

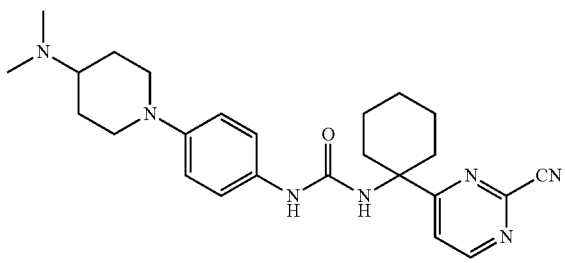 [SMILES: CN(C)C1CCN(c2ccc(NC(=O)NC3(c4ccnc(C#N)n4)CCCCC3)cc2)CC1]

¹H NMR (400 MHz, MeOD) δ 8.80 (d, J=5.44 Hz, 1H), 7.82 (d, J=5.44 Hz, 1H), 7.35 (s, 2H), 7.21 (s, 2H), 3.79 (s, 2H), 3.52 (m, 1H), 3.20 (m, 2H), 2.93 (s, 6H), 2.22 (m, 2H), 2.06 (m, 2H), 1.80 (m, 5H), 1.44 (m, 1H). [M+H]⁺=448.1.

Example 142: 1-(1-(2-cyanopyrimidin-4-yl)cyclohexyl)-3-(4-(4-isopropylpiperazin-1-yl)phenyl)urea

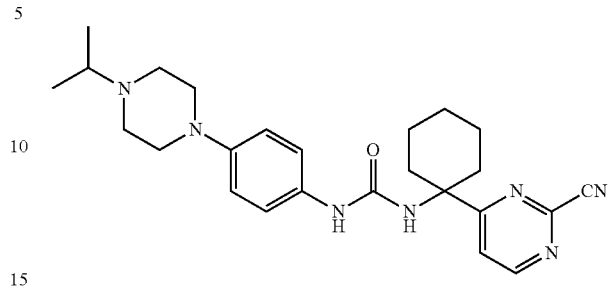

¹H NMR (400 MHz, MeOD) δ 8.79 (d, J=5.44 Hz, 1H), 7.82 (d, J=5.44 Hz, 1H), 7.24 (d, J=8.92 Hz, 2H), 6.96 (d, J=8.96 Hz, 2H), 3.78 (d, J=13.0 Hz, 2H), 3.60 (m, 3H), 3.02 (m, 2H), 2.21 (d, J=13.08 Hz, 2H), 2.01 (m, 2H), 1.80 (m, 5H), 1.43 (d, J=6.64 Hz, 7H). [M+H]⁺=448.0.

Example 143: 1-(4-(4-(tert-butyl)piperazin-1-yl)phenyl)-3-(1-(2-cyanopyrimidin-4-yl)cyclohexyl)urea

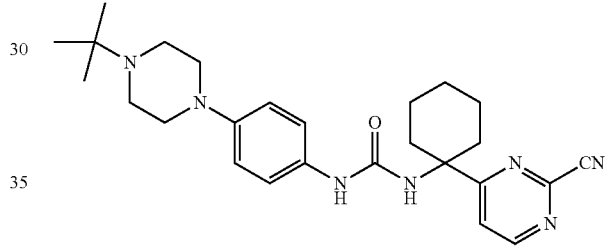

¹H NMR (400 MHz, DMSO-d₆) δ 8.90 (d, J=5.44 Hz, 1H), 7.85 (d, J=5.48 Hz, 1H), 7.16 (d, J=8.88 Hz, 2H), 6.80 (d, J=8.96 Hz, 2H), 3.00 (s, 4H), 2.68 (d, J=1.8 Hz, 4H), 2.08 (d, J=13.12 Hz, 2H), 1.85 (m, 2H), 1.63 (m, 5H), 1.29 (m, 1H), 1.06 (s, 9H). [M+H]⁺=462.15.

Example 144: 1-(1-(2-cyanopyrimidin-4-yl)cyclohexyl)-3-(4-(4-cyclopropylpiperazin-1-yl)phenyl)urea

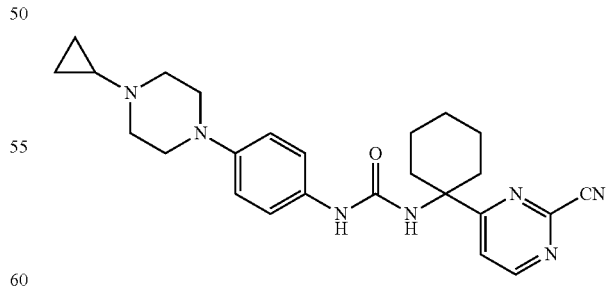

¹H NMR (400 MHz, DMSO-d₆) δ 8.89 (d, J=5.44 Hz, 1H), 8.41 (s, 1H), 7.85 (d, J=5.40 Hz, 1H), 7.14 (d, J=8.84 Hz, 2H), 6.79 (d, J=8.92 Hz, 2H), 6.64 (s, 1H), 2.95 (s, 4H), 2.64 (s, 4H), 2.07 (m, 2H), 1.84 (m, 2H), 1.62 (m, 5H), 1.28 (m, 1H), 0.43 (d, J=4.28 Hz, 2H), 0.32 (d, J=2.52 Hz, 2H). [M+H]⁺=446.05.

Example 145: 1-(1-(2-cyanopyrimidin-4-yl)cyclohexyl)-3-(4-(4-isopropylpiperidin-1-yl)phenyl)urea

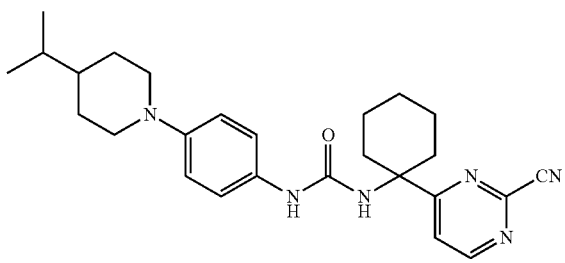 [SMILES: CC(C)C1CCN(c2ccc(NC(=O)NC3(c4ccnc(C#N)n4)CCCCC3)cc2)CC1]

$^1$H NMR (400 MHz, DMSO-d$_6$) δ 8.98 (s, 1H), 8.91 (d, J=5.44 Hz, 1H), 7.86 (d, J=5.44 Hz, 1H), 7.43 (s, 4H), 6.95 (s, 1H), 2.10 (d, J=6.32 Hz, 2H), 1.90 (m, 4H), 1.65 (m, 9H), 1.29 (s, 1H), 0.90 (d, J=6.68 Hz, 6H). [M+H]$^+$=447.10.

Example 146: 1-(1-(2-cyanopyrimidin-4-yl)cyclohexyl)-3-(4-(4-ethylpiperazin-1-yl)phenyl)urea

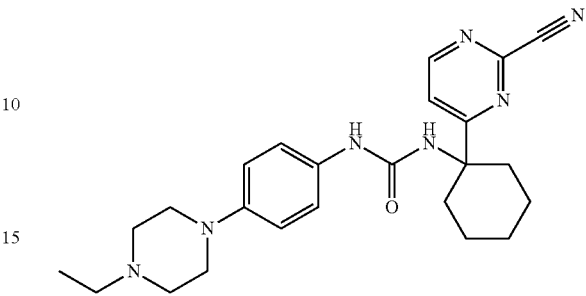

$^1$H NMR (400 MHz, DMSO-d$_6$) δ 8.89 (d, J=5.4 Hz, 1H), 8.45 (s, 1H), 7.85 (d, J=5.4 Hz, 1H), 7.14 (d, J=8.9 Hz, 2H), 6.79 (d, J=8.9 Hz, 2H), 6.68 (s, 1H), 3.00 (s, 4H), 2.47-2.34 (m, 4H), 2.06 (d, J=12.8 Hz, 2H), 1.81 (td, J=13.0, 4.1 Hz, 2H), 1.71-1.52 (m, J=32.6, 17.9 Hz, 5H), 1.33-1.21 (m, J=11.4 Hz, 1H), 1.03 (t, J=6.9 Hz, 3H), HPLC purity=99%, LRMS(ESI): m/z=434 [M+H]+

Example 147: 4'-(3-(1-(2-cyanopyrimidin-4-yl)cyclohexyl)ureido)-N-(2-methoxyethyl)-[1,1'-biphenyl]-4-carboxamide

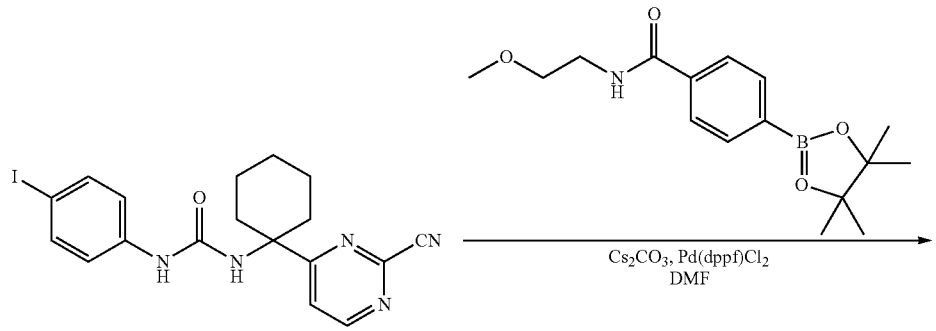

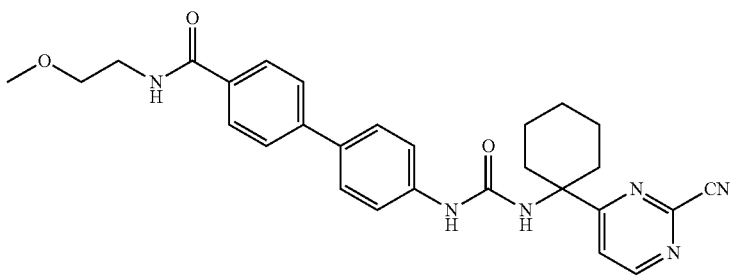

A solution of 1-(1-(2-cyanopyrimidin-4-yl)cyclohexyl)-3-(4-iodophenyl)urea (30 mg, 0.067 mmol) prepared in Example 132, cesium carbonate (54.6 mg, 0.168 mmol), N-(2-methoxyethyl)-4-(4,4,5,5-tetramethyl-1,3,2-dioxaborolan-2-yl)benzamide (20.47 mg, 0.067 mmol), and PdCl$_2$ (dppf) (5.48 mg, 0.0671 mmol) in a mixed solvent of dimethylformamide and water (5:1) (0.6 ml) was reacted at 120° C. for 30 minutes using microwave. After the completion of the reaction, water and ethyl acetate were added thereto and the organic layer was extracted. The organic layer was washed with a sodium bicarbonate solution and brine, dried on magnesium sulfate, and then distilled under reduced pressure. The resulting residue was purified by Prep-HPLC to give 3.4 mg of the titled compound (white solid, Yield: 10%).

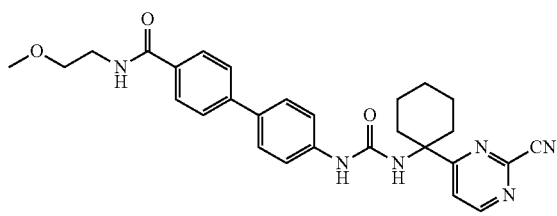 [SMILES: COCCNC(=O)c1ccc(-c2ccc(NC(=O)NC3(c4ccnc(C#N)n4)CCCCC3)cc2)cc1]

$^1$H NMR (400 MHz, DMSO-d$_6$) δ 8.92 (d, J=5.4 Hz, 1H), 8.85 (s, 1H), 8.55 (t, J=5.2 Hz, 1H), 7.93-7.84 (m, 3H), 7.73-7.65 (m, 2H), 7.64-7.56 (m, 2H), 7.45-7.37 (m, 2H), 6.85 (s, 1H), 3.27 (s, 4H), 2.10 (d, J=13.2 Hz, 2H), 1.84 (t, J=13.0 Hz, 2H), 1.63 (q, J=12.8 Hz, 5H), 1.29 (d, J=12.4 Hz, 1H). [M+H]$^+$=499.

The compounds of Examples 148 to 161 were prepared in accordance with the same procedures as in Example 147, using 1-(1-(2-cyanopyrimidin-4-yl)cyclohexyl)-3-(4-iodophenyl)urea prepared in Example 132 as a starting material and using the corresponding boronic acid or boronic ester instead of N-(2-methoxyethyl)-4-(4,4,5,5-tetramethyl-1,3,2-dioxaborolan-2-yl)benzamide used in Example 147.

Example 148: 4'-(3-(1-(2-cyanopyrimidin-4-yl)cyclohexyl)ureido)-N-cyclopropyl-[1,1'-biphenyl]-4-sulfonamide

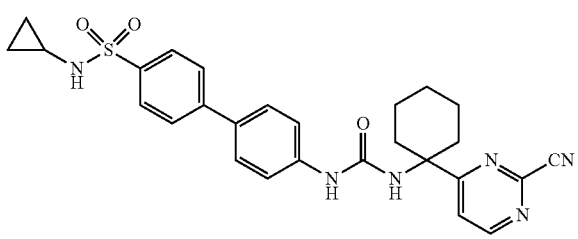 [SMILES: N#Cc1nccc(C2(NC(=O)Nc3ccc(-c4ccc(S(=O)(=O)NC5CC5)cc4)cc3)CCCCC2)n1]

$^1$H NMR (400 MHz DMSO-d) 8.95-8.85 (m, 2H), 7.93 (d, J=2.6 Hz, 1H), 7.89 (d, J=5.5 Hz, 1H), 7.84 (s, 2H), 7.63 (d, J=8.8 Hz, 2H), 7.44 (d, J=8.7 Hz, 2H), 6.87 (s, 1H), 2.10 (dt, J=10.3, 3.2 Hz, 2H), 1.90-1.79 (m, 4H), 1.63 (q, J=12.8 Hz, 5H), 1.29 (d, J=11.9 Hz, 1H), 0.49 (td, J=7.0, 6.5, 4.8 Hz, 2H), 0.40 (q, J=4.0 Hz, 2H). [M+H]$^+$=517.

Example 149: 4'-(3-(1-(2-cyanopyrimidin-4-yl)cyclohexyl)ureido)-N-cyclopropyl-[1,1'-biphenyl]-4-carboxamide

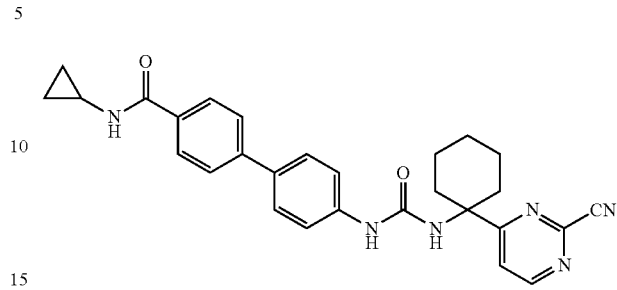

$^1$H NMR (400 MHz, DMSO-d$_6$) δ 8.92 (d, J=5.4 Hz, 1H), 8.85 (s, 1H), 8.46 (d, J=4.2 Hz, 1H), 7.93-7.80 (m, 3H), 7.74-7.55 (m, 4H), 7.48-7.34 (m, 2H), 6.85 (s, 1H), 2.85 (tq, J=7.6, 4.0 Hz, 1H), 2.14-2.04 (m, 2H), 1.84 (t, J=11.6 Hz, 2H), 1.63 (q, J=12.9, 12.4 Hz, 5H), 1.31 (s, 1H), 0.70 (td, J=7.1, 4.7 Hz, 2H), 0.61-0.53 (m, 2H). [M+H]$^+$=481.

Example 150: 1-(3'-chloro-4'-(pyrrolidin-1-carbonyl)-[1,1'-biphenyl]-4-yl)-3-(1-(2-cyanopyrimidin-4-yl)cyclohexyl)urea

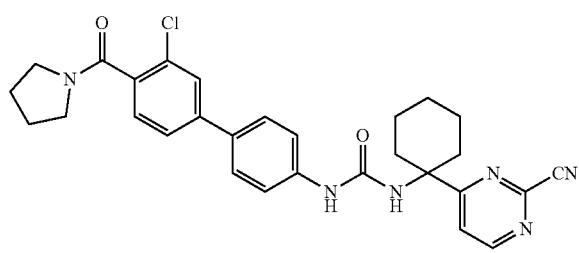 [SMILES: N#Cc1nccc(C2(NC(=O)Nc3ccc(-c4ccc(C(=O)N5CCCC5)c(Cl)c4)cc3)CCCCC2)n1]

$^1$H NMR (400 MHz, MeOD) δ 8.82 (d, J=5.4 Hz, 1H), 7.85 (d, J=5.5 Hz, 1H), 7.72 (d, J=1.7 Hz, 1H), 7.65 (dd, J=8.0, 1.7 Hz, 1H), 7.60-7.53 (m, 2H), 7.48-7.39 (m, 3H), 3.64 (t, J=6.9 Hz, 2H), 2.23 (d, J=13.3 Hz, 2H), 2.07-1.93 (m, 5H), 1.74 (d, J=26.1 Hz, 5H), 1.42 (d, J=11.4 Hz, 1H). [M+H]$^+$=529.

Example 151: N-((4'-(3-(1-(2-cyanopyrimidin-4-yl)cyclohexyl)ureido)-[1,1'-biphenyl]-4-yl)methyl)acetamide

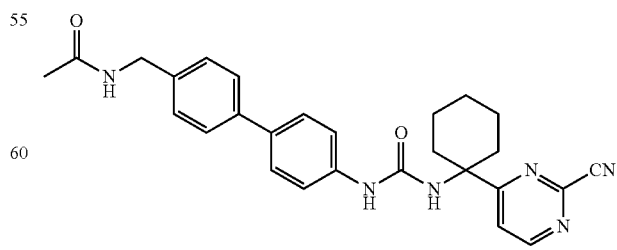

$^1$H NMR (400 MHz, MeOD) δ 8.81 (d, J=5.4 Hz, 1H), 7.84 (d, J=5.4 Hz, 1H), 7.54 (m, 4H), 7.35 (m, 4H), 4.39 (d,

J=5.5 Hz, 2H), 2.12-2.08 (m, 2H), 1.93-1.85 (m, 2H), 1.64-1.52 (m, 4H), 1.35-1.25 (m, 2H), [M+1]⁺=469

Example 152: 1-(1-(2-cyanopyrimidin-4-yl)cyclohexyl)-3-(4'-((4-(2-methoxyethyl)phenoxy)methyl)-[1,1'-biphenyl]-4-yl)urea

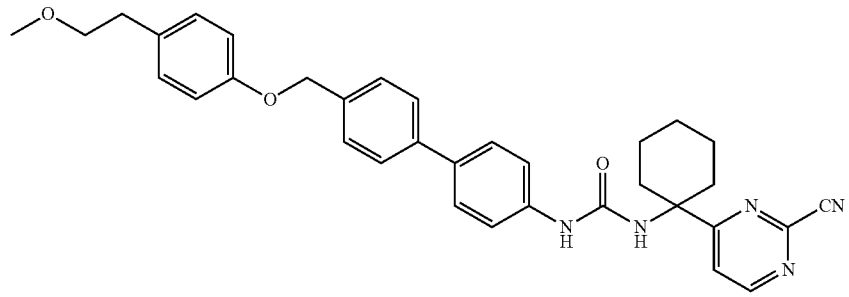 [SMILES: COCCc1ccc(OCc2ccc(-c3ccc(NC(=O)NC4(c5ccnc(C#N)n5)CCCCC4)cc3)cc2)cc1]

¹H NMR (400 MHz, MeOD) δ 8.81 (d, J=5.4 Hz, 1H), 7.84-7.33 (m, 8H), 7.15 (m, 2H), 6.93 (m, 2H), 5.12 (s, 2H), 3.59 (m, 2H), 2.81 (m, 2H), 2.12-2.08 (m, 2H), 1.93-1.85 (m, 2H), 1.64-1.52 (m, 4H), 1.35-1.25 (m, 2H), [M+1]⁺= 562.

Example 153: 1-(1-(2-cyanopyrimidin-4-yl)cyclohexyl)-3-(4'-(2-(dimethylamino)ethoxy)-[1,1'-biphenyl]-4-yl)urea

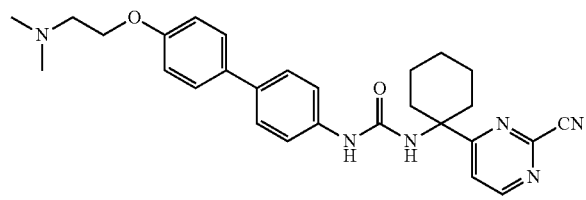 [SMILES: CN(C)CCOc1ccc(-c2ccc(NC(=O)NC3(c4ccnc(C#N)n4)CCCCC3)cc2)cc1]

¹H NMR (400 MHz, DMSO-d₆) δ 8.91 (d, J=5.4 Hz, 1H), 8.78 (s, 1H), 7.88 (d, J=5.4 Hz, 1H), 7.59-7.55 (m, 2H), 7.50-7.45 (m, 2H), 7.37 (d, J=8.5 Hz, 2H), 7.08-7.03 (m, 2H), 6.84 (s, 1H), 4.33 (t, J=5.0 Hz, 2H), 2.87 (d, J=3.6 Hz, 6H), 2.10 (d, J=13.2 Hz, 2H), 1.84 (t, J=12.0 Hz, 2H), 1.70-1.58 (m, 5H). [M+H]⁺=485.

Example 154: 1-(1-(2-cyanopyrimidin-4-yl)cyclohexyl)-3-(4'-(4-isopropylpiperazin-1-yl)-[1,1'-biphenyl]-4-yl)urea

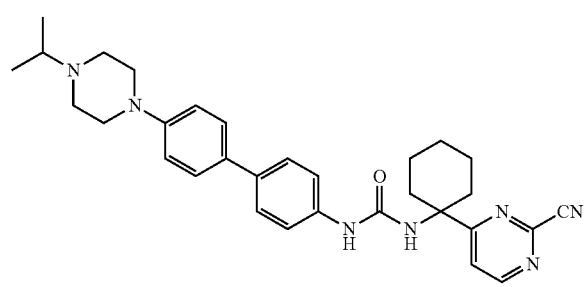 [SMILES: CC(C)N1CCN(c2ccc(-c3ccc(NC(=O)NC4(c5ccnc(C#N)n5)CCCCC4)cc3)cc2)CC1]

¹H NMR (400 MHz, DMSO-d₆) δ 8.91 (d, J=5.4 Hz, 1H), 8.76 (s, 1H), 7.88 (d, J=5.5 Hz, 1H), 7.49 (dd, J=20.0, 8.8 Hz, 4H), 7.35 (d, J=8.7 Hz, 2H), 7.06 (d, J=8.9 Hz, 2H), 6.83 (s, 1H), 3.91 (d, J=13.1 Hz, 2H), 3.53 (d, J=12.1 Hz, 2H), 3.17 (t, J=11.2 Hz, 2H), 2.97 (t, J=12.3 Hz, 2H), 2.10 (d, J=13.3 Hz, 2H), 1.88-1.78 (m, 2H), 1.71-1.56 (m, 5H), 1.30 (d, J=6.6 Hz, 6H). [M+H]⁺=524.

Example 155. 1-(4'(4-acetylpiperazin-1-yl)-[1,1'-biphenyl]-4-yl)-3-(1-(2-cyanopyrimidin-4-yl)cyclohexyl)urea

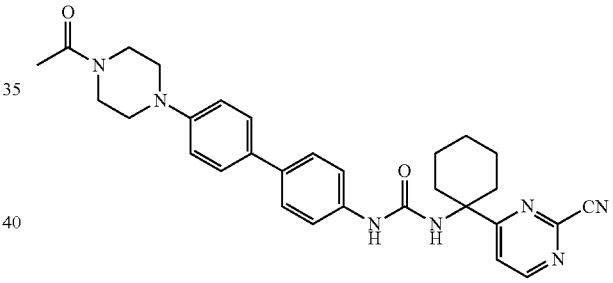

¹H NMR (400 MHz, DMSO-d₆) δ 8.89 (d, J=5.5 Hz, 1H), 8.72 (s, 1H), 7.86 (d, J=5.5 Hz, 1H), 7.45 (dd, J=10.3, 8.6 Hz, 4H), 7.33 (d, J=8.6 Hz, 2H), 7.00 (d, J=8.7 Hz, 2H), 6.79 (s, 1H), 3.14 (dt, J=27.0, 5.2 Hz, 4H), 2.11-2.05 (m, 2H), 2.03 (s, 3H), 1.83 (td, J=13.0, 4.4 Hz, 2H), 1.62 (dq, J=22.8, 13.0, 12.2 Hz, 5H), 1.31-1.24 (m, 1H). [M+H]⁺=523.

Example 156: methyl 2-(4'-(3-(1-(2-cyanopyrimidin-4-yl)cyclohexyl)ureido)-[1,1'-biphenyl]-4-yl)acetate

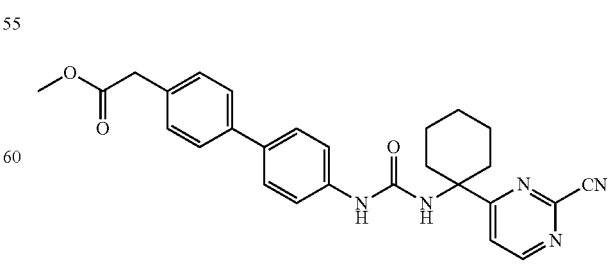

¹H NMR (400 MHz, DMSO-d₆) δ 8.90 (d, J=5.5 Hz, 1H), 8.78 (s, 1H), 7.87 (d, J=5.5 Hz, 1H), 7.58-7.46 (m, 4H), 7.38

(d, J=8.7 Hz, 2H), 7.29 (d, J=8.0 Hz, 2H), 6.82 (s, 1H), 3.69 (s, 2H), 3.61 (s, 3H), 2.13-2.05 (m, 2H), 1.83 (dt, J=13.0, 7.3 Hz, 2H), 1.72-1.53 (m, 5H), 1.28 (d, J=12.1 Hz, 1H). [M+H]⁺=470.

Example 157: 1-(1-(2-cyanopyrimidin-4-yl)cyclohexyl)-3-(4'-((2-methoxyethoxy)methyl)-[1,1'-biphenyl]-4-yl)urea

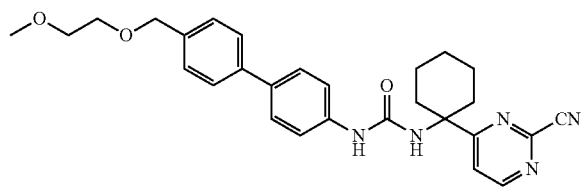 [SMILES: COCCOCc1ccc(-c2ccc(NC(=O)NC3(c4ccnc(C#N)n4)CCCCC3)cc2)cc1]

¹H NMR (400 MHz, DMSO-d₆) δ 8.90 (d, J=5.4 Hz, 1H), 8.78 (s, 1H), 7.88 (d, J=5.4 Hz, 1H), 7.57 (d, J=8.2 Hz, 2H), 7.51 (d, J=8.7 Hz, 2H), 7.36 (dd, J=12.6, 8.6 Hz, 4H), 6.82 (s, 1H), 4.49 (s, 2H), 3.55 (dd, J=5.8, 3.3 Hz, 2H), 3.48 (dd, J=5.8, 3.3 Hz, 2H), 3.25 (s, 3H), 2.11-2.05 (m, 2H), 1.83 (dt, J=13.2, 6.6 Hz, 2H), 1.60 (d, J=23.6 Hz, 5H), 1.30-1.25 (m, 1H). [M+H]⁺=486.

Example 158: 4'-(3-(1-(2-cyanopyrimidin-4-yl)cyclohexyl)ureido)-N-((tetrahydrofuran-2-yl)methyl)-[1,1'-biphenyl]-4-carboxamide

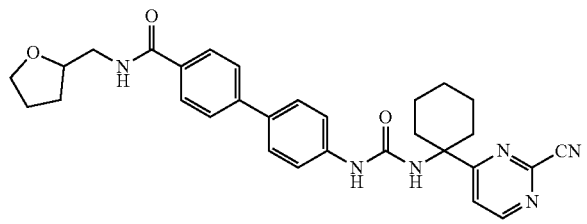 [SMILES: N#Cc1nccc(C2(NC(=O)Nc3ccc(-c4ccc(C(=O)NCC5CCCO5)cc4)cc3)CCCCC2)n1]

¹H NMR (400 MHz, DMSO-d₆) δ 8.90 (d, J=5.5 Hz, 1H), 8.82 (s, 1H), 8.54 (t, J=5.9 Hz, 1H), 7.94-7.83 (m, 3H), 7.67 (d, J=8.2 Hz, 2H), 7.58 (d, J=8.7 Hz, 2H), 7.39 (d, J=8.5 Hz, 2H), 6.83 (s, 1H), 3.96 (p, J=6.2 Hz, 1H), 3.76 (q, J=7.0 Hz, 1H), 3.61 (q, J=7.3 Hz, 1H), 2.08 (d, J=13.1 Hz, 2H), 1.92-1.74 (m, 5H), 1.70-1.50 (m, 6H), 1.28 (s, 1H). [M+H]⁺= 525.

Example 159: 4'-(3-(1-(2-cyanopyrimidin-4-yl)cyclohexyl)ureido)-N-(2-(dimethylamino)ethyl)-[1,1'-biphenyl]-4-carboxamide

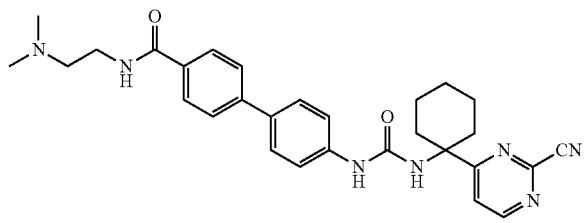

¹H NMR (400 MHz, DMSO-d₆) δ 8.91 (d, J=5.8 Hz, 2H), 8.70 (t, J=5.7 Hz, 1H), 7.95-7.84 (m, 3H), 7.74 (d, J=8.3 Hz, 2H), 7.61 (d, J=8.6 Hz, 2H), 7.42 (d, J=8.5 Hz, 2H), 6.90 (s, 1H), 3.61 (q, J=5.9 Hz, 2H), 3.27 (q, J=5.8 Hz, 2H), 2.85 (d, J=4.7 Hz, 6H), 2.10 (d, J=13.1 Hz, 2H), 1.84 (td, J=13.0, 4.2 Hz, 2H), 1.62 (q, J=12.6 Hz, 5H), 1.33-1.26 (m, 1H). [M+H]⁺=512.

Example 160: 1-(1-(2-cyanopyrimidin-4-yl)cyclohexyl)-3-(4'-(4-ethylpiperazin-1-yl)-[1,1'-biphenyl]-4-yl)urea

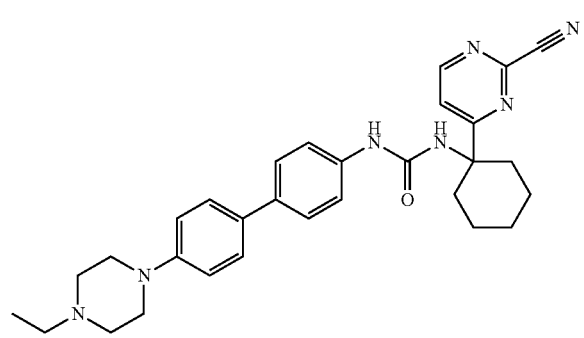 [SMILES: CCN1CCN(c2ccc(-c3ccc(NC(=O)NC4(c5ccnc(C#N)n5)CCCCC4)cc3)cc2)CC1]

¹H NMR (400 MHz, MeOD) δ 8.67 (d, J=5.4 Hz, 1H), 7.71 (d, J=5.4 Hz, 1H), 7.41-7.31 (m, 4H), 7.22 (d, J=8.7 Hz, 2H), 6.90 (d, J=8.8 Hz, 2H), 3.16-3.07 (m, 4H), 2.60-2.47 (m, 4H), 2.40 (q, J=7.2 Hz, 2H), 2.09 (d, J=13.2 Hz, 2H), 1.87 (td, J=13.1, 4.3 Hz, 2H), 1.63 (dd, J=27.8, 16.3 Hz, 5H), 1.35-1.24 (m, 1H), 1.05 (t, J=7.2 Hz, 3H), HPLC purity=96%, LRMS(ESI): m/z=510 [M+H]+.

Example 161: 2-(4'-(3-(1-(2-cyanopyrimidin-4-yl)cyclohexyl)ureido)-[1,1'-biphenyl]-4-yl)acetic acid

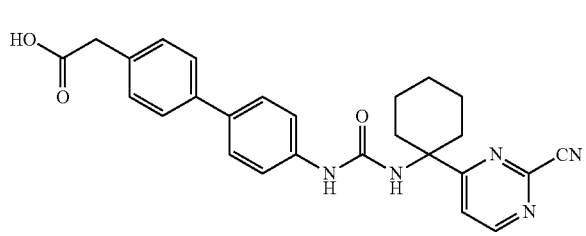 [SMILES: N#Cc1nccc(C2(NC(=O)Nc3ccc(-c4ccc(CC(=O)O)cc4)cc3)CCCCC2)n1]

¹H NMR (400 MHz, MeOD) δ 8.81 (d, J=5.36 Hz, 1H), 7.85 (d, J=5.40 Hz, 1H), 7.55 (m, 4H), 7.39 (m, 4H), 3.64 (s, 2H), 2.23 (d, J=11.96 Hz, 2H), 2.02 (m, 2H), 1.76 (m, 5H), 1.43 (m, 1H). [M+H]⁺=456.05.

The compounds of Examples 162 and 163 were prepared in accordance with the same procedures as in Example 147, using 1-(4-bromo-3-(trifluoromethyl)phenyl)-3-(1-(2-cyanopyrimidin-4-yl)cyclohexyl)urea prepared in Example 133 as a starting material and using (4-(methylsulfonyl)phenyl) boronic acid or 4-boronobenzoic acid instead of N-(2-methoxyethyl)-4-(4,4,5,5-tetramethyl-1,3,2-dioxaborolan-2-yl)benzamide used in Example 147.

Example 162: 1-(1-(2-cyanopyrimidin-4-yl)cyclohexyl)-3-(4'-(methylsulfonyl)-2-(trifluoromethyl)-[1,1'-biphenyl]-4-yl)urea

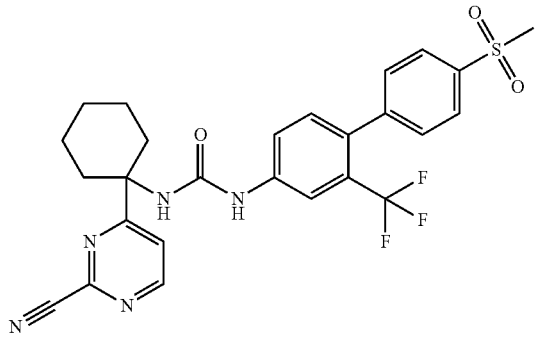 [SMILES: CS(=O)(=O)c1ccc(-c2ccc(NC(=O)NC3(c4ccnc(C#N)n4)CCCCC3)cc2C(F)(F)F)cc1]

¹H NMR (400 MHz, DMSO-d₆) δ 9.18 (s, 1H), 8.93 (d, J=5.5 Hz, 1H), 8.00-7.95 (m, J=5.4 Hz, 3H), 7.90 (d, J=5.5 Hz, 1H), 7.54 (d, J=8.3 Hz, 2H), 7.51 (dd, J=8.4, 2.1 Hz, 1H), 7.29 (d, J=8.4 Hz, 1H), 6.98 (s, 1H), 3.29 (s, 3H), 2.12-2.08 (m, 2H), 1.91-1.84 (m, 2H), 1.67-1.57 (m, 4H), 1.35-1.25 (m, 2H)

HPLC purity=99%

LRMS(ESI): m/z=544 [M+H]+

Example 163: 4'-(3-(1-(2-cyanopyrimidin-4-yl)cyclohexyl)ureido)-2'-(trifluoromethyl)-[1,1'-biphenyl]-4-carboxylic acid

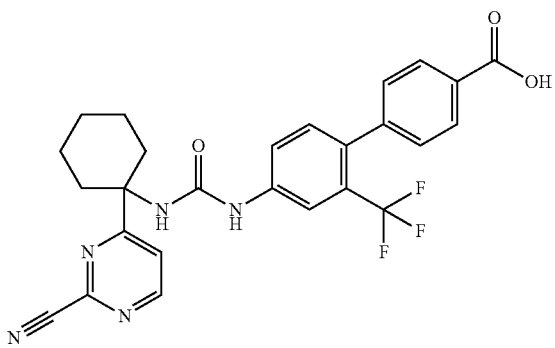 [SMILES: N#Cc1nccc(C2(NC(=O)Nc3ccc(-c4ccc(C(=O)O)cc4)c(C(F)(F)F)c3)CCCCC2)n1]

¹H NMR (400 MHz, MeOD) δ 8.72 (d, J=5.44 Hz, 2H), 7.95 (d, J=8.36 Hz, 2H), 7.77 (d, J=2.2 Hz, 1H), 7.75 (d, J=5.44 Hz, 1H), 7.44 (dd, J=2.12 Hz, J=8.4 Hz, 1H), 7.3 (d, J=8.16 Hz, 2H), 7.16 (d, J=8.44 Hz, 1H), 2.15-2.12 (m, 2H), 1.94-1.87 (m, 2H), 1.67-1.6 (m, 4H), 1.37-1.24 (m, 2H)

HPLC purity=99%

LRMS(ESI): m/z=510 [M+H]+

The compounds of Examples 164 to 168 were prepared in accordance with the same procedures as in Example 147, using 1-(1-(2-cyanopyrimidin-4-yl)cyclohexyl)-3-(3-fluoro-4-iodophenyl)urea prepared in Example 137 as a starting material and using the corresponding boronic acid instead of N-(2-methoxyethyl)-4-(4,4,5,5-tetramethyl-1,3,2-dioxaborolan-2-yl)benzamide used in Example 147.

Example 164: N-(4'-(3-(1-(2-cyanopyrimidin-4-yl)cyclohexyl)ureido)-2'-fluoro-[1,1'-biphenyl]-4-yl)acetamide

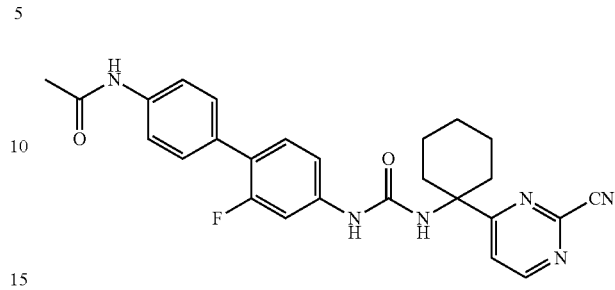

¹H NMR (400 MHz, MeOD) δ 8.81 (d, J=5.4 Hz, 1H), 7.84 (d, J=5.4 Hz, 1H), 7.62 (d, J=8.7 Hz, 2H), 7.46 (d, J=7.3 Hz, 2H), 7.33 (m, 2H), 7.06 (dd, J=2.1 Hz, J=8.4 Hz 1H), 2.12-2.08 (m, 2H), 2.15 (s, 3H), 1.93-1.85 (m, 2H), 1.64-1.52 (m, 4H), 1.35-1.25 (m, 2H), [M+1]⁺=473.

Example 165: N-((4'-(3-(1-(2-cyanopyrimidin-4-yl)cyclohexyl)ureido)-2'-fluoro-[1,1'-biphenyl]-4-yl)methyl)acetamide

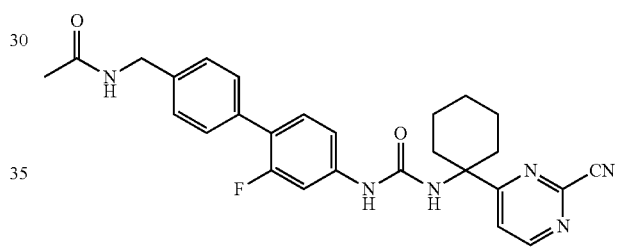

¹H NMR (400 MHz, MeOD) δ 8.81 (d, J=5.4 Hz, 1H), 7.84 (d, J=5.4 Hz, 1H), 7.62 (d, J=8.7 Hz, 2H), 7.46 (d, J=7.3 Hz, 2H), 7.35 (m, 2H), 7.06 (dd, J=2.1 Hz, J=8.4 Hz 1H), 4.40 (s, 2H), 2.12-2.08 (m, 2H), 1.93-1.85 (m, 2H), 1.64-1.52 (m, 4H), 1.35-1.25 (m, 2H), [M+1]⁺=487.

Example 166: 1-(1-(2-cyanopyrimidin-4-yl)cyclohexyl)-3-(2-fluoro-4'-(4-isopropylpiperazin-1-yl)-[1,1'-biphenyl]-4-yl)urea

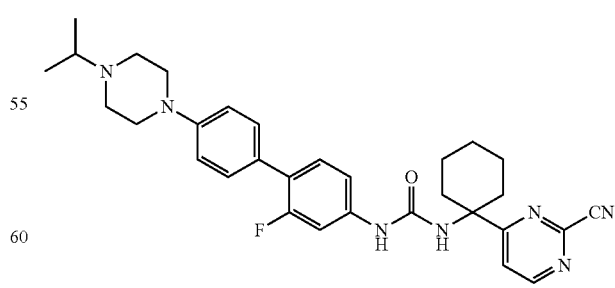

¹H NMR (400 MHz, DMSO-d₆) δ 8.98 (s, 1H), 8.92 (d, J=5.4 Hz, 1H), 7.88 (d, J=5.5 Hz, 1H), 7.44-7.29 (m, 4H), 7.13-7.01 (m, 3H), 6.93 (s, 1H), 3.93 (d, J=13.1 Hz, 2H), 3.53 (d, J=13.1 Hz, 2H), 3.18 (q, J=11.5 Hz, 2H), 2.99 (t,

J=12.4 Hz, 2H), 2.10 (d, J=13.1 Hz, 2H), 1.84 (t, J=12.8 Hz, 2H), 1.71-1.54 (m, 5H), 1.30 (d, J=6.6 Hz, 6H). [M+H]⁺= 542.4.

Example 167: 1-(1-(2-cyanopyrimidin-4-yl)cyclohexyl)-3-(2-fluoro-4'-(methylsulfonyl)-[1,1'-biphenyl]-4-yl)urea

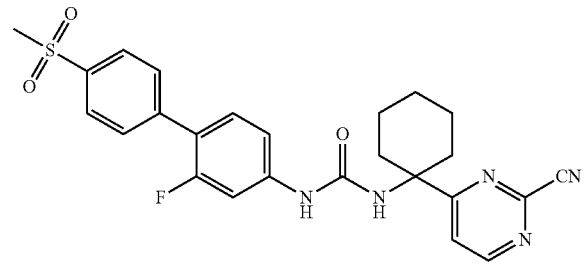 [SMILES: CS(=O)(=O)c1ccc(-c2ccc(NC(=O)NC3(c4ccnc(C#N)n4)CCCCC3)cc2F)cc1]

¹H NMR (400 MHz, DMSO-d₆) δ 9.09 (s, 1H), 8.93 (d, J=5.4 Hz, 1H), 8.02-7.95 (m, 2H), 7.89 (d, J=5.5 Hz, 1H), 7.76 (dd, J=8.4, 1.6 Hz, 2H), 7.53-7.42 (m, 2H), 7.13 (dd, J=8.5, 2.1 Hz, 1H), 6.97 (s, 1H), 3.25 (s, 3H), 2.16-2.05 (m, 2H), 1.89-1.80 (m, 2H), 1.74-1.53 (m, 5H), 1.30 (s, 1H). [M+H]⁺=494.1.

Example 168: 1-(1-(2-cyanopyrimidin-4-yl)cyclohexyl)-3-(4'-(1-cyclopropylpiperidin-4-yl)-2-fluoro-[1,1'-biphenyl]-4-yl)urea

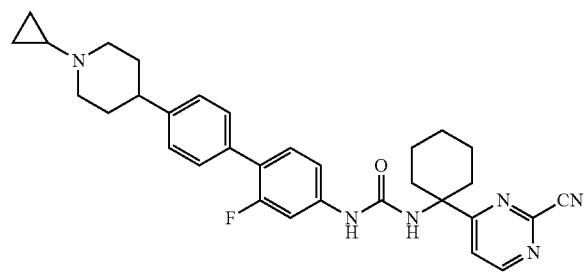 [SMILES: N#Cc1nccc(C2(NC(=O)Nc3ccc(-c4ccc(C5CCN(C6CC6)CC5)cc4)c(F)c3)CCCCC2)n1]

¹H NMR (400 MHz, MeOD) δ 8.82 (d, J=5.44 Hz, 1H), 7.84 (d, J=5.44 Hz, 1H), 7.49 (d, J=7.40 Hz, 2H), 7.36 (m, 4H), 7.08 (m, 1H), 3.80 (d, J=12.48 Hz, 2H), 3.39 (d, J=11.32 Hz, 2H), 3.01 (m, 1H), 2.88 (s, 1H), 2.23 (t, J=14.54 Hz, 4H), 2.03 (m, 4H), 1.75 (m, 5H), 1.45 (m, 1H), 1.03 (d, J=5.1 Hz, 4H). [M+H]⁺=539.30.

Example 169: 1-(1-(2-cyanopyrimidin-4-yl)cyclohexyl)-3-(4'-((trifluoromethyl)sulfonyl)-[1,1'-biphenyl]-4-yl)urea Step 1: 1-(1-(2-cyanopyrimidin-4-yl)cyclohexyl)-3-(4-(4,4,5,5-tetramethyl-1,3,2-dioxaborolan-2-yl)phenyl)urea

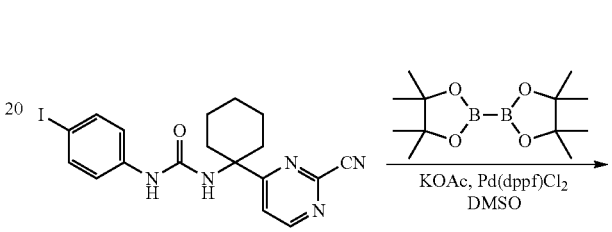

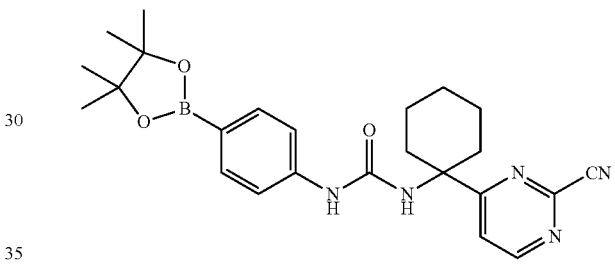

A mixture of 1-(1-(2-cyanopyrimidin-4-yl)cyclohexyl)-3-(4-iodophenyl)urea (150 mg, 0.335 mmol) prepared in Example 132, bis(pinacolato)diboron (52 mg, 0.503 mmol), potassium acetate (48.6 mg, 0.495 mmol), and PdCl₂(dppf) (27.4 mg, 0.034 mmol) in dimethyl sulfoxide (2 ml) was stirred at 90° C. for 4 hours. The reaction mixture was dried on magnesium sulfate and then distilled under reduced pressure. The resulting residue was purified by MPLC to give 75 mg of the titled compound (Yield: 50%). [M+1]⁺=448.

Step 2: 1-(1-(2-cyanopyrimidin-4-yl)cyclohexyl)-3-(4'-((trifluoromethyl)sulfonyl)-[1,1'-biphenyl]-4-yl)urea

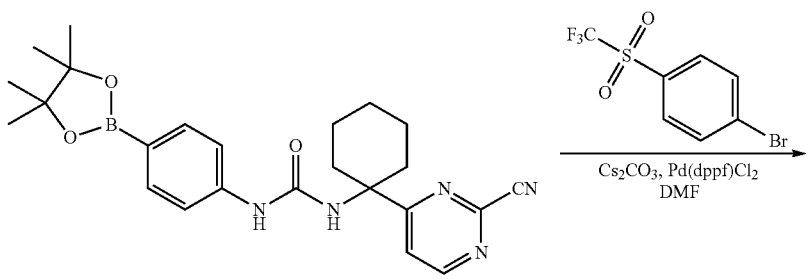

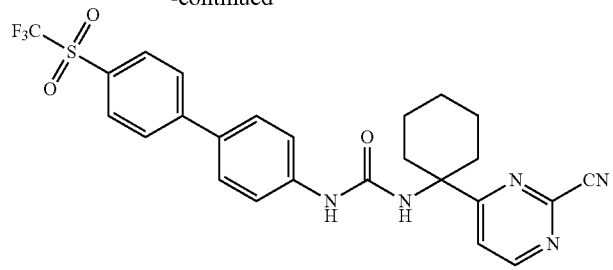

A mixture of 1-(1-(2-cyanopyrimidin-4-yl)cyclohexyl)-3-(4-(4,4,5,5-tetramethyl-1,3,2-dioxaborolan-2-yl)phenyl)urea (6 mg, 0.013 mmol) prepared in Step 1, 1-bromo-4-((trifluoromethyl)sulfonyl)benzene (3.25 mg, 10.73 μmol), cesium carbonate (10.92 mg, 0.034 mmol), and PdCl$_2$(dppf)-CH$_2$Cl$_2$ adduct (2.66 mg, 3.25 μmol) in dimethylformamide (1000 μl) and water (100 μl) was reacted at 120° C. for 30 minutes using microwave. The reaction mixture was extracted with water and ethyl acetate. The organic layer was dried on magnesium sulfate and then distilled under reduced pressure. The resulting residue was purified by Prep-HPLC to give 1.5 mg of the titled compound (Yield: 17%).

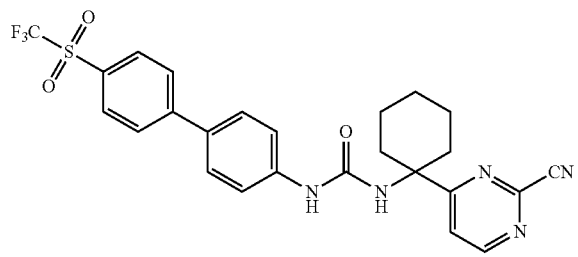 [SMILES: N#Cc1nccc(C2(NC(=O)Nc3ccc(-c4ccc(S(=O)(=O)C(F)(F)F)cc4)cc3)CCCCC2)n1]

$^1$H NMR (400 MHz, MeOD) δ 8.70 (d, J=5.4 Hz, 1H), 7.98 (d, J=8.4 Hz, 2H), 7.89 (d, J=9.2 Hz, 2H), 7.73 (d, J=5.4 Hz, 1H), 7.58 (d, J=8.7 Hz, 2H), 7.37 (d, J=8.6 Hz, 2H), 2.12-2.08 (m, 2H), 1.93-1.85 (m, 2H), 1.64-1.52 (m, 4H), 1.35-1.25 (m, 2H), [M+1]$^+$=530.

The compounds of Examples 170 to 175 were prepared in accordance with the same procedures as in Example 169, using the corresponding bromides instead of 1-bromo-4-((trifluoromethyl)sulfonyl)benzene used in Step 2 of Example 169.

Example 170: 1-(1-(2-cyanopyrimidin-4-yl)cyclohexyl)-3-(3'-fluoro-4'-(methylsulfonyl)-[1,1'-biphenyl]-4-yl)urea

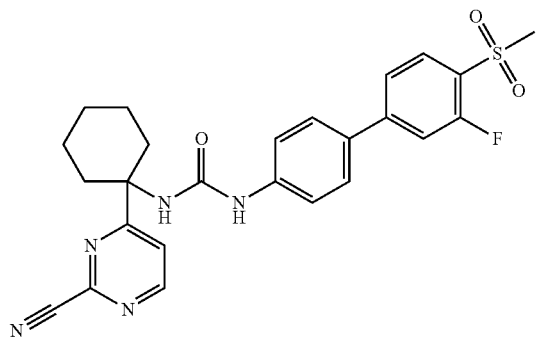 [SMILES: CS(=O)(=O)c1ccc(-c2ccc(NC(=O)NC3(c4ccnc(C#N)n4)CCCCC3)cc2)cc1F]

$^1$H NMR (400 MHz, CDCl$_3$) δ 8.77 (d, J=5.4 Hz, 2H), 7.97 (t, 2H), 7.67 (d, J=5.4 Hz, 1H), 7.54-7.45 (m, J=14.1, 5.5 Hz, 3H), 7.41-7.33 (m, J=8.6 Hz, 3H), 6.64 (s, 1H), 5.23 (s, 1H), 3.26 (s, 3H), 2.12-2.08 (m, 2H), 1.91-1.84 (m, 2H), 1.67-1.57 (m, 4H), 1.35-1.25 (m, 2H)

HPLC purity=96%

LRMS(ESI): m/z=494 [M+H]+

Example 171: 1-(1-(2-cyanopyrimidin-4-yl)cyclohexyl)-3-(4'-(methylsulfonyl)-3'-(trifluoromethyl)-[1,1'-biphenyl]-4-yl)urea

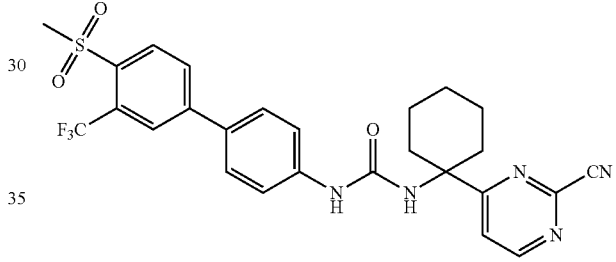

$^1$H NMR (400 MHz, DMSO-d$_6$) δ 8.93 (d, J=5.5 Hz, 1H), 8.25 (d, J=8.1 Hz, 1H), 8.15 (s, 1H), 7.90 (d, J=5.1 Hz, 1H), 7.76 (d, J=8.9 Hz, 2H), 7.48 (d, J=8.8 Hz, 2H), 2.12-2.08 (m, 2H), 1.93-1.85 (m, 2H), 1.64-1.52 (m, 4H), 1.35-1.25 (m, 2H), [M]$^+$=543.

Example 172: 1-(1-(2-cyanopyrimidin-4-yl)cyclohexyl)-3-(2'-(trifluoromethyl)-[1,1'-biphenyl]-4-yl)urea

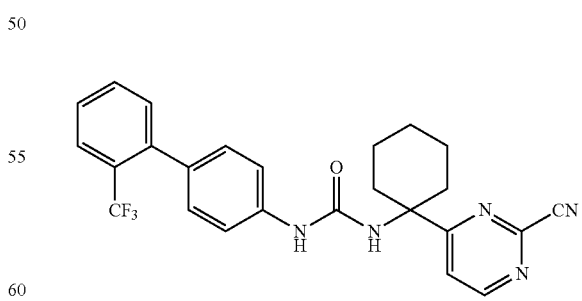

$^1$H NMR (400 MHz, MeOD) δ8.67 (d, J=5.4 Hz, 1H), 7.73 (d, J=5.4 Hz, 1H), 7.64 (d, J=7.8 Hz, 1H), 7.51 (t, J=7.3 Hz, 1H), 7.40 (t, J=7.6 Hz, 1H), 7.25 (m, 3H), 7.08 (d, J=8.4 Hz, 1H), 2.12-2.08 (n, 2H), 1.93-1.85 (n, 2H), 1.64-1.52 (m, 4H), 1.35-1.25 (m, 2H), [M+1]$^+$=466.

Example 173: 4'-(3-(1-(2-cyanopyrimidin-4-yl)cy-clohexyl)ureido)-[1,1'-biphenyl]-4-sulfonamide

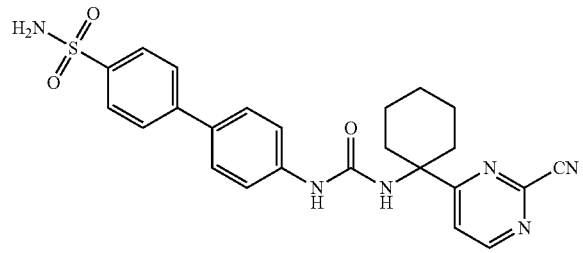 [SMILES: N#Cc1nccc(C2(NC(=O)Nc3ccc(-c4ccc(S(N)(=O)=O)cc4)cc3)CCCCC2)n1]

¹H NMR (400 MHz, MeOD) δ 8.82 (d, J=5.4 Hz, 1H), 7.95 (d, J=8.4 Hz, 2H), 7.86 (d, J=5.4 Hz, 1H), 7.78 (d, J=8.5 Hz, 2H), 7.61 (d, J=8.7 Hz, 2H), 7.44 (d, J=8.7 Hz, 2H), 2.12-2.08 (m, 2H), 1.93-1.85 (m, 2H), 1.64-1.52 (m, 4H), 1.35-1.25 (m, 2H), [M+1]⁺=477.

Example 174: N-(4'-(3-(1-(2-cyanopyrimidin-4-yl)cyclohexyl)ureido)-[1,1'-biphenyl]-4-yl)methane-sulfonamide

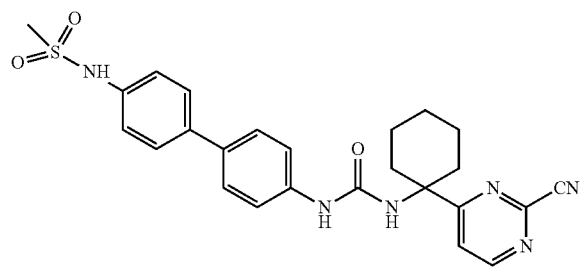 [SMILES: CS(=O)(=O)Nc1ccc(-c2ccc(NC(=O)NC3(c4ccnc(C#N)n4)CCCCC3)cc2)cc1]

¹H NMR (400 MHz, Pyridine-d₅) δ 8.80 (m, 2H), 7.95 (d, J=8.4 Hz, 7.86 (d, J=5.4 Hz, 1H), 7.78 (d, J=8.5 Hz, 2H), 7.61 (d, J=8.7 Hz, 2H), 7.44 (d, J=8.7 Hz, 2H), 2.12-2.08 (m, 2H), 1.93-1.85 (m, 2H), 1.64-1.52 (m, 4H), 1.35-1.25 (m, 2H), [M+1]⁺=491.

Example 175: methyl 5-(4'-(3-(1-(2-cyanopyrimi-din-4-yl)cyclohexyl)ureido)-[1,1'-biphenyl]-4-yl)pent-4-ynoate

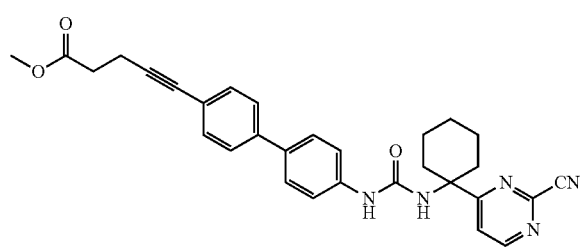 [SMILES: COC(=O)CCC#Cc1ccc(-c2ccc(NC(=O)NC3(c4ccnc(C#N)n4)CCCCC3)cc2)cc1]

¹H NMR (400 MHz, MeOD) δ 8.81 (d, J=5.4 Hz, 1H), 7.85 (d, J=5.4 Hz, 1H), 7.52 (m, 4H), 7.39 (m, 4H), 2.73 (t, J=7.6 Hz, 2H), 2.65 (t, J=7.6 Hz, 2H), 2.12-2.08 (m, 2H), 1.93-1.85 (m, 2H), 1.64-1.52 (m, 4H), 1.35-1.25 (m, 2H), [M+1]⁺=508.

Example 176: 1-(2,2'-bis(trifluoromethyl)-[1,1'-biphenyl]-4-yl)-3-(1-(2-cyanopyrimidin-4-yl)cyclohexyl)urea Step 1: 1-(1-(2-cyanopyrimidin-4-yl)cyclohexyl)-3-(4-(4,4,5,5-tetramethyl-1,3,2-dioxaborolan-2-yl)-3-(trifluoromethyl)phenyl)urea

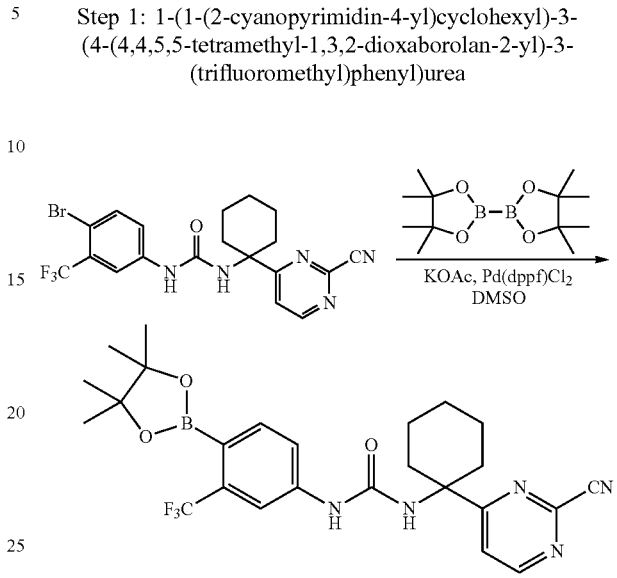

A mixture of 1-(4-bromo-3-(trifluoromethyl)phenyl)-3-(1-(2-cyanopyrimidin-4-yl)cyclohexyl)urea (237 mg, 0.507 mmol) prepared in Example 133, bis(pinacolato)diboron (142 mg, 0.558 mmol), potassium acetate (174 mg, 1.776 mmol), and PdCl₂(dppf) (21 mg, 0.025 mmol) in dimethyl sulfoxide (2 ml) was stirred at 120° C. for 30 minutes using microwave. The reaction mixture was dried on magnesium sulfate and then distilled under reduced pressure. The resulting residue was purified by MPLC to give 100 mg of the titled compound (Yield: 38%). [M+1]⁺=516.

Step 2: 1-(2,2'-bis(trifluoromethyl)-[1,1'-biphenyl]-4-yl)-3-(1-(2-cyanopyrimidin-4-yl)cyclohexyl)urea

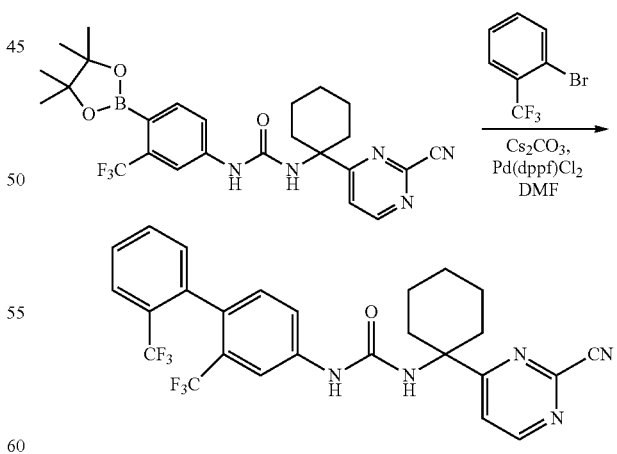

A mixture of 1-(1-(2-cyanopyrimidin-4-yl)cyclohexyl)-3-(4-(4,4,5,5-tetramethyl-1,3,2-dioxaborolan-2-yl)-3-(trifluoromethyl)phenyl)urea (5 mg, 9.70 μmol) prepared in Step 1, 1-bromo-2-(trifluoromethyl)benzene (1.211 μl, 8.94 μmol), cesium carbonate (7.90 mg, 0.024 mmol), and PdCl₂(dppf)-CH₂Cl₂ adduct (2.66 mg, 3.25 μmol) in dimethylformamide (900 μl) and water (100 μl) was reacted at 120° C. for 30 minutes using microwave. The reaction mixture was extracted with water and ethyl acetate. The organic layer was dried on magnesium sulfate and then distilled under reduced pressure. The resulting residue was purified by Prep-HPLC to give 1.0 mg of the titled compound (Yield: 19%).

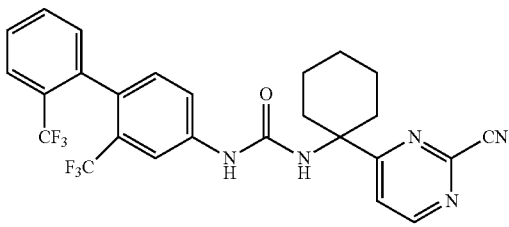 [SMILES: N#Cc1nccc(C2(NC(=O)Nc3ccc(-c4ccccc4C(F)(F)F)c(C(F)(F)F)c3)CCCCC2)n1]

$^1$H NMR (400 MHz, MeOD) δ 8.70 (d, J=5.4 Hz, 1H), 7.74 (m, 2H), 7.65 (d, J=7.8 Hz, 1H), 7.48 (m, 2H), 7.38 (dd, J=2.0 Hz, J=8.4 Hz 1H), 7.19 (d, J=7.4 Hz, 1H), 7.06 (d, J=8.4 Hz, 1H), 2.12-2.08 (m, 2H), 1.93-1.85 (m, 2H), 1.64-1.52 (m, 4H), 1.35-1.25 (m, 2H), [M+1]$^+$=534.

The compounds of Examples 177 to 180 were prepared in accordance with the same procedures as in Example 176, using the corresponding bromides instead of 1-bromo-2-(trifluoromethyl)benzene used in Step 2 of Example 176.

Example 177: 1-(1-(2-cyanopyrimidin-4-yl)cyclohexyl)-3-(2-(trifluoromethyl)-4'-((trifluoromethyl)sulfonyl)-[1,1'-biphenyl]-4-yl)urea

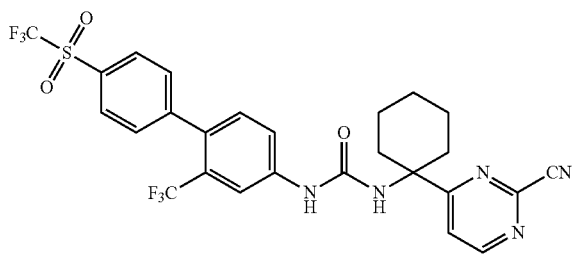 [SMILES: N#Cc1nccc(C2(NC(=O)Nc3ccc(-c4ccc(S(=O)(=O)C(F)(F)F)cc4)c(C(F)(F)F)c3)CCCCC2)n1]

$^1$H NMR (400 MHz, MeOD) δ 8.71 (d, J=5.4 Hz, 1H), 8.02 (d, J=8.3 Hz, 2H), 7.81 (d, J=1.8 Hz, 1H), 7.74 (d, J=5.4 Hz, 1H), 7.61 (d, J=8.3 Hz, 2H), 7.48 (dd, J=1.8 Hz, J=8.4 Hz 1H), 7.21 (d, J=8.4 Hz, 1H), 2.12-2.08 (m, 2H), 1.93-1.85 (m, 2H), 1.64-1.52 (m, 4H), 1.35-1.25 (m, 2H), [M+1]$^+$=598.

Example 178: 1-(1-(2-cyanopyrimidin-4-yl)cyclohexyl)-3-(4'-(methylsulfonyl)-2,3'-bis(trifluoromethyl)-[1,1'-biphenyl]-4-yl)urea

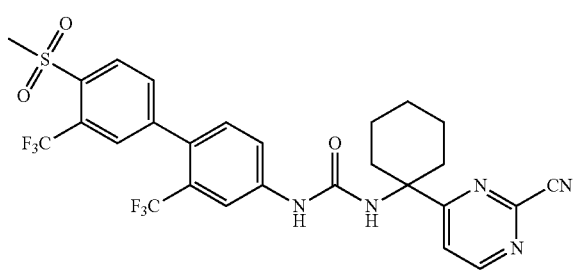 [SMILES: CS(=O)(=O)c1ccc(-c2ccc(NC(=O)NC3(c4ccnc(C#N)n4)CCCCC3)cc2C(F)(F)F)cc1C(F)(F)F]

$^1$H NMR (400 MHz, MeOD) 8.71 (d, J=5.4 Hz, 1H), 7.82 (d, J=1.7 Hz, 1H), 7.74 (s, 1H), 7.72 (m, 2H), 7.49 (dd, J=1.0 Hz, J=9.3 Hz 1H), 7.21 (d, J=8.4 Hz, 1H), 2.12-2.08 (m, 2H), 1.93-1.85 (m, 2H), 1.64-1.52 (m, 4H), 1.35-1.25 (m, 2H), [M+1]$^+$=612.

Example 179: 4'-(3-(1-(2-cyanopyrimidin-4-yl)cyclohexyl)ureido)-2'-(trifluoromethyl)-[1,1'-biphenyl]-4-sulfonamide

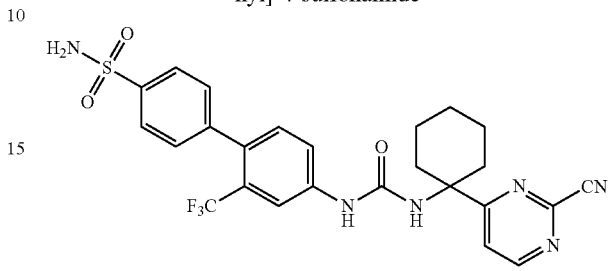

$^1$H NMR (400 MHz, MeOD) δ 8.71 (d, J=5.4 Hz, 1H), 7.82 (d, J=8.3 Hz, 2H), 7.77 (d, J=2.0 Hz 1H), 7.74 (d, J=5.4 Hz, 1H), 7.44 (dd, J=2.0 Hz, J=8.3 Hz 1H), 7.17 (m, 5H), 2.12-2.08 (m, 2H), 1.93-1.85 (m, 2H), 1.64-1.52 (m, 4H), 1.35-1.25 (m, 2H), [M+1]$^+$=545.

Example 180: N-(4'-(3-(1-(2-cyanopyrimidin-4-yl)cyclohexyl)ureido)-2'-(trifluoromethyl)-[1,1'-biphenyl]-4-yl)methanesulfonamide

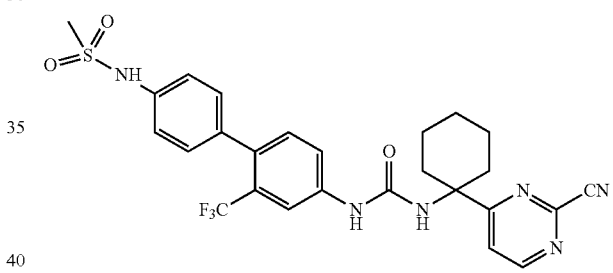

$^1$H NMR (400 MHz, MeOD) δ 8.71 (d, J=5.4 Hz, 1H), 7.73 (m, 2H), 7.44 (dd, J=2.0 Hz, J=8.3 Hz 1H), 7.35 (d, J=8.2 Hz, 2H), 7.15 (d, J=8.4 Hz, 1H), 2.12-2.08 (m, 2H), 1.93-1.85 (m, 2H), 1.64-1.52 (m, 4H), 1.35-1.25 (m, 2H), [M+1]$^+$=559.

Example 181: 1-(1-(2-cyanopyrimidin-4-yl)cyclohexyl)-3-((4'-(4-isopropylpiperazin-1-yl)-[1,1'-biphenyl]-4-yl)methyl)urea

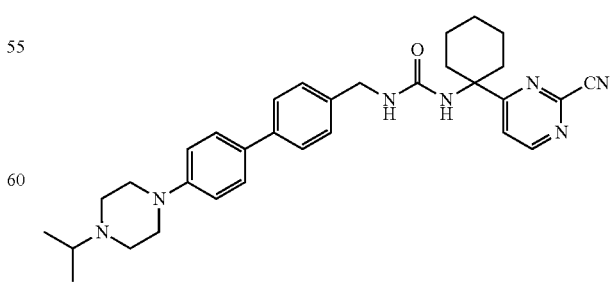

4-Nitrophenyl 4-iodobenzylcarbamate was prepared in accordance with the same procedures as in Example 132 using (4-iodophenyl)methanamine instead of 4-iodoaniline used in Step 3 of Example 132. The 4-nitrophenyl 4-iodobenzylcarbamate was reacted with the intermediate prepared in Step 2, i.e., 4-(1-aminocyclohexyl)pyrimidine-2-carbonitrile, to prepare 1-(1-(2-cyanopyrimidin-4-yl)cyclohexyl)-3-(4-(iodobenzyl)urea. The titled compound (0.8 mg) was prepared in accordance with the same procedures as in Example 147, using 1-isopropyl-4-(4-(4,4,5,5-tetramethyl-1,3,2-dioxaborolan-2-yl)phenyl)piperazine (Yield: 1.373%).

$^1$H NMR (400 MHz, MeOD) δ 8.78 (d, J=5.40 Hz, 1H), 7.99 (s, 1H), 7.77 (d, J=5.44 Hz, 1H), 7.60 (t, J=8.0 Hz, 4H), 7.33 (d, J=8.12 Hz, 2H), 7.13 (d, J=8.84 Hz, 2H), 4.28 (s, 2H), 3.98 (d, J=12.68 Hz, 2H), 3.63 (m, 3H), 3.15 (m, 2H), 2.23 (m, 2H), 1.96 (m, 2H), 1.72 (m, 5H), 1.46 (d, J=6.68 Hz, 6H). [M+H]$^+$=538.35.

Example 182: 5-(4-(3-(1-(2-cyanopyrimidin-4-yl)cyclohexyl)ureido)phenyl)pent-4-ynoic acid 1-(1-(2-Cyanopyrimidin-4-yl)cyclohexyl)-3-(4-iodophenyl)urea (10 mg, 0.011 mmol) prepared in Example 132, bis(triphenylphosphine)palladium(II) chloride (0.392 mg, 1.118 μmol), and copper(I) iodide (0.213 mg, 1.118 μmol) were dissolved in dimethylformamide (1.5 ml). Triethylamine (0.016 ml, 0.112 mmol) was slowly added thereto. Pent-4-ynoic acid (2.193 mg, 0.022 mmol) was added to the reaction mixture, which was then stirred at 80° C. for 4 hours. The reaction mixture was extracted with water and ethyl acetate. The organic layer was dried on magnesium sulfate and then distilled under reduced pressure. The resulting residue was purified by Prep-HPLC to give 2 mg of the titled compound (Yield: 21%).

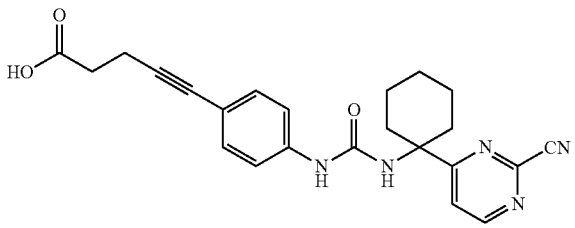 [SMILES: N#Cc1nccc(C2(NC(=O)Nc3ccc(C#CCCC(=O)O)cc3)CCCCC2)n1]

$^1$H NMR (400 MHz, MeOD) δ 8.80 (d, J=5.4 Hz, 1H), 7.81 (d, J=5.4 Hz, 1H), 7.24 (m, 4H), 2.68 (t, J=7.6 Hz, 2H), 2.58 (t, J=7.6 Hz, 2H), 2.12-2.08 (m, 2H), 1.93-1.85 (m, 2H), 1.64-1.52 (m, 4H), 1.35-1.25 (m, 2H), [M+1]$^+$=418

Example 183: 1-(1-(2-cyanopyrimidin-4-yl)cyclohexyl)-3-(4-((4-(hydroxymethyl)phenyl)ethynyl)phenyl)urea 1-(1-(2-Cyanopyrimidin-4-yl)cyclohexyl)-3-(4-iodophenyl)urea (10 mg, 0.011 mmol) prepared in Example 132, bis(triphenylphosphine)palladium(II) chloride (0.392 mg, 1.118 μmol), and copper(I) iodide (0.213 mg, 1.118 μmol) were dissolved in dimethylformamide (1.5 ml). Triethylamine (0.016 ml, 0.112 mmol) was slowly added thereto. (4-Ethynylphenyl)methanol (2.95 mg, 0.022 mmol) was added to the reaction mixture, which was then stirred at 80° C. for 4 hours. The reaction mixture was extracted with water and ethyl acetate. The organic layer was dried on magnesium sulfate and then distilled under reduced pressure. The resulting residue was purified by Prep-HPLC to give 0.5 mg of the titled compound (Yield: 5%).

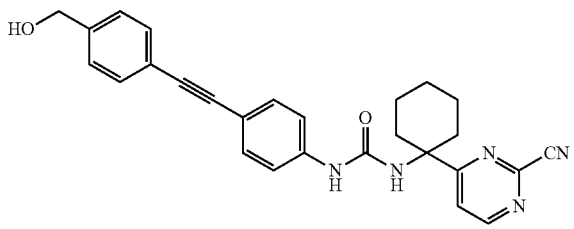 [SMILES: N#Cc1nccc(C2(NC(=O)Nc3ccc(C#Cc4ccc(CO)cc4)cc3)CCCCC2)n1]

$^1$H NMR (400 MHz, MeOD) δ 8.80 (d, J=5.4 Hz, 1H), 7.82 (d, J=5.4 Hz, 1H), 7.47 (d, J=8.2 Hz, 2H), 7.38 (m, 6H), 4.63 (s, 2H), 2.12-2.08 (m, 2H), 1.93-1.85 (m, 2H), 1.64-1.52 (m, 4H), 1.35-1.25 (m, 2H), [M+1]$^+$=452

Example 184: N-(2-(1H-imidazol-4-yl)ethyl)-4'-(3-(1-(2-cyanopyrimidin-4-yl)cyclohexyl)ureido)-[1,1'-biphenyl]-4-carboxamide Step 1: 4'-(3-(1-(2-cyanopyrimidin-4-yl)cyclohexyl)ureido)-[1,1'-biphenyl]-4-carboxylic acid

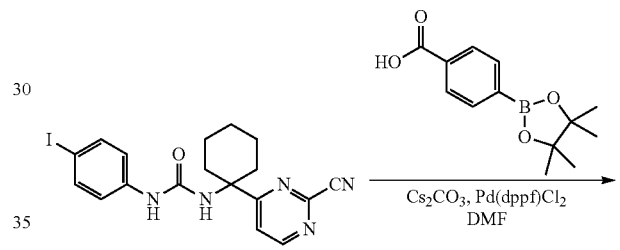

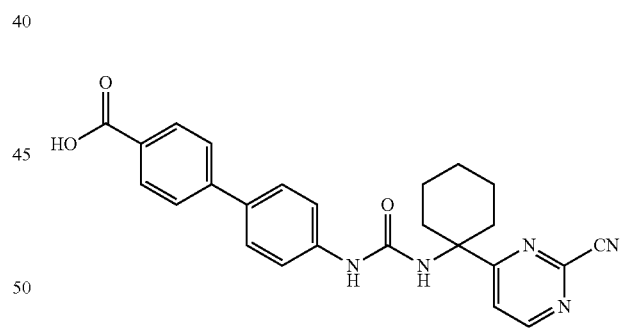

A solution of 1-(1-(2-cyanopyrimidin-4-yl)cyclohexyl)-3-(4-iodophenyl)urea (30 mg, 0.067 mmol) prepared in Example 132, cesium carbonate (54.6 mg, 0.168 mmol), 4-(4,4,5,5,-tetramethyl-1,3,2-dioxaborolan-2-yl)benzoic acid (11 mg, 0.067 mmol), and PdCl$_2$(dppf) (5.48 mg, 0.0671 mmol) in a mixed solvent of dimethylformamide and water (5:1) (0.6 mL) was reacted at 120° C. for 30 minutes using microwave. After the completion of the reaction, water and ethyl acetate were added thereto and the organic layer was extracted. The organic layer was washed with a sodium bicarbonate solution and brine, dried on magnesium sulfate, and then distilled under reduced pressure. The resulting residue was purified by Prep-HPLC to give 3.5 mg of the titled compound (white solid, Yield: 10%).

Step 2: N-(2-(1H-imidazol-4-yl)ethyl)-4'-(3-(1-(2-cyanopyrimidin-4-yl)cyclohexyl)ureido)-[1,1'-biphenyl]-4-carboxamide

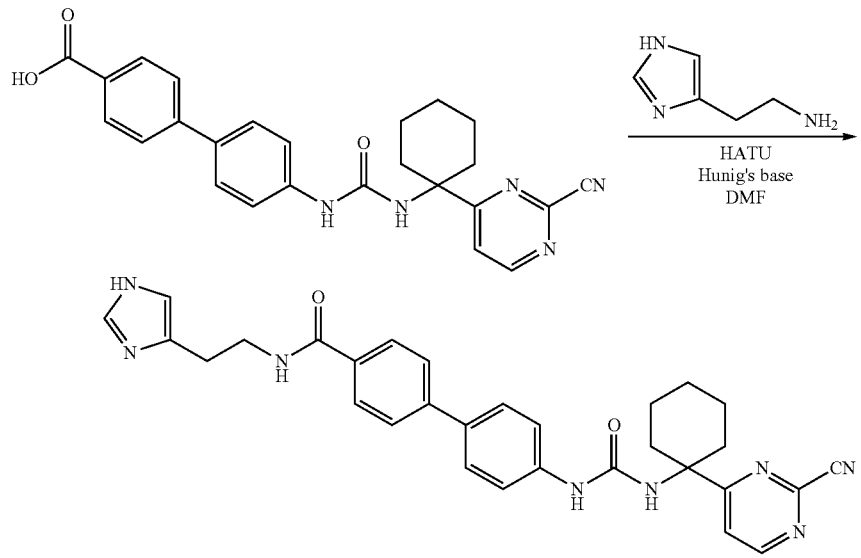

4'-(3-(1-(2-Cyanopyrimidin-4-yl)cyclohexyl)ureido)-[1,1'-biphenyl]-4-carboxylic acid (3 mg, 6.80 μmol) prepared in Step 1 was dissolved in dimethylformamide (1 ml). 2-(1H-Imidazol-4-yl)ethanamine dihydrochloride (1.251 mg, 6.80 μmol), 2-(3H-[1,2,3]triazolo[4,5-b]pyridin-3-yl)-1,1,3,3-tetramethylisouronium hexafluorophosphate(V) (3.10 mg, 8.15 μmol) and Hunig's base (5.93 μl, 0.034 mmol) were sequentially slowly added thereto. The reaction mixture was extracted with water and ethyl acetate. The organic layer was dried on magnesium sulfate and then distilled under reduced pressure. The resulting residue was purified by Prep-HPLC to give 2 mg of the titled compound (Yield: 55%).

Example 185: N-(2-(1H-imidazol-1-yl)ethyl)-4'-(3-(1-(2-cyanopyrimidin-4-yl)cyclohexyl)ureido)-[1,1'-biphenyl]-4-carboxamide 4'-(3-(1-(2-Cyanopyrimidin-4-yl)cyclohexyl)ureido)-[1,1'-biphenyl]-4-carboxylic acid (3 mg, 6.80 μmol) prepared in Step 1 of Example 184 was dissolved in dimethylformamide (1 ml). 2-(1H-Imidazol-1-yl)ethanamine (0.755 mg, 6.80 μmol), 2-(3H-[1,2,3]triazolo[4,5-b]pyridin-3-yl)-1,1,3,3-tetramethylisouronium hexafluorophosphate(V) (3.10 mg, 8.15 μmol) and Hunig's base (5.93 μl, 0.034 mmol) were sequentially slowly added thereto. The reaction mixture was extracted with water and ethyl acetate. The organic layer was dried on magnesium sulfate and then distilled under reduced pressure. The resulting residue was purified by Prep-HPLC to give 1.5 mg of the titled compound (Yield: 41%).

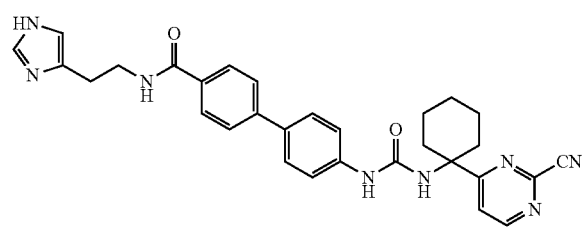 [SMILES: N#Cc1nccc(C2(NC(=O)Nc3ccc(-c4ccc(C(=O)NCCc5c[nH]cn5)cc4)cc3)CCCCC2)n1]

$^1$H NMR (400 MHz, MeOD) δ 8.83 (d, J=5.4 Hz, 1H), 8.81 (s, 1H), 7.85 (m, 3H), 7.69 (d, J=8.5 Hz, 2H), 7.59 (d, J=8.7 Hz, 2H), 7.42 (d, J=8.7 Hz, 2H), 7.38 (s, 1H), 3.73 (t, J=6.7 Hz, 2H), 3.06 (t, J=5.5 Hz, 2H), 2.12-2.08 (m, 2H), 1.93-1.85 (m, 2H), 1.64-1.52 (m, 4H), 1.35-1.25 (m, 2H), [M+1]$^+$=535

$^1$H NMR (400 MHz, MeOD) δ 8.92 (s, 1H), 8.81 (d, J=5.4 Hz, 1H), 7.85 (m, 3H), 7.68 (m, 3H), 7.58 (m, 3H), 7.42 (d, J=8.6 Hz, 2H), 4.50 (t, J=5.5 Hz, 2H), 3.87 (t, J=5.5 Hz, 2H), 2.12-2.08 (m, 2H), 1.93-1.85 (m, 2H), 1.64-1.52 (m, 4H), 1.35-1.25 (m, 2H), [M+1]$^+$=535.

Example 186: N-(2-(1H-imidazol-1-yl)ethyl)-4'-(3-(1-(2-cyanopyrimidin-4-yl)cyclohexyl)ureido)-2'-fluoro-[1,1'-biphenyl]-4-carboxamide

Step 1: 4'-(3-(1-(2-cyanopyrimidin-4-yl)cyclohexyl)ureido)-2'-fluoro-[1,1'-biphenyl]-4-carboxylic acid

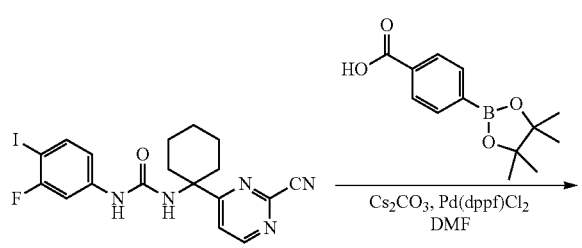

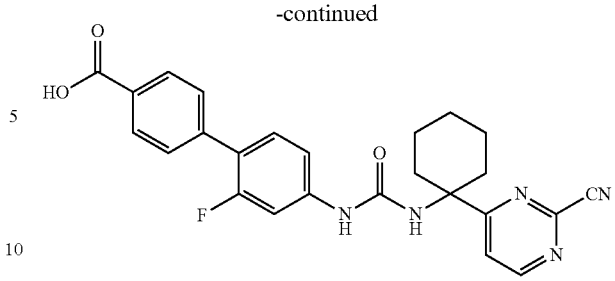

A solution of 1-(1-(2-cyanopyrimidin-4-yl)cyclohexyl)-3-(3-fluoro-4-iodophenyl)urea (100 mg, 0.215 mmol) prepared in Example 137, cesium carbonate (175 mg, 0.537 mmol), 4-(4,4,5,5,-tetramethyl-1,3,2-dioxaborolan-2-yl)benzoic acid (53 mg, 0.215 mmol), and PdCl$_2$(dppf) (17.55 mg, 0.021 mmol) in a mixed solvent of dimethylformamide and water (5:1) (1 mL) was reacted at 120° C. for 30 minutes using microwave. After the completion of the reaction, water and ethyl acetate were added thereto and the organic layer was extracted. The organic layer was washed with a sodium bicarbonate solution and brine, dried on magnesium sulfate, and then distilled under reduced pressure. The resulting residue was purified by Prep-HPLC to give 39.6 mg of the titled compound (white solid, Yield: 40%).

Step 2: N-(2-(1H-imidazol-1-yl)ethyl)-4'-(3-(1-(2-cyanopyrimidin-4-yl)cyclohexyl)ureido)-2'-fluoro-[1,1'-biphenyl]-4-carboxamide

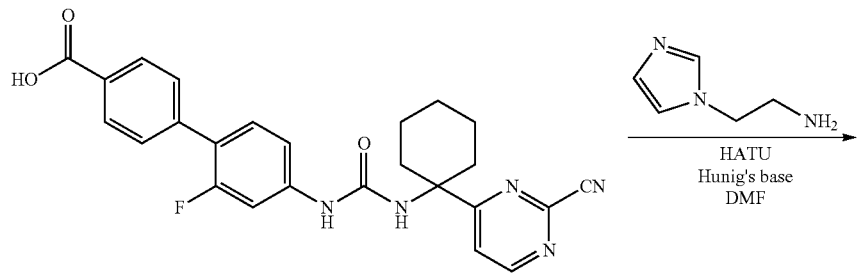

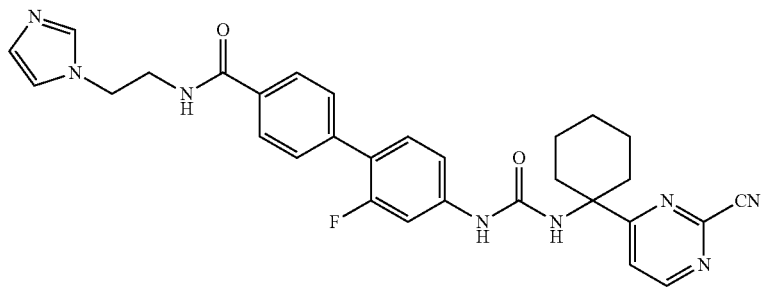

4'-(3-(1-(2-Cyanopyrimidin-4-yl)cyclohexyl)ureido)-2'-fluoro-[1,1'-biphenyl]-4-carboxylic acid (30 mg, 0.065 mmol) prepared in Step 1 was dissolved in dimethylformamide (1 ml). 2-(1H-Imidazol-1-yl)ethanamine (7.26 mg, 0.065 mmol), 2-(3H-[1,2,3]triazolo[4,5-b]pyridin-3-yl)-1,1,3,3-tetramethylisouronium hexafluorophosphate(V) (29.8 mg, 0.078 mmol) and Hunig's base (57.0 µl, 0.326 mmol) were sequentially slowly added thereto. The reaction mixture was extracted with water and ethyl acetate. The organic layer was dried on magnesium sulfate and then distilled under reduced pressure. The resulting residue was purified by Prep-HPLC to give 7 mg of the titled compound (Yield: 19.4%).

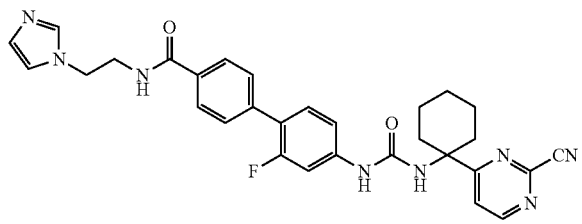 [SMILES: N#Cc1nccc(C2(NC(=O)Nc3ccc(-c4ccc(C(=O)NCCn5ccnc5)cc4)cc3)CCCCC2)n1]

$^1$H NMR (400 MHz, MeOD) δ 9.00 (s, 1H), 8.81 (d, J=5.4 Hz, 1H), 7.83 (m, 3H), 7.58 (m, 4H), 7.41 (m, 2H), 7.09 (dd, J=2.1 Hz, J=8.4 Hz, 1H), 4.50 (t, J=5.6 Hz, 2H), 4.50 (t, J=5.6 Hz, 2H), 2.12-2.08 (m, 2H), 1.93-1.85 (m, 2H), 1.64-1.52 (m, 4H), 1.35-1.25 (m, 2H), [M+1]$^+$=553.

Example 187: N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide 4'-(3-(1-(2-Cyanopyrimidin-4-yl)cyclohexyl)ureido)-2'-fluoro-[1,1'-biphenyl]-4-carboxylic acid (30 mg, 0.065 mmol) prepared in Step 1 of Example 186 was dissolved in dimethylformamide (1 ml). 2-(1H-1,2,3-Triazol-1-yl)ethanamine (7.32 mg, 0.065 mmol), 2-(3H-[1,2,3]triazolo[4,5-b]pyridin-3-yl)-1,1,3,3-tetramethylisouronium hexafluorophosphate(V) (29.8 mg, 0.078 mmol) and Hunig's base (57.0 µl, 0.326 mmol) were sequentially slowly added thereto. The reaction mixture was extracted with water and ethyl acetate. The organic layer was dried on magnesium sulfate and then distilled under reduced pressure. The resulting residue was purified by Prep-HPLC to give 6 mg of the titled compound (Yield: 17%).

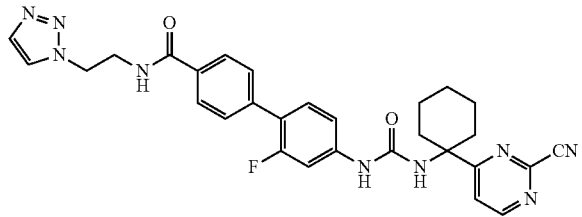 [SMILES: N#Cc1nccc(C2(NC(=O)Nc3ccc(-c4ccc(C(=O)NCCn5ccnn5)cc4)c(F)c3)CCCCC2)n1]

$^1$H NMR (400 MHz, MeOD): 8.81 (d, J=5.4 Hz, 1H), 8.03 (s, 1H), 7.83 (m, 3H), 7.76 (s, 1H), 7.41 (m, 2H), 7.09 (dd, J=2.1 Hz, J=8.4 Hz 1H), 4.72 (t, J=5.6 Hz, 2H), 3.89 (t, J=56 Hz, 2H) 2.12-2.08 (m, 2H), 1.93-1.85 (m, 2H), 1.64-1.52 (m, 4H), 1.35-1.25 (m, 2H), [M+1]$^+$=554.

Example 188: N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide 4'-(3-(1-(2-Cyanopyrimidin-4-yl)cyclohexyl)ureido)-2'-fluoro-[1,1'-biphenyl]-4-carboxylic acid (30 mg, 0.065 mmol) prepared in Step 1 of Example 186 was dissolved in dimethylformamide (1 ml). 2-(2H-1,2,3-triazol-2-yl)ethane-1-amine (7.32 mg, 0.065 mmol), 2-(3H-[1,2,3]triazolo[4,5-b]pyridin-3-yl)-1,1,3,3-tetramethylisouronium hexafluorophosphate(V) (29.8 mg, 0.078 mmol) and Hunig's base (57.0 µl, 0.326 mmol) were sequentially slowly added thereto. The reaction mixture was extracted with water and ethyl acetate. The organic layer was dried on magnesium sulfate and then distilled under reduced pressure. The resulting residue was purified by Prep-HPLC to give 3.5 mg of the titled compound (Yield: 10%).

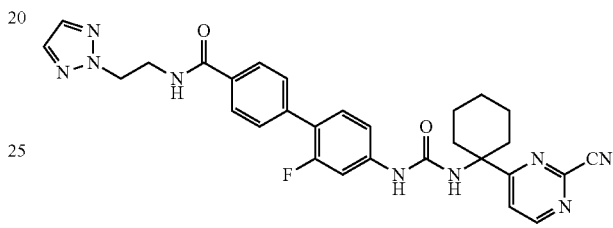

$^1$H NMR (400 MHz, MeOD): 8.70 (d, J=5.4 Hz, 1H), 7.71 (m, 3H), 7.67 (s, 2H), 7.48 (m, 2H), 7.28 (m, 2H), 6.97 (dd, J=2.1 Hz, J=8.4 Hz 1H), 4.61 (t, J=5.6 Hz, 2H), 3.78 (t, J=5.6 Hz, 2H), 2.12-2.08 (m, 2H), 1.93-1.85 (m, 2H), 1.64-1.52 (m, 4H), 1.35-1.25 (m, 2H), [M+1]$^+$=554.

Example 189: N-(2-(1H-imidazol-4-yl)ethyl)-4'-(3-(1-(2-cyanopyrimidin-4-yl)cyclohexyl)ureido)-2'-(trifluoromethyl)-[1,1'-biphenyl]-4-carboxamide 4'-(3-(1-(2-Cyanopyrimidin-4-yl)cyclohexyl)ureido)-2'-(trifluoromethyl)-[1,1'-biphenyl]-4-carboxylic acid (10 mg, 0.02 mmol) prepared in Example 163 was dissolved in dimethylformamide (0.2 ml). 2-(1H-Imidazol-4-yl)ethanamine dihydrochloride (3.61 mg, 0.02 mmol), 2-(3H-[1,2,3]triazolo[4,5-b]pyridin-3-yl)-1,1,3,3-tetramethylisouronium hexafluorophosphate(V) (8.96 mg, 0.024 mmol), and diisopropylethylamine (17 uL, 0.098 mmol) were sequentially slowly added thereto, followed by stirring overnight. The reaction mixture was purified by Prep-HPLC to give 5.6 mg of the titled compound (brown solid, Yield 47%).

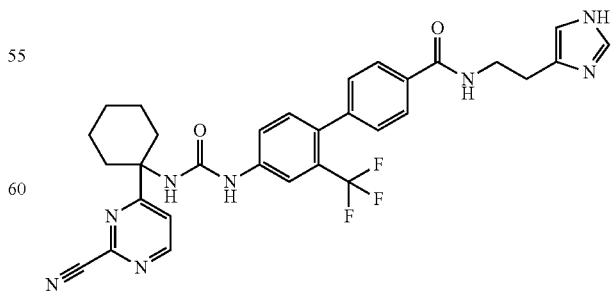

$^1$H NMR (400 MHz, MeOD) δ 8.72-8.70 (m, 2H), 7.74 (d, J=5.44 Hz, 2H), 7.7 (d, J=8.28 Hz, 2H), 7.43 (dd, J=8.4 Hz,

J=1.9 Hz, 1H), 7.28 (d, J=1.96 Hz, 2H), 7.26 (s, 1H), 7.12 (d, J=8.4 Hz, 1H), 3.62 (t, J=6.66 Hz, 2H), 2.95 (t, J=6.64 Hz, 2H), 2.14-2.10 (m, 2H), 1.93-1.84 (m, 2H), 1.66-1.56 (m, 4H), 1.35-1.27 (m, 2H)

HPLC purity=93%

LRMS(ESI): m/z=603 [M+H]+

Example 190: 1-(4'-(2-aminoethoxy)-[1,1'-biphenyl]-4-yl)-3-(1-(2-cyanopyrimidin-4-yl)cyclohexyl) urea

Step 1: 1-(1-(2-cyanopyrimidin-4-yl)cyclohexyl)-3-(4'-hydroxy-[1,1'-biphenyl]-4-yl)urea

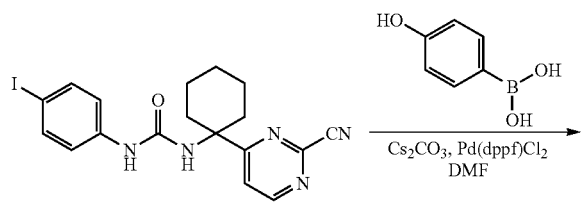

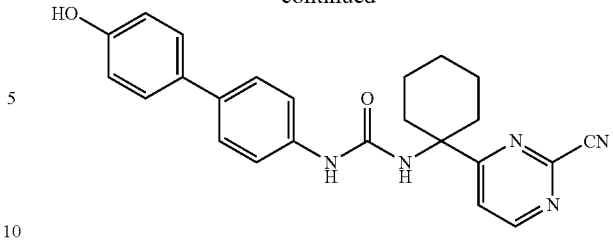

A solution of 1-(1-(2-cyanopyrimidin-4-yl)cyclohexyl)-3-(4-iodophenyl)urea (100 mg, 0.224 mmol) prepared in Example 132, cesium carbonate (182 mg, 0.560 mmol), (4-hydroxyphenyl)boronic acid (30.8 mg, 0.224 mmol), and PdCl$_2$(dppf) (18 mg, 0.022 mmol) in a mixed solvent of dimethylformamide and water (5:1) (1 mL) was reacted at 120° C. for 30 minutes using microwave. After the completion of the reaction, water and ethyl acetate were added thereto and the organic layer was extracted. The organic layer was washed with a sodium bicarbonate solution and brine, dried on magnesium sulfate, and then distilled under reduced pressure. The resulting residue was purified by Prep-HPLC to give 52 mg of the titled compound (white solid, Yield: 56%).

Step 2: 1-(4'-(2-aminoethoxy)-[1,1'-biphenyl]-4-yl)-3-(1-(2-cyanopyrimidin-4-yl)cyclohexyl)urea

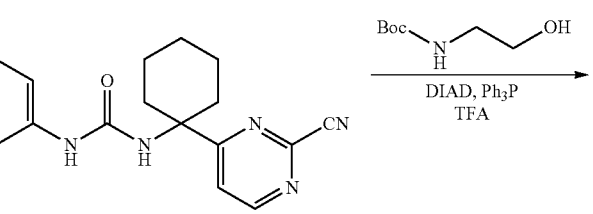

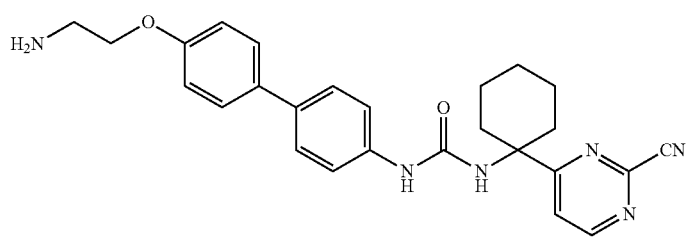

tert-Butyl (2-hydroxyethyl)carbamate (17.54 mg, 0.109 mmol) and triphenylphosphine (28.5 mg, 0.109 mmol) were added to methylene chloride (0.363 ml). Diisopropyl azodicarboxylate (21.43 μl, 0.109 mmol) was added at 0° C. to the mixture, which was then stirred for 10 minutes. A solution of 1-(1-(2-cyanopyrimidin-4-yl)cyclohexyl)-3-(4'-hydroxy-[1,1'-biphenyl]-4-yl)urea (15 mg, 0.036 mmol) prepared in Step 1 in methylene chloride (0.363 ml) was added at 0° C. to the mixture, which was then stirred for 12 hours. The reaction mixture was distilled under reduced pressure. The resulting residue was extracted with water and ethyl acetate. The organic layer was dried on magnesium sulfate and then distilled under reduced pressure. The resulting residue was dissolved in methylene chloride (0.5 ml) and then 2,2,2-trifluoroacetic acid (0.1 ml) was added thereto under stirring. The reaction mixture was distilled under reduced pressure. The resulting residue was purified by Prep-HPLC to give 1.5 mg of the titled compound (Yield: 8.95%).

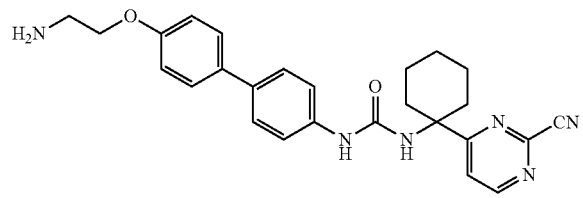 [SMILES: N#Cc1nccc(C2(NC(=O)Nc3ccc(-c4ccc(OCCN)cc4)cc3)CCCCC2)n1]

$^1$H NMR (400 MHz, MeOD) δ 8.81 (d, J=5.44 Hz, 1H), 7.84 (d, J=5.44 Hz, 1H), 7.55 (d, J=8.80 Hz, 2H), 7.48 (d, J=8.72 Hz, 2H), 7.36 (d, J=8.72 Hz, 2H), 7.08 (d, J=8.80 Hz, 2H), 4.28 (m, 2H), 3.40 (m, 2H), 2.24 (d, J=13.2 Hz, 2H), 2.05 (m, 2H), 1.70 (m, 5H), 1.47 (m, 1H). [M+H]$^+$=457.10.

Example 191: 1-(1-(2-cyanopyrimidin-4-yl)cyclohexyl)-3-(4'-(2-(methylamino)ethoxy)-[1,1'-biphenyl]-4-yl)urea tert-Butyl (2-hydroxyethyl)(methyl)carbamate (66.1 mg, 0.377 mmol) and triphenylphosphine (99 mg, 0.377 mmol) were added to methylene chloride (1.258 ml). Diisopropyl azodicarboxylate (74.3 μl, 0.377 mmol) was added at 0° C. to the mixture, which was then stirred for 10 minutes. A solution of 1-(1-(2-cyanopyrimidin-4-yl)cyclohexyl)-3-(4'-hydroxy-[1,1'-biphenyl]-4-yl)urea (52 mg, 0.126 mmol) prepared in Step 1 of Example 190 in methylene chloride (1.258 ml) was added at 0° C. to the mixture, which was then stirred for 12 hours. The reaction mixture was distilled under reduced pressure. The resulting residue was extracted with water and ethyl acetate. The organic layer was dried on magnesium sulfate and then distilled under reduced pressure. The resulting residue was dissolved in methylene chloride (4 ml) and then 2,2,2-trifluoroacetic acid (0.4 ml) was added thereto under stirring. The reaction mixture was distilled under reduced pressure. The resulting residue was purified by Prep-HPLC to give 32 mg of the titled compound (Yield: 99.6%).

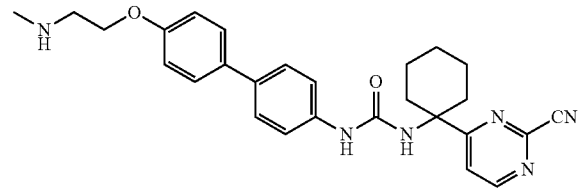

$^1$H NMR (400 MHz, DMSO-d$_6$) δ 8.92 (d, J=5.48 Hz, 1H), 8.80 (s, 1H), 8.64 (s, 2H), 7.88 (d, J=5.44 Hz, 1H), 7.57 (m, 2H), 7.48 (d, J=8.76 Hz, 2H), 7.38 (d, J=8.76 Hz, 2H), 7.05 (d, J=8.80 Hz, 2H), 6.86 (s, 1H), 4.26 (m, 2H), 3.37 (m, 2H), 2.66 (t, J=5.44 Hz, 3H), 2.12 (d, J=12.40 Hz, 2H), 1.88 (m, 2H), 1.70 (s, 5H), 1.39 (s, 1H), 1.34 (m, 1H). [M+H]$^+$=471.0.

Experimental Example: Inhibitory Activity Assay Against Cathepsin K, B, L, and S In order to measure the enzyme activity of cathepsin K, a buffer solution (pH 5.5) consisting of 50 mM 2-(N-morpholino)ethanesulfonic acid (MES), 2 mM dithiothreitol (DTT), 2.5 mM ethylenediaminetetraacetic acid (EDTA), 0.01% Triton X-100, and 10% dimethyl sulfoxide (DMSO) was prepared. The substrate, the test material, and the enzyme were mixed in the buffer solution in a predetermined concentration. The Z-Phe-Arg-AMC substrate was used in the final concentration of 10 μM. The test material was used in the final concentrations of 10.0 μM, 3.33 μM, 1.11 μM, 0.370 μM, 0.123 μM, 0.0412 μM, 0.0137 μM, 0.00457 μM, 0.00152 μM, and 0.000508 μM, respectively. The cathepsin K enzyme was used in the final concentration of 1 nM. The final volume of the enzyme reaction solution was 10 μL. After reacting the mixture of substrate, test material, and enzyme for 30 minutes, the enzyme activity was measured with the Synergy Neo (Biotek) microplate reader at an absorption wavelength of 355 nm and an emission wavelength of 460 nm. IC$_{50}$ values were determined using 4-parameter logistic curve fit program of GraphPad Prism.

In order to measure the enzyme activity of cathepsin B, a buffer solution (pH 6.0) consisting of 50 mM MES, 5 mM DTT, 2.5 mM EDTA, 0.005% Polysorbate 20, and 10% DMSO was prepared. The substrate, the test material, and the enzyme were mixed in the buffer solution in a predetermined concentration. The Z-Arg-Arg-AMC substrate was used in the final concentration of 40 μM. The test material was used in the final concentrations of 10.0 μM, 3.33 μM, 1.11 μM, 0.370 μM, 0.123 μM, 0.0412 μM, 0.0137 μM, 0.00457 μM, 0.00152 μM, and 0.000508 μM, respectively. The cathepsin B enzyme was used in the final concentration of 1 nM. The final volume of the enzyme reaction solution was 10 μL. After reacting the mixture of substrate, test material, and enzyme for 90 minutes, the enzyme activity was measured with the EnVision (Perkin Elmer) microplate reader at an absorption wavelength of 340 nm and an emission wavelength of 460 nm. IC$_{50}$ values were determined using 4-parameter logistic curve fit program of GraphPad Prism.

In order to measure the enzyme activity of cathepsin L, a buffer solution (pH 5.5) consisting of 50 mM MES, 2.5 mM DTT, 2.5 mM EDTA, 0.005% Polysorbate 20, and 10% DMSO was prepared. The substrate, the test material, and the enzyme were mixed in the buffer solution in a predetermined concentration. The Z-Phe-Arg-AMC substrate was used in the final concentration of 2 μM. The test material was used in the final concentrations of 10.0 μM, 3.33 μM, 1.11 μM, 0.370 μM, 0.123 μM, 0.0412 μM, 0.0137 μM, 0.00457 μM, 0.00152 μM, and 0.000508 μM, respectively. The cathepsin L enzyme was used in the final concentration of 3 nM. The final volume of the enzyme reaction solution was 10 μL. After reacting the mixture of substrate, test material, and enzyme for 30 minutes, the enzyme activity was measured with the EnVision (Perkin Elmer) microplate reader at an absorption wavelength of 340 nm and an emission wavelength of 460 nm. IC$_{50}$ values were determined using 4-parameter logistic curve fit program of GraphPad Prism.

In order to measure the enzyme activity of cathepsin S, a buffer solution (pH 6.5) consisting of 50 mM MES, 2.5 mM DTT, 1.0 mM EDTA, 0.001% bovine serum albumin (BSA), and 10% DMSO was prepared. The substrate, the test material, and the enzyme were mixed in the buffer solution in a predetermined concentration. The Z-Phe-Arg-AMC substrate was used in the final concentration of 70 μM. The test material was used in the final concentrations of 10.0 μM, 3.33 μM, 1.11 μM, 0.370 μM, 0.123 μM, 0.0412 μM, 0.0137 μM, 0.00457 μM, 0.00152 μM, and 0.000508 μM, respectively. The cathepsin S enzyme was used in the final concentration of 3 nM. The final volume of the enzyme reaction solution was 10 μL.

After reacting the mixture of substrate, test material, and enzyme for 45 minutes, the enzyme activity was measured with the EnVision (Perkin Elmer) microplate reader at an absorption wavelength of 340 nm and an emission wavelength of 460 nm. IC$_{50}$ values were determined using 4-parameter logistic curve fit program of GraphPad Prism.

The IC$_{50}$ values against the cathepsin K, B, L, and S enzymes obtained by measuring as above are shown in the following tables 1 to 7.

TABLE 1

| Compound No. | Cathepsin K | Cathepsin B | Cathepsin L | Cathepsin S |
|---|---|---|---|---|
| Example 1 | 23.0 | | | |
| Example 2 | 21.8 | >10000 | >10000 | >10000 |
| Example 3 | 507.0 | >10000 | 6388 | >10000 |
| Example 4 | 1150.0 | >10000 | >10000 | >10000 |
| Example 5 | 161.0 | | | |
| Example 6 | 179.4 | | | |
| Example 7 | 56.3 | >10000 | 3549 | >10000 |
| Example 8 | 284.9 | | | |
| Example 9 | 490.4 | | | |
| Example 10 | 5.6 | >10000 | 1176 | 7013 |
| Example 11 | 18.8 | >10000 | >10000 | >10000 |
| Example 12 | 168.2 | >10000 | 6910 | >10000 |
| Example 13 | 240.9 | >10000 | 5080 | >10000 |
| Example 14 | 3700.0 | >10000 | 9230 | >10000 |
| Example 15 | 45.5 | >10000 | 1620 | 8600 |
| Example 16 | 277.3 | >10000 | 4610 | >10000 |
| Example 17 | 58.4 | >10000 | 1420 | >10000 |
| Example 18 | 60.8 | | 1740 | 8320 |
| Example 19 | 18.0 | >10000 | 1059 | 5846 |
| Example 20 | 32.9 | >10000 | 2014 | 9232 |
| Example 21 | 83.8 | >10000 | 2860 | >10000 |
| Example 22 | 37.2 | >10000 | >10000 | >10000 |
| Example 23 | 19.9 | >10000 | >10000 | >10000 |
| Example 24 | 37.9 | >10000 | >10000 | >10000 |
| Example 25 | 41.0 | >10000 | >10000 | >10000 |
| Example 26 | 61.7 | >10000 | 5950 | >10000 |
| Example 27 | 22.4 | >10000 | 895 | 7780 |
| Example 28 | 35.8 | >10000 | 8780 | >10000 |
| Example 29 | 1570.0 | >10000 | >10000 | >10000 |

TABLE 2

| Compound No. | Cathepsin K | Cathepsin B | Cathepsin L | Cathepsin S |
|---|---|---|---|---|
| Example 30 | 355.0 | >10000 | >10000 | 9447 |
| Example 31 | 934.0 | >10000 | >10000 | >10000 |
| Example 32 | 10000.0 | | | |
| Example 33 | 1620.0 | >10000 | >10000 | >10000 |
| Example 34 | 2040.0 | | | |

TABLE 2-continued

| Compound No. | Cathepsin K | Cathepsin B | Cathepsin L | Cathepsin S |
|---|---|---|---|---|
| Example 35 | 492.0 | >10000 | >10000 | >10000 |
| Example 36 | 31.9 | >10000 | >10000 | 7347 |
| Example 37 | 112.9 | | | |
| Example 38 | 69.6 | >10000 | 8060 | >10000 |
| Example 39 | 108.3 | | | |
| Example 40 | 93.3 | >10000 | 9230 | >10000 |
| Example 41 | 39.9 | >10000 | 8181 | >10000 |
| Example 42 | 31.2 | >10000 | 7544 | >10000 |
| Example 43 | 462.0 | >10000 | >10000 | >10000 |
| Example 44 | 18.5 | >10000 | >10000 | >10000 |
| Example 45 | 3430.0 | | | |
| Example 46 | 13.2 | >10000 | 5966 | >10000 |
| Example 47 | 105.5 | | | |
| Example 48 | 49.6 | >10000 | >10000 | >10000 |
| Example 49 | 589.5 | | | |
| Example 50 | 4.3 | >10000 | 2673 | >10000 |
| Example 51 | 38.8 | >10000 | 4173 | >10000 |
| Example 52 | 607.6 | | | |
| Example 53 | 319.5 | | | |
| Example 54 | 76.0 | >10000 | >10000 | >10000 |
| Example 55 | 19.5 | 5662 | >10000 | >10000 |
| Example 56 | 100.5 | >10000 | >10000 | >10000 |
| Example 57 | 517.0 | | | |

TABLE 3

| Compound No. | Cathepsin K | Cathepsin B | Cathepsin L | Cathepsin S |
|---|---|---|---|---|
| Example 58 | 115.7 | | | |
| Example 59 | 174.2 | | | |
| Example 60 | 21.6 | 8778 | >10000 | >10000 |
| Example 61 | 292.3 | | | |
| Example 62 | 83.7 | >10000 | >10000 | >10000 |
| Example 63 | 64.3 | >10000 | >10000 | >10000 |
| Example 64 | 75.9 | 5890 | 5510 | >10000 |
| Example 65 | 46.6 | >10000 | >10000 | >10000 |
| Example 66 | 3.4 | >10000 | >10000 | >10000 |
| Example 67 | 64.6 | >10000 | >10000 | >10000 |
| Example 68 | 219.4 | | | |
| Example 69 | 552.2 | | | |
| Example 70 | 270.2 | | | |
| Example 71 | 546.8 | | | |
| Example 72 | 331.2 | | | |
| Example 73 | 315.0 | | | |
| Example 74 | 27.0 | >10000 | >10000 | >10000 |
| Example 75 | 41.0 | >10000 | >10000 | >10000 |
| Example 76 | 573.4 | | | |
| Example 77 | 95.1 | >10000 | >10000 | >10000 |
| Example 78 | 51.8 | >10000 | >10000 | >10000 |
| Example 79 | 3076.0 | | | |
| Example 80 | 156.9 | | | |
| Example 81 | 161.8 | | | |
| Example 82 | 54.5 | 7610 | >10000 | >10000 |
| Example 83 | 17.0 | >10000 | >10000 | >10000 |
| Example 84 | 44.3 | >10000 | 3410 | 1680 |
| Example 85 | 28.2 | >10000 | >10000 | >10000 |

TABLE 4

| Compound No. | Cathepsin K | Cathepsin B | Cathepsin L | Cathepsin S |
|---|---|---|---|---|
| Example 86 | 38.9 | >10000 | 2461 | 7107 |
| Example 87 | 3.6 | >10000 | 898 | 6260 |
| Example 88 | 31.6 | >10000 | 7137 | >10000 |
| Example 89 | 3.8 | >10000 | 6894 | >10000 |
| Example 90 | 68.2 | >10000 | >10000 | >10000 |
| Example 91 | 32.2 | >10000 | 4766 | >10000 |
| Example 92 | 40.9 | >10000 | >10000 | >10000 |

TABLE 4-continued

| Compound No. | Cathepsin K | Cathepsin B | Cathepsin L | Cathepsin S |
|---|---|---|---|---|
| Example 93 | 23.9 | >10000 | >10000 | >10000 |
| Example 94 | 9.0 | >10000 | 1131 | 8239 |
| Example 95 | 18.3 | >10000 | >10000 | >10000 |
| Example 96 | 10.2 | >10000 | 6504 | >10000 |
| Example 97 | 4.9 | >10000 | >10000 | >10000 |
| Example 98 | 61.7 | >10000 | >10000 | 4480 |
| Example 99 | 3.2 | >10000 | 1100 | >10000 |
| Example 100 | 15.4 | >10000 | >10000 | >10000 |
| Example 101 | 21.7 | >10000 | >10000 | >10000 |
| Example 102 | 63.2 | >10000 | 3440 | 6240 |
| Example 103 | 4.6 | >10000 | >10000 | >10000 |
| Example 104 | 12.4 | >10000 | 5590 | 3540 |
| Example 105 | 2.1 | >10000 | 2980 | 3630 |
| Example 106 | 3.1 | >10000 | >10000 | >10000 |
| Example 107 | 6.8 | >10000 | 1470 | 4750 |
| Example 108 | 6.9 | >10000 | 2270 | 9850 |
| Example 109 | 11.0 | >10000 | 1920 | 7620 |
| Example 110 | 22.9 | >10000 | >10000 | >10000 |
| Example 111 | 71.5 | >10000 | >10000 | >10000 |
| Example 112 | 147.1 | | | |
| Example 113 | 12.2 | >10000 | >10000 | >10000 |

TABLE 5

| Compound No. | Cathepsin K | Cathepsin B | Cathepsin L | Cathepsin S |
|---|---|---|---|---|
| Example 114 | 69.7 | >10000 | >10000 | >10000 |
| Example 115 | 9.2 | >10000 | >10000 | >10000 |
| Example 116 | 2.1 | >10000 | >10000 | >10000 |
| Example 117 | 4.1 | >10000 | >10000 | >10000 |
| Example 118 | 16.6 | >10000 | >10000 | >10000 |
| Example 119 | 9.6 | >10000 | 6790 | >10000 |
| Example 120 | 3.9 | 9280 | >10000 | >10000 |
| Example 121 | 17.2 | >10000 | >10000 | >10000 |
| Example 122 | 16.9 | >10000 | >10000 | >10000 |
| Example 123 | 10.2 | >10000 | >10000 | >10000 |
| Example 124 | 6.9 | >10000 | >10000 | >10000 |
| Example 125 | 15.2 | >10000 | >10000 | 5420 |
| Example 126 | 25.1 | >10000 | >10000 | 5750 |
| Example 127 | 10.9 | >10000 | >10000 | >10000 |
| Example 128 | 13.6 | >10000 | >10000 | 9060 |
| Example 129 | 4.9 | >10000 | >10000 | >10000 |
| Example 130 | 7.8 | >10000 | >10000 | 9069 |
| Example 131 | 15.9 | >10000 | >10000 | 3931 |
| Example 132 | 15.9 | >10000 | >10000 | >10000 |
| Example 133 | 63.7 | >10000 | >10000 | >10000 |
| Example 134 | 5.3 | >10000 | >10000 | >10000 |
| Example 135 | 110.9 | | | |
| Example 136 | 24.5 | >10000 | >10000 | >10000 |
| Example 137 | 38.2 | >10000 | >10000 | 6222 |
| Example 138 | 5.8 | >10000 | 4201 | 10000 |
| Example 139 | 12.2 | >10000 | 7035 | >10000 |
| Example 140 | 21.5 | >10000 | 6568 | >10000 |
| Example 141 | 4.5 | >10000 | >10000 | >10000 |

TABLE 6

| Compound No. | Cathepsin K | Cathepsin B | Cathepsin L | Cathepsin S |
|---|---|---|---|---|
| Example 142 | 17.9 | >10000 | >10000 | >10000 |
| Example 143 | 2.3 | >10000 | >10000 | >10000 |
| Example 144 | 18.3 | >10000 | >10000 | >10000 |
| Example 145 | 76.0 | | | |
| Example 146 | 3.9 | >10000 | >10000 | >10000 |
| Example 147 | 5.2 | >10000 | >10000 | 7926 |
| Example 148 | 16.8 | >10000 | >10000 | 8583 |
| Example 149 | 6.4 | >10000 | >10000 | 7297 |

TABLE 6-continued

| Compound No. | Cathepsin K | Cathepsin B | Cathepsin L | Cathepsin S |
|---|---|---|---|---|
| Example 150 | 6.6 | >10000 | 8921 | >10000 |
| Example 151 | 2.0 | >10000 | >10000 | >10000 |
| Example 152 | 2404.0 | | | |
| Example 153 | 0.2 | 4800 | 6720 | >10000 |
| Example 154 | 0.3 | 3209 | 4282 | >10000 |
| Example 155 | 2.0 | 7343 | >10000 | >10000 |
| Example 156 | 4.3 | >10000 | >10000 | >10000 |
| Example 157 | 6.4 | >10000 | >10000 | 4624 |
| Example 158 | 6.6 | 5648 | >10000 | 9425 |
| Example 159 | 0.6 | 1890 | 4086 | >10000 |
| Example 160 | 0.1 | 1838 | 8810 | >10000 |
| Example 161 | 61.1 | >10000 | >10000 | >10000 |
| Example 162 | 8.3 | >10000 | 6520 | 3950 |
| Example 163 | 25.2 | >10000 | >10000 | 3367 |
| Example 164 | 6.2 | >10000 | >10000 | 4637 |
| Example 165 | 5.7 | >10000 | >10000 | >10000 |
| Example 166 | 0.4 | 2413 | 3440 | 5937 |
| Example 167 | 8.0 | >10000 | >10000 | 1110 |
| Example 168 | 0.3 | >10000 | >10000 | >10000 |
| Example 169 | 74.0 | >10000 | >10000 | 3600 |

TABLE 7

| Compound No. | Cathepsin K | Cathepsin B | Cathepsin L | Cathepsin S |
|---|---|---|---|---|
| Example 170 | 39.5 | >10000 | >10000 | >10000 |
| Example 171 | 24.0 | >10000 | >10000 | 2190 |
| Example 172 | 108.1 | >10000 | >10000 | 8020 |
| Example 173 | 13.8 | >10000 | >10000 | >10000 |
| Example 174 | 11.7 | >10000 | >10000 | >10000 |
| Example 175 | 135.7 | | | |
| Example 176 | 121.7 | >10000 | >10000 | 5840 |
| Example 177 | 204.9 | >10000 | >10000 | 6140 |
| Example 178 | 21.2 | >10000 | >10000 | 5600 |
| Example 179 | 11.5 | >10000 | 7530 | 2760 |
| Example 180 | 10.9 | >10000 | >10000 | >10000 |
| Example 181 | 1.9 | >10000 | >10000 | >10000 |
| Example 182 | 10.5 | >10000 | >10000 | >10000 |
| Example 183 | 22.0 | >10000 | >10000 | >10000 |
| Example 184 | 0.2 | 2152 | 2421 | 8053 |
| Example 185 | 0.1 | 1758 | 4403 | >10000 |
| Example 186 | 0.1 | 2740 | 2020 | >10000 |
| Example 187 | 10.0 | >10000 | >10000 | 3377 |
| Example 188 | 16.1 | >10000 | >10000 | 4329 |
| Example 189 | 0.6 | 5402 | 1190 | >10000 |
| Example 190 | 0.3 | 7867 | >10000 | >10000 |
| Example 191 | 0.1 | 4759 | >10000 | >10000 |

As can be seen from the results of Tables 1 to 7, the compounds according to the present invention showed selective inhibitory activity against Cathepsin K, and therefore can be usefully applied for preventing and treating osteoporosis.

The invention claimed is:

1. A compound of Formula 1 or pharmaceutically acceptable salt thereof:

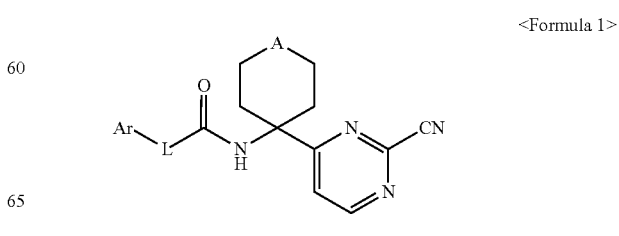

<Formula 1> wherein,

A is a bond, —CH$_2$—, —O—, or —C(CH$_3$)$_2$—,

L is —(CH$_2$)$_m$—O—, —(CH$_2$)$_n$—NH—, —CH(CH$_3$)—NH—, or —N(CH$_3$)—, m is 1 or 2, n is 0, 1, or 2,

Ar is an aromatic ring selected from the group consisting of phenyl, phenoxy-phenyl, pyridinyl-phenyl, indazolyl-phenyl, morpholinyl-phenyl, piperazinyl-phenyl, piperidinyl-phenyl, pyrazolyl-phenyl, benzyl-phenyl, phenylaminophenyl, biphenyl, piperazinyl-biphenyl, morpholinyl-biphenyl, naphthyl, benzodioxolyl, furanyl, indazolyl, quinoxalinyl, and indanyl, and the aromatic ring is optionally substituted with one to three substituents selected from the group consisting of halogen, cyano, hydroxy, trifluoromethyl, C$_1$~C$_4$ alkyl, C$_3$~C$_6$ cycloalkyl, C$_1$~C$_4$ alkoxy, hydroxy-C$_1$~C$_4$ alkyl, C$_1$~C$_4$ alkoxy-C$_1$~C$_4$ alkyl, hydroxycarbonyl-C$_1$~C$_4$ alkyl, C$_1$~C$_4$ alkoxycarbonyl-C$_1$~C$_4$ alkyl, C$_1$~C$_4$ alkoxy-C$_1$~C$_4$ alkoxy-C$_1$~C$_4$ alkyl, C$_1$~C$_4$ alkylcarbonylamino-C$_1$~C$_4$ alkyl, amino-C$_1$~C$_4$ alkoxy, mono- or di-C$_1$~C$_4$ alkylamino-C$_1$~C$_4$ alkoxy, aminosulfonyl, C$_1$~C$_4$ alkyl-sulfonyl, trifluoromethylsulfonyl, C$_3$~C$_6$ cycloalkylaminosulfonyl, mono- or di-C$_1$~C$_4$ alkylamino, C$_1$~C$_4$ alkylcarbonylamino, methanesulfonylamino, C$_1$~C$_4$ alkylcarbonyl, hydroxycarbonyl, mono- or di-C$_1$~C$_4$ alkylaminocarbonyl, oxolanyl-C$_1$~C$_4$ alkylaminocarbonyl, di-C$_1$~C$_4$ alkylamino-C$_1$~C$_4$ alkylaminocarbonyl, imidazolyl-C$_1$~C$_4$ alkylaminocarbonyl, C$_1$~C$_4$ alkoxy-C$_1$~C$_4$ alkylaminocarbonyl, C$_3$~C$_6$ cycloalkylaminocarbonyl, pyrrolidinylcarbonyl, triazolyl-C$_1$~C$_4$ alkylaminocarbonyl, C$_1$~C$_4$ alkoxycarbonyl-C$_2$~C$_4$ alkynyl, hydroxycarbonyl-C$_2$~C$_4$ alkynyl, hydroxy-C$_1$~C$_4$ alkylphenyl-C$_2$~C$_4$ alkynyl, and C$_1$~C$_4$ alkoxy-C$_1$~C$_4$ alkyl-phenoxymethyl.

2. The compound or pharmaceutically acceptable salt thereof according to claim 1, wherein the aromatic ring is optionally substituted with one to three substituents selected from the group consisting of halogen, cyano, hydroxy, trifluoromethyl, C$_1$~C$_4$ alkyl, C$_3$~C$_6$ cycloalkyl, C$_1$~C$_4$ alkoxy, hydroxymethyl, methoxymethyl, hydroxycarbonylmethyl, hydroxycarbonylethyl, methoxycarbonylmethyl, methoxyethoxymethyl, acetylaminomethyl, aminoethoxy, methylaminoethoxy, dimethylaminoethoxy, aminosulfonyl, methanesulfonyl, trifluoromethylsulfonyl, cyclopropylaminosulfonyl, mono- or di-C$_1$~C$_4$ alkylamino, acetylamino, methanesulfonylamino, acetyl, hydroxycarbonyl, dimethylaminocarbonyl, oxolanylmethylaminocarbonyl, dimethylaminoethylaminocarbonyl, imidazolylethylaminocarbonyl, methoxyethylaminocarbonyl, cyclopropylaminocarbonyl, pyrrolidinylcarbonyl, triazolylethylam inocarbonyl, methoxycarbonylbutynyl, hydroxycarbonylbutynyl, hydroxymethylphenylethynyl, and methoxyethylphenoxymethyl.

3. The compound or pharmaceutically acceptable salt thereof according to claim 1, wherein the aromatic ring is substituted with one or two substituents selected from the group consisting of halogen, C$_1$~C$_4$ alkyl, and acetyl.

4. The compound or pharmaceutically acceptable salt thereof according to claim 1, wherein A is —CH$_2$—, L is —(CH$_2$)$_n$—NH—, n is 0, Ar is an aromatic ring selected from the group consisting of biphenyl, piperazinyl-biphenyl, and morpholinyl-biphenyl, and the aromatic ring is substituted with one or two substituents selected from the group consisting of halogen, C$_1$~C$_4$ alkyl, and acetyl.

5. The compound or pharmaceutically acceptable salt thereof according to claim 1, wherein A is —CH$_2$—, L is —(CH$_2$)$_n$—NH—, n is 0, Ar is a piperazinyl-biphenyl group substituted with one or two substituents selected from the group consisting of halogen and C$_1$~C$_4$ alkyl.

6. The compound or pharmaceutically acceptable salt thereof according to claim 1, wherein the compound is selected from the group consisting of:

benzyl (1-(2-cyanopyrimidin-4-yl)cyclopentyl)carbamate;

4-bromobenzyl (1-(2-cyanopyrimidin-4-yl)cyclopentyl)carbamate;

3-bromobenzyl (1-(2-cyanopyrimidin-4-yl)cyclopentyl)carbamate;

phenethyl (1-(2-cyanopyrimidin-4-yl)cyclopentyl)carbamate;

3-methylbenzyl (1-(2-cyanopyrimidin-4-yl)cyclopentyl)carbamate;

3-methoxybenzyl (1-(2-cyanopyrimidin-4-yl)cyclopentyl)carbamate;

3-fluorobenzyl (1-(2-cyanopyrimidin-4-yl)cyclopentyl)carbamate;

3-chlorobenzyl (1-(2-cyanopyrimidin-4-yl)cyclopentyl)carbamate;

3-cyanobenzyl (1-(2-cyanopyrimidin-4-yl)cyclopentyl)carbamate;

benzyl (1-(2-cyanopyrimidin-4-yl)cyclohexyl)carbamate;

4-bromobenzyl (1-(2-cyanopyrimidin-4-yl)cyclohexyl)carbamate;

3-bromobenzyl (1-(2-cyanopyrimidin-4-yl)cyclohexyl)carbamate;

3-methylbenzyl (1-(2-cyanopyrimidin-4-yl)cyclohexyl)carbamate;

3-(trifluoromethyl)benzyl (1-(2-cyanopyrimidin-4-yl)cyclohexyl)carbamate;

3-fluorobenzyl (1-(2-cyanopyrimidin-4-yl)cyclohexyl)carbamate;

3-chlorobenzyl (1-(2-cyanopyrimidin-4-yl)cyclohexyl)carbamate;

2-methylbenzyl (1-(2-cyanopyrimidin-4-yl)cyclohexyl)carbamate;

2-fluorobenzyl (1-(2-cyanopyrimidin-4-yl)cyclohexyl)carbamate;

2-bromobenzyl (1-(2-cyanopyrimidin-4-yl)cyclohexyl)carbamate;

2-(trifluoromethyl)benzyl (1-(2-cyanopyrimidin-4-yl)cyclohexyl)carbamate;

2-methoxybenzyl (1-(2-cyanopyrimidin-4-yl)cyclohexyl)carbamate;

4-methylbenzyl (1-(2-cyanopyrimidin-4-yl)cyclohexyl)carbamate;

4-chlorobenzyl (1-(2-cyanopyrimidin-4-yl)cyclohexyl)carbamate;

4-(trifluoromethyl)benzyl (1-(2-cyanopyrimidin-4-yl)cyclohexyl)carbamate;

4-methoxybenzyl (1-(2-cyanopyrimidin-4-yl)cyclohexyl)carbamate;

naphthalen-1-ylmethyl (1-(2-cyanopyrimidin-4-yl)cyclohexyl)carbamate;

4-fluorobenzyl (1-(2-cyanopyrimidin-4-yl)cyclohexyl)carbamate;

2-chlorobenzyl (1-(2-cyanopyrimidin-4-yl)cyclohexyl)carbamate;
(4'-(methylsulfonyl)-[1,1'-biphenyl]-4-yl)methyl (1-(2-cyanopyrimidin-4-yl)cyclopentyl)carbamate;
(4'-(methylsulfonyl)-[1,1'-biphenyl]-3-yl)methyl (1-(2-cyanopyrimidin-4-yl)cyclopentyl)carbamate;
(4'-morpholino-[1,1'-biphenyl]-4-yl)methyl (1-(2-cyanopyrimidin-4-yl)cyclopentyl)carbamate;
(4'-morpholino-[1,1'-biphenyl]-3-yl)methyl (1-(2-cyanopyrimidin-4-yl)cyclopentyl)carbamate;
4-(6-fluoropyridin-3-yl)benzyl (1-(2-cyanopyrimidin-4-yl)cyclopentyl)carbamate;
4-(1-methyl-1H-indazol-6-yl)benzyl (1-(2-cyanopyrimidin-4-yl)cyclopentyl)carbamate;
3-(6-fluoropyridin-3-yl)benzyl (1-(2-cyanopyrimidin-4-yl)cyclopentyl)carbamate;
3-(1-methyl-1H-indazol-6-yl)benzyl (1-(2-cyanopyrimidin-4-yl)cyclopentyl)carbamate;
1-(1-(2-cyanopyrimidin-4-yl)cyclopentyl)-3-(ortho-tolyl)urea;
1-(1-(2-cyanopyrimidin-4-yl)cyclopentyl)-3-(meta-tolyl)urea;
1-(1-(2-cyanopyrimidin-4-yl)cyclopentyl)-3-(para-tolyl)urea;
1-(1-(2-cyanopyrimidin-4-yl)cyclopentyl)-3-(2-fluorobenzyl)urea;
1-(1-(2-cyanopyrimidin-4-yl)cyclopentyl)-3-phenylurea;
1-benzyl-3-(1-(2-cyanopyrimidin-4-yl)cyclopentyl)urea;
1-(benzo[d][1,3]dioxol-5-ylmethyl)-3-(1-(2-cyanopyrimidin-4-yl)cyclopentyl)urea;
1-(1-(2-cyanopyrimidin-4-yl)cyclopentyl)-3-(4-phenoxyphenyl)urea;
4-(2-(3-(1-(2-cyanopyrimidin-4-yl)cyclopentyl)ureido)ethyl)benzenesulfonamide;
1-(1-(2-cyanopyrimidin-4-yl)cyclopentyl)-3-(2-methylbenzyl)urea;
1-(1-(2-cyanopyrimidin-4-yl)cyclopentyl)-3-(3-methylbenzyl)urea;
1-(1-(2-cyanopyrimidin-4-yl)cyclopentyl)-3-(4-methylbenzyl)urea;
1-(1-(2-cyanopyrimidin-4-yl)cyclopentyl)-3-(3,4-dimethoxybenzyl)urea;
1-(1-(2-cyanopyrimidin-4-yl)cyclopentyl)-3-(2,5-dimethylphenyl)urea;
1-(1-(2-cyanopyrimidin-4-yl)cyclopentyl)-3-(1-phenylethyl)urea;
1-(1-(2-cyanopyrimidin-4-yl)cyclopentyl)-3-(4-(piperazin-1-yl)phenyl)urea;
1-(1-(2-cyanopyrimidin-4-yl)cyclopentyl)-3-(furan-3-ylmethyl)urea;
1-(1-(2-cyanopyrimidin-4-yl)cyclopentyl)-3-(4-fluorobenzyl)urea;
1-(1-(2-cyanopyrimidin-4-yl)cyclopentyl)-3-(naphthalen-1-ylmethyl)urea;
1-(1-(2-cyanopyrimidin-4-yl)cyclopentyl)-3-(2-(trifluoromethyl)benzyl)urea;
1-(1-(2-cyanopyrimidin-4-yl)cyclopentyl)-3-(3-(trifluoromethyl)benzyl)urea;
1-(1-(2-cyanopyrimidin-4-yl)cyclopentyl)-3-(4-(trifluoromethyl)benzyl)urea;
1-(1-(2-cyanopyrimidin-4-yl)cyclopentyl)-3-(2-(trifluoromethyl)phenyl)urea;
1-(1-(2-cyanopyrimidin-4-yl)cyclopentyl)-3-(3-(trifluoromethyl)phenyl)urea;
1-(1-(2-cyanopyrimidin-4-yl)cyclopentyl)-3-(4-(trifluoromethyl)phenyl)urea;
1-(1-(2-cyanopyrimidin-4-yl)cyclopentyl)-3-(3,4-dimethylphenyl)urea;
1-(1-(2-cyanopyrimidin-4-yl)cyclopentyl)-3-(3,5-dimethylphenyl)urea;
1-(1-(2-cyanopyrimidin-4-yl)cyclopentyl)-3-(2,3-dimethylphenyl)urea;
1-(1-(2-cyanopyrimidin-4-yl)cyclopentyl)-3-(2,5-difluorophenyl)urea;
1-(1-(2-cyanopyrimidin-4-yl)cyclopentyl)-3-(2-methyl-5-(trifluoromethyl)phenyl)urea;
1-(1-(2-cyanopyrimidin-4-yl)cyclopentyl)-3-(5-fluoro-2-(trifluoromethyl)phenyl)urea;
1-(1-(2-cyanopyrimidin-4-yl)cyclopentyl)-3-(2-methoxybenzyl)urea;
1-(1-(2-cyanopyrimidin-4-yl)cyclopentyl)-3-(3-methoxybenzyl)urea;
1-(1-(2-cyanopyrimidin-4-yl)cyclopentyl)-3-(4-methoxybenzyl)urea;
1-(1-(2-cyanopyrimidin-4-yl)cyclopentyl)-3-(3-hydroxyphenyl)urea;
4-(3-(1-(2-cyanopyrimidin-4-yl)cyclopentyl)ureido)benzenesulfonamide;
1-(1-(2-cyanopyrimidin-4-yl)cyclopentyl)-3-(2-hydroxyphenyl)urea;
1-(1-(2-cyanopyrimidin-4-yl)cyclopentyl)-3-(naphthalen-1-yl)urea;
1-(1-(2-cyanopyrimidin-4-yl)cyclopentyl)-3-(naphthalen-2-yl)urea;
1-(1-(2-cyanopyrimidin-4-yl)cyclopentyl)-3-(1-methyl-1H-indazol-5-yl)urea;
1-(1-(2-cyanopyrimidin-4-yl)cyclopentyl)-3-(quinoxalin-6-yl)urea;
1-(benzo[d][1,3]dioxol-5-yl)-3-(1-(2-cyanopyrimidin-4-yl)cyclopentyl)urea;
1-(1-(2-cyanopyrimidin-4-yl)cyclopentyl)-3-(2-methoxyphenyl)urea;
1-(1-(2-cyanopyrimidin-4-yl)cyclopentyl)-3-(3-methoxyphenyl)urea;
1-(1-(2-cyanopyrimidin-4-yl)cyclopentyl)-3-(4-methoxyphenyl)urea;
1-(1-(2-cyanopyrimidin-4-yl)cyclopentyl)-3-(2,3-dihydro-1H-inden-5-yl)urea;
1-(1-(2-cyanopyrimidin-4-yl)cyclopentyl)-3-(2-fluoro-5-(trifluoromethyl)phenyl)urea;
1-(1-(2-cyanopyrimidin-4-yl)-4,4-dimethylcyclohexyl)-3-(2,5-dimethylphenyl)urea;
1-(4-(2-cyanopyrimidin-4-yl)tetrahydro-2H-pyran-4-yl)-3-(4-fluoro-3-(trifluoromethyl)phenyl)urea;
1-(1-(2-cyanopyrimidin-4-yl)cyclohexyl)-3-phenylurea;
1-(1-(2-cyanopyrimidin-4-yl)cyclohexyl)-3-(2,5-dimethylphenyl)urea;
1-benzyl-3-(1-(2-cyanopyrimidin-4-yl)cyclohexyl)urea;
1-(1-(2-cyanopyrimidin-4-yl)cyclohexyl)-3-(3-(trifluoromethyl)phenyl)urea;
1-(1-(2-cyanopyrimidin-4-yl)cyclohexyl)-3-(4-(trifluoromethyl)phenyl)urea;
1-(1-(2-cyanopyrimidin-4-yl)cyclohexyl)-3-(2-(trifluoromethyl)benzyl)urea;
1-(1-(2-cyanopyrimidin-4-yl)cyclohexyl)-3-(2-(trifluoromethyl)phenyl)urea;
1-(4-chloro-3-(trifluoromethyl)phenyl)-3-(1-(2-cyanopyrimidin-4-yl)cyclohexyl)urea;
1-(1-(2-cyanopyrimidin-4-yl)cyclohexyl)-3-(2-fluoro-5-methylphenyl)urea;
1-(3,5-bis(trifluoromethyl)phenyl)-3-(1-(2-cyanopyrimidin-4-yl)cyclohexyl)urea;

1-(1-(2-cyanopyrimidin-4-yl)cyclohexyl)-3-(4-fluoro-3-(trifluoromethyl)phenyl)urea;
1-(1-(2-cyanopyrimidin-4-yl)cyclohexyl)-3-(2-fluoro-5-(trifluoromethyl)phenyl)urea;
2-(3-(1-(2-cyanopyrimidin-4-yl)cyclohexyl)ureido)-4-(trifluoromethyl)benzoic acid;
1-(1-(2-cyanopyrimidin-4-yl)cyclohexyl)-3-(2-methyl-5-(trifluoromethyl)phenyl)urea;
1-(4-benzylphenyl)-3-(1-(2-cyanopyrimidin-4-yl)cyclohexyl)urea;
1-(1-(2-cyanopyrimidin-4-yl)cyclohexyl)-3-(4-(phenylamino)phenyl)urea;
1-(1-(2-cyanopyrimidin-4-yl)cyclohexyl)-3-(2-hydroxyphenyl)urea;
1-(2,5-bis(trifluoromethyl)phenyl)-3-(1-(2-cyanopyrimidin-4-yl)cyclohexyl)urea;
3-(1-(2-cyanopyrimidin-4-yl)cyclohexyl)-1-methyl-1-phenylurea;
3-(1-(2-cyanopyrimidin-4-yl)cyclohexyl)-1-(4-fluoro-3-(trifluoromethyl)phenyl)-1-methylurea;
1-(1-(2-cyanopyrimidin-4-yl)cyclohexyl)-3-(2,4-difluoro-5-(trifluoromethyl)phenyl)urea;
1-(1-(2-cyanopyrimidin-4-yl)cyclohexyl)-3-(2-(methoxymethyl)-5-(trifluoromethyl)phenyl)urea;
1-(1-(2-cyanopyrimidin-4-yl)cyclohexyl)-3-(2-(hydroxymethyl)-5-(trifluoromethyl)phenyl)urea;
1-(3-bromophenyl)-3-(1-(2-cyanopyrimidin-4-yl)cyclohexyl)urea;
1-(4-bromophenyl)-3-(1-(2-cyanopyrimidin-4-yl)cyclohexyl)urea;
1-([1,1'-biphenyl]-3-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-3-yl)urea;
1-([1,1'-biphenyl]-4-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-4-yl)urea;
1-(1-(2-cyanopyrimidin-4-yl)cyclohexyl)-3-(4'-hydroxy-[1,1'-biphenyl]-4-yl)urea;
1-(1-(2-cyanopyrimidin-4-yl)cyclohexyl)-3-(4'-(methylsulfonyl)-[1,1'-biphenyl]-4-yl)urea;
1-(1-(2-cyanopyrimidin-4-yl)cyclohexyl)-3-(4'-morpholino-[1,1'-biphenyl]-4-yl)urea;
1-(1-(2-cyanopyrimidin-4-yl)cyclohexyl)-3-(4-(1-methyl-1H-indazol-6-yl)phenyl)urea;
1-(1-(2-cyanopyrimidin-4-yl)cyclohexyl)-3-(4-(pyridin-4-yl)phenyl)urea;
1-(1-(2-cyanopyrimidin-4-yl)cyclohexyl)-3-(4-(1-methyl-1H-pyrazol-4-yl)phenyl)urea;
1-(1-(2-cyanopyrimidin-4-yl)cyclohexyl)-3-(4'-fluoro-[1,1'-biphenyl]-4-yl)urea;
1-(1-(2-cyanopyrimidin-4-yl)cyclohexyl)-3-(4'-ethynyl-[1,1'-biphenyl]-4-yl)urea;
1-(1-(2-cyanopyrimidin-4-yl)cyclohexyl)-3-(3'-fluoro-[1,1'-biphenyl]-4-yl)urea;
1-(1-(2-cyanopyrimidin-4-yl)cyclohexyl)-3-(2'-fluoro-[1,1'-biphenyl]-4-yl)urea;
1-(1-(2-cyanopyrimidin-4-yl)cyclohexyl)-3-(4-(6-fluoropyridin-3-yl)phenyl)urea;
1-(1-(2-cyanopyrimidin-4-yl)cyclohexyl)-3-(4-(6-(trifluoromethyl)pyridin-3-yl)phenyl)urea;
1-(1-(2-cyanopyrimidin-4-yl)cyclohexyl)-3-(4-(6-methoxypyridin-3-yl)phenyl)urea;
1-(1-(2-cyanopyrimidin-4-yl)cyclohexyl)-3-(4-(pyridin-3-yl)phenyl)urea;
N-(4'-(3-(1-(2-cyanopyrimidin-4-yl)cyclohexyl)ureido)-[1,1'-biphenyl]-4-yl)acetamide;
4'-(3-(1-(2-cyanopyrimidin-4-yl)cyclohexyl)ureido)-N,N-dimethyl-[1,1'-biphenyl]-4-carboxamide;
3-(4'-(3-(1-(2-cyanopyrimidin-4-yl)cyclohexyl)ureido)-[1,1'-biphenyl]-4-yl)propanoic acid;
1-(1-(2-cyanopyrimidin-4-yl)cyclohexyl)-3-(4-iodophenyl)urea;
1-(4-bromo-3-(trifluoromethyl)phenyl)-3-(1-(2-cyanopyrimidin-4-yl)cyclohexyl)urea;
1-(4-bromo-2-fluorophenyl)-3-(1-(2-cyanopyrimidin-4-yl)cyclohexyl)urea;
4-(3-(1-(2-cyanopyrimidin-4-yl)cyclohexyl)ureido)benzoic acid;
1-(1-(2-cyanopyrimidin-4-yl)cyclohexyl)-3-(4-iodo-3-(trifluoromethyl)phenyl)urea;
1-(1-(2-cyanopyrimidin-4-yl)cyclohexyl)-3-(3-fluoro-4-iodophenyl)urea;
1-(1-(2-cyanopyrimidin-4-yl)cyclohexyl)-3-(4-(4-methylpiperazin-1-yl)phenyl)urea;
1-(1-(2-cyanopyrimidin-4-yl)cyclohexyl)-3-(4-morpholinophenyl)urea;
1-(1-(2-cyanopyrimidin-4-yl)cyclohexyl)-3-(4-(piperazin-1-yl)phenyl)urea;
1-(1-(2-cyanopyrimidin-4-yl)cyclohexyl)-3-(4-(4-(dimethylamino)piperidin-1-yl)phenyl)urea;
1-(1-(2-cyanopyrimidin-4-yl)cyclohexyl)-3-(4-(4-isopropylpiperazin-1-yl)phenyl)urea;
1-(4-(4-(tert-butyl)piperazin-1-yl)phenyl)-3-(1-(2-cyanopyrimidin-4-yl)cyclohexyl)urea;
1-(1-(2-cyanopyrimidin-4-yl)cyclohexyl)-3-(4-(4-cyclopropylpiperazin-1-yl)phenyl)urea;
1-(1-(2-cyanopyrimidin-4-yl)cyclohexyl)-3-(4-(4-isopropylpiperidin-1-yl)phenyl)urea;
1-(1-(2-cyanopyrimidin-4-yl)cyclohexyl)-3-(4-(4-ethylpiperazin-1-yl)phenyl)urea;
4'-(3-(1-(2-cyanopyrimidin-4-yl)cyclohexyl)ureido)-N-(2-methoxyethyl)-[1,1'-biphenyl]-4-carboxamide;
4'-(3-(1-(2-cyanopyrimidin-4-yl)cyclohexyl)ureido)-N-cyclopropyl-[1,1'-biphenyl]-4-sulfonamide;
4'-(3-(1-(2-cyanopyrimidin-4-yl)cyclohexyl)ureido)-N-cyclopropyl-[1,1'-biphenyl]-4-carboxamide;
1-(3'-chloro-4'-(pyrrolidin-1-carbonyl)-[1,1'-biphenyl]-4-yl)-3-(1-(2-cyanopyrimidin-4-yl)cyclohexyl)urea;
N-((4'-(3-(1-(2-cyanopyrimidin-4-yl)cyclohexyl)ureido)-[1,1'-biphenyl]-4-yl)methyl)acetamide;
1-(1-(2-cyanopyrimidin-4-yl)cyclohexyl)-3-(4'-((4-(2-methoxyethyl)phenoxy)methyl)-[1,1'-biphenyl]-4-yl)urea;
1-(1-(2-cyanopyrimidin-4-yl)cyclohexyl)-3-(4'-(2-(dimethylamino)ethoxy)-[1,1'-biphenyl]-4-yl)urea;
1-(1-(2-cyanopyrimidin-4-yl)cyclohexyl)-3-(4'-(4-isopropylpiperazin-1-yl)-[1,1'-biphenyl]-4-yl)urea;
1-(4'-(4-acetylpiperazin-1-yl)-[1,1'-biphenyl]-4-yl)-3-(1-(2-cyanopyrimidin-4-yl)cyclohexyl)urea;
methyl 2-(4'-(3-(1-(2-cyanopyrimidin-4-yl)cyclohexyl)ureido)-[1,1'-biphenyl]-4-yl)acetate;
1-(1-(2-cyanopyrimidin-4-yl)cyclohexyl)-3-(4'-((2-methoxyethoxy)methyl)-[1,1'-biphenyl]-4-yl)urea;
4'-(3-(1-(2-cyanopyrimidin-4-yl)cyclohexyl)ureido)-N-((tetrahydrofuran-2-yl)methyl)-[1,1'-biphenyl]-4-carboxamide;
4'-(3-(1-(2-cyanopyrimidin-4-yl)cyclohexyl)ureido)-N-(2-(dimethylamino)ethyl)-[1,1'-biphenyl]-4-carboxamide;
1-(1-(2-cyanopyrimidin-4-yl)cyclohexyl)-3-(4'-(4-ethylpiperazin-1-yl)-[1,1'-biphenyl]-4-yl)urea;

2-(4'-(3-(1-(2-cyanopyrimidin-4-yl)cyclohexyl)ureido)-[1,1'-biphenyl]-4-yl)acetic acid;
1-(1-(2-cyanopyrimidin-4-yl)cyclohexyl)-3-(4'-(methylsulfonyl)-2-(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-carboxylic acid;
N-(4'-(3-(1-(2-cyanopyrimidin-4-yl)cyclohexyl)ureido)-2'-fluoro-[1,1'-biphenyl]-4-yl)acetamide;
N-((4'-(3-(1-(2-cyanopyrimidin-4-yl)cyclohexyl)ureido)-2'-fluoro-[1,1'-biphenyl]-4-yl)methyl)acetamide;
1-(1-(2-cyanopyrimidin-4-yl)cyclohexyl)-3-(2-fluoro-4'-(4-isopropylpiperazin-1-yl)-[1,1'-biphenyl]-4-yl)urea;
1-(1-(2-cyanopyrimidin-4-yl)cyclohexyl)-3-(2-fluoro-4'-(methylsulfonyl)-[1,1'-biphenyl]-4-yl)urea;
1-(1-(2-cyanopyrimidin-4-yl)cyclohexyl)-3-(4'-(1-cyclopropylpiperidin-4-yl)-2-fluoro-[1,1'-biphenyl]-4-yl)urea;
1-(1-(2-cyanopyrimidin-4-yl)cyclohexyl)-3-(4'-((trifluoromethyl)sulfonyl)-[1,1'-biphenyl]-4-yl)urea;
1-(1-(2-cyanopyrimidin-4-yl)cyclohexyl)-3-(3'-fluoro-4'-(methylsulfonyl)-[1,1'-biphenyl]-4-yl)urea;
1-(1-(2-cyanopyrimidin-4-yl)cyclohexyl)-3-(4'-(methylsulfonyl)-3'-(trifluoromethyl)-[1,1'-biphenyl]-4-yl)urea;
1-(1-(2-cyanopyrimidin-4-yl)cyclohexyl)-3-(2'-(trifluoromethyl)-[1,1'-biphenyl]-4-yl)urea;
4'-(3-(1-(2-cyanopyrimidin-4-yl)cyclohexyl)ureido)-[1,1'-biphenyl]-4-sulfonamide;
N-(4'-(3-(1-(2-cyanopyrimidin-4-yl)cyclohexyl)ureido)-[1,1'-biphenyl]-4-yl)methanesulfonamide;
methyl 5-(4'-(3-(1-(2-cyanopyrimidin-4-yl)cyclohexyl)ureido)-[1,1'-biphenyl]-4-yl)pent-4-ynoate;
1-(2,2'-bis(trifluoromethyl)-[1,1'-biphenyl]-4-yl)-3-(1-(2-cyanopyrimidin-4-yl)cyclohexyl)urea;
1-(1-(2-cyanopyrimidin-4-yl)cyclohexyl)-3-(2-(trifluoromethyl)-4'-((trifluoromethyl)sulfonyl)-[1,1'-biphenyl]-4-yl)urea;
1-(1-(2-cyanopyrimidin-4-yl)cyclohexyl)-3-(4'-(methylsulfonyl)-2,3'-bis(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-sulfonamide;
N-(4'-(3-(1-(2-cyanopyrimidin-4-yl)cyclohexyl)ureido)-2'-(trifluoromethyl)-[1,1'-biphenyl]-4-yl)methanesulfonamide;
1-(1-(2-cyanopyrimidin-4-yl)cyclohexyl)-3-((4'-(4-isopropylpiperazin-1-yl)-[1,1'-biphenyl]-4-yl)methyl)urea;
5-(4-(3-(1-(2-cyanopyrimidin-4-yl)cyclohexyl)ureido)phenyl)pent-4-ynoic acid;
1-(1-(2-cyanopyrimidin-4-yl)cyclohexyl)-3-(4-((4-(hydroxymethyl)phenyl)ethynyl)phenyl)urea;
N-(2-(1H-imidazol-4-yl)ethyl)-4'-(3-(1-(2-cyanopyrimidin-4-yl)cyclohexyl)ureido)-[1,1'-biphenyl]-4-carboxamide;
N-(2-(1H-imidazol-1-yl)ethyl)-4'-(3-(1-(2-cyanopyrimidin-4-yl)cyclohexyl)ureido)-[1,1'-biphenyl]-4-carboxamide;
N-(2-(1H-imidazol-1-yl)ethyl)-4'-(3-(1-(2-cyanopyrimidin-4-yl)cyclohexyl)ureido)-2'-fluoro-[1,1'-biphenyl]-4-carboxamide;
N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;

N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;
N-(2-(1H-imidazol-4-yl)ethyl)-4'-(3-(1-(2-cyanopyrimidin-4-yl)cyclohexyl)ureido)-2'-(trifluoromethyl)-[1,1'-biphenyl]-4-carboxamide;
1-(4'-(2-aminoethoxy)-[1,1'-biphenyl]-4-yl)-3-(1-(2-cyanopyrimidin-4-yl)cyclohexyl)urea; and
1-(1-(2-cyanopyrimidin-4-yl)cyclohexyl)-3-(4'-(2-(methylamino)ethoxy)-[1,1'-biphenyl]-4-yl)urea.

7. The compound or pharmaceutically acceptable salt according to claim 1, wherein the compound is selected from the group consisting of:
1-([1,1'-biphenyl]-3-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-3-yl)urea;
1-([1,1'-biphenyl]-4-yl)-3-(1-(2-cyanopyrimidin-4-yl)cyclohexyl)urea;
1-(1-(2-cyanopyrimidin-4-yl)cyclohexyl)-3-(4'-(trifluoromethyl)-[1,1'-biphenyl]-4-yl)urea;
1-(1-(2-cyanopyrimidin-4-yl)cyclohexyl)-3-(4'-hydroxy-[1,1'-biphenyl]-4-yl)urea;
1-(1-(2-cyanopyrimidin-4-yl)cyclohexyl)-3-(4'-(methylsulfonyl)-[1,1'-biphenyl]-4-yl)urea;
1-(1-(2-cyanopyrimidin-4-yl)cyclohexyl)-3-(4'-morpholino-[1,1'-biphenyl]-4-yl)urea;
1-(1-(2-cyanopyrimidin-4-yl)cyclohexyl)-3-(4'-fluoro-[1,1'-biphenyl]-4-yl)urea;
1-(1-(2-cyanopyrimidin-4-yl)cyclohexyl)-3-(4'-ethynyl-[1,1'-biphenyl]-4-yl)urea;
1-(1-(2-cyanopyrimidin-4-yl)cyclohexyl)-3-(3'-fluoro-[1,1'-biphenyl]-4-yl)urea;
1-(1-(2-cyanopyrimidin-4-yl)cyclohexyl)-3-(2'-fluoro-[1,1'-biphenyl]-4-yl)urea;
N-(4'-(3-(1-(2-cyanopyrimidin-4-yl)cyclohexyl)ureido)-[1,1'-biphenyl]-4-yl)acetamide;
4'-(3-(1-(2-cyanopyrimidin-4-yl)cyclohexyl)ureido)-N,N-dimethyl-[1,1'-biphenyl]-4-carboxamide;
3-(4'-(3-(1-(2-cyanopyrimidin-4-yl)cyclohexyl)ureido)-[1,1'-biphenyl]-4-yl)propanoic acid;
4'-(3-(1-(2-cyanopyrimidin-4-yl)cyclohexyl)ureido)-N-(2-methoxyethyl)-[1,1'-biphenyl]-4-carboxamide;
4'-(3-(1-(2-cyanopyrimidin-4-yl)cyclohexyl)ureido)-N-cyclopropyl-[1,1'-biphenyl]-4-sulfonamide;
4'-(3-(1-(2-cyanopyrimidin-4-yl)cyclohexyl)ureido)-N-cyclopropyl-[1,1'-biphenyl]-4-carboxamide;
1-(3'-chloro-4'-(pyrrolidin-1-carbonyl)-[1,1'-biphenyl]-4-yl)-3-(1-(2-cyanopyrimidin-4-yl)cyclohexyl)urea;
N-((4'-(3-(1-(2-cyanopyrimidin-4-yl)cyclohexyl)ureido)-[1,1'-biphenyl]-4-yl)methyl)acetamide;
1-(1-(2-cyanopyrimidin-4-yl)cyclohexyl)-3-(4'-((4-(2-methoxyethyl)phenoxy)methyl)-[1,1'-biphenyl]-4-yl)urea;
1-(1-(2-cyanopyrimidin-4-yl)cyclohexyl)-3-(4'-(2-(dimethylamino)ethoxy)-[1,1'-biphenyl]-4-yl)urea;
1-(1-(2-cyanopyrimidin-4-yl)cyclohexyl)-3-(4'-(4-isopropylpiperazin-1-yl)-[1,1'-biphenyl]-4-yl)urea;
1-(4'-(4-acetylpiperazin-1-yl)-[1,1'-biphenyl]-4-yl)-3-(1-(2-cyanopyrimidin-4-yl)cyclohexyl)urea;
methyl 2-(4'-(3-(1-(2-cyanopyrimidin-4-yl)cyclohexyl)ureido)-[1,1'-biphenyl]-4-yl)acetate;
1-(1-(2-cyanopyrimidin-4-yl)cyclohexyl)-3-(4'-((2-methoxyethoxy)methyl)-[1,1'-biphenyl]-4-yl)urea;
4'-(3-(1-(2-cyanopyrimidin-4-yl)cyclohexyl)ureido)-N-((tetrahydrofuran-2-yl)methyl)-[1,1'-biphenyl]-4-carboxamide;

4'-(3-(1-(2-cyanopyrimidin-4-yl)cyclohexyl)ureido)-N-(2-(dimethylamino)ethyl)-[1,1'-biphenyl]-4-carboxamide;
1-(1-(2-cyanopyrimidin-4-yl)cyclohexyl)-3-(4'-(4-ethylpiperazin-1-yl)-[1,1'-biphenyl]-4-yl)urea;
2-(4'-(3-(1-(2-cyanopyrimidin-4-yl)cyclohexyl)ureido)-[1,1'-biphenyl]-4-yl)acetic acid;
1-(1-(2-cyanopyrimidin-4-yl)cyclohexyl)-3-(4'-(methylsulfonyl)-2-(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-carboxylic acid;
N-(4'-(3-(1-(2-cyanopyrimidin-4-yl)cyclohexyl)ureido)-2'-fluoro-[1,1'-biphenyl]-4-yl)acetamide;
N-((4'-(3-(1-(2-cyanopyrimidin-4-yl)cyclohexyl)ureido)-2'-fluoro-[1,1'-biphenyl]-4-yl)methyl)acetamide;
1-(1-(2-cyanopyrimidin-4-yl)cyclohexyl)-3-(2-fluoro-4'-(4-isopropylpiperazin-1-yl)-[1,1'-biphenyl]-4-yl)urea;
1-(1-(2-cyanopyrimidin-4-yl)cyclohexyl)-3-(2-fluoro-4'-(methylsulfonyl)-[1,1'-biphenyl]-4-yl)urea;
1-(1-(2-cyanopyrimidin-4-yl)cyclohexyl)-3-(4'-(1-cyclopropylpiperidin-4-yl)-2-fluoro-[1,1'-biphenyl]-4-yl)urea;
1-(1-(2-cyanopyrimidin-4-yl)cyclohexyl)-3-(4'-((trifluoromethyl)sulfonyl)-[1,1'-biphenyl]-4-yl)urea;
1-(1-(2-cyanopyrimidin-4-yl)cyclohexyl)-3-(3'-fluoro-4'-(methylsulfonyl)-[1,1'-biphenyl]-4-yl)urea;
1-(1-(2-cyanopyrimidin-4-yl)cyclohexyl)-3-(4'-(methylsulfonyl)-3'-(trifluoromethyl)-[1,1'-biphenyl]-4-yl)urea;
1-(1-(2-cyanopyrimidin-4-yl)cyclohexyl)-3-(2'-(trifluoromethyl)-[1,1'-biphenyl]-4-yl)urea;
4'-(3-(1-(2-cyanopyrimidin-4-yl)cyclohexyl)ureido)-[1,1'-biphenyl]-4-sulfonamide;
N-(4'-(3-(1-(2-cyanopyrimidin-4-yl)cyclohexyl)ureido)-[1,1'-biphenyl]-4-yl)methanesulfonamide;
methyl 5-(4'-(3-(1-(2-cyanopyrimidin-4-yl)cyclohexyl)ureido)-[1,1'-biphenyl]-4-yl)pent-4-ynoate;
1-(2,2'-bis(trifluoromethyl)-[1,1'-biphenyl]-4-yl)-3-(1-(2-cyanopyrimidin-4-yl)cyclohexyl)urea;
1-(1-(2-cyanopyrimidin-4-yl)cyclohexyl)-3-(2-(trifluoromethyl)-4'-((trifluoromethyl)sulfonyl)-[1,1'-biphenyl]-4-yl)urea;
1-(1-(2-cyanopyrimidin-4-yl)cyclohexyl)-3-(4'-(methylsulfonyl)-2,3'-bis(trifluoromethyl)-[1,1'-biphenyl]-4-yl)urea;
4'-(3-(1-(2-cyanopyrimidin-4-yl)cyclohexyl)ureido)-2'-(trifluoromethyl)-[1,1'-biphenyl]-4-sulfonamide;
N-(4'-(3-(1-(2-cyanopyrimidin-4-yl)cyclohexyl)ureido)-2'-(trifluoromethyl)-[1,1'-biphenyl]-4-yl)methanesulfonamide;
1-(1-(2-cyanopyrimidin-4-yl)cyclohexyl)-3-((4'-(4-isopropylpiperazin-1-yl)-[1,1'-biphenyl]-4-yl)methyl)urea;
N-(2-(1H-imidazol-4-yl)ethyl)-4'-(3-(1-(2-cyanopyrimidin-4-yl)cyclohexyl)ureido)-[1,1'-biphenyl]-4-carboxamide;
N-(2-(1H-imidazol-1-yl)ethyl)-4'-(3-(1-(2-cyanopyrimidin-4-yl)cyclohexyl)ureido)-[1,1'-biphenyl]-4-carboxamide;
N-(2-(1H-imidazol-1-yl)ethyl)-4'-(3-(1-(2-cyanopyrimidin-4-yl)cyclohexyl)ureido)-2'-fluoro-[1,1'-biphenyl]-4-carboxamide;
N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;
N-(2-(2H-1,2,3-triazol-2-yl)ethyl)-4'-(3-(1-(2-cyanopyrimidin-4-yl)cyclohexyl)ureido)-2'-fluoro-[1,1'-biphenyl]-4-carboxamide;
N-(2-(1H-imidazol-4-yl)ethyl)-4'-(3-(1-(2-cyanopyrimidin-4-yl)cyclohexyl)ureido)-2'-(trifluoromethyl)-[1,1'-biphenyl]-4-carboxamide;
1-(4'-(2-aminoethoxy)-[1,1'-biphenyl]-4-yl)-3-(1-(2-cyanopyrimidin-4-yl)cyclohexyl)urea; and
1-(1-(2-cyanopyrimidin-4-yl)cyclohexyl)-3-(4'-(2-(methylamino)ethoxy)-[1,1'-biphenyl]-4-yl)urea.

8. The compound or pharmaceutically acceptable salt according to claim 1, wherein the compound is selected from the group consisting of:

1-(1-(2-cyanopyrimidin-4-yl)cyclohexyl)-3-(4'-(4-isopropylpiperazin-1-yl)-[1,1'-biphenyl]-4-yl)urea;
1-(4'-(4-acetylpiperazin-1-yl)-[1,1'-biphenyl]-4-yl)-3-(1-(2-cyanopyrimidin-4-yl)cyclohexyl)urea;
1-(1-(2-cyanopyrimidin-4-yl)cyclohexyl)-3-(4'-(4-ethylpiperazin-1-yl)-[1,1'-biphenyl]-4-yl)urea; and
1-(1-(2-cyanopyrimidin-4-yl)cyclohexyl)-3-(2-fluoro-4'-(4-isopropylpiperazin-1-yl)-[1,1'-biphenyl]-4-yl)urea.

9. The compound or pharmaceutically acceptable salt according to claim 1, wherein the compound is 1-(1-(2-cyanopyrimidin-4-yl)cyclohexyl)-3-(4'-(4-isopropylpiperazin-1-yl)-[1,1'-biphenyl]-4-yl)urea.

10. The compound or pharmaceutically acceptable salt according to claim 1, wherein the compound is 1-(1-(2-cyanopyrimidin-4-yl)cyclohexyl)-3-(2-fluoro-4'-(4-isopropylpiperazin-1-yl)-[1,1'-biphenyl]-4-yl)urea.

11. A method for preventing or treating osteoporosis comprising administering to a subject a pharmaceutical composition comprising a therapeutically effective amount of the compound or pharmaceutically acceptable salt thereof according to claim 1; and a pharmaceutically acceptable carrier.

12. A reagent composition for inhibiting cathepsin K comprising the compound or salt thereof according to claim 1.

* * * * *